(12) United States Patent
Condon et al.

(10) Patent No.: US 8,481,495 B2
(45) Date of Patent: Jul. 9, 2013

(54) IAP INHIBITORS

(75) Inventors: Stephen M. Condon, Malvern, PA (US); Yijun Deng, Malvern, PA (US); Matthew D. Alexander, Malvern, PA (US); Matthew G. Laporte, Malvern, PA (US)

(73) Assignee: TetraLogic Pharmaceuticals Corporation, Malvern, PA (US)

( * ) Notice: Subject to any disclaimer, the term of this patent is extended or adjusted under 35 U.S.C. 154(b) by 0 days.

(21) Appl. No.: 13/322,588

(22) PCT Filed: May 25, 2010

(86) PCT No.: PCT/US2010/036046
§ 371 (c)(1),
(2), (4) Date: Dec. 14, 2011

(87) PCT Pub. No.: WO2010/138496
PCT Pub. Date: Dec. 2, 2010

(65) Prior Publication Data
US 2012/0094917 A1 Apr. 19, 2012

Related U.S. Application Data

(60) Provisional application No. 61/181,875, filed on May 28, 2009.

(51) Int. Cl.
*A01N 43/46* (2006.01)
*A61K 31/40* (2006.01)

(52) U.S. Cl.
USPC ....... 514/18.7; 514/18.9; 514/19.3; 514/19.8; 514/19.2

(58) Field of Classification Search
None
See application file for complete search history.

(56) References Cited

FOREIGN PATENT DOCUMENTS

| WO | 2005097791 A1 | 10/2005 |
|---|---|---|
| WO | WO 2005097791 A1 * | 10/2005 |
| WO | 2006010118 | 1/2006 |
| WO | 2006017925 | 2/2006 |
| WO | 2008014240 A2 | 1/2008 |
| WO | 2010033531 | 3/2010 |

OTHER PUBLICATIONS

Hunter, A.M., et al., "The inhibitors of apoptosis (IAPs) as cancer targets" Apoptosis 12:1542-1568 (2007).*
Dean et al., "Novel therapeutic targets in lung cancer: inhibitor apoptosis proteins from laboratory to clinic," Cancer Treat. Rev. 33:203-212 (2007).*
Sykes et al., "Treatment of severe autoimmune disease by stem-cell transplantation," Nature 435:620-627 (2005).*
Tarner et al., "Treatment of autoimmune diases by adoptive cellular gene therapy," Ann. N. Y. Acad. Sci. 998:512-219 (2003).*
Traub et al., "Psoriasis—pathophysiology, conventional, and alternative approaches to treatment," Alt. Med. Rev. 112:319-330 (2007).*
George, "Management of patients with refractory immune thrombocytopenic purpura," J. Throm. Haemost. 4:1664-1672 (2006).*
Liu et al., Structural basis for binding of Smac/DIABLO to the XIAP BIR3 domain, 2000, Nature vol. 408, pp. 1004-1008; p. 1004-p. 1007.
Extended European Search Report dated Nov. 28, 2012 in EP App. No. 10 78 1080 dated Nov. 28, 2012.

* cited by examiner

*Primary Examiner* — Christina Bradley
*Assistant Examiner* — Kristina M Hellman
(74) *Attorney, Agent, or Firm* — Banner & Witcoff, Ltd.

(57) ABSTRACT

The present invention describes compounds of the formula

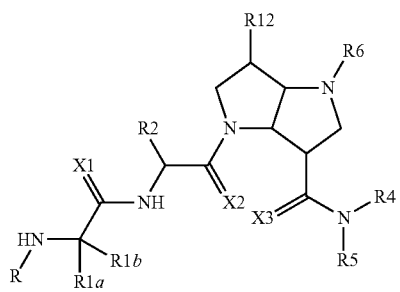

pharmaceutically acceptable salts thereof, processes for their preparation, pharmaceutical compositions containing them, and their use in therapy.

28 Claims, No Drawings

IAP INHIBITORS

BACKGROUND OF THE INVENTION

1. Field of the Invention

The present invention describes compounds that are inhibitors of IAPs (inhibitors of apoptosis proteins), processes for their preparation, pharmaceutical compositions containing them, and their use in therapy. The compounds of the present invention are useful in the treatment of cancer, autoimmune diseases and other disorders.

2. Description of Related Art

Apoptosis (programmed cell death) plays a central role in the development and homeostasis of all multi-cellular organisms. Apoptosis can be initiated within a cell from an external factor such as a chemokine (an extrinsic pathway) or via an intracellular event such a DNA damage (an intrinsic pathway). Alterations in apoptotic pathways have been implicated in many types of human pathologies, including developmental disorders, cancer, autoimmune diseases, as well as neurodegenerative disorders. One mode of action of chemotherapeutic drugs is cell death via apoptosis.

Apoptosis is conserved across species and executed primarily by activated caspases, a family of cysteine proteases with aspartate specificity in their substrates. These cysteine containing aspartate specific proteases ("caspases") are produced in cells as catalytically inactive zymogens and are proteolytically processed to become active proteases during apoptosis. Once activated, effector caspases are responsible for proteolytic cleavage of a broad spectrum of cellular targets that ultimately lead to cell death. In normal surviving cells that have not received an apoptotic stimulus, most caspases remain inactive. If caspases are aberrantly activated, their proteolytic activity can be inhibited by a family of evolutionarily conserved proteins called IAPB (inhibitors of apoptosis proteins).

The IAP family of proteins suppresses apoptosis by preventing the activation of procaspases and inhibiting the enzymatic activity of mature caspases. Several distinct mammalian IAPB including XIAP, c-IAP1, c-IAP2, ML-IAP, NAIP (neuronal apoptosis inhibiting protein), Bruce, and survivin, have been identified, and they all exhibit anti-apoptotic activity in cell culture. IAPs were originally discovered in baculovirus by their functional ability to substitute for P35 protein, an anti-apoptotic gene. IAPs have been described in organisms ranging from Drosophila to human, and are known to be overexpressed in many human cancers. Generally speaking, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion. It is the BIR domain that is believed to cause the anti-apoptotic effect by inhibiting the caspases and thus inhibiting apoptosis. XIAP is expressed ubiquitously in most adult and fetal tissues. Overexpression of XIAP in tumor cells has been demonstrated to confer protection against a variety of pro-apoptotic stimuli and promotes resistance to chemotherapy. Consistent with this, a strong correlation between XIAP protein levels and survival has been demonstrated for patients with acute myelogenous leukemia. Down-regulation of XIAP expression by antisense oligonucleotides has been shown to sensitize tumor cells to death induced by a wide range of pro-apoptotic agents, both in vitro and in vivo In normal cells signaled to undergo apoptosis, however, the IAP-mediated inhibitory effect must be removed, a process at least in part performed by a mitochondrial protein named Smac (second mitochondrial activator of caspases). Smac (or, DIABLO), is synthesized as a precursor molecule of 239 amino acids; the N-terminal 55 residues serve as the mitochondria targeting sequence that is removed after import. The mature form of Smac contains 184 amino acids and behaves as an oligomer in solution. Smac and various fragments thereof have been proposed for use as targets for identification of therapeutic agents.

Smac is synthesized in the cytoplasm with an N-terminal mitochondrial targeting sequence that is proteolytically removed during maturation to the mature polypeptide and is then targeted to the inter-membrane space of mitochondria. At the time of apoptosis induction, Smac is released from mitochondria into the cytosol, together with cytochrome c, where it binds to IAPs, and enables caspase activation, therein eliminating the inhibitory effect of IAPs on apoptosis. Whereas cytochrome c induces multimerization of Apaf-1 to activate procaspase-9 and -3, Smac eliminates the inhibitory effect of multiple IAPs. Smac interacts with essentially all IAPs that have been examined to date including XIAP, c-IAP1, c-IAP2, ML-IAP, and survivin. Thus, Smac appears to be a master regulator of apoptosis in mammals.

It has been shown that Smac promotes not only the proteolytic activation of procaspases, but also the enzymatic activity of mature caspase, both of which depend upon its ability to interact physically with IAPs. X-ray crystallography has shown that the first four amino acids (AVPI) of mature Smac bind to a portion of IAPs. This N-terminal sequence is essential for binding IAPs and blocking their anti-apoptotic effects.

Currently, there are drug discovery efforts aimed at identifying compounds that interfere with the role played by IAPs in disease states where a defect in apoptosis is implicated, such as in cancers and autoimmune diseases. Indeed, a number of IAP inhibitors that mimic the interactions of the Smac tetrapeptide are now known and possess pro-apoptotic activity in vitro and in vivo. The art continues to look for additional compounds that may function as IAP inhibitors.

SUMMARY OF THE INVENTION

The present invention provides IAP inhibitors (Smac mimetics), as well as therapeutic methods of using these inhibitors to modulate apoptosis.

In one embodiment, the elements of which can be practiced either separately, or in combination with the other embodiments disclosed below, the present invention provides compounds of Formula (I):

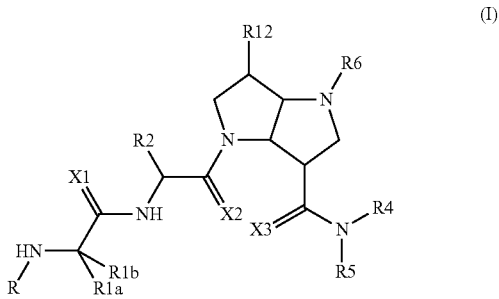

or pharmaceutically acceptable salts thereof, wherein:

X1, X2 and X3 are each independently O or S:

R is selected from H, alkyl, substituted alkyl, alkenyl, substituted alkenyl, cycloalkyl, substituted cycloalkyl, aryl, substituted aryl, heteroaryl, or substituted heteroaryl;

R1a and R1b are each independently selected from H, alkyl, or substituted alkyl;

R2 is selected from H, alkyl, substituted alkyl, cycloalkyl, substituted cycloalkyl, heterocycloalkyl, substituted heterocycloalkyl, aryl, substituted aryl, heteroaryl, or substituted heteroaryl;

R4 and R5 are each independently selected from H, alkyl, substituted alkyl, cycloalkyl, substituted cycloalkyl, aryl, substituted aryl, heterocycloalkyl, substituted heterocycloalkyl, heteroaryl, or substituted heteroaryl, or R4 and R5 together with the nitrogen to which they are attached represent heterocycloalkyl, or substituted heterocycloalkyl;

R6 is selected from H, alkyl, substituted alkyl, alkoxy, substituted alkoxy, alkylsulfonyl, arylsulfonyl, cycloalkyl, substituted cycloalkyl, heterocycloalkyl, substituted heterocycloalkyl, aryl, substituted aryl, heteroaryl, or substituted heteroaryl; and R12 is selected from H or hydroxy.

In another embodiment, the elements of which can be practiced either separately, or in combination with the other embodiments disclosed above and below, the various substituents of Formula (I) are defined as follows:

X1, X2 and X3 are O;

R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;

R1a and R1b are each independently selected from H, alkyl, or substituted alkyl, wherein the substitutents are selected from the group consisting of halogen, hydroxy, oxo, mercapto, carboxyl, cycloalkyl, aryl, alkoxy, amino, heteroaryl, and nitro;

R2 is alkyl; substituted alkyl, wherein the substituents are selected from the group consisting of halogen, hydroxy, oxo, alkoxy, cycloalkyl, aryl, heterocycloalkyl and heteroaryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the substituents are selected from the group consisting of halogen, hydroxy, mercapto, carboxyl, alkyl, cycloalkyl, aryl, alkoxy, amino, heteroaryl, and nitro;

R4 and R5 are each independently selected from H; alkyl; substituted alkyl, wherein the substituents are selected from the groups consisting of oxo, alkoxy, carboxy, carboalkoxy, cycloalkyl, aryl, and substituted aryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

In another embodiment, the elements of which can be practiced either separately, or in combination with the other embodiments disclosed above and below, X1, X2 and X3 are O.

In another embodiment, the elements of which can be practiced either separately, or in combination with the other embodiments disclosed above and below, the various substituents of Formula (I) are defined as follows:

X1, X2 and X3 are O;

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;

R1a and R1b are each independently selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R4 and R5 are each independently selected from H; alkyl; substituted alkyl, wherein the substituents are selected from the groups consisting of oxo, alkoxy, carboxy, carboalkoxy, cycloalkyl, aryl, and substituted aryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

In one embodiment, the elements of which can be practiced either separately, or in combination with the other embodiments disclosed above and below, the compounds of Formula (I) where X1, X2 and X3 are O, or their pharmaceutically acceptable salts, have the absolute configuration of formula (I-S) as follows:

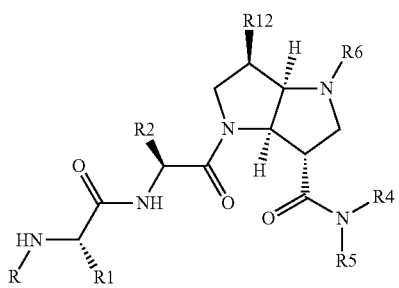

(I-S)

wherein:
R is selected from H, alkyl, substituted alkyl, alkenyl, substituted alkenyl, cycloalkyl, substituted cycloalkyl, aryl, substituted aryl, heteroaryl, or substituted heteroaryl;
R1 is selected from alkyl, or substituted alkyl;
R2 is selected from H, alkyl, substituted alkyl, cycloalkyl, substituted cycloalkyl, heterocycloalkyl, substituted heterocycloalkyl, aryl, substituted aryl, heteroaryl, or substituted heteroaryl;
R4 and R5 are each independently selected from H; alkyl, substituted alkyl, cycloalkyl; substituted cycloalkyl; aryl; substituted aryl; heterocycloalkyl, substituted heterocycloalkyl heteroaryl, or substituted heteroaryl, or R4 and R5 together with the nitrogen to which they are attached represent heterocycloalkyl, or substituted heterocycloalkyl;
R6 is selected from H, alkylsulfonyl, arylsulfonyl, alkyl, substituted alkyl, alkoxy, substituted alkoxy, cycloalkyl, substituted cycloalkyl, heterocycloalkyl, substituted heterocycloalkyl, aryl, substituted aryl, heteroaryl, or substituted heteroaryl; and
R12 is selected from H or hydroxy.

In related compounds, the elements of which can be practiced either separately, or in combination with the other embodiments disclosed above and below, the compounds and pharmaceutically acceptable salts of Formula (I) where X1, X2 and X3 are O have the absolute configuration of formula (I-R) as follows (with the various substituents having the same definitions presented above in connection with formula (I-S):

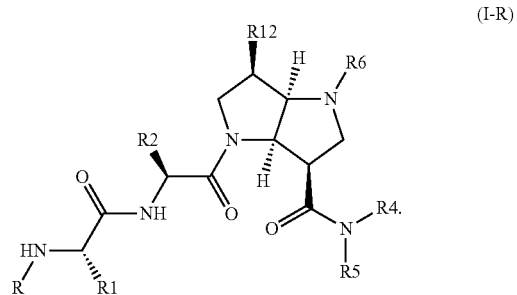

(I-R)

In another embodiment, the elements of which can be practiced either separately, or in combination with the other embodiments disclosed above and below, the various substituents of Formula (I-S) and (I-R) are defined as follows:
R is selected from H, alkyl, substituted alkyl, alkenyl, substituted alkenyl, aryl, substituted aryl, cycloalkyl, substituted cycloalkyl, heteroaryl, or substituted heteroaryl; wherein the substitutents are selected from the group consisting of halogen, hydroxy, oxo, mercapto, carboxyl, alkyl, cycloalkyl, aryl, alkoxy, amino, heteroaryl, and nitro;
R1 is alkyl, or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;
R2 is alkyl; substituted alkyl, wherein the substituents are selected from the group consisting of halogen, hydroxy, oxo, alkoxy, cycloalkyl, aryl, heterocycloalkyl and heteroaryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the substituents are selected from the group consisting of halogen, hydroxy, mercapto, carboxyl, alkyl, cycloalkyl, aryl, alkoxy, amino, heteroaryl, and nitro;

R4 and R5 are each independently selected from H; alkyl; substituted alkyl, wherein the substituents are selected from the groups consisting of oxo, alkoxy, carboxy, carboalkoxy, cycloalkyl, aryl, and substituted aryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl, or substituted heterocycloalkyl, wherein the substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

In another embodiment, the elements of which can be practiced either separately, or in combination with the other embodiments disclosed above and below, the various substitutents of Formula (I-S) and (I-R) are defined as follows:

R is selected from H, alkyl, substituted alkyl, alkenyl, or substituted alkenyl; wherein the substitutents are selected from the group consisting of halogen, hydroxy, oxo, mercapto, carboxyl, alkyl, cyclopropyl, alkoxy, amino, and nitro;

R1 is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R2 is alkyl, cycloalkyl, aryl, heterocycloalkyl, heteroaryl, or substituted alkyl, wherein the substituents are selected from the group consisting of halogen, hydroxy, oxo, alkoxy, cycloalkyl, aryl, heterocycloalkyl and heteroaryl;

R4 and R5 are each independently selected from H; alkyl; substituted alkyl, wherein the substituents are selected from the groups consisting of oxo, alkoxy, carboxy, carboalkoxy, cycloalkyl, aryl, and substituted aryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl, or substituted heterocycloalkyl, wherein the substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the substituents are selected from the group consisting of halogen, hydroxy, mercapto, carboxyl, alkyl, cycloalkyl, aryl, alkoxy, amino, heteroaryl, and nitro; and R12 is selected from H or hydroxy.

In other embodiments, the elements of which can be practiced either separately, or in combination with the other embodiments disclosed above and below, the present invention provides compounds of Formula (I), or pharmaceutically acceptable salts thereof, wherein:

X1, X2 and X3 are O;

R is selected from H, or lower alkyl;

R1a and R1b are each independently selected from H, or lower alkyl;

R2 is selected from H; lower alkyl; cycloalkyl; or substituted lower alkyl wherein the substituents are selected from the group consisting of hydroxy, and alkoxy;

R4 and R5 are each independently selected from H; alkyl; substituted alkyl, wherein the substituents are selected from the groups consisting of oxo, alkoxy, carboxy, carboalkoxy, cycloalkyl, aryl, and substituted aryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl, or substituted heterocycloalkyl, wherein the substituents are selected from the group consisting of halogen, hydroxy, mercapto, carboxyl, alkyl, cycloalkyl, aryl, alkoxy, amino, heteroaryl, and nitro;

R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; and R12 is H or hydroxy.

In other embodiments, the elements of which can be practiced either separately, or in combination with the other embodiments disclosed above and below, the present invention provides compounds of Formula (I-S), or (I-R), or pharmaceutically acceptable salts thereof, wherein:

R is selected from H, or lower alkyl;

R1 is lower alkyl;

R2 is selected from lower alkyl; cycloalkyl; or substituted lower alkyl, wherein the substituents are selected from the group consisting of hydroxy, and alkoxy;

R4 and R5 are each independently selected from H; alkyl; substituted alkyl, wherein the substituents are selected from the groups consisting of oxo, alkoxy, carboxy, carboalkoxy, cycloalkyl, aryl, and substituted aryl; cycloalkyl; substituted cycloalkyl, wherein the substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl, or substituted heterocycloalkyl, wherein the substituents are selected from the group consisting of halogen, hydroxy, mercapto, carboxyl, alkyl, cycloalkyl, aryl, alkoxy, amino, heteroaryl, and nitro;

R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen; and R12 is H or hydroxy.

In all of the embodiments identified above and below, dimers are also encompassed within the scope of this invention. Dimerization of monomeric Smac mimetics has been shown to provide useful Smac mimetics. See, e.g., U.S. Pat. No. 7,517,906, US20080020986, WO200814236, WO200814238, and WO200814240, all of which are incorporated herein by reference as though fully set forth.

Dimeric Smac mimetics of the invention generally comprise the formula "Formula (I) -L- Formula (I)", as depicted here:

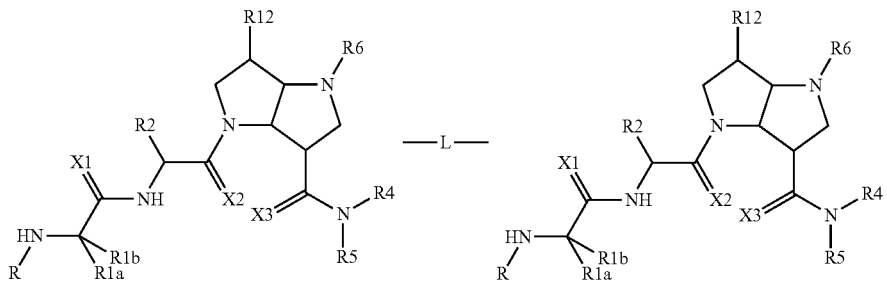

or Formula (I-S) -L- Formula (I-S) or Formula (I-S) -L- Formula (I-R).

L is A "Linker" (L), i.e., bond or linking group whereby two chemical moieties are directly covalently linked one to the other or are indirectly linked via a chemical moiety that covalently links the two chemical moieties, in either case, to form a homo- or heterodimer. A Linker, therefore, is a single or double covalent bond or is a contiguous chain, branched or unbranched, substituted or unsubstituted, of 1 to about 100 atoms, typically 1 to about 30 atoms and typically up to about 500 MW, e.g., optionally substituted alkyl, alkylene, alkylyne, cycloalkyl, alkylcycloalkyl, alkylarylalkyl chain of 2 to 20 atoms with 1-4 heteroatoms selected from —O—, —NH— and —S—. Illustrative Linkers are described, e.g., in U.S. Pat. Nos. 7,517,906, 7,309,792, US20080020986, WO200814236, WO200814238, and WO200814240, US 20050197403, U.S. Pat. No. 7,589,118, WO2010031171, WO2007131366, WO2007104162, and WO2008134679 all of which are incorporated herein by reference as though fully set forth.

Illustrative -L- groups include the following:
1) —C1-C10 alkyl-,
2) —C2-C6 alkenyl-,
3) —C2-C4 alkynyl-,
4) —C3-C7 cycloalkyl-,
5) -phenyl-,
6) -biphenyl-,
7) -heteroaryl-,
8) -heterocyclyl-,
9) —C1-C6 alkyl-(C2-C6 alkenyl)-C1-C6 alkyl-,
10) —C1-C6 alkyl-(C2-C4 alkynyl)-C1-C6 alkyl-,
11) —C1-C6 alkyl-(C3-C7 cycloalkyl)-C1-C6 alkyl-,
12) —C1-C6 alkyl-phenyl-C1-C6 alkyl-,
13) —C1-C6 alkyl-biphenyl-C1-C6 alkyl-,
14) —C1-C6 alkyl-heteroaryl-C1-C6 alkyl-,
15) —C1-C6 alkyl-heterocyclyl-C1-C6 alkyl-,
16) —C1-C6 alkyl-O—C1-C6 alkyl-,
17) —C(O)—N—C(O)— wherein N is cyclohexyl, phenyl, naphthyl or biphenyl optionally substituted with Rx and Rx is C1-C6 alkyl or C6-C10 aryl optionally substituted with C1-C6 alkyl,
18) —C(O)CH$_2$NHC(O)C(O)NHCH$_2$C(O)—.

For additional linkers, see, e.g., WO2007131366 and WO2007104162.

More specifically, in this embodiment, the invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:
X1 is O or S:
X2 is O or S:
X3 is O or S:
R is selected from H; alkyl; substituted alkyl; alkenyl; substituted alkenyl; cycloalkyl; substituted cycloalkyl; aryl; substituted aryl; heteroaryl; or substituted heteroaryl;
R1a is H; alkyl; or substituted alkyl;
R1b is H; alkyl; or substituted alkyl;
R1 is H; alkyl; or substituted alkyl;
both R2 groups together, or both R6 groups together, form -L-, linking the two monomers;
when both R6 groups together form -L-, then each R2 is independently selected from H; alkyl; substituted alkyl; cycloalkyl; substituted cycloalkyl; heterocycloalkyl; substituted heterocycloalkyl; aryl; substituted aryl; heteroaryl; or substituted heteroaryl;
R4 is H; alkyl; substituted alkyl; cycloalkyl; substituted cycloalkyl; aryl; substituted aryl; heterocycloalkyl; substituted heterocycloalkyl; heteroaryl; or substituted heteroaryl and R5 is H; alkyl; substituted alkyl; cycloalkyl; substituted cycloalkyl; aryl; substituted aryl; heterocycloalkyl; substituted heterocycloalkyl; heteroaryl; or substituted heteroaryl or R4 and R5 together with the nitrogen to which each are attached represent heterocycloalkyl; or substituted heterocycloalkyl;
when both R2 groups together form -L-, each R6 is independently selected from H; alkyl; substituted alkyl; alkoxy; substituted alkoxy; alkylsulfonyl; arylsulfonyl; cycloalkyl; substituted cycloalkyl; heterocycloalkyl; substituted heterocycloalkyl; aryl; substituted aryl; heteroaryl; or substituted heteroaryl; and
R12 is H or hydroxy;
L is a single or double covalent bond or is a contiguous chain, branched or unbranched, substituted or unsubstituted, of 1 to about 100 atoms In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:
in R, the alkyl, alkenyl, aryl, cycloalkyl, and heteroaryl substitutents are selected from the group consisting of halogen, hydroxy, oxo, mercapto, carboxyl, alkyl, cycloalkyl, aryl, alkoxy, amino, heteroaryl, and nitro;
in R1a, R1b and R1, the alkyl substitutents are selected from the group consisting of halogen, hydroxy, oxo, mercapto, carboxyl, cycloalkyl, aryl, alkoxy, amino, heteroaryl, and nitro;
in R2, the alkyl substituents are selected from the group consisting of halogen, hydroxy, oxo, alkoxy, cycloalkyl, aryl, heterocycloalkyl and heteroaryl; cycloalkyl; the cycloalkyl substituents are selected from the group consisting of halogen, hydroxy, oxo, mercapto, carboxyl, alkyl, cycloalkyl, aryl, alkoxy, amino, heteroaryl, and nitro; aryl; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro;
in R4, the alkyl substituents are selected from the groups consisting of oxo, alkoxy, carboxy, carboalkoxy, cycloalkyl, aryl, and substituted aryl; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro;
in R5, the alkyl substituents are selected from the groups consisting of oxo, alkoxy, carboxy, carboalkoxy, cycloalkyl, aryl, and substituted aryl; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro;
in R6, the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, oxo, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

X1, X2 and X3 are O;

R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;

R1a is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R1b is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R1 is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R2 is alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

R4 and R5 are each independently selected from H; alkyl; substituted alkyl, wherein the alkyl substituents are selected from the group consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;

both R6 groups together form -L-;

L is a single or double covalent bond or is a contiguous chain, branched or unbranched, substituted or unsubstituted, of 1 to 100 atoms.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

R is selected from H or lower alkyl;

R1a is H or lower alkyl;

R1b is H or lower alkyl;

R1 is H or lower alkyl;

R2 is selected from H; lower alkyl; cycloalkyl; or substituted lower alkyl, wherein the substituents are selected from the group consisting of hydroxy, cycloalkyl and alkoxy;

R4 is H or methyl and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;

both R6 groups together form -L-;

L is a single or double covalent bond or is a contiguous chain, branched or unbranched, substituted or unsubstituted, of 1 to 100 atoms.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

R is methyl;

R1a is H;

R1b is methyl;

R1 is methyl;

R2 is lower alkyl or cycloalkyl;

R4 is H and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;

R6 is selected from H; methylsulfonyl; substituted lower alkyl, wherein the substituents are selected from the group consisting of oxo, lower alkoxy, —NH$_2$, mono-lower alkyl amino, and heteroaryl optionally substituted with lower alkyl or halogen;

L is optionally substituted alkyl, alkylene, alkylyne, cycloalkyl, alkylcycloalkyl, alkylarylalkyl chain of 2 to 20 atoms with 1-3 heteroatoms selected from —O—, —NH— and —S—.

In other embodiments, the elements of which can be practiced either separately, or in combination with the other embodiments disclosed above and below, the present invention provides a compound that is a dimer of two monomers of Formula (I), or two monomers of Formula (I-S) or one monomer of Formula (I-S) and one monomer of Formula (I-R), or a pharmaceutically acceptable salt thereof, wherein:

R1a is —H
R1b is methyl;
R1 is methyl;
R2 is selected from t-butyl or cyclohexyl;
R4 is H and R5 is selected from cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;
R12 is —H;
L is —C(O)CH$_2$NHC(O)C(O)NHCH$_2$C(O)—.

In all of the embodiments identified above, the pharmaceutically acceptable salts of the compounds embraced by the foregoing formulae are also included in each of the embodiments.

In another embodiment, the present invention is directed specifically to compounds of formula (I) and/or formula (I-S) where the structure

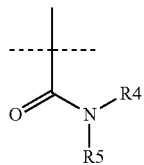

consists of a residue of an L-amino acid or an L-amino acid ester. In such instance one of R4 or R5 is H and the other one of R4 or R5 constitutes the moiety (or an ester derivative thereof) attached to the amino group of the amino acid. An abbreviated list of examples illustrative of the phrases "residue of an L-amino acid" and "residue of an ester of an L-amino acid" are shown in the following table where —C(O)OR is —C(O)OH or —C(O)O-lower alkyl:

| Amino Acid | Example Of Residues of amino acids or amino acid esters |
|---|---|
| Glycine | 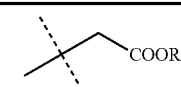 |
| β-alanine | 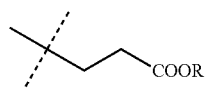 |

| Amino Acid | Example Of Residues of amino acids or amino acid esters |
|---|---|
| α-alanine | |
| Valine | |
| Leucine | |
| Isoleucine | |
| Phenylalanine | |

For simplicity and illustrative purposes, the principles of the invention are described by referring mainly to specific illustrative embodiments thereof. In addition, in the following description, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

DEFINITIONS

"Alkyl" (monovalent) and "alkylene" (divalent) when alone or as part of another term (e.g., alkoxy) mean branched or unbranched, saturated aliphatic hydrocarbon group, having up to 12 carbon atoms unless otherwise specified. Examples of particular alkyl groups include, but are not limited to, methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The term, "lower," when used to modify alkyl, alkenyl, etc., means 1 to 4 carbon atoms, branched or linear so that, e.g., the terms "lower alkyl", "C$_1$-C$_4$ alkyl" and "alkyl of 1 to 4 carbon atoms" are synonymous and used interchangeably to mean methyl, ethyl, 1-propyl, isopropyl, 1-butyl, sec-butyl or t-butyl. Examples of alkylene groups include, but are not limited to, methylene, ethylene, n-propylene, n-butylene and 2-methyl-butylene.

The term substituted alkyl refers to alkyl moieties having substituents replacing one or more hydrogens on one or more (often no more than four) carbon atoms of the hydrocarbon backbone. Such substituents are independently selected from the group consisting of: a halogen (e.g., I, Br, Cl, or F, particularly fluoro (F)), hydroxy, amino, cyano, mercapto, alkoxy (such as a $C_1$-$C_6$ alkoxy, or a lower ($C_1$-$C_4$) alkoxy, e.g., methoxy or ethoxy to yield an alkoxyalkyl), aryloxy (such as phenoxy to yield an aryloxyalkyl), nitro, oxo (e.g., to form a carbonyl), carboxyl (which is actually the combination of an oxo and hydroxy substituent on a single carbon atom), carbamoyl (an aminocarbonyl such as $NR_2C(O)$—, which is the substitution of an oxo and an amino on a single carbon atom), cycloalkyl (e.g., a cycloalkylalkyl), aryl (resulting for example in aralkyls such as benzyl or phenylethyl), heterocyclylalkyl (e.g., heterocycloalkylalkyl), heteroaryl (e.g., heteroarylalkyl), alkylsulfonyl (including lower alkylsulfonyl such as methylsulfonyl), arylsulfonyl (such as phenylsulfonyl), and —$OCF_3$ (which is a halogen substituted alkoxy). The invention further contemplates that several of these alkyl substituents, including specifically alkoxy, cycloalkyl, aryl, heterocyclyalkyl and heteroaryl, are optionally further substituted as defined in connection with each of their respective definitions provided below. In addition, certain alkyl substituent moieties result from a combination of such substitutions on a single carbon atom. For example, an ester moiety, e.g., an alkoxycarbonyl such as methoxycarbonyl, or tert-butoxycarbonyl (Boc) results from such substitution. In particular, methoxycarbonyl and Boc are substituted alkyls that result from the substitution on a methyl group (—$CH_3$) of both an oxo (=O) and an unsubstituted alkoxy, e.g., a methoxy ($CH_3$—O—) or a tert-butoxy (($CH_3$)$_3$C—O—), respectively replacing the three hydrogens. Similarly, an amide moiety, e.g., an alkylaminocarbonyl, such as dimethlyaminocarbonyl or methylaminocarbonyl, is a substituted alkyl that results from the substitution on a methyl group (—$CH_3$) of both an oxo (=O) and a mono-unsubstitutedalkylamino or, diunsubstitutedalkylamino, e.g., dimethylamino (—N—($CH_3$)$_2$), or methylamino (—NH—($CH_3$)) replacing the three hydrogens (similarly an arylaminocarbonyl such as diphenylaminocarbonyl is a substituted alkyl that results from the substitution on a methyl group (—$CH_3$) of both an oxo (=O) and a mono-unsubstitutedaryl(phenyl)amino). Exemplary substituted alkyl groups further include cyanomethyl, nitromethyl, hydroxyalkyls such as hydroxymethyl, trityloxymethyl, propionyloxymethyl, aminoalkyls such as aminomethyl, carboxylalkyls such as carboxymethyl, carboxyethyl, carboxypropyl, 2,3-dichloropentyl, 3-hydroxy-5-carboxyhexyl, acetyl (e.g., an alkanoyl, where in the case of acetyl the two hydrogen atoms on the —$CH_2$ portion of an ethyl group are replaced by an oxo (=O)), 2-aminopropyl, pentachlorobutyl, trifluoromethyl, methoxyethyl, 3-hydroxypentyl, 4-chlorobutyl, 1,2-dimethyl-propyl, pentafluoroethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro (n-butyl), 2-amino (iso-propyl), cycloalkylcarbonyl (e.g., cuclopropylcarbonyl) and 2-carbamoyloxyethyl. Particular substituted alkyls are substituted methyl groups. Examples of substituted methyl group include groups such as hydroxymethyl, protected hydroxymethyl (e.g., tetrahydropyranyl-oxymethyl), acetoxymethyl, carbamoyloxymethyl, trifluoromethyl, chloromethyl, carboxymethyl, carboxyl (where the three hydrogen atoms on the methyl are replaced, two of the hydrogens are replaced by an oxo (=O) and the other hydrogen is replaced by a hydroxy (—OH)), tert-butoxycarbonyl (where the three hydrogen atoms on the methyl are replaced, two of the hydrogens are replaced by an oxo (=O) and the other hydrogen is replaced by a tert-butoxy (—O—C($CH_3$)$_3$), bromomomethyl and iodomethyl. When the specification and especially the claims refer to a particular substituent for an alkyl, that substituent can potentially occupy one or more of the substitutable positions on the allyl. For example, reciting that an alkyl has a fluoro substituent, would embrace mono-, di-, and possibly a higher degree of substitution on the alkyl moiety.

The term substituted alkylene refers to alkylene moieties having substituents replacing one or more hydrogens on one or more (often no more than four) carbon atoms of the hydrocarbon backbone where the alkylene is similarly substituted with groups as set forth above for alkyl.

Alkoxy is —O-alkyl. A substituted alkoxy is —O-substituted alkyl, where the alkoxy is similarly substituted with groups as set forth above for alkyl. One substituted alkoxy is acetoxy where two of the hydrogens in ethoxy (e.g., —O—$CH_2$—$CH_3$) are replaced by an oxo, (=O) to yield —O—C(O)—$CH_3$; another is an aralkoxy where one of the hydrogens in the alkoxy is replaced by an aryl, such as benzyloxy, and another is a carbamate where two of the hydrogens on methoxy (e.g., —O—$CH_3$) are replaced by oxo (=O) and the other hydrogen is replaced by an amino (e.g., —$NH_2$, —NHR or —NRR) to yield, for example, —O—C(O)—$NH_2$. A lower alkoxy is —O-lower alkyl.

"Alkenyl" (monovalent) and "alkenylene" (divalent) when alone or as part of another term mean an unsaturated hydrocarbon group containing at least one carbon-carbon double bond, typically 1 or 2 carbon-carbon double bonds, which may be linear or branched and which have at least 2 and up to 12 carbon atoms unless otherwise specified. Representative alkenyl groups include, by way of example, vinyl, allyl, isopropenyl, but-2-enyl, n-pent-2-enyl, and n-hex-2-enyl.

The terms substituted alkenyl and substituted alkenylene refer to alkenyl and alkenylene moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, oxo, carbamoyl, cycloalkyl, aryl, heterocyclyl, heteroaryl, alkylsulfonyl, arylsulfonyl and —$OCF_3$.

"Alkynyl" means a monovalent unsaturated hydrocarbon group containing at least one carbon-carbon triple bond, typically 1 carbon-carbon triple bond, which may be linear or branched and which have at least 2 and up to 12 carbon atoms unless otherwise specified. Representative alkynyl groups include, by way of example, ethynyl, propargyl, and but-2-ynyl.

"Cycloalkyl" when alone or as part of another term means a saturated or partially unsaturated cyclic aliphatic hydrocarbon group (carbocycle group), having up to 12 carbon atoms unless otherwise specified, such as cyclopropyl, cyclobutyl, cyclopentyl and cyclohexyl, and further includes polycyclic, including fused cycloalkyls such as 1,2,3,4-tetrahydronaphthalenyls (1,2,3,4-tetrahydronaphthalen-1-yl, and 1,2,3,4-tetrahydronaphthalen-2-yl), indanyls (indan-1yl, and indan-2-yl), isoindenyls (isoinden-1-yl, isoinden-2-yl, and isoinden-3-yl) and indenyls (inden-1-yl, inden-2-yl and inden-3-yl). A lower cycloalkyl has from 3 to 6 carbon atoms and includes cyclopropyl, cyclobutyl, cyclopentyl and cyclohexyl.

The term substituted cycloalkyl refers to cycloalkyl moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, mercapto, carboxyl, oxo, carbamoyl, alkyl, substituted alkyls such as trifluoromethyl, aryl, substituted aryls, heterocyclyl, heteroaryl, alkylsulfonyl, arylsulfonyl and —OCF$_3$. When the specification and especially the claims refer to a particular substituent for a cycloalkyl, that substituent can potentially occupy one or more of the substitutable positions on the cycloalkyl. For example, reciting that a cycloalkyl has a fluoro substituent, would embrace mono-, di-, and a higher degree of substitution on the cycloalkyl moiety. Examples of cycloalkyls include cyclopropy, cyclobutyl, cyclopentyl, cyclohexyl, tetrahydronaphthyl and indanyl.

"Amino" denotes primary (i.e., —NH$_2$), secondary (i.e., —NHR) and tertiary (i.e., —NRR) amines, where the R groups can be the same or different and can be selected from a variety of moieties, usually an alkyl, a substituted alkyl, an aryl, a substituted aryl, a cycloalkyl, or a substituted cyclosalkyl and especially a lower alkyl and an aryl (phenyl), including substituted phenyl. Particular secondary and tertiary aminos are alkylaminos, dialkylaminos, arylaminos, diarylaminos, aralkylaminos and diaralkylaminos. Particular secondary and tertiary amines are methylamino, ethylamino, propylamino, isopropylamino, phenylamino, benzylamino dimethylamino, diethylamino, dipropylamino and disopropylamino.

"Aryl" when used alone or as part of another term means an aromatic carbocyclic group whether or not fused having the number of carbon atoms designated, or if no number is designated, from 6 up to 14 carbon atoms. Particular aryl groups include phenyl, naphthyl, biphenyl, phenanthrenyl, naphthacenyl, and the like (see e.g. Lang's Handbook of Chemistry (Dean, J. A., ed) 13$^{th}$ ed. Table 7-2 [1985]). Phenyl and naphthyl groups are generally preferred.

The term substituted aryl refers to aryl moieties having substituents replacing one or more hydrogens on one or more (usually no more than six) carbon atoms of the aromatic hydrocarbon core. Such substituents are independently selected from the group consisting of: halo (e.g., I, Br, Cl, F), hydroxy, amino, cyano, alkoxy (such as $C_1$-$C_6$ alkoxy and particularly lower alkoxy), substituted alkoxy, aryloxy (such as phenoxy), nitro, mercapto, carboxyl, carbamoyl, alkyl, substituted alkyl (such as trifluoromethyl), aryl, —OCF$_3$, alkylsulfonyl (including lower alkylsulfonyl), arylsulfonyl, heterocyclyl and heteroaryl. Examples of such substituted phenyls include but are not limited to a mono- or di (halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl; 3-fluorophenyl, 4-fluorophenyl, a mono- or di (hydroxy)phenyl group such as 4-hydroxyphenyl, 3-hydroxyphenyl, 2,4-dihydroxyphenyl, the protected-hydroxy derivatives thereof; a nitrophenyl group such as 3- or 4-nitrophenyl; a cyanophenyl group, for example, 4-cyanophenyl; a mono- or di (lower alkyl)phenyl group such as 4-methylphenyl, 2,4-dimethylphenyl, 2-methylphenyl, 4-(iso-propyl)phenyl, 4-ethylphenyl, 3-(n-propyl)phenyl; a mono or di (alkoxy) phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl; 3- or 4-trifluoromethylphenyl; a mono- or dicarboxyphenyl or (protected carboxy)phenyl group such 4-carboxyphenyl; a mono- or di (hydroxymethyl)phenyl or (protected hydroxymethyl)phenyl such as 3-(protected hydroxymethyl)phenyl or 3,4-di (hydroxymethyl)phenyl; a mono- or di (aminomethyl) phenyl or (protected aminomethyl)phenyl such as 2-(aminomethyl) phenyl or 2,4-(protected aminomethyl)phenyl; or a mono- or di (N-(methylsulfonylamino)) phenyl such as 3-(N-methylsulfonylamino) phenyl. Also, the substituents, such as in a disubstituted phenyl groups, can be the same or different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, as well as for trisubstituted phenyl groups where the substituents are different, as for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups are 2-chlorophenyl, 2-aminophenyl, 2-bromophenyl, 3-methoxyphenyl, 3-ethoxyphenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl) benzyloxy-phenyl, 3-methoxy-4-(1-chloromethyl)benzyloxy-6-methyl sulfonyl aminophenyl groups. When the specification and especially the claims refer to a particular substituent for an aryl, that substituent can potentially occupy one or more of the substitutable positions on the aryl. For example, reciting that an aryl has a fluoro substituent, would embrace mono-, di-, tri, tetra and a higher degree of substitution on the aryl moiety. Fused aryl rings may also be substituted with the substituents specified herein, for example with 1, 2 or 3 substituents, in the same manner as substituted alkyl groups. The terms aryl and substituted aryl do not include moieties in which an aromatic ring is fused to a saturated or partially unsaturated aliphatic ring.

Aryloxy is —O-aryl. A substituted aryloxy is —O-substituted aryl, where the suitable substituents are those described for a substituted aryl.

"Heterocyclic group", "heterocyclic", "heterocycle", "heterocyclyl", "heterocycloalkyl" or "heterocyclo" alone and when used as a moiety in a complex group, are used interchangeably and refer to any mono-, bi-, or tricyclic, saturated or unsaturated, non-aromatic hetero-atom-containing ring system having the number of atoms designated, or if no number is specifically designated then from 5 to about 14 atoms, where the ring atoms are carbon and at least one heteroatom and usually not more than four heteroatoms (i.e., nitrogen, sulfur or oxygen). Included in the definition are any bicyclic groups where any of the above heterocyclic rings are fused to an aromatic ring (i.e., an aryl (e.g., benzene) or a heteroaryl ring). In a particular embodiment the group incorporates 1 to 4 heteroatoms. Typically, a 5-membered ring has 0 to 1 double bonds and a 6- or 7-membered ring has 0 to 2 double bonds and the nitrogen or sulfur heteroatoms may optionally be oxidized (e.g. SO, SO$_2$), and any nitrogen heteroatom may optionally be quaternized. Particular unsubstituted non-aromatic heterocycles include morpholinyl (morpholino), pyrrolidinyls, oxiranyl, indolinyl (e.g., 2,3-dihydroindolyl), isoindolinyls, tetrahydroquinolinyls, tetrahydroisoquinolinyls, oxetanyl, tetrahydrofuranyls, 2,3-dihydrofuranyl, 2H-pyranyls, tetrahydropyranyls, aziridinyls, azetidinyls, 1-methyl-2-pyrrolyl, piperazinyls and piperidinyls.

The term substituted heterocyclo refers to heterocyclo moieties having substituents replacing one or more hydrogens on one or more (usually no more than six) atoms of the heterocyclo backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, carboxyl, oxo, carbamoyl, alkyl, substituted alkyl (such as trifluoromethyl), —OCF$_3$, aryl, substituted aryl, alkylsulfonyl (including lower alkylsulfonyl), and arylsulfonyl. When the specification and especially the claims refer to a particular substituent for a heterocycloalkyl, that substituent can potentially occupy one or more of the substitutable positions on the heterocycloalkyl. For example, reciting that a heterocycloalkyl has a fluoro substituent, would embrace mono-, di-, tri, tetra and a higher degree of substitution on the heterocycloalkyl moiety.

"Heteroaryl" alone and when used as a moiety in a complex group refers to any mono-, bi-, or tricyclic aromatic ring system having the number of atoms designated, or if no number is specifically designated then at least one ring is a 5-, 6- or 7-membered ring and the total number of atoms is from 5 to about 14 and containing from one to four heteroatoms selected from the group consisting of nitrogen, oxygen, and sulfur (Lang's Handbook of Chemistry, supra). Included in the definition are any bicyclic groups where any of the above heteroaryl rings are fused to a benzene ring. The following ring systems are examples of the heteroaryl groups denoted by the term "heteroaryl": thienyls (alternatively called thiophenyl), furyls, imidazolyls, pyrazolyls, thiazolyls, isothiazolyls, oxazolyls, isoxazolyls, triazolyls, thiadiazolyls, oxadiazolyls, tetrazolyls, thiatriazolyls, oxatriazolyls, pyridyls, pyrimidinyls (e.g., pyrimidin-2-yl), pyrazinyls, pyridazinyls, thiazinyls, oxazinyls, triazinyls, thiadiazinyls, tetraoxadiazinyls, dithiazinyls, dioxazinyls, oxathiazinyls, tetrazinyls, thiatriazinyls, oxatriazinyls, dithiadiazinyls, imidazolinyls, dihydropyrimidyls, tetrahydropyrimidyls, tetrazolo[1, 5-b]pyridazinyl and purinyls, as well as benzo-fused derivatives, for example benzoxazolyls, benzofuryls, benzothienyls, benzothiazolyls, benzothiadiazolyl, benzotriazolyls, benzoimidazolyls, isoindolyls, indazolyls, indolizinyls, indolyls, naphthyridines, pyridopyrimidines, phthalazinyls, quinolyls, isoquinolyls and quinazolinyls.

The term substituted heteroaryl refers to heteroaryl moieties (such as those identified above) having substituents replacing one or more hydrogens on one or more (usually no more than six) atoms of the heteroaryl backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, carbamoyl, alkyl, substituted alkyl (such as trifluoromethyl), —$OCF_3$, aryl, substituted aryl, alkylsulfonyl (including lower alkylsulfonyl), and arylsulfonyl. When the specification and especially the claims refer to a particular substituent for a heteroaryl, that substituent can potentially occupy one or more of the substitutable positions on the heteroaryl. For example, reciting that a heteroaryl has a fluoro substituent, would embrace mono-, di-, tri, tetra and a higher degree of substitution on the heteroaryl moiety.

Particular "heteroaryls" (including "substituted heteroaryls") include; 1H-pyrrolo[2,3-b]pyridine, 1,3-thiazol-2-yl, 4-(carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl, 1, 3-oxazol-2-yl, 1,3, 4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino) eth-2-yl)-1H-tetrazol-5-yl, 1-(carboxymethyl)-1H-tetrazol-5-yl, 1-(methylsulfonic acid)-1H-tetrazol-5-yl, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl, 2,5-dihydro-5-oxo-6-hydroxy-2-methyl-astriazin-3-yl, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl, 8-aminotetrazolo[1,5-b]-pyridazin-6-yl, quinol-2-yl, quinol-3-yl, quinol-4-yl, quinol-5-yl, quinol-6-yl, quinol-8-yl, 2-methyl-quinol-4-yl, 6-fluoro-quinol-4-yl, 2-methyl, 8-fluoro-quinol-4-yl, isoquinol-5-yl, isoquinol-8-yl, isoquinol-1-yl, and quinazolin-4-yl. An alternative group of "heteroaryl" includes: 5-methyl-2-phenyl-2H-pyrazol-3-yl, 4-(carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(methylsulfonic acid)-1H-tetrazol-5-yl, 1,2,3-triazol-5-yl, 1,4,5,6-tetrahydro-5,6-dioxo-4-methyl-as-triazin-3-yl, 1,4,5, 6-tetrahydro-4-(2-formylmethyl)-5,6-dioxo-as-triazin-3-yl, 2,5-dihydro-5-oxo-6-hydroxy-2-methyl-as-triazin-3-yl, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"IAP Inhibitor" or "IAP antagonist" means a compound (1) which interferes with the physiological function of an IAP protein, including the binding of IAP proteins to caspase proteins, for example by reducing or preventing the binding of IAP proteins to caspase proteins, or (2) which reduces or prevents the inhibition of apoptosis by an IAP protein, or (3) which binds to an IAP BIR domain in a manner similar to the binding of the amino terminal portion of Smac, or (4) has any two, or all three of the preceding functions.

As used herein, the terms "pharmaceutically acceptable", "physiologically tolerable" and grammatical variations thereof, as they refer to compositions, excipients, carriers, diluents and reagents, are used interchangeably and represent that the materials can be administered to a subject or patient, especially a human patient.

"Pharmaceutically acceptable salts" include both acid and base addition salts.

"Pharmaceutically acceptable acid addition salt" refers to those non-toxic salts which retain the biological effectiveness and essential properties of the associated free bases and which are not biologically or otherwise undesirable, and are formed with inorganic acids and with organic acids. The acid addition salts of the basic compounds are prepared by contacting the free base form of the compound with a sufficient amount of the desired acid to produce the salt in the conventional manner. The free base form may be regenerated by contacting the salt form with a base and isolating the free base in the conventional manner. The free base forms generally differ from their respective salt forms somewhat in certain physical properties such as solubility in polar solvents.

"Pharmaceutically acceptable base addition salts" refer to those non-toxic salts which retain the biological effectiveness and essential properties of the associated free acids and which are not biologically or otherwise undesirable and are formed with metals or amines, such as alkali and alkaline earth metal hydroxides, or with organic amines. The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms usually differ from their respective salt forms somewhat in certain physical properties such as solubility in polar solvents.

The terms "treating", "treat" or "treatment" and the like include preventative (e.g., prophylactic) and palliative treatment.

As used herein "subject" or "patient" refers to an animal or mammal including, but not limited to, human, dog, cat, horse, cow, pig, sheep, goat, chicken, monkey, rabbit, rat, and mouse.

As used herein, the term "therapeutic" refers to the amelioration of, the prevention of, an improvement of, or a delay in the onset of one or more symptoms of an unwanted condition or disease of a patient. Embodiments of the present invention are directed to therapeutic treatments by promoting apoptosis, and thus cell death.

The terms "therapeutically effective amount" or "effective amount", as used herein, means an amount of a compound, or a pharmaceutically acceptable salt thereof, often as part of a pharmaceutical composition, sufficient to inhibit, halt, ameliorate, attenuate, delay the onset of, or cause an improvement in one or more symptoms of the disease being treated when administered alone or in conjunction with another pharmaceutical agent for treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "excipient" means any pharmaceutically acceptable additive, carrier, diluent, adjuvant, or other ingredient, other than the active pharmaceutical ingredient (API), which is typically included for formulation and/or administration to a patient.

DETAILED DESCRIPTION OF THE INVENTION

It has been demonstrated in accordance with the present invention that the IAP-binding compounds of the present invention, which are Smac mimetics, are capable of potentiating apoptosis of cells.

Compounds of the present invention can be used in their free base or free acid forms or in the form of their pharmaceutically-acceptable salts. In the practice of the present invention, compounds of the present invention in their free base or free acid forms generally will have a molecular weight of 1000 or below, most often a molecular weight of 800 or below and often a molecular weight of 600 or below.

The following preparations and schemes are illustrative of synthesis of compounds of the present invention. Abbreviations which are used throughout these schemes and in the application generally, are identified in the following table:

| ABBREVIATION | MEANING |
| --- | --- |
| ACN | Acetonitrile |
| Ac₂O | Acetic anhydride |
| Cbz and Z | Benzyloxycarbonyl |
| Boc and/or boc | tert-butyloxycarbonyl |
| THF | Tetrahydrofuran |
| DCM | Dichloromethane |
| DDQ | 2,3-dichloro-5,6-dicyano-1,4-benzoquinone |
| mCPBA | 3-chloroperbenzoic acid |

-continued

| ABBREVIATION | MEANING |
| --- | --- |
| Cbz—Cl | Benzyloxycarbonyl chloride |
| Hex | Hexanes |
| HPLC | high performance liquid chromatography |
| TLC | thin layer chromatography |
| EtOAc | ethyl acetate |
| Ph | Phenyl |
| HATU | 2-(7-Aza-1H-benzotriazole-1-yl)-1,1,3,3-tetramethyluronium hexafluorophosphate |
| Me | Methyl* |
| iPr | Iso-propyl |
| cPr | Cyclopropyl |
| (2R—EtOMe) and/or R—MeCHOMe | 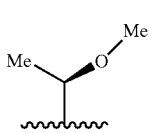 |
| TBAF | tetrabutyl ammonium fluoride |
| OMs | Methanesulfonyloxy |
| TBDMSCl | tert-butyl-dimethyl-silyl chloride |
| Ph₃P | Triphenylphosphine |
| n-Bu | Normal butyl |
| Swern[O] | Swern Oxidation |
| TBA-Cl | Tetra-n-butyl ammonium chloride |
| NP-HPLC | Normal phase-high performance liquid chromatography |
| EDCI | N-3-(dimethylaminopropyl)-N'-ethylcarbodiimide hydrochloride 1-Ethyl-3-(3-Dimethylaminopropyl)carbodiimide-HCl |
| Et₂O | Ethylene oxide 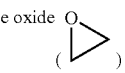 |
| TES | Triethylsilane |
| MeNO₂ | Nitromethane |
| EtOH | Ethanol |
| DCE, or EDC | Dichloroethane, Ethylenedichloride |
| NaHMDS | Sodium hexamethyldisilazide or sodium bis(trimethylsilyl)amide |
| Boc-Chg-OH (Boc-L-cyclohexylglcine) | 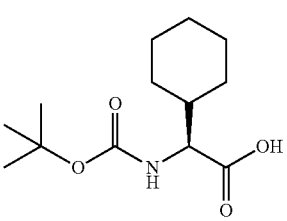 [SMILES: CC(C)(C)OC(=O)N[C@H](C(=O)O)C1CCCCC1] |
| Boc-N(Me)Ala-OH | 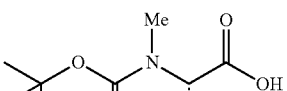 |
| Boc-Abu-OH | 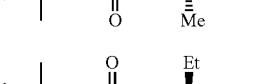 |
| Boc-Ser-OH | 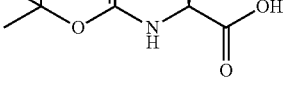 |

-continued

| ABBREVIATION | MEANING |
|---|---|
| Boc-Ser(Me)-OH | (structure) |
| Boc-Thr(tBu)-OH | (structure) |
| Boc-Thr(Me)-OH | (structure) |
| h | hour |
| NMP | N-methylpyrrolidinone |
| PhCOCl | Benzoyl chloride |
| DIAD | diisopropyl azo dicarboxylate |
| DIBAL | Diisobutylaluminium hydride |
| DMAP | 4-dimethylamino pyridine |
| DMF | Dimethylformamide |
| DMSO | dimethyl sulfoxide |
| TFA | trifluoroacetic acid |
| TFAA | trifluoroactic anhydride |
| HOAc or AcOH | acetic acid |
| DIPEA | Diisopropylethylamine |
| NMM | N-methylmorpholine |
| NCS | N-chlorosuccinimide |
| TEA (Et$_3$N) | Triethylamine |
| MsCl | Methane-sulfonylchloride |
| Et | Ethyl |
| tBu or tert-Bu | tert-butyl |
| cHex | Cyclohexyl |
| (2R—EtOH) and/or R—MeCHOH | (structure) |
| MsCl | Methanesulfonyl chloride |
| OTs | —O—SO$_2$—Ph—Me |
| OTBS | tert-butyl-dimethyl-silanyloxy |
| Ac | Acetyl |
| DMA | Dimethylamine |
| HWE | Honer-Wadsworth-Emmons reaction |
| DMS | Dimethylsulfide |
| Meldrum's Acid | 2,2-dimethyl-1,3-dioxane-4,6-dione |
| Imid. | Imidazole |
| HOBT, or HBT | Hydroxybenzotriazole |
| RT | Room Temperature |
| MeOH | Methanol |
| NaOAc | Sodium acetate |
| ClCO$_2$Me | Ethyl chloroformate |
| TBSCl | tert-butyl-dimethyl-silanyl chloride |
| Cbz—N(Me)Ala-OH Z-N(Me)Ala-OH | (structure) |
| Boc-Tle-OH | (structure) |
| Boc-Val-OH | (structure) |
| Cbz-Ser(tBu)-OH | (structure) |
| Cbz-Thr(tBu)-OH | (structure) |
| Boc-Thr-OH | (structure) |
| PSI | Pounds per Square Inch (Guage) |
| NaOMe | Sodium methoxide |

*As is a commonly accepted convention, depending on the context, which will be apparent to those skilled in the art, a vacant terminal bond may be used to indicate either a methyl group, or the point of attachment to another structure for a radical.

Abbreviations for NMR data reported in the following examples are as follows: s=singlet, d=doublet, t=triplet, q=quartet, m=multiplet, dd=doublet of doublets, ddd=doublet of doublet of doublets, dt=doublet of triplets, app=apparent, br=broad, δ indicates the chemical shift; J and $J_{CF}$ indicate NMR coupling constants measured in Hertz.

The binding affinities of compounds of the present invention to XIAP BIR-3 or to cIAP-1 BIR-3 (as reported below as ranges) were determined substantially as described by Nikolovska-Coleska, Z. et.al. (Analytical Biochemistry (2004), vol. 332:261-273 and incorporated herein by reference) using as the fluorogenic substrate: the fluorescently labeled peptide AbuRPF-K(5-Fam)-NH$_2$. The binding affinities of the compounds are reported as a K$_D$ value (μM). Briefly, various concentrations of test peptides were mixed with 5 nM of the fluorescently labeled peptide (i.e., a mutated N-terminal Smac peptide-AbuRPF-K(5-Fam)-NH$_2$) and 40 nM of the respective IAP BIR3 for 15 min at RT in 100 mL of 0.1M Potassium Phosphate buffer, pH 7.5 containing 100 mg/ml bovine g-globulin. Following incubation, the polarization values (mP) were measured on a Victor2V™ (available from PerkinElmer® Life Sciences) using a 485 nm excitation filter and a 520 nm emission filter. The reported binding affinities ($K_D$ values) are supplied as ranges (A=<0.1 µM, B=0.1 µM to 1 µM, C=>1 µM to 10 µM, D=>10 µM).

Compounds of the invention also were tested for their ability to inhibit the growth of an ovarian cancer cell line, SK-OV-3. A known assay previously used for measuring cell growth (as described in Hansen, M. B., Nielsen, S. E., and Berg, K. (1989) *J. Immunol. Methods* 119, 203-210 and incorporated herein by reference in its entirety) was used. Briefly, SK-OV-3 cells are seeded in 96-well plates in McCoy's medium containing 10% fetal bovine serum albumin (5,000 per well) and incubated overnight at 37° C. The next day, test compounds are added at various concentrations (0.003-10 µM) and the plates are incubated at 37° C. for an additional 72 hrs. This incubation time was considered to be optimal for measuring inhibitory effects of the different compounds tested. 50 microliters of 5 mg/mL MTT reagent is added to each well and the plates are incubated at 37° C. for another three (3) hours. At the end of the three (3) hour incubation period, 50 microliters of DMSO is added to each well to dissolve cells and the optical density (OD) of the wells is measured with a microplate reader (Victor² 1420™, Wallac, Finland) at 535 nm. Cell survival (CS) was calculated using the following equation:

$CS=(OD$ treated well/mean $OD$ control wells$)\times 100\%$.

The $CC_{50}$ (reported in the following tables), is defined as the drug concentration that results in 50% cell survival (CS), and is derived by calculating the point where the dose-response curve crosses the 50% CS point using GraphPad Prism® graphing software. The reported $CC_{50}$ values are supplied as ranges (A=<0.1 µM, B=0.1 µM to 1 µM, C=>1 µM to 10 µM, D=>10 µM).

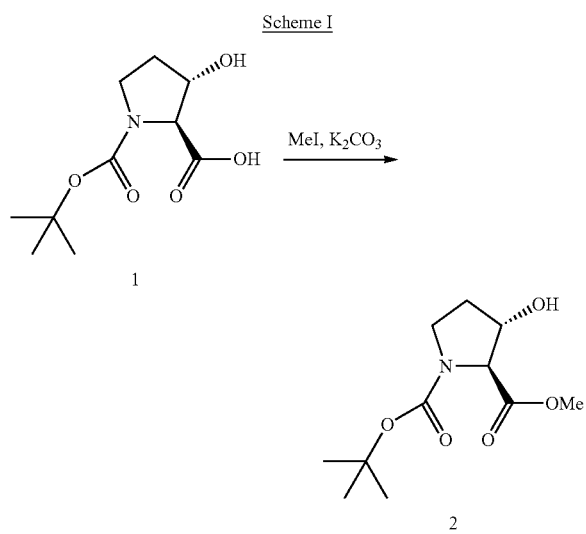

3-Hydroxy-pyrrolidine-1,2-dicarboxylic acid 1-tert-butyl ester 2-methyl ester (2): A solution containing 3-hydroxy-pyrrolidine-1,2-dicarboxylic acid 1-tert-butyl ester (1, 16 g, 71 mmol). See: Hodges, J. A.; Raines, R. T. *J. Am. Chem. Soc.* 2005, 45, 15923) in DMF (100 mL) was cooled to 0° C. To this solution was added $K_2CO_3$ (16 g, 116 mmol) followed by iodomethane (5.4 mL, 87 mmol). The reaction mixture was slowly warmed to ambient temperature over 1 h at which time it became a yellow heterogeneous solution. This mixture was heated at 90° C. for 1 h and then cooled to ambient temperature. The solution was diluted with brine, extracted with diethyl ether, dried over anhydrous $Na_2SO_4$, filtered, and concentrated to afford 14.8 g (87%) of 3-hydroxypyrrolidine-1,2-dicarboxylic acid 1-tert-butyl ester 2-methyl ester (2) as a yellow oil (See: Demange, L.; Cluzeau, J.; Menez, A.; Dugave, C. *Tetrahedron Lett.* 2001, 42, 651).

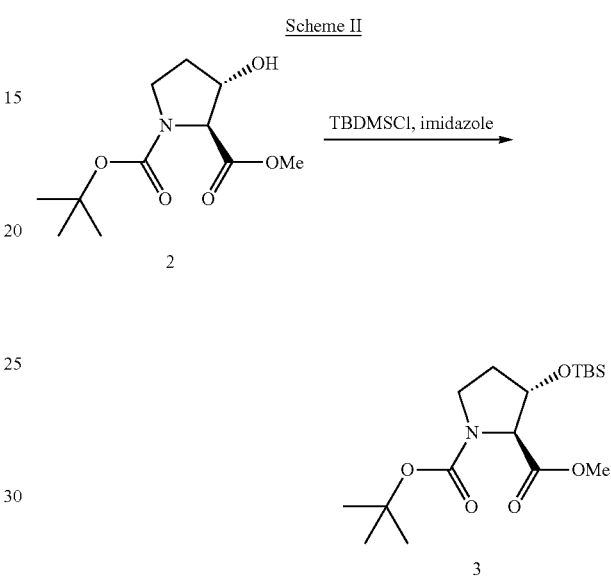

3-(tert-Butyl-dimethyl-silanyloxy)-pyrrolidine-1,2-dicarboxylic acid 1-tert-butyl ester 2-methyl ester (3): A solution containing 3-hydroxypyrrolidine-1,2-dicarboxylic acid 1-tert-butyl ester 2-methyl ester (2, 14.8 g, 60 mmol) in DCM (150 mL) was cooled to 0° C. To this solution was added imidazole (5.4 g, 79 mmol) followed by t-butyl-dimethylsilyl-chloride (10 g, 66 mmol) in two portions. The reaction mixture was warmed to ambient temperature over 1 h. After 5 h, the reaction mixture was diluted with 1M HCl and extracted twice with DCM. The combined organic extracts were dried over anhydrous $Na_2SO_4$, filtered, and concentrated to afford 21.2 g (99%) of 3-(tert-butyldimethylsilanyloxy)pyrrolidine-1,2-dicarboxylic acid 1-tert-butyl ester 2-methyl ester (3) as a yellow oil. ¹H NMR (CDCl₃, 300 MHz): δ4.38-4.34 (m, 1H), 4.18 (br s, rotomers, 0.5H), 4.04 (app d, J=2.1 Hz, rotomers, 0.5H), 3.74 (s, 3H), 3.62-3.50 (m, 2H), 2.04-1.96 (m, 1H), 1.85-1.78 (m, 1H), 1.46 (s, minor rotomer), 1.41 (s, 9H), 0.92 (s, minor rotomer), 0.86 (s, 9H), 0.11 (s, 6H), 0.09 (s, minor rotomer) ppm.

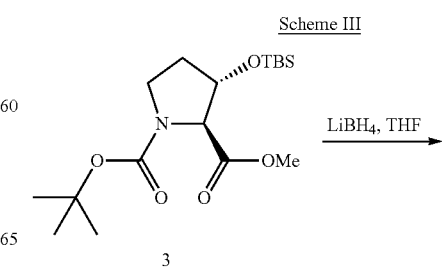

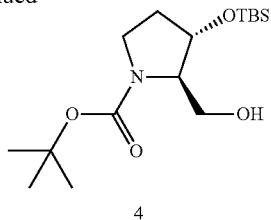

3-(tert-Butyl-dimethyl-silanyloxy)-2-hydroxymethyl-pyrrolidine-1-carboxylic acid tert-butyl ester (4): A solution containing 3-(tert-Butyldimethylsilanyloxy)pyrrolidine-1,2-dicarboxylic acid 1-tert-butyl ester 2-methyl ester (3, 12 g, 33 mmol) in THF (50 mL) was cooled to 0° C. LiBH$_4$ in THF (2M, 20 mL) was added in a dropwise fashion. After 1 h, the solution was warmed to ambient temperature. After 2 h, the solution was diluted with MeOH, then H$_2$O, and concentrated. The residue was extracted with EtOAc, washed with 1M HCl, saturated aqueous NaHCO$_3$, brine, dried over anhydrous Na$_2$SO$_4$, filtered, and concentrated to afford 9.5 g (87%) of 3-(tert-Butyldimethylsilanyloxy)-2-hydroxymethylpyrrolidine-1-carboxylic acid tert-butyl ester (4) as a colorless oil (See: Herdeis, C.; Hubmann, H. P.; Lotter, H. *Tetrahedron: Asymmetry*, 1994, 5, 119).

Scheme IV

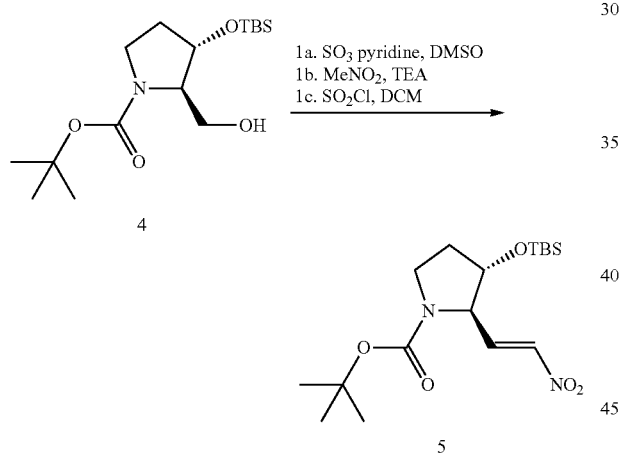

3S-(tert-Butyl-dimethyl-silanyloxy)-2R-(2-nitro-vinyl)-pyrrolidine-1-carboxylic acid tert-butyl ester (5): To a stirred solution containing alcohol 4 (5.7 g, 17.2 mmol) in DCM (60 mL) was added at ambient temperature Et$_3$N (14 mL, 103 mmol) and DMSO (50 mL). The reaction mixture was cooled to 0° C. and a solution of SO$_3$.pyridine (11.0 g, 69 mmol) in DMSO (50 mL) was added in a dropwise fashion. After 1 h, the reaction was warmed to ambient temperature. After 1 h, the reaction mixture was poured onto a 30% citric acid/ice mixture. The aqueous layer was extracted with DCM (3×250 mL) and the combined organic extracts were washed with brine (400 mL), dried over anhydrous Na$_2$SO$_4$, filtered, and concentrated to afford 5.6 g (99%) of crude N-Boc-(3S-OTBS)-2R-prolinal as a yellow-colored oil.

To a stirred solution containing crude N-Boc-(3S-OTBS)-2R-prolinal (5.6 g, 17 mmol) in nitromethane (30 mL) was added Et$_3$N (1.5 mL). After 12 h, the reaction mixture was concentrated in vacuo to afford 6.6 g (99%) of the intermediate carbinol as a yellow-colored oil.

To a solution containing crude carbinol (6.6 g, 17 mmol) at −78° C. in DCM (30 mL) was added thionyl chloride (2.60 g, 21.9 mmol) in CH$_2$Cl$_2$ (15 mL). After 1 h, TEA (6.96 mL, 68.8 mmol) was added and, after an additional 1 h at −78° C., the reaction mixture was quenched with MeOH (15 mL), H$_2$O (20 mL), and saturated aqueous NaHCO$_3$ (20 mL) followed by warming to 0° C. After 1 h, the reaction mixture was concentrated in vacuo and extracted with EtOAc (3×200 mL). The combined organic extracts were washed with brine (300 mL), dried over anhydrous Na$_2$SO$_4$, filtered, and concentrated to afford 6.1 g (98%) of 5 as an orange-colored oil. $^1$H NMR (CDCl$_3$, 300 MHz): δ7.04 (dd, J=13.2, 6.5 Hz, 1H), 6.91 (d, J=13.2 Hz, 1H), 4.08 (m, 1H), 3.54 (m, 2H), 3.37 (m, 1H), 1.80 (m, 2H), 1.35 (d, J=13.2 Hz, 6H), 0.80 (s, 9H), 0.00 (s, 9H) ppm. Mass spectrum, m/z calcd for C$_{12}$H$_{24}$NO$_3$Si [M+H]$^{30}$ 272.53, found 272.84.

Scheme V

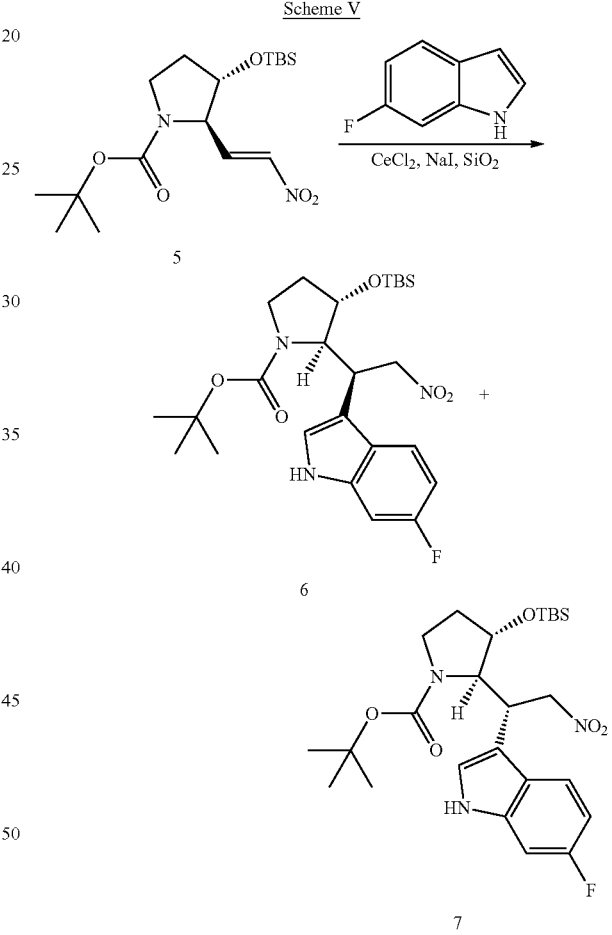

3S-(tert-Butyl-dimethyl-silanyloxy)-2R-[1S-(6-F-indol-3-yl)-2-nitro-ethyl]-pyrrolidine-1-carboxylic acid tert-butyl ester (6) and 3S-(tert-Butyl-dimethyl-silanyloxy)-2R-[1R-(6-F-indol-3-yl)-2-nitro-ethyl]-pyrrolidine-1-carboxylic acid tert-butyl ester (7): (See: Bartoli, G.; et al. *J. Org. Chem.* 2005, 70, 1941) A 1 L round-bottomed flask was charged with CeCl$_3$.7H$_2$O (10.3 g, 27.7 mmol), NO (4.2 g, 27.7 mmol), and reagent grade MeOH (200 mL). To the clear, water-white solution was added silica gel (Fisher Grade 60, 230-400 mesh, 45 g) and the white, heterogeneous mixture was concentrated in vacuo (rotovap bath temp: 40° C.). To the white, free-flowing CeCl$_2$/NaI/SiO$_2$ was added 5 (25.8 g, 69.2 mmol) and 6-F-indole (11.2 g, 83.1 mmol) in anhydrous ACN (160 mL) and the pale orange mixture was concentrated under high vacuum (bath temp: 40° C.). The orange-brown solid was allowed to stand at ambient temperature. After 16 h, the solid residue was poured atop a short column of silica gel and the products were eluted (20% EtOAc/hexanes to 40% EtOAc/hexanes). The diastereomers were separated by normal phase HPLC (2" Dynamax® SiO$_2$; 10-50% EtOAc/hexanes over 30 min; Flow: 40 mL/min) to afford 12 g (34%) of isomer 6, and 10 g (28%) of isomer 7 together with some recovered 5 [TLC analysis, SiO$_2$, 4:1 hexanes/EtOAc; R$_f$(5) =0.6; R$_f$(6)=0.48; R$_f$(7)=0.45].

6: $^1$H NMR (CDCl$_3$, 300 MHz), ~3:2 mixture of carbamate rotamers: δ 8.86 (br s, 0.4H, minor rotamer), 8.83 (br s, 0.6H, major rotamer), 8.15 (dd, J=5.1, 8.7 Hz, 0.6H, major rotamer), 8.04 (dd, J=5.4, 9.0 Hz, 0.4H, minor rotamer), 7.55 (d, J=2.4 Hz, 0.6H, major rotamer), 7.53 (br s, 1H), 7.50 (d, J=2.1 Hz, 0.4H, minor rotamer), 7.40 (app t, J=8.7 Hz, 0.6H, major rotamer), 7.39 (app t, J=9.3 Hz, 0.4H, minor rotamer), 5.74-5.35 (m, 1H), 5.29-5.20 (m, 1H), 4.68 (app t, J=11.4 Hz, 1H), 4.43 (m, 1H), 4.24-3.95 (m, 2H), 3.82 (t, J=9.6 Hz, 1H), 2.61 (m, 1H), 2.28 (m, 1H), 2.08 (s, 3H, minor rotamer), 1.99 (s, 6H, major rotamer), 1.14 (s, 9H), 0.10 (s, 1H, minor rotamer), 0.09 (s, 2H, major rotamer), 0.01 (s, 2H, major rotamer), 0.00 (s, 1H, minor rotamer) ppm; $^{13}$C NMR (300 MHz, CDCl$_3$), ~3:2 mixture of carbamate rotamers: δ 171.2, 161.3, 157.5 (d, J$_{CF}$=102.4 Hz), 157.1 (d, J$_{CF}$=164.2 Hz), 136.7 (d, J$_{CF}$=11.1 Hz), 136.5 (d, J$_{CF}$=12.3 Hz), 123.3 (d, J$_{CF}$=18.3 Hz), 122.3 (d, J$_{CF}$=18.9 Hz), 119.3 (d, J$_{CF}$=30.9 Hz), 111.3 (d, J$_{CF}$=37.2 Hz), 108.3 (d, J$_{CF}$=25.5 Hz), 98.1 (d, J$_{CF}$=23.1 Hz), 97.8 (d, J$_{CF}$=24.6 Hz), 80.8, 79.4, 74.2, 73.8, 68.9, 68.8, 60.3, 45.2, 44.9, 40.4, 39.9, 32.0, 31.1, 28.3, 28.2, 25.2, 20.7, 17.5, 13.9, −5.6, −5.7 ppm. Mass spectrum, m/z [408.2] (M-Boc)+.

7: $^1$H NMR (CDCl$_3$, 300 MHz), ~3:2 mixture of carbamate rotamers: δ 9.03 (br s, 0.4H, minor rotamer), 8.92 (br s, 0.6H, major rotamer), 8.03 (m, 1H), 7.52-7.44 (m, 2H), 7.36 (app t, J=8.4 Hz, 1H), 5.42-5.19 (m, 2H), 4.79 (m, 1H), 4.63 (m, 2H), 4.07-3.86 (m, 1H), 3.63-3.46 (m, 1H), 2.06 (s, 3H, minor rotamer), 1.99 (s, 6H, major rotamer), 1.95 (m, 1H), 1.65 (m, 1H), 1.27 (s, 6H, major rotamer), 1.20 (s, 3H, minor rotamer), 0.38-0.25 (m, 6H) ppm; $^{13}$C NMR (300 MHz, CDCl$_3$), ~3:2 mixture of carbamate rotamers: δ 171.4, 161.5, 157.3 (d, J$_{CF}$=151.9 Hz), 157.1 (d, J$_{CF}$=186.9 Hz), 136.2 (d, J$_{CF}$=12.3 Hz), 123.2, 122.5 (d, J$_{CF}$=24.9 Hz), 119.5 (d, J$_{CF}$=36.0), 110.8, 108.5 (d, J$_{CF}$=24.3 Hz), 97.8 (d, J$_{CF}$=28.9 Hz), 81.2, 79.9, 78.0, 75.1, 68.8, 60.4, 46.3, 38.8, 37.9, 33.2, 32.5, 28.4, 25.5, 25.4, 20.9, 17.7, 14.1, −5.1, −5.4 ppm. Mass spectrum, m/z [408.2] (M-Boc)+.

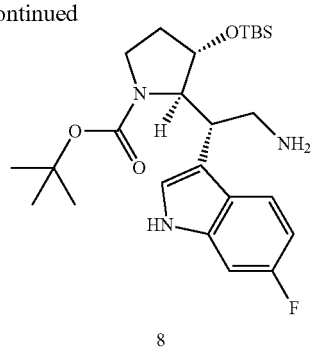

8

2R-[2-Amino-1S-(6-F-indol-3-yl)-ethyl]-3S-(tert-butyl-dimethyl-silanyloxy)-pyrrolidine-1-carboxylic acid tert-butyl ester (8): A Parr bottle was charged with 7 (12 g, 23.7 mmol) and Raney Ni (20 mL, 2400 Ni slurry in H$_2$O) in EtOH (120 mL) and subjected to 50 PSI H$_2$ pressure (379.2 KPa). Rapid absorption of H$_2$ was observed and the reaction was twice recharged to 50 PSI H$_2$ (379.2 KPa). After 1.5 h, the reaction mixture was filtered through diatomaceous earth (Celite®) and the solids were washed with EtOH. The filtrate was concentrated and the residue was dissolved in EtOAc, washed with saturated NaHCO$_3$, brine, dried over anhydrous Na$_2$SO$_4$, filtered and concentrated to give 8 (10.7, 95%) as a yellow foam. $^1$H NMR (CDCl$_3$, 300 MHz), mixture of carbamate rotamers: δ 9.30 (br s, 0.5H), 9.07 (br s, 0.5H), 7.86-7.75 (m, 1H), 7.24 (app t, J=6.6 Hz, 1H), 7.15 (s, 1H), 7.08 (ap t, J=9.0 Hz, 1H), 4.38-4.30 (m, 3H), 3.86-3.61 (m, 2H), 3.44-3.28 (m, 3H), 1.71 (s, 9H), 0.96 (s, 9H), 0.06 (s, 3H), 0.001 (s, 3H) ppm; $^{13}$C NMR (CDCl$_3$, 75 MHz), mixture of carbamate rotamers: δ 166.5 & 163.4, 161.3 (J$_{CF}$=13.5 Hz), 141.7 (J$_{CF}$=12.1 Hz), 129.4, 127.6 & 127.3, 125.1 (J$_{CF}$=10.4 Hz) & 124.8 (J$_{CF}$=10.4 Hz), 119.1 & 118.5, 113.2 & 112.9, 102.8 (J$_{CF}$=17.6 Hz) & 102.5 (J$_{CF}$=16.6 Hz), 85.1 & 84.4, 80.4 & 80.1, 74.7 & 74.1, 51.4 & 51.1, 48.5, 38.5 & 37.7, 33.6 & 30.7, 22.9, 0.09 ppm. Mass spectrum, m/z [478.3] (M+H)+.

Scheme VII

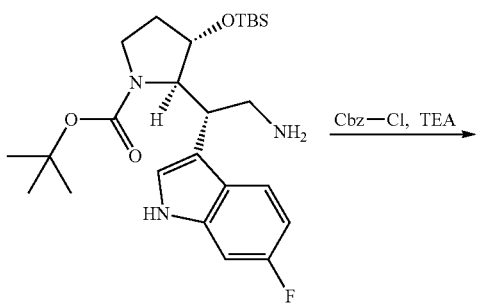

8

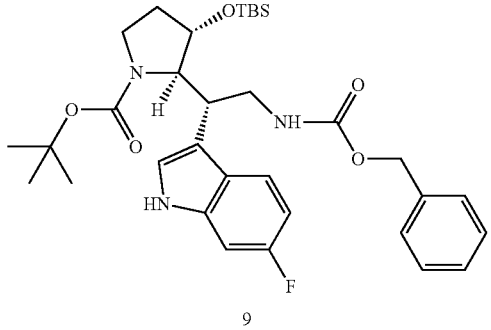

9

Scheme VI

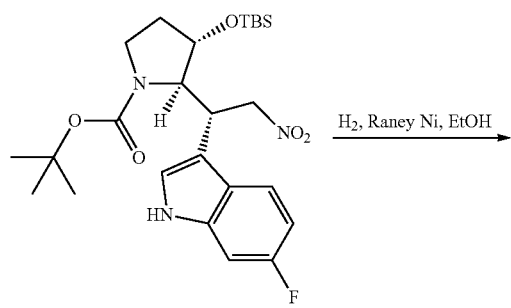

7

2R-[2-Benzyloxycarbonylamino-1S-(6-fluoro-1H-indol-3-yl)-ethyl]-3S-(tert-butyl-dimethyl-silanyloxy)-pyrrolidine-1-carboxylic acid tert-butyl ester (9): To a solution of DCM (10 mL) containing crude 8 (10.7 g, 22.4 mmol) at 0° C. was added TEA (4.8 mL, 34.5 mmol) followed by Cbz-Cl (3.5 mL, 25 mmol). After 1 h, the reaction was warmed to room temperature. After 1.5 h, the reaction mixture was diluted with DCM, washed successively with 1N HCl and brine, dried over anhydrous Na$_2$SO$_4$, filtered, and concentrated to afford 9 (13.5 g, 98%). $^1$H NMR (CDCl$_3$, 300 MHz): δ8.73 (br s, 1H), 7.57 (app q, J=5.1 Hz, 1H), 7.48-7.32 (m, 5H), 7.10 (m, 1H), 6.91 (m, 1H), 6.45 (br s, 1H), 5.20 (s, 2H), 4.24-4.09 (m, 2H), 3.65-3.40 (m, 4H), 3.02 (app t, J=9.6 Hz, 1H), 1.57 (s, 9H), 0.87 (s, 9H), 0.00 (s, 6H) ppm. Mass spectrum, m/z [612.4] (M+H)+.

Scheme VIII

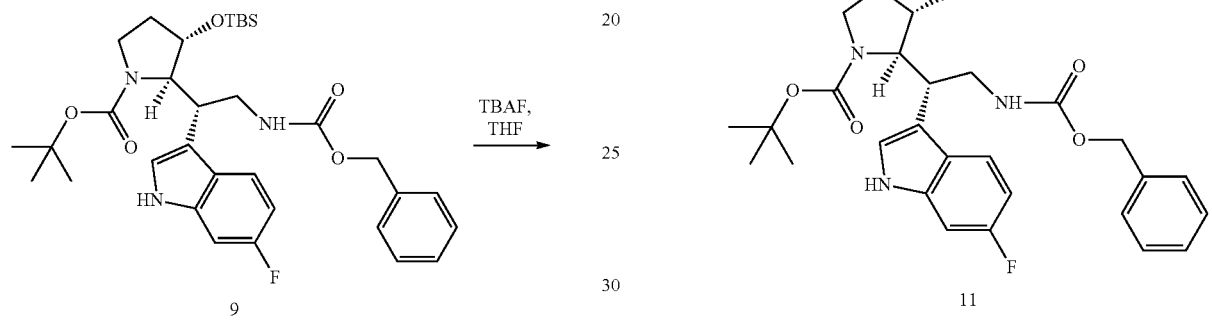

2R-[2-Benzyloxycarbonylamino-1S-(6-fluoro-1H-indol-3-yl)-ethyl]-3S-hydroxy-pyrrolidine-1-carboxylic acid tert-butyl ester (10): A solution of 9 (13.5 g, 22.0 mmol) in THF (60 mL) was treated with TBAF (45 mL, 1M in THF, 45 mmol) at ambient temperature. After 5 h, the reaction mixture was warmed for 1 h at 45° C. and then diluted with EtOAc, washed successively with 1N HCl and brine, dried over anhydrous Na$_2$SO$_4$, filtered, and concentrated to afford crude 10 which was purified by flash silica gel chromatography (1:2 hexanes/EtOAc) to afford 10.1 g (93%) of 10 as light peach-colored foam. $^1$H NMR (CDCl$_3$, 300 MHz): δ8.88 (s, 1H), 7.40-7.31 (m, 5H), 6.94 (app d, J=9.6 Hz, 1H), 6.81-6.75 (m, 1H), 6.67 (s, 1H), 6.45 (m, 1H), 5.12 (app q, J=11.7 Hz, 2H), 4.18-4.03 (m, 2H), 3.51-3.34 (m, 4H), 2.92 (app t, J=9.9 Hz, 1H), 2.33 (br s, 1H), 1.48 (s, 9H), 0.91-0.86 (m, 1H) ppm; $^{13}$C NMR (CDCl$_3$, 75 MHz) δ158.5, 157.2, 157.0, 136.9, 136.5, 136.3, 128.7, 128.3, 123.7, 122.8, 120.6, 113.6, 108.7, 108.4, 98.0, 97.7, 80.1, 75.7, 67.3, 66.9, 46.5, 43.4, 41.1, 32.3, 28.7 ppm. Mass spectrum, m/z [498.2] (M+H)+.

Scheme IX

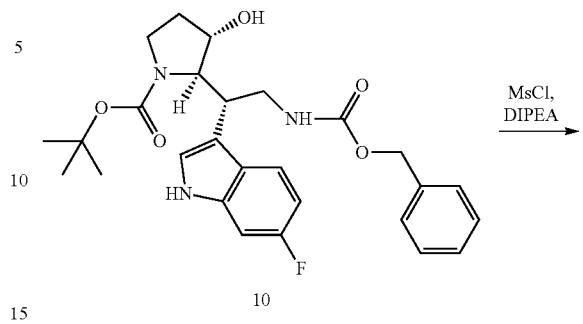

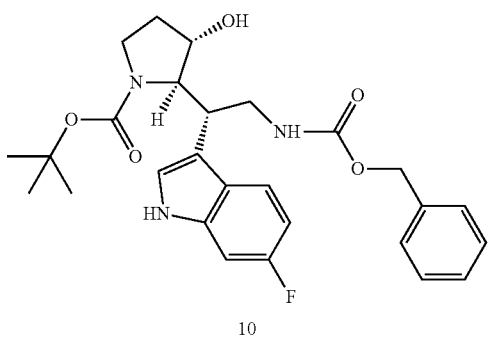

2R-[2-Benzyloxycarbonylamino-1S-(6-fluoro-1H-indol-3-yl)-ethyl]-3S-methanesulfonyloxy-pyrrolidine-1-carboxylic acid tert-butyl ester (11): A solution of 10 (10.0 g, 20.1 mmol) in DCM (100 mL) was cooled to 0° C. A solution of MsCl (1.5 mL, 19.4 mmol) in DCM (3 mL) was added dropwise followed by the addition of DMAP (250 mg, 2.0 mmol). After 3 h at 0° C., the reaction mixture was diluted with DCM, washed successively with 1N HCl, water, and brine, dried over anhydrous Na$_2$SO$_4$, filtered, and concentrated to afford 11 (10.4 g, 90%) as a light peach colored foam. $^1$H NMR (CDCl$_3$, 300 MHz): δ8.71 (s, 1H), 7.50 (app q, J=5.4 Hz, 1H), 7.38-7.32 (m, 5H), 7.00 (app d, J=8.4 Hz, 1H), 6.89-6.81 (m, 2H), 6.29 (br s, 1H), 5.14 (s, 2H), 4.92 (app d, J=3.9 Hz, 1H), 4.52 (s, 1H), 3.55-3.39 (m, 4H), 3.04 (app t, J=9.9 Hz, 1H), 2.79 (s, 3H), 1.82 (app q, J=7.5 Hz, 1H), 1.52 (s, 9H), 1.14 (m, 1H) ppm. Mass spectrum, m/z [576.3] (M+H)+.

Scheme X

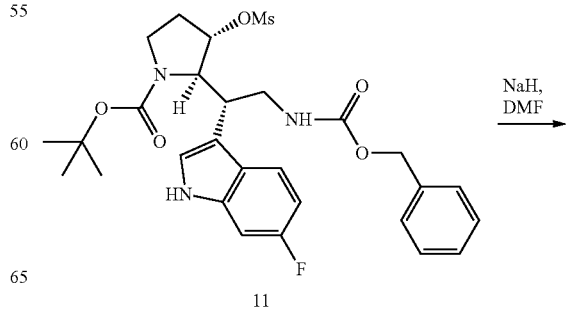

-continued

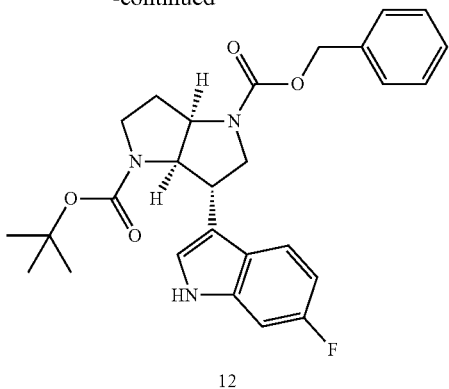

12

(3aR,6aR)-6S-(6-fluoro-1H-Indol-3-yl)-hexahydro-pyrrolo[3,2-b]pyrrole-1-carboxylic acid tert-butyl ester (12): A solution of 11 (10.4 g, 18 mmol) in DMF (30 mL) was added to a suspension of NaH (1.9 g, 60%, 46 mmol) in DMF (100 mL) at 0° C. After 1 h, the reaction mixture was diluted with H₂O, extracted with diethyl ether, washed with brine, dried over anhydrous Na₂SO₄, filtered, and concentrated to give 12 (8.3 g, 97%) as a light tan colored solid. ¹H NMR (CDCl₃, 300 MHz), mixture of carbamate rotamers: δ8.25 (br s, 0.5 H), 8.16 (s, 0.5 H), 8.04 (dd, J=8.4, 14.1 Hz, 0.5 H), 7.95 (dd, J=7.8, 13.5 Hz, 0.5 H), 7.71 (m, 0.5 H), 7.64 (m, 0.5 H), 7.34 (m, 4H), 6.99 (app t, J=13.2 Hz, 1H), 6.91-6.84 (m, 1H), 6.81-6.76 (m, 0.5 H), 6.68-6.61 (m, 0.5 H), 5.24-5.15 (m, 2H), 4.46-4.31 (m, 2H), 4.20-4.02 (m, 1H), 3.96 (m, 1H), 3.84-3.68 (m, 1H), 3.63 (app q, J=5.7 Hz, 1H), 3.25 (m, 1H), 2.31 (dd, J=6.0, 13.5 Hz, 0.5 H), 2.14 (dd, J=5.7, 13.5 Hz, 0.5 H), 1.94-1.84 (m, 1H), 1.52 (s, 7H), 1.31-1.26 (m, 2H), 0.91-0.83 (m, 2H) ppm.

Scheme XI

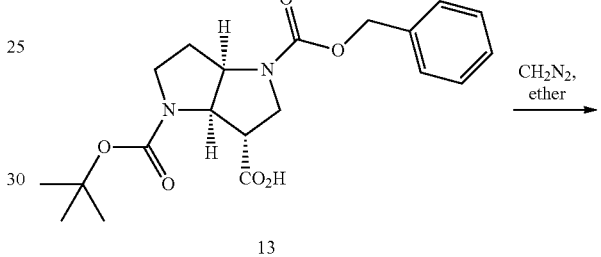

Hexahydro-pyrrolo[3,2-b]pyrrole-1,3,4-tricarboxylic acid 1-benzyl ester 4-tert-butyl ester (13): A solution of 12 (0.5 g, 1.1 mmol) was dissolved in NMP (5 mL). To this solution was added ACN (10 mL), CCl₄ (10 mL), and H₂O (20 mL). To this biphasic solution was added NaIO₄ (3.4 g, 16 mmol). After 10 min, RuCl₃·hydrate (29 mg, 0.14 mmol) was added and the solution immediately turned dark orange. Precipitation was observed after about 10 min. After 3.5 h, the solution was diluted with EtOAc and washed with brine (2×). The combined organic extracts were dried over anhydrous Na₂SO₄, filtered and concentrated to give crude 13 as a dark brown-colored oil (470 mg) which was diluted with EtOAc (10 mL) and treated with DMSO (0.15 mL) and stirred at ambient temperature overnight. The solution was then concentrated and used without further purification. ¹H NMR (CDCl₃, 300 MHz): δ7.36-7.29 (m, 5H), 5.14 (m, 2H), 4.55 (m, 2H), 3.75-3.53 (m, 1H), 3.32-3.17 (m, 1H), 2.38 (app t, J=8.4 Hz, 1H), 1.47 (s, 9H) ppm. Mass spectrum, m/z [391.2] (M+H)+.

Scheme XII

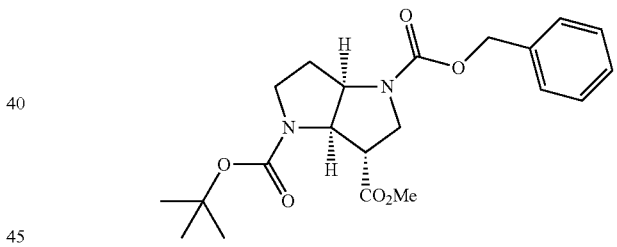

Hexahydro-pyrrolo[3,2-b]pyrrole-1,3,4-tricarboxylic acid 1-benzyl ester 4-tert-butyl ester 3-methyl ester (14): To a solution of crude 13 (0.47 g) in EtOAc (10 mL) and Et₂O (10 mL) was added an ethereal solution of diazomethane that was prepared by treatment of N-nitroso-N-methyl urea (0.5 g) in Et₂O (10 mL) with 1M KOH (10 mL). After consumption of starting material (monitored by TLC), the reaction mixture was diluted with HOAc. The solution was extracted with EtOAc, washed with saturated NaHCO₃, brine, dried over anhydrous Na₂SO₄, filtered and concentrated to give a dark oil that was purified by HPLC (2″ Dynamax® SiO₂, 10% EtOAc/hexane to 100% EtOAc over 30 min) to give 14 (0.19 g) as a yellow-colored oil. ¹H NMR (CDCl₃, 300 MHz): δ7.40-7.29 (m, 5H), 5.23-5.09 (m, 2H), 4.56-4.52 (m, 2H), 4.11-4.04 (m, 1H), 3.69 (s, 3H), 3.45-3.42 (m, 1H), 3.22-3.12 (m, 1H), 2.27-2.10 (m, 1H), 1.96 (m, 1H), 1.47 (s, 9H) ppm. Mass spectrum, m/z [405.2] (M+H)+.

Scheme XIII

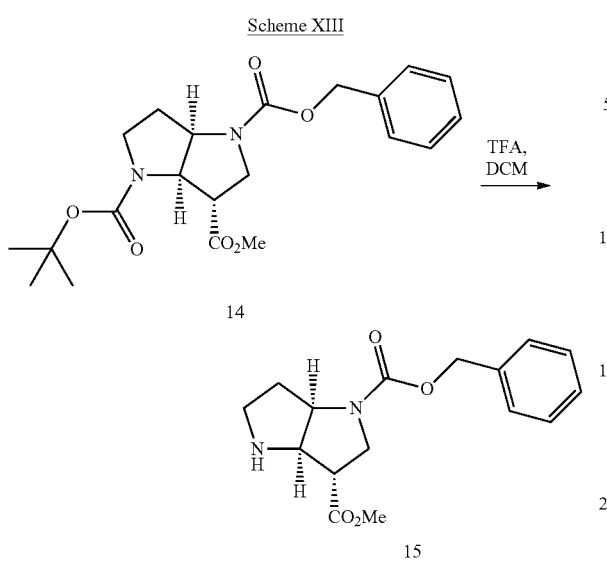

Hexahydro-pyrrolo[3,2-b]pyrrole-1,3-dicarboxylic acid 1-benzyl ester 3-methyl ester (15): A solution of 14 (480 mg, 1.2 mmol) in DCM (10 mL) was treated with TFA (3 mL) at ambient temperature. After 75 min, the solution was concentrated, diluted with EtOAc, washed with saturated NaHCO$_3$, brine. The aqueous washes were back extracted with DCM and the combined organic extracts were dried over anhydrous Na$_2$SO$_4$, filtered and concentrated to afford crude 15 (309 mg) as an orange-colored oil that was used without further purification. Mass spectrum, m/z [305.2] (M+H)+.

Scheme XIV

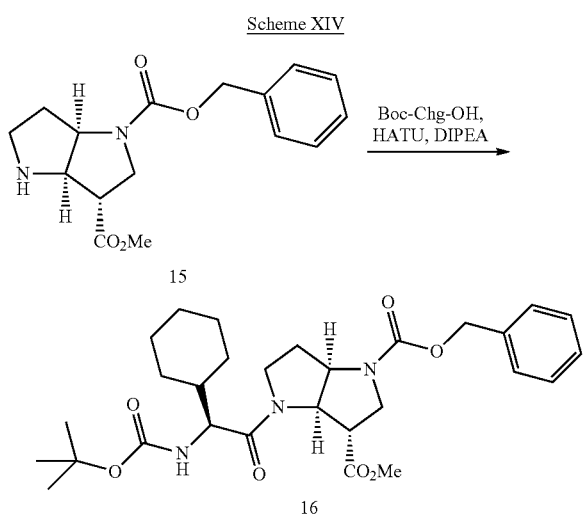

4-(2-tert-Butoxycarbonylamino-2-cyclohexyl-acetyl)-hexahydro-pyrrolo[3,2-b]pyrrole-1,3-dicarboxylic acid 1-benzyl ester 3-methyl ester (16): A solution of Boc-L-cyclohexylglycine (257 mg, 1 mmol) in NMP (5 mL) was cooled to 0° C. and treated with HATU (380 mg, 1 mmol) followed by DIPEA (0.3 mL, 1.7 mmol). After 10 min, 15 (309 mg, 1.0 mmol) in NMP (5 mL) was added. The reaction mixture was allowed to warm to ambient temperature overnight. The solution was diluted with EtOAc, washed successively with 1M HCl, saturated NaHCO$_3$, dried over anhy- drous Na$_2$SO$_4$, filtered and concentrated to afford 16 as an orange-colored foam (578 mg) which was used without further purification. Mass spectrum, m/z [544.4] (M+H)+.

Scheme XV

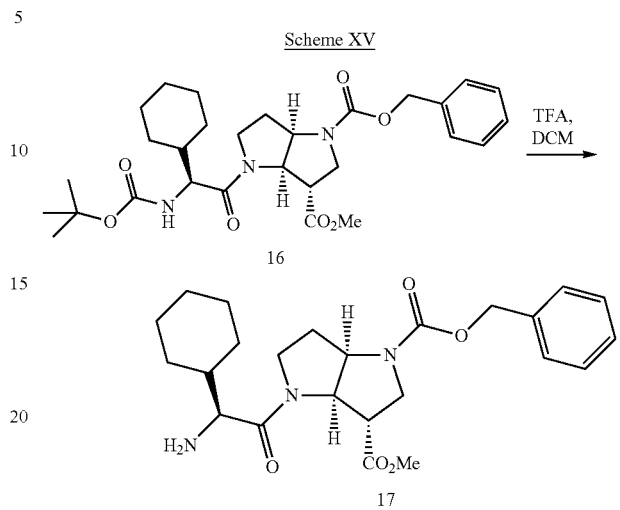

4-(2-Amino-2-cyclohexyl-acetyl)-hexahydro-pyrrolo[3,2-b]pyrrole-1,3-dicarboxylic acid 1-benzyl ester 3-methyl ester (17): A solution of 16 (346 mg, 0.64 mmol) in DCM (10 mL) was treated with TFA (3 mL) at ambient temperature. After 1 h, the solution was concentrated, diluted with EtOAc, and washed with saturated NaHCO$_3$. The aqueous phase was back extracted with DCM and the combined organic extracts were washed with brine, dried over anhydrous Na$_2$SO$_4$, filtered and concentrated to afford 17 (245 mg) as an orange-colored foam that was used without further purification. Mass spectrum, m/z [444.4] (M+H)+.

Scheme XVI

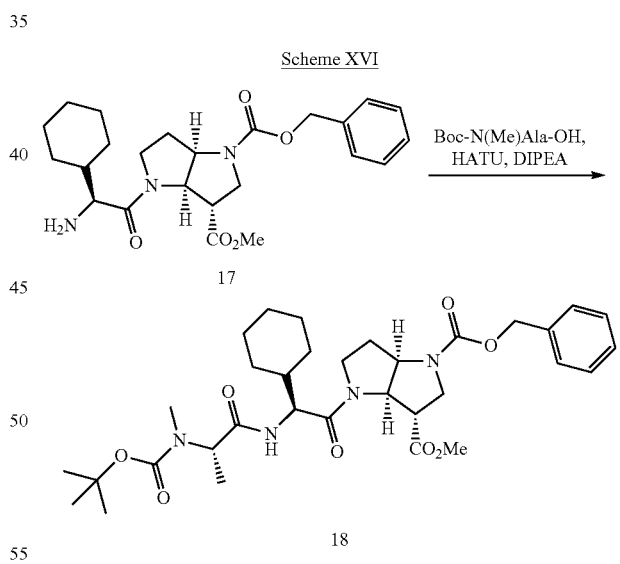

4-{2-[2-(tert-Butoxycarbonyl-methyl-amino)-propionylamino]-2-cyclohexyl-acetyl}-hexahydro-pyrrolo[3,2-b]pyrrole-1,3-dicarboxylic acid 1-benzyl ester 3-methyl ester (18): A solution of Boc-N(Me)Ala-OH (113 mg, 0.56 mmol) in NMP (4 mL) was cooled to 0° C. and treated with HATU (207 mg, 0.54 mmol) followed by DIPEA (0.15 mL, 0.87 mmol). After 10 min, 17 (245 mg, 0.55 mmol) in NMP (5 mL) was added. The reaction mixture was allowed to warm to ambient temperature overnight. The solution was diluted with EtOAc, washed successively with 1M HCl, saturated NaHCO$_3$, dried over anhydrous Na$_2$SO$_4$, filtered and concentrated to afford 18 as an orange-colored oil (400 mg) which was used without further purification.

Scheme XVII

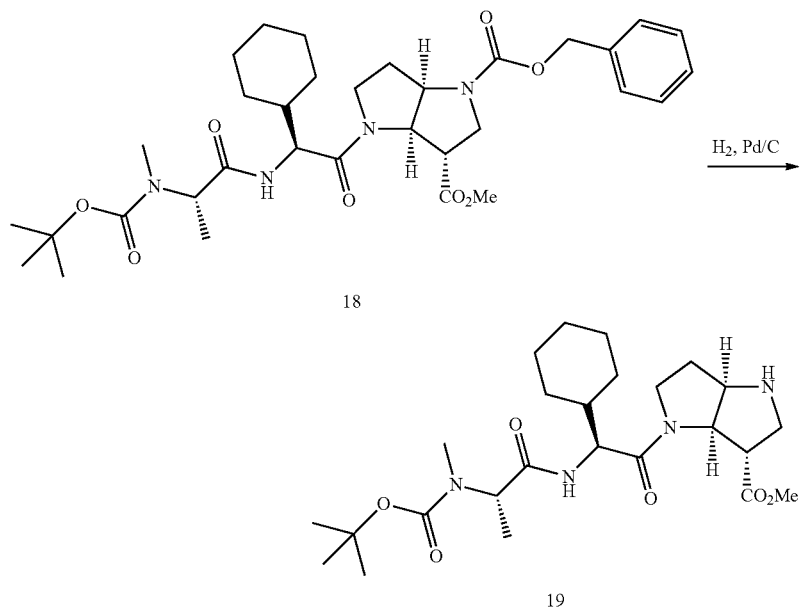

4-{2-[2-(tert-Butoxycarbonyl-methyl-amino)-propionylamino]-2-cyclohexyl-acetyl}-octahydro-pyrrolo[3,2-b]pyrrole-3-carboxylic acid methyl ester (19): A solution of 18 (0.4 g, 0.64 mmol) in MeOH (20 mL) was treated with 10% Pd/C (wet, 216 mg) and reduced under an $H_2$ atmosphere (50 psi) using a Parr apparatus. After 1.5 h, the mixture was filtered through a nylon filter cartridge and the solids were washed with MeOH. The filtrate was concentrated to afford 19 (0.31 g) as an orange-colored oil which was used without further purification. Mass spectrum, m/z [495.4] (M+H)+.

(20): A solution of 19 (0.31 g, 0.63 mmol) in DCM (10 mL) was cooled to 0° C. and treated with DIPEA (0.2 mL, 1.2 mmol) and DMAP (5 mg, 0.04 mmol). Methanesulfonyl chloride (0.08 mL, 1 mmol) was added. After 2 h, the solution was diluted with DCM, washed successively with 1M HCl, brine, dried over anhydrous $Na_2SO_4$, filtered and concentrated to afford 20 as an orange-colored oil (362 mg) which was used without further purification.

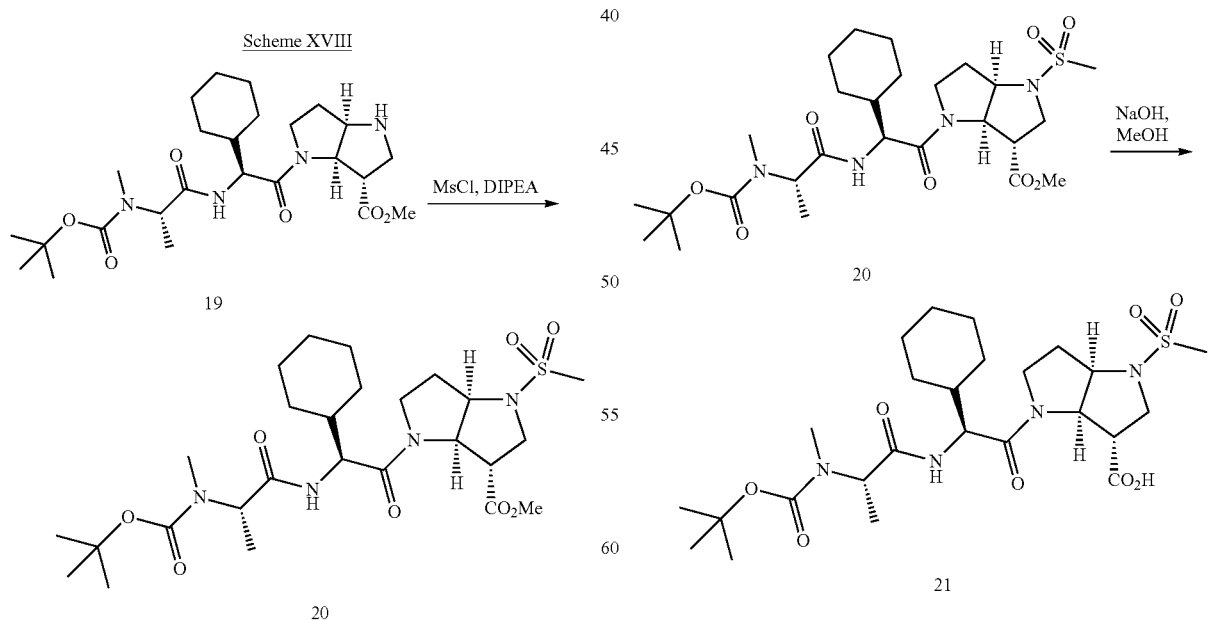

4-{2-[2-(tert-Butoxycarbonyl-methyl-amino)-propionylamino]-2-cyclohexyl-acetyl}-1-methanesulfonyl-octahydro-pyrrolo[3,2-b]pyrrole-3-carboxylic acid methyl ester 4-{2-[2-(tert-Butoxycarbonyl-methyl-amino)-propionylamino]-2-cyclohexyl-acetyl}-1-methanesulfonyl-octahydro-pyrrolo[3,2-b]pyrrole-3-carboxylic acid (21): A solution of 20 (362 mg, 0.63 mmol) in MeOH (10 mL) was treated with 1M NaOH (2 mL) at ambient temperature. After 1 h, the solution was concentrated and diluted with EtOAc and 1M HCl. The layers were separated and the aqueous phase was extracted with EtOAc. The combined organic extracts were washed successively with 1M HCl, brine, dried over anhydrous $Na_2SO_4$, filtered and concentrated to afford 21 as a yellow-colored foam (278 mg) which was used without further purification.

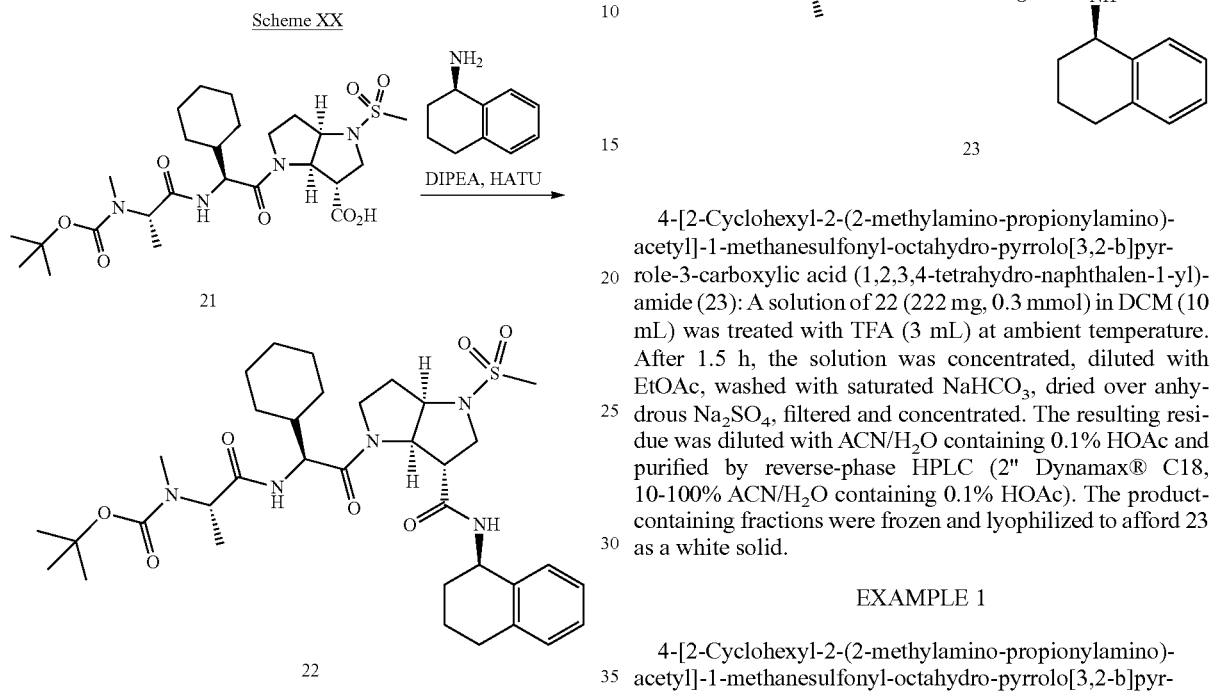

(1-{1-Cyclohexyl-2-[4-methanesulfonyl-6-(1,2,3,4-tetrahydro-naphthalen-1-ylcarbamoyl)-hexahydro-pyrrolo[3,2-b]pyrrol-1-yl]-2-oxo-ethylcarbamoyl}-ethyl)-methyl-carbamic acid tert-butyl ester (22): A solution of crude 21 (106 mg, 0.19 mmol) in NMP (5 mL) was cooled to 0° C. and treated with HATU (73 mg, 0.19 mmol) and DIPEA (0.1 mL, 0.57 mmol). After 10 min, (1R)-1,2,3,4-tetrahydro-naphthalen-1-ylamine (0.05 mL, 0.35 mmol) in NMP (3 mL) was added. The reaction was allowed to warm to ambient temperature. After 16 h, the solution was diluted with EtOAc, washed successively with 1M HCl, brine, dried over anhydrous $Na_2SO_4$, filtered and concentrated to afford 22 which was used without further purification. Mass spectrum, m/z [688.5] (M+H)+.

4-[2-Cyclohexyl-2-(2-methylamino-propionylamino)-acetyl]-1-methanesulfonyl-octahydro-pyrrolo[3,2-b]pyrrole-3-carboxylic acid (1,2,3,4-tetrahydro-naphthalen-1-yl)-amide (23): A solution of 22 (222 mg, 0.3 mmol) in DCM (10 mL) was treated with TFA (3 mL) at ambient temperature. After 1.5 h, the solution was concentrated, diluted with EtOAc, washed with saturated $NaHCO_3$, dried over anhydrous $Na_2SO_4$, filtered and concentrated. The resulting residue was diluted with $ACN/H_2O$ containing 0.1% HOAc and purified by reverse-phase HPLC (2" Dynamax® C18, 10-100% $ACN/H_2O$ containing 0.1% HOAc). The product-containing fractions were frozen and lyophilized to afford 23 as a white solid.

EXAMPLE 1

4-[2-Cyclohexyl-2-(2-methylamino-propionylamino)-acetyl]-1-methanesulfonyl-octahydro-pyrrolo[3,2-b]pyrrole-3-carboxylic acid (1,2,3,4-tetrahydro-naphthalen-1-yl)-amide (23): $^1$H NMR (CDCl$_3$, 300 MHz), ~3:1 mixture of rotamers: δ8.67 (d, J=8.4 Hz, 0.25 H), 7.83 (d, J=10.2 Hz, 0.25 H), 7.60 (d, J=8.7 Hz, 0.75H), 7.27-7.03 (m, 5H), 5.16-5.14 (m, 1H), 4.54-4.43 (m, 2H), 4.21 (app t, J=5.4 Hz, 0.75H), 4.13 (app t, J=9.3 Hz, 0.25H), 4.07-3.95 (m, 1H), 3.78-3.51 (m, 2H), 3.33-3.28 (m, 0.25H), 3.11 (s, 0.75H), 3.08 (s, 2.25H), 2.81-2.79 (m, 2H), 2.64-2.58 (m, 1H), 2.37 (s, 2.25H), 2.34 (s, 0.75H), 2.09-2.02 (m, 3H), 1.93-1.54 (m, 9H), 1.31 (d, J=7.2 Hz, 2.25H), 1.18 (d, J=6.9 Hz, 0.75H), 1.24-0.96 (m, 4H) ppm; $^{13}$C NMR (CDCl$_3$, 75 MHz), mixture of rotomers: δ175.4, 175.3, 172.1, 171.5, 170.7, 170.4, 137.6, 137.2, 136.6, 136.5, 129.4, 129.2, 129.0, 128.9, 127.6, 127.5, 126.5, 69.0, 68.0, 65.8, 63.3, 60.4, 60.2, 55.2, 51.7, 51.4, 49.9, 48.5, 47.6, 47.4, 46.0, 44.7, 41.8, 40.7, 35.8, 35.4, 35.2, 34.8, 33.4, 33.2, 30.3, 30.1, 29.9, 29.8, 29.5, 29.3, 29.3, 29.0, 26.4, 26.2, 26.1, 26.0, 19.9, 19.7 ppm. Mass spectrum, m/z [588.6] (M+H)+.

EXAMPLES 2 through 6 were prepared using the chemistries described in Schemes XIV through XXI by replacing (1R)-1,2,3,4-tetrahydro-naphthalen-1-ylamine with benzylamine, 4-fluorobenzylamine, (1S)-1,2,3,4-tetrahydro-naphthalen-1-ylamine, cyclohexylamine, and 1,1-diphenylmethylamine.

EXAMPLE 2

4-[2-Cyclohexyl-2-(2-methylamino-propionylamino)-acetyl]-1-methanesulfonyl-octahydro-pyrrolo[3,2-b]pyrrole-3-carboxylic acid benzylamide: $^1$H NMR (CDCl$_3$, 300 MHz), ~3:1 mixture of rotamers: δ8.90 (dd, J=5.1, 7.5 Hz, 0.25H), 7.89 (d, J=10.5 Hz, 0.25H), 7.67 (d, J=8.1 Hz, 0.75

H), 7.40-7.25 (m, 5.75 H), 4.47-4.67 (m, 0.25 H), 4.52-4.37 (m, 3H), 4.25-4.11 (m, 2H), 4.04-3.93 (m, 1H), 4.04-3.93 (m, 1H), 3.75-3.50 (m, 2H), 3.36-3.29 (m, 0.5H), 3.23-3.12 (m, 1H), 3.09 (s, 0.75H), 3.02 (s, 2.25H), 2.63-2.49 (m, 2H), 2.38 (s, 3H), 2.09-2.02 (m, 1H), 1.74-1.57 (m, 5H), 1.32-0.99 (m, 9H) ppm; $^{13}$C NMR (CDCl$_3$, 75 MHz), mixture of rotomers: δ175.3, 174.9, 172.1, 171.4, 170.9, 170.0, 138.3, 138.0, 128.7, 128.7, 127.8, 127.6, 127.5, 127.4, 68.4, 67.7, 65.4, 63.0, 60.1, 55.0, 51.1, 49.7, 48.3, 45.9, 44.5, 43.6, 43.2, 41.6, 40.6, 35.5, 35.1, 34.9, 34.5, 33.1, 32.9, 29.6, 29.4, 28.8, 28.8, 26.0, 25.8, 25.8, 25.6, 19.5, 19.3 ppm. Mass spectrum, m/z [548.4] (M+H)+.

EXAMPLE 3

4-[2-Cyclohexyl-2-(2-methylamino-propionylamino)-acetyl]-1-methanesulfonyl-octahydro-pyrrolo[3,2-b]pyrrole-3-carboxylic acid 4-fluoro-benzylamide: $^1$H NMR (CDCl$_3$, 300 MHz), ~3:1 mixture of rotomers: δ8.93 (dd, J=6.9, 7.5 Hz, 0.25H), 7.93 (d, J=10.2 Hz, 0.25H), 7.64 (d, J=9.0 Hz, 0.75H), 7.45 (app t, J=5.4 Hz, 0.75H), 7.31-7.24 (m, 2H), 7.04-6.98 (m, 2H), 4.70-4.63 (m, 0.25H), 4.51-4.30 (m, 4H), 4.22-4.12 (m, 2H), 4.05-3.92 (m, 1H), 3.74-3.51 (m, 2H), 3.37-3.27 (m, 0.25H), 3.18-3.12 (m, 1H), 3.10 (s, 0.75H), 3.02 (s, 2.25H), 2.64-2.52 (m, 4H), 2.38 (s, 3H), 2.12-2.06 (m, 1H), 1.80-1.56 (m, 6H), 1.32-0.99 (m, 8H) ppm; $^{13}$C NMR (CDCl$_3$, 75 MHz), mixture of rotomers: δ175.7, 175.3, 172.3, 171.8, 171.2, 170.2, 162.4 (J$_{CF}$=246 Hz), 134.4 (J$_{CF}$=3.5 Hz), 134.0 (J$_{CF}$=3.2 Hz), 129.8 (J$_{CF}$=8.1 Hz), 129.5 (J$_{CF}$=8.4 Hz), 115.8 (J$_{CF}$=4.3 Hz), 115.6 (J$_{CF}$=4.1 Hz), 68.7, 67.9, 65.6, 63.3, 60.4, 60.3, 55.2, 51.4, 51.3, 49.8, 48.6, 46.1, 44.7, 43.2, 42.8, 41.8, 40.8, 35.7, 35.4, 35.2, 34.7, 33.3, 33.0, 29.9, 29.7, 29.2, 29.0, 26.2, 26.1, 26.0, 25.9, 25.8, 19.8, 19.7 ppm. Mass spectrum, m/z [566.5] (M+H)+.

EXAMPLE 4

4-[2-Cyclohexyl-2-(2-methylamino-propionylamino)-acetyl]-1-methanesulfonyl-octahydro-pyrrolo[3,2-b]pyrrole-3-carboxylic acid (1,2,3,4-tetrahydro-naphthalen-1-yl)-amide: $^1$H NMR (CDCl$_3$, 300 MHz), ~1:1 mixture of rotomers: δ8.95 (d, J=9.0 Hz, 0.5H), 7.75 (d, J=9.3 Hz, 0.5H), 7.59 (d, J=8.4 Hz, 0.5H), 7.31-7.05 (m, 5.5H), 5.22-5.19 (m, 0.5H), 5.12-5.09 (m, 0.5H), 4.54-4.45 (m, 2H), 4.26-4.10 (m, 1H), 4.05-3.96 (m, 1H), 3.79-3.51 (m, 2H), 3.32-3.27 (m, 0.5H), 3.19-3.16 (m, 0.5H), 2.81-2.76 (m, 1.5H), 2.64-2.51 (m, 0.5H), 2.34 (s, 1.5H), 2.30 (s, 1.5H), 2.11-1.67 (m, 3.15 (s, 1.5H), 3.07 (s, 1.5H), 2.11-1.50 (m, 12H), 1.33-1.06 (m, 12H), 0.88-0.83 (m, 5H) ppm; $^{13}$C NMR (CDCl$_3$, 75 MHz), mixture of rotomers: δ175.2, 171.5, 170.7, 170.3, 137.8, 137.5, 136.5, 129.5, 129.4, 128.7, 128.3, 127.5, 127.4, 126.4, 68.8, 68.2, 65.6, 63.3, 60.5, 60.2, 55.2, 51.3, 51.2, 49.9, 48.6, 48.2, 46.6, 46.0, 44.6, 41.8, 40.8, 35.7, 35.4, 35.2, 34.9, 33.4, 33.2, 30.4, 30.3, 29.9, 29.8, 29.4, 29.3, 29.2, 29.0, 28.6, 26.2, 26.1, 25.8, 20.3, 19.7, 19.2 ppm. Mass spectrum, m/z [588.6] (M+H)+.

EXAMPLE 5

4-[2-Cyclohexyl-2-(2-methylamino-propionylamino)-acetyl]-1-methanesulfonyl-octahydro-pyrrolo[3,2-b]pyrrole-3-carboxylic acid cyclohexylamide: $^1$H NMR (CDCl$_3$, 300 MHz), ~1:1 mixture of rotomers: δ8.44 (d, J=8.1 Hz, 0.5H), 7.93 (d, J=9.9 Hz, 0.5 H), 7.67 (d, J=8.4 Hz, 0.5 H), 6.71 (d, J=8.4 Hz, 0.5 H), 4.52-4.45 (m, 2H), 4.17 (app t, J=4.8 Hz, 1H), 4.02 (dd, J=7.5, 11.7 Hz, 0.5H), 3.92 (dd, J=2.7, 11.7 Hz, 0.5H), 3.72-3.46 (m, 2.5H), 3.38-3.28 (m, 0.5H), 3.16-3.14 (m, 1H), 3.09 (s, 1.5H), 3.03 (s, 1.5H), 2.62-2.50 (m, 1H), 2.40 (s, 3H), 2.07-2.00 (m, 1H), 1.87-1.58 (14H), 1.35-0.9 (m, 15H) ppm; $^{13}$C NMR (CDCl$_3$, 75 MHz), mixture of rotomers: δ175.4, 175.2, 171.4, 171.3, 170.1, 68.7, 68.0, 65.5, 63.0, 60.3, 60.2, 54.9, 54.8, 51.2, 51.1, 49.6, 48.5, 48.3, 47.9, 45.8, 44.4, 41.6, 40.6, 35.4, 35.3, 35.1, 34.6, 33.1, 33.0, 32.9, 32.8, 32.7, 32.5, 29.7, 29.7, 29.3, 28.8, 26.1, 26.0, 25.9, 25.8, 25.7, 25.5, 24.7, 24.6, 24.4, 19.7, 19.6 ppm. Mass spectrum, m/z [540.5] (M+H)+.

EXAMPLE 6

4-[2-Cyclohexyl-2-(2-methylamino-propionylamino)-acetyl]-1-methanesulfonyl-octahydro-pyrrolo[3,2-b]pyrrole-3-carboxylic acid benzhydryl-amide: $^1$H NMR (CDCl$_3$, 300 MHz), ~1:1 mixture of rotomers: δ9.44 (d, J=9.0 Hz, 0.5 H), 8.12 (d, J=8.4 Hz, 0.5H), 7.90 (d, J=10.2 Hz, 0.5H), 7.68 (d, J=8.7 Hz, 0.5H), 7.37-7.22 (m, 10H), 6.25-6.20 (m, 1H), 4.55-4.36 (m, 2H), 4.15-3.89 (m, 2H), 3.75-3.54 (m, 2H), 3.40-3.20 (m, 1.5H), 3.06 (s, 1.5H), 2.93 (s, 1.5H), 2.62-2.49 (m, 1H), 2.39 (s, 3H), 2.10-2.01 (m, 0.5H), 1.74-1.60 (m, 5H), 1.33-1.04 (m, 7H), 0.84-0.77 (m, 0.5H), 0.45-0.41 (m, 0.5H) ppm; $^{13}$C NMR (CDCl$_3$, 75 MHz), mixture of rotomers: δ175.5, 175.4, 171.8, 171.6, 170.4, 170.2, 142.4, 141.9, 141.5, 141.4, 129.0, 128.9, 128.8, 127.7, 127.6, 127.5, 127.4, 127.3, 68.4, 68.0, 65.7, 63.4, 60.6, 60.1, 57.3, 57.1, 55.3, 55.2, 51.4, 51.2, 49.9, 48.8, 46.1, 44.7, 41.7, 40.7, 35.8, 35.4, 35.2, 34.5, 33.3, 33.0, 29.9, 29.6, 29.1, 29.0, 26.2, 26.1, 26.0, 25.9, 25.8, 19.9, 19.6 ppm. Mass spectrum, m/z [624.5] (M+H)+.

TABLE 1

| Example | Structure | XIAP, nM | cIAP1, nM | SKOV3, nM | Mass Spectrum, m/z |
|---|---|---|---|---|---|
| 1 | 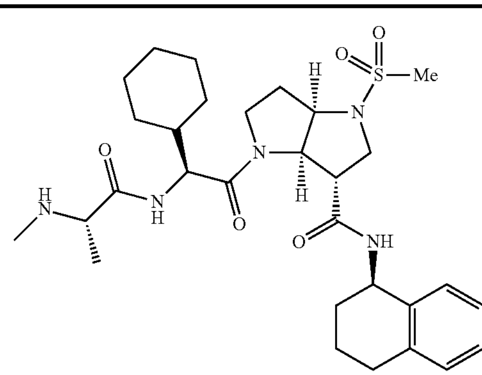 | A | A | A | 588.6 (M + H) |

TABLE 1-continued
| Example | Structure | XIAP, nM | cIAP1, nM | SKOV3, nM | Mass Spectrum, m/z |
|---|---|---|---|---|---|
| 2 | 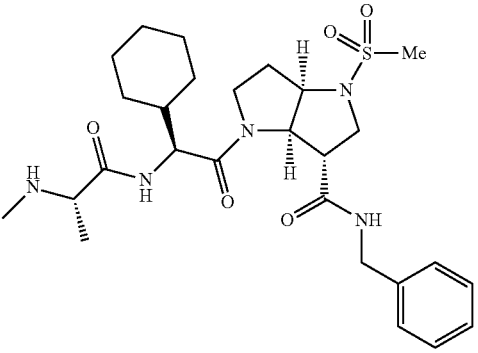 [SMILES: CN[C@@H](C)C(=O)N[C@H](C(=O)N1CC[C@@H]2[C@H]1[C@@H](C(=O)NCc1ccccc1)CN2S(C)(=O)=O)C1CCCCC1] | A | A | A | 548.4 (M + H) |
| 3 | 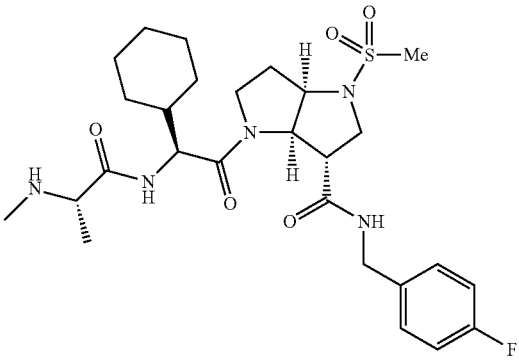 [SMILES: CN[C@@H](C)C(=O)N[C@H](C(=O)N1CC[C@@H]2[C@H]1[C@@H](C(=O)NCc1ccc(F)cc1)CN2S(C)(=O)=O)C1CCCCC1] | A | A | A | 566.5 (M + H) |
| 4 | 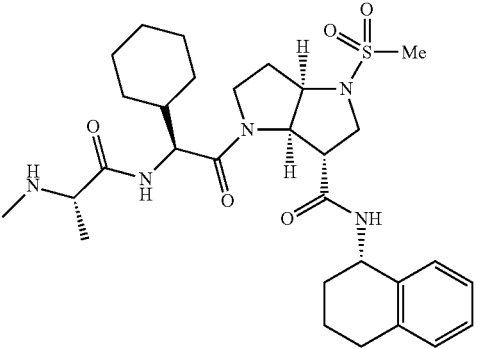 [SMILES: CN[C@@H](C)C(=O)N[C@H](C(=O)N1CC[C@@H]2[C@H]1[C@@H](C(=O)N[C@H]1CCCc3ccccc31)CN2S(C)(=O)=O)C1CCCCC1] | A | A | B | 588.6 (M + H) |
| 5 | 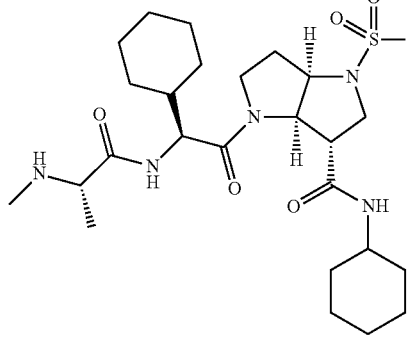 | C | A | C | 540.5 (M + H) |

| Example | Structure | XIAP, nM | cIAP1, nM | SKOV3, nM | Mass Spectrum, m/z |
|---|---|---|---|---|---|
| 6 | 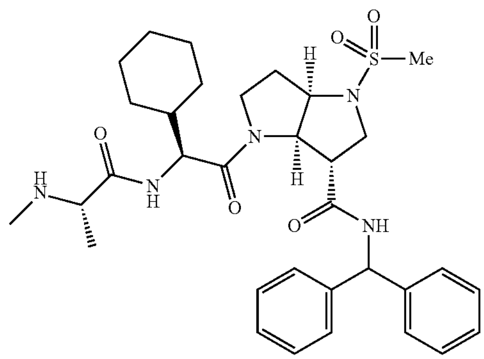 [SMILES: CN[C@@H](C)C(=O)N[C@H](C(=O)N1CC[C@@H]2[C@H]1[C@@H](C(=O)NC(c1ccccc1)c1ccccc1)CN2S(C)(=O)=O)C1CCCCC1] | A | A | B | 624.5 (M + H) |

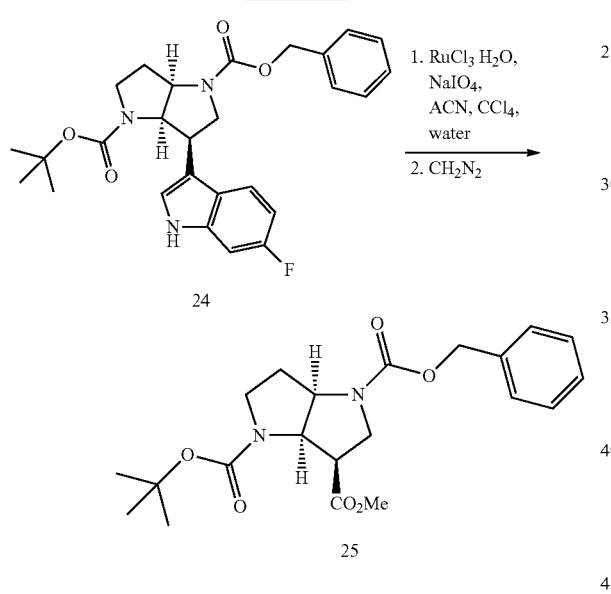

Scheme XXII

Hexahydro-pyrrolo[3,2-b]pyrrole-1,3,4-tricarboxylic acid 1-benzyl ester 4-tert-butyl ester 3-methyl ester (25): Indole 24 (0.5 g, 1.1 mmol) [prepared from compound 6 using the procedures described in Schemes VI through X] was dissolved in ACN (5 mL), CCl$_4$ (5 mL), and H$_2$O (10 mL). To this biphasic solution was added NaIO$_4$ (3.4 g, 16 mmol). After 10 min, RuCl$_3$.hydrate (23 mg, 0.14 mmol) was added and the solution immediately turned dark orange. Precipitation was observed after about 10 min. After 3.5 h, the solution was diluted with EtOAc and washed with brine (2×). The combined organic extracts were dried over anhydrous Na$_2$SO$_4$, filtered and concentrated to give the crude acid as a dark brown oil (460 mg) which was diluted with EtOAc (10 mL) and treated with DMSO (0.10 mL) and stirred at ambient temperature overnight. The solution was then concentrated and used without further purification.

To a solution of the crude acid (0.47 g) in Et$_2$O (5 mL) was added an ethereal solution of diazomethane that was prepared by treatment of N-nitroso-N-methyl urea (0.6 g) in Et$_2$O (10 mL) with 1M KOH (10 mL). After consumption of starting material (monitored by TLC), the reaction mixture was diluted with HOAc (5 mL). The solution was extracted with EtOAc, washed with saturated NaHCO$_3$, brine, dried over anhydrous Na$_2$SO$_4$, filtered and concentrated to give a dark oil that was purified by HPLC (2" Dynamax® SiO$_2$, 10% EtOAc/hexane to 100% EtOAc over 30 min) to give 25 (0.15 g) as a yellow-colored oil. $^1$H NMR (CDCl$_3$, 300 MHz): δ7.35 (m, 5H), 5.19-5.08 (m, 2H), 4.69 (m, 1H), 4.53-4.49 (m, 1H), 3.92-3.84 (m, 2H), 3.69 (s, 3H), 3.25-3.08 (m, 2H), 2.22-1.95 (m, 2H), 1.42 (s, 9H) ppm. Mass spectrum, m/z [405.2] (M+H)+.

Scheme XXIII

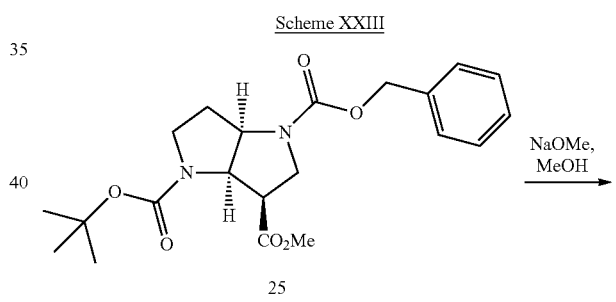

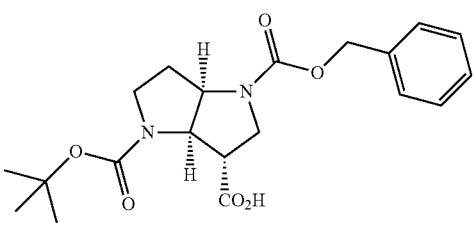

Hexahydro-pyrrolo[3,2-b]pyrrole-1,3,4-tricarboxylic acid 1-benzyl ester 4-tert-butyl ester (13): A solution of 25 (1.4 g, 3.5 mmol) in MeOH (20 mL) was added to a solution of NaOMe (0.34 g, 6.3 mmol) in MeOH at ambient temperature. The reaction mixture was stirred for 16 h and then concentrated. The residue was diluted with EtOAc, washed successively with 1M HCl, brine, dried over anhydrous Na$_2$SO$_4$, filtered and concentrated to afford 13 as an orange-colored foam (1.39 g) that was used without further purification.

Scheme XXIV

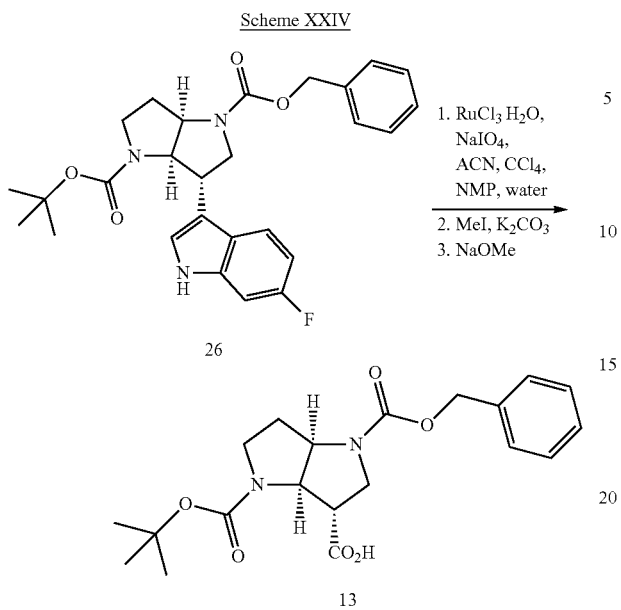

Scheme XXV

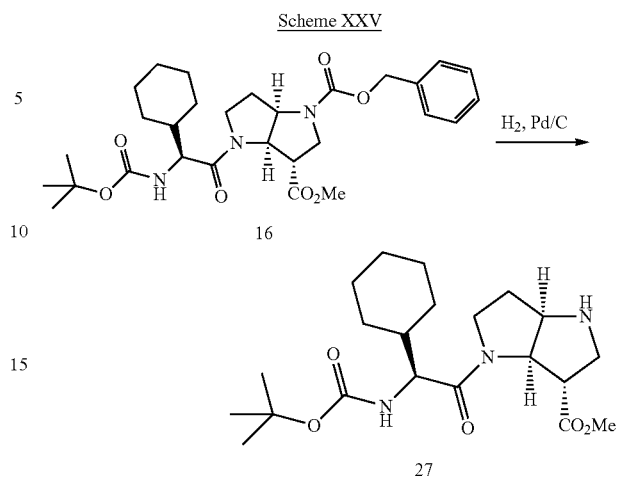

Hexahydro-pyrrolo[3,2-b]pyrrole-1,3,4-tricarboxylic acid 1-benzyl ester 4-tert-butyl ester (13): A solution of 26 (mixture of diastereomers, 1.5 g, 3.1 mmol) [The mixture of diastereomers was prepared from the mixture of diastereomers (6 and 7) generated in Scheme V using the procedures described in Schemes VI through X on the diastereomeric mixture produced in each step] in NMP (5 mL), MeCN (10 mL), CCl$_4$ (10 mL) and H$_2$O (20 mL) was treated with NaIO$_4$ (9.3 g, 44 mmol) in one portion. After 10 min, RuCl$_3$·H$_2$O (57 mg, 0.28 mmol) was added and the solution immediately turned dark orange. After ~10 min, the reaction mixture became warm and precipitation was observed. After 7.5 h, the solution was diluted with EtOAc and 1M HCl and filtered through Celite®, and rinsed with EtOAc. The filtrate was extracted with EtOAc, washed successively with 1M HCl, 10% Na$_2$S$_2$O$_3$, brine, dried over anhydrous Na$_2$SO$_4$, filtered and concentrated to give a mixture of crude acids as a dark brown oil (1.4 g) which was used without further purification.

A solution of crude acids (1.4 g, 3.6 mmol) in DMF (20 mL) was cooled to 0° C. and treated with K$_2$CO$_3$ (2.5 g, 18.1 mmol). After 10 min, this suspension was treated with CH$_3$I (0.65 mL, 10.4 mmol) and the reaction mixture was allowed to warm to ambient temperature. After consumption of starting material (approximately 2 h, monitored by TLC), the reaction mixture was diluted with EtOAc, and 1M HCl. The layers were separated and the aqueous phase was extracted with EtOAc. The combined organic extracts were washed successively with 1M HCl, 10% Na$_2$S$_2$O$_3$, brine, dried over anhydrous Na$_2$SO$_4$, filtered and concentrated to give a dark brown residue. The dark residue was absorbed onto SiO$_2$ and purified by flash chromatography (1:1 hexane/EtOAc) to afford 0.69 g of a mixture of methyl esters (55%, 2 steps) as a yellow-colored foam.

To a suspension of NaOMe (2.0 g, 37 mmol) in MeOH (20 mL) was added a solution of methyl esters (1.3 g, 3.2 mmol) in a dropwise fashion at ambient temperature. The reaction mixture was stirred for 16 h and then concentrated. The residue was diluted with EtOAc, washed successively with 1M HCl, and brine, dried over anhydrous Na$_2$SO$_4$, filtered and concentrated to afford 13 as an orange-colored foam (1.1 g) that was used without further purification.

4-(2-tert-Butoxycarbonylamino-2-cyclohexyl-acetyl)-octahydro-pyrrolo[3,2-b]pyrrole-3-carboxylic acid methyl ester (27): A solution of 16 (1.2 g, 2.2 mmol) in MeOH (30 mL) was treated with Pd/C (10% wet, 354 mg) and placed under H$_2$ (50 psi) using a Parr apparatus. After 1.5 h, the reaction mixture was filtered through syringe filter disc (Acrodisc-PSF-0.45 μM) and rinsed with MeOH. The filtrate was concentrated to afford crude 27 (0.9 g) as a glassy solid which was used without further purification. $^1$H NMR (CDCl$_3$, 300 MHz): δ5.23 (d, J=9.0 Hz, 1H), 4.83 (dd, J=2.1, 6.0 Hz, 1H), 4.32-4.21 (m, 2H), 4.03 (app t, J=9.9 Hz, 1H), 3.77 (s, 3H), 3.86-3.32 (m, 1H), 3.25-3.23 (m, 1H), 2.49-2.42 (m, 1H), 2.27-2.13 (m, 1H), 1.72-1.59 (m, 6H), 1.42 (s, 9H), 1.31-0.99 (m, 6H) ppm; $^{13}$C NMR (CDCl$_3$, 75 MHz): δ172.1, 171.5, 156.1, 79.9, 65.4, 61.8, 56.8, 52.9, 50.2, 49.3, 46.4, 41.0, 30.4, 29.9, 28.5, 28.3, 26.2, 26.1, 26.0 ppm.

Scheme XXVI

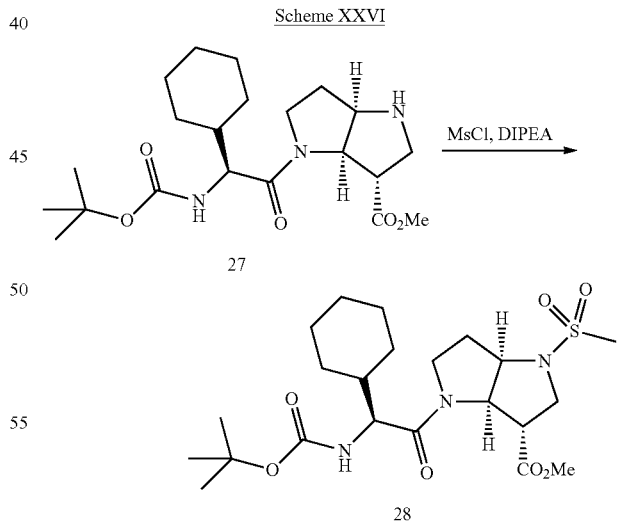

4-(2-tert-Butoxycarbonylamino-2-cyclohexyl-acetyl)-1-methanesulfonyl-octahydro-pyrrolo[3,2-b]pyrrole-3-carboxylic acid methyl ester (28): A solution of 27 (0.9 g, 2.2 mmol) in DCM (20 mL) was cooled to 0° C. and treated with DIPEA (0.75 mL, 4.3 mmol) and DMAP (31 mg, 0.25 mmol). Methanesulfonyl chloride (0.3 mL, 3.9 mmol) was then added. After 1.5 h, the solution was diluted with DCM, washed successively with 1M HCl, brine, dried over anhydrous Na$_2$SO$_4$, filtered and concentrated to afford sulfonamide 28 as an off-white foam (1.1 g) which was used without further purification. $^1$H NMR (CDCl$_3$, 300 MHz): δ5.23 (d, J=9.0 Hz, 1H), 4.74 (d, J=5.1 Hz, 1H), 4.31-4.28 (m, 2H), 4.03 (app t, J=9.3 Hz, 1H), 3.83-3.76 (m, 1H), 3.76 (s, 3H), 3.59-3.47 (m, 2H), 3.42-3.4 (m, 1H), 2.91 (s, 3H), 2.51 (dd, J=5.7, 13.8 Hz, 1H), 2.09-2.05 (m, 1H), 1.75-1.53 (m, 6H), 1.43 (s, 9H), 1.26-1.04 (m, 6H) ppm; $^{13}$C NMR (CDCl$_3$, 75 MHz): δ172.7, 171.6, 155.9, 79.8, 66.1, 63.1, 56.9, 52.8, 50.7, 47.2, 46.2, 41.2, 35.6, 33.3, 29.8, 28.5, 28.4, 26.2, 26.1, 26.0 ppm.

Scheme XXVII

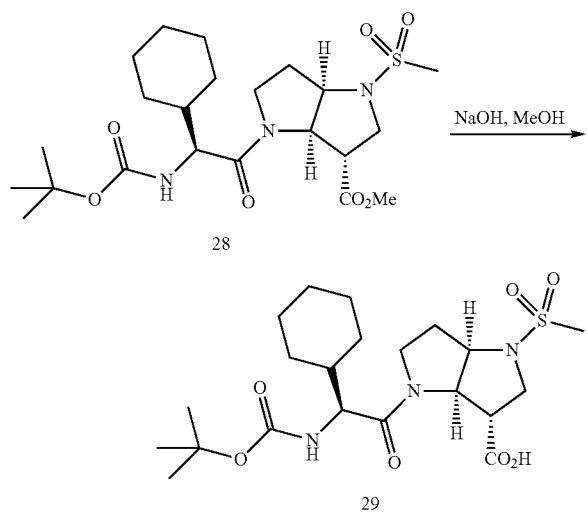

4-(2-tert-Butoxycarbonylamino-2-cyclohexyl-acetyl)-1-methanesulfonyl-octahydro-pyrrolo[3,2-b]pyrrole-3-carboxylic acid (29): A solution of 28 (1.1 g, 2.3 mmol) in MeOH (20 mL) was treated with 1M NaOH (10 mL) at ambient temperature. After 40 min, the solution was concentrated, acidified with 1M HCl until pH~2, and extracted with EtOAc. The organic extracts were washed with brine, dried over anhydrous Na$_2$SO$_4$, filtered and concentrated to afford 29 (1.0 g) as a light yellow-colored foam which was used without further purification. $^1$H NMR (CDCl$_3$, 300 MHz): δ5.23 (d, J=9.0 Hz, 1H), 4.71 (d, J=6.3 Hz, 1H), 4.33-4.16 (m, 2H), 4.16-4.06 (m, 2H), 3.82-3.78 (m, 1H), 3.73-3.66 (m, 2H), 3.17 (m, 1H), 2.92 (s, 3H), 2.66 (dd, J=5.1, 13.5 Hz, 1H), 2.13 (m, 1H), 1.77-1.55 (m, 6H), 1.43 (s, 9H), 1.29-1.01 (m, 6H) ppm.

Scheme XXVIII

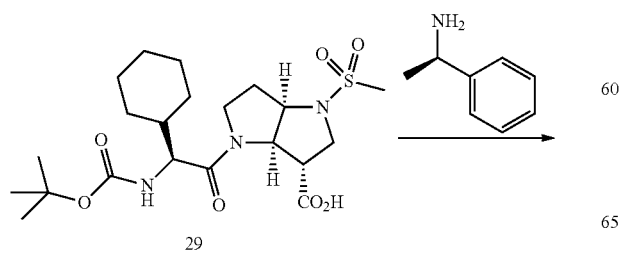

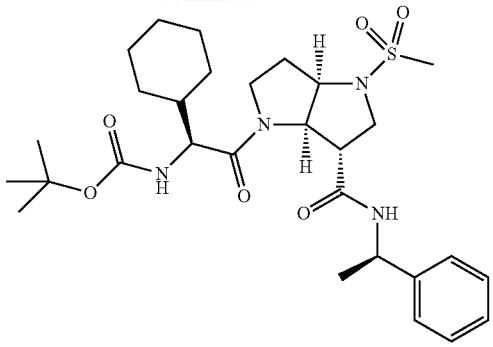

{1-Cyclohexyl-2-[4-methanesulfonyl-6-(1-phenyl-ethyl-carbamoyl)-hexahydro-pyrrolo[3,2-b]pyrrol-1-yl]-2-oxo-ethyl}-carbamic acid tert-butyl ester (30): A solution of 29 (115 mg, 0.24 mmol) in DCM (6 mL) was cooled to 0° C. and treated with (R)-(+)-α-methylbenzylamine (36 μL, 0.28 mmol), EDC (71 mg, 0.37 mmol), and HOBT (51 mg, 0.37 mmol). To this solution was then added DIPEA (0.2 mL, 1.2 mmol). The reaction mixture was allowed to warm to ambient temperature. After 16 h, the solution was diluted with DCM, washed with 1M HCl, dried over anhydrous Na$_2$SO$_4$, filtered and concentrated to give crude 30 as an off-white foam. The crude residue was diluted with ACN/H$_2$O containing 0.1% HOAc and purified by reverse-phase HPLC (2" Dynamax® C18, 10% ACN/H$_2$O to 100% ACN over 30 min). The product-containing fractions were combined and concentrated, diluted with EtOAc and washed successively with saturated NaHCO$_3$ and brine. The combined aqueous layers were back-extracted with DCM and the combined organic extracts were dried over anhydrous Na$_2$SO$_4$, filtered and concentrated to afford 30 as an off-white foam. Mass spectrum, m/z [577.6] (M+H)+.

Scheme XXIX

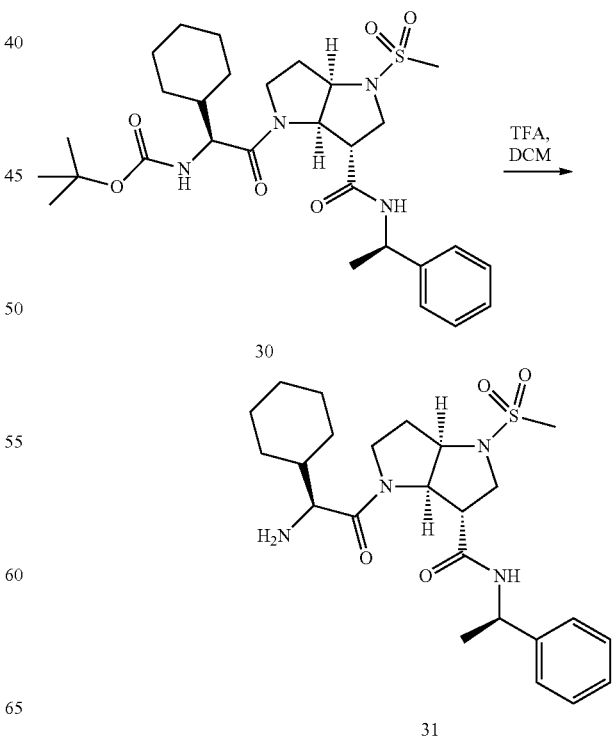

4-(2-Amino-2-cyclohexyl-acetyl)-1-methanesulfonyl-octahydro-pyrrolo[3,2-b]pyrrole-3-carboxylic acid (1-phenyl-ethyl)-amide (31): A solution of 30 (81 mg, 0.14 mmol) in DCM (10 mL) was treated with TFA (3 mL) at 0° C. After 1 h, the reaction mixture was warmed to ambient temperature. After 30 min, the solution was concentrated, diluted with EtOAc, washed with saturated NaHCO$_3$, and brine. The aqueous layers were back-extracted with DCM and the combined organic extracts were dried over anhydrous Na$_2$SO$_4$, filtered and concentrated to afford 31 (60 mg) as an off-white foam. $^1$H NMR (CDCl$_3$, 300 MHz): δ7.42-7.27 (m, 5H), 5.10-5.01 (m, 1H), 4.57 (d, J=4.5 Hz, 1H), 4.22 (m, 1H), 3.86 (d, J=11.1 Hz, 1H), 3.78 (m, 1H), 3.64-3.46 (m, 2H), 3.19 (m, 1H), 2.96 (s, 3H), 2.62-2.56 (m, 1H), 1.77-1.67 (m, 6H), 1.53 (d, J=6.9 Hz, 3H), 1.19-1.15 (m, 6H) ppm. Mass spectrum, m/z [477.5] (M+H)+.

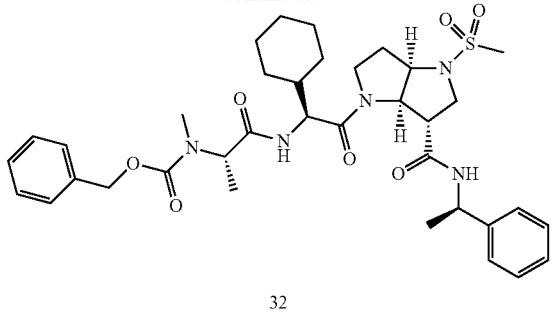

32

Scheme XXX

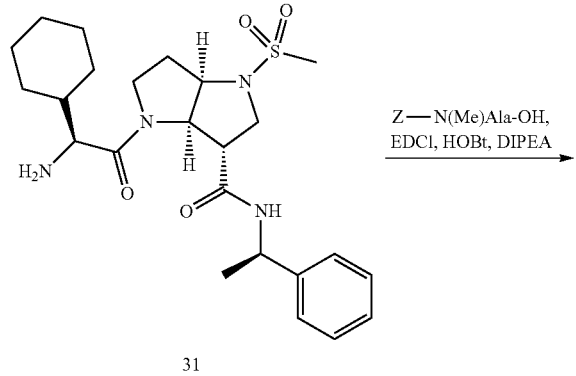

31

Z—N(Me)Ala-OH,
EDCl, HOBt, DIPEA (1-{1-Cyclohexyl-2-[4-methanesulfonyl-6-(1-phenyl-ethylcarbamoyl)-hexahydro-pyrrolo[3,2-b]pyrrol-1-yl]-2-oxo-ethylcarbamoyl}-ethyl)-methyl-carbamic acid benzyl ester (32): A solution of 31 (60 mg, 0.12 mmol) in DCM (5 mL) was cooled to 0° C. and treated with Z—N(Me)Ala-OH (32 mg, 0.14 mmol), EDC (34 mg, 0.18 mmol), and HOBt (25 mg, 0.19 mmol) followed by the addition of DIPEA (0.1 mL, 0.58 mmol). The reaction mixture was allowed to warm to ambient temperature. After 16 h, the reaction mixture was diluted with DCM, washed with 1M HCl, dried over anhydrous Na$_2$SO$_4$, filtered and concentrated to afford 32 (113 mg) as a light yellow-colored oil that was used without further purification. Mass spectrum, m/z [696.8] (M+H)+.

Scheme XXXI

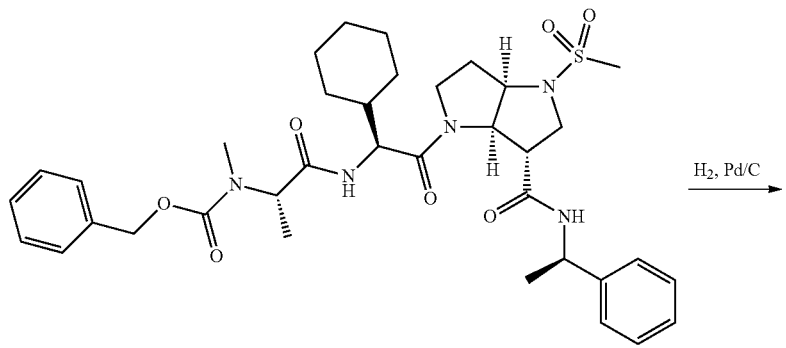

32

H$_2$, Pd/C

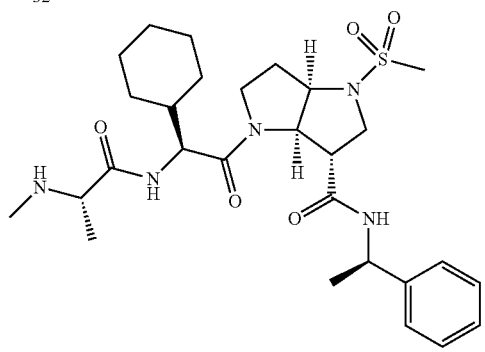

33

4-[2-Cyclohexyl-2-(2-methylamino-propionylamino)-acetyl]-1-methanesulfonyl-octahydro-pyrrolo[3,2-b]pyrrole-3-carboxylic acid (1-phenyl-ethyl)-amide (33): A solution of 32 (113 mg, 0.16 mmol) in MeOH (15 mL) was treated with 10% Pd/C (wet, 151 mg) and pressurized under $H_2$ atmosphere (50 psi) using a Parr apparatus. After 2.5 h, the reaction mixture was filtered through a filter disc (Acrodisc-PSF-0.45 μM) and rinsed with MeOH. The filtrate was concentrated to afford the crude amine 33 which was diluted with ACN/$H_2O$ containing 0.1% HOAc and purified by reverse phase HPLC (2" Dynamax® C18, 10% ACN/$H_2O$ to 100% ACN over 30 min). The product-containing fractions were combined, frozen, and lyophilized to afford 33 as a white solid.

EXAMPLE 7

4-[2-Cyclohexyl-2-(2-methylamino-propionylamino)-acetyl]-1-methanesulfonyl-octahydro-pyrrolo[3,2-b]pyrrole-3-carboxylic acid (1-phenyl-ethyl)-amide (33): $^1$H NMR (CDCl$_3$, 300 MHz), ~1:1 mixture of rotomers: δ8.97 (d, J=8.4 Hz, 0.5H), 7.96 (d, J=10.2 Hz, 0.5H), 7.68 (d, J=8.7 Hz, 1H), 7.38-7.27 (m, 5H), 5.09-4.99 (m, 2H), 4.60-4.46 (m, 4H), 4.22-4.16 (m, 2H), 4.04 (dd, J=7.8, 12.0 Hz, 0.5H), 3.85 (dd, J=3.0, 11.4 Hz, 0.5H), 3.66-3.47 (m, 4H), 3.38-3.28 (m, 0.5H), 3.21 (d, J=6.6 Hz, 0.5H), 3.14-3.07 (m, 2H), 3.02 (s, 1.5 Hz), 2.94 (s, 1.5H), 2.62-2.56 (m, 1H), 2.43 (s, 2H), 2.41 (s, 1H), 2.05-1.71 (m, 6H), 1.52-1.49 (s, 3H), 1.35-1.32 (m, 3H), 1.23-1.04 (m, 6H) ppm; $^{13}$C NMR (CDCl$_3$, 75 MHz), mixture of rotomers: δ175.5, 175.1, 171.6, 171.5, 170.4, 170.3, 143.4, 143.4, 128.9, 128.8, 127.7, 127.5, 126.4, 126.3, 68.5, 68.1, 65.7, 63.4, 60.4, 60.2, 55.3, 55.2, 51.5, 51.3, 49.9, 49.5, 49.3, 48.6, 46.1, 44.7, 41.9, 40.8, 35.7, 35.4, 35.2, 34.7, 33.4, 33.1, 30.0, 29.9, 29.6, 29.0, 26.3, 26.2, 26.1, 26.0, 25.9, 23.2, 22.4, 19.7 ppm. Mass spectrum, m/z [562.6] (M+H)+.

EXAMPLES 8 through 28 were prepared using the chemistries described in Schemes XXVI through XXXI by replacing Boc-Chg-OH with Boc-Tle-OH and/or (R)-(+)-α-methylbenzylamine with aniline, N-methylbenzylamine, methyl phenylalaninate, (S)-(+)-α-methylbenzylamine, indan-1S-ylamine, 2,3-dihydro-1H-isoindole, indan-1R-ylamine, 2,3-dihydro-1H-indole, phenethylamine, naphthalen-1-ylamine, naphthalen-2-ylamine, cyclohexyl-methylamine, benzylamine, 4-fluorobenzylamine, and (1S)-1,2,3,4-tetrahydro-naphthalen-1-ylamine(1R)-1,2,3,4-tetrahydro-naphthalen-1-ylamine, 5-methyl-2-phenyl-2H-pyrazol-3-ylamine, and 1S-cyclohexyl-ethylamine.

EXAMPLE 8

4-[2-Cyclohexyl-2-(2-methylamino-propionylamino)-acetyl]-1-methanesulfonyl-octahydro-pyrrolo[3,2-b]pyrrole-3-carboxylic acid phenylamide: $^1$H NMR (CDCl$_3$, 300 MHz), ~3:2 mixture of rotomers: δ10.48 (s, 0.4H), 9.54 (s, 0.6H), 8.07 (d, J=10.2 Hz, 0.4H), 7.76 (d, J=8.4 Hz, 0.6H), 7.64 (d, J=9.0 Hz, 1H), 7.56 (d, J=8.7 Hz, 1H), 7.35-7.26 (m, 2H), 7.16-7.11 (m, 1H), 4.66-4.49 (m, 2H), 4.20-4.14 (m, 1H), 4.08-4.01 (m, 1H), 3.84-3.59 (m, 2H), 3.42-3.33 (m, 0.4H), 3.28-3.25 (m, 0.6H), 3.14 (s, 1.8H), 3.03 (s, 1.2H), 2.66-2.54 (m, 1H), 2.45 (s, 1.8H), 2.43 (s, 1.2H), 2.12-2.01 (m, 3H), 1.90-1.57 (m, 6H), 1.41 (d, J=6.6 Hz, 1.2H), 1.36 (d, J=6.6 Hz, 1.8H), 1.31-1.00 (m, 6H) ppm; $^{13}$C NMR (CDCl$_3$, 75 MHz), mixture of rotomers: δ175.9, 175.2, 172.1, 170.8, 170.2, 169.1, 138.5, 138.2, 129.3, 129.2, 124.7, 124.6, 120.1, 120.0, 68.6, 68.0, 65.6, 63.3, 60.5, 60.4, 55.3, 55.2, 52.3, 51.4, 49.9, 49.4, 46.2, 44.8, 41.9, 40.8, 36.0, 35.5, 35.2, 34.6, 33.3, 32.9, 30.0, 29.6, 29.4, 29.0, 26.2, 26.1, 26.0, 25.9, 25.8, 19.8, 19.7 ppm. Mass spectrum, m/z [534.6] (M+H)+.

EXAMPLE 9

4-[2-Cyclohexyl-2-(2-methylamino-propionylamino)-acetyl]-1-methanesulfonyl-octahydro-pyrrolo[3,2-b]pyrrole-3-carboxylic acid benzyl-methyl-amide: $^1$H NMR (CDCl$_3$, 300 MHz), ~1:1 mixture of rotomers: δ7.64-7.61 (m, 1H), 7.34-7.26 (m, 3H), 7.22-7.14 (m, 2H), 5.40 (d, J=10.8 Hz, 0.5H), 4.62 (d, J=14.7 Hz, 0.5H), 4.55-4.44 (m, 2H), 4.33-4.32 (m, 1H), 4.21-4.09 (m, 1H), 3.78-3.62 (m, 2H), 3.55-3.49 (m, 1H), 3.30-3.26 (m, 0.5 H), 3.24 (s, 2H), 3.15-3.10 (m, 1H), 3.07-3.03 (m, 4H), 2.68-2.57 (m, 1H), 2.52 (m, 3H), 2.39 (s, 3H), 2.04-1.97 (m, 1H), 1.73-1.64 (m, 6H), 1.31 (d, J=6.6 Hz, 3H), 1.22-0.99 (m, 6H) ppm; $^{13}$C NMR (CDCl$_3$, 75 MHz), mixture of rotomers: δ174.7, 174.6, 173.0, 171.8, 171.4, 171.2, 137.4, 136.7, 128.9, 128.7, 127.8, 127.6, 126.2, 67.4, 67.3, 63.8, 63.6, 60.1, 60.0, 55.4, 55.2, 53.6, 51.7, 51.5, 51.3, 46.2, 46.0, 43.9, 43.6, 40.7, 40.6, 35.5, 35.4, 35.3, 35.2, 34.8, 32.7, 32.5, 29.7, 29.6, 28.8, 28.7, 26.1, 26.0, 25.9, 25.8, 19.3, 19.2 ppm. Mass spectrum, m/z [562.6] (M+H)+.

EXAMPLE 10

2-({4-[2-Cyclohexyl-2-(2-methylamino-propionylamino)-acetyl]-1-methanesulfonyl-octahydro-pyrrolo[3,2-b]pyrrole-3-carbonyl}-amino)-3-phenyl-propionic acid methyl ester: $^1$H NMR (CDCl$_3$, 300 MHz), ~1:1 mixture of rotomers: δ8.90 (d, J=6.9 Hz, 0.5H), 8.01 (d, J=6.8 Hz, 0.5H), 7.80 (d, J=7.8 Hz, 0.5H), 7.72 (d, J=7.8 Hz, 0.5H), 7.32-7.21 (m, 5H), 4.73-4.66 (m, 1.5H), 4.59-4.50 (m, 1H), 4.39 (m, 0.5H), 4.14 (app t, J=4.8 Hz, 0.5H), 4.04 (app t, J=8.4 Hz, 0.5H), 3.80-3.76 (m, 0.5H), 3.75 (s, 1.5H), 3.72 (s, 1.5H), 3.63-3.44 (m, 2H), 3.31-3.18 (m, 2H), 3.11-2.96 (m, 0.5H), 2.92 (s, 1.5H), 2.88 (s, 1.5H), 2.59 (s, 1.5H), 2.50 (s, 1.5H), 2.09-2.00 (m, 0.5H), 1.76 (m, 6H), 1.50 (d, J=6.9 Hz, 1.5H), 1.45 (d, J=7.2 Hz, 1.5H), 1.28-1.06 (m, 6H) ppm; $^{13}$C NMR (CDCl$_3$, 75 MHz), mixture of rotomers: δ173.9, 173.2, 172.4, 171.9, 171.4, 171.0, 170.5, 137.0, 136.5, 129.4, 129.4, 128.9, 128.7, 127.4, 127.2, 67.9, 67.4, 65.5, 63.4, 59.8, 59.2, 55.9, 55.5, 54.4, 54.2, 52.6, 52.6, 51.0, 49.9, 48.3, 46.2, 44.7, 42.0, 40.6, 37.9, 37.5, 35.7, 35.0, 34.5, 33.4, 33.4, 32.9, 29.9, 29.0, 28.9, 26.2, 26.1, 26.0, 18.7, 18.0 ppm., Mass spectrum, m/z [620.7] (M+H)+.

EXAMPLE 11

4-[2-Cyclohexyl-2-(2-methylamino-propionylamino)-acetyl]-1-methanesulfonyl-octahydro-pyrrolo[3,2-b]pyrrole-3-carboxylic acid (1-phenyl-ethyl)-amide: $^1$H NMR (CDCl$_3$, 300 MHz), ~1:1 mixture of rotomers: δ8.92 (d, J=8.4 Hz, 0.5H), 7.91 (d, J=10.2 Hz, 0.5H), 7.69 (d, J=9.0 Hz, 0.5H), 7.58 (d, J=8.1 Hz, 0.5H), 7.39-7.24 (m, 5H), 5.10-5.05 (m, 1H), 4.52 (app t, J=8.1 Hz, 0.5H), 4.41-4.38 (m, 1H), 4.34 (m, 0.5H), 4.15-3.91 (m, 2H), 3.76-3.52 (m, 2H), 3.46 (m, 1H), 3.36-3.27 (m, 0.5H), 3.21-3.14 (m, 1.5H), 3.09 (s, 1.5H), 2.96 (s, 1.5H), 2.61-2.47 (m, 1H), 2.42 (s, 1.5H), 2.40 (s, 1.5H), 2.09-1.97 (m, 1H), 1.77-1.73 (m, 2.5H), 1.63-1.60 (m, 2.5H), 1.54-1.48 (m, 1.5H), 1.37-1.32 (m, 1.5H), 1.26-0.97 (m, 6H), 0.88-0.68 (m, 0.5H), 0.54-0.42 (m, 0.5H) ppm; $^{13}$C NMR (CDCl$_3$, 75 MHz), mixture of rotomers: δ175.5, 175.2, 171.7, 171.3, 170.3, 170.1, 143.9, 143.6, 128.9, 128.8, 127.5, 127.4, 126.4, 126.1, 68.6, 67.9, 65.6, 65.2, 60.4, 60.2, 55.3, 51.3, 49.8, 49.4, 49.2, 48.7, 46.1, 44.7, 41.8, 40.7, 35.7, 35.4, 35.0, 34.5, 33.2, 32.9, 30.0, 29.6, 29.0, 26.2, 26.1, 26.0, 25.9, 25.8, 23.1, 22.7, 19.8, 19.7 ppm. Mass spectrum, m/z [562.6] (M+H)+.

EXAMPLE 12

4-[2-Cyclohexyl-2-(2-methylamino-propionylamino)-acetyl]-1-methanesulfonyl-octahydro-pyrrolo[3,2-b]pyrrole-3-carboxylic acid indan-1-ylamide: $^1$H NMR (CDCl$_3$, 300 MHz), ~1:1 mixture of rotomers: δ 8.88 (d, J=8.1 Hz, 0.5H), 7.89 (d, J=10.2 Hz, 0.5H), 7.68 (d, J=8.1 Hz, 0.5H), 7.33 (d, J=6.3 Hz, 0.5H), 7.34-7.17 (m, 5H), 5.47-5.37 (m, 1H), 4.58-4.46 (m, 2H), 4.31-4.25 (m, 2H), 4.15-3.96 (m, 2H), 3.76 (d, J=11.7 Hz, 0.5H), 3.69-3.52 (m, 1H), 3.37-3.24 (m, 0.5H), 3.21-3.19 (m, 0.5H), 3.13 (s, 1.5H), 3.08 (s, 1.5H), 3.06-2.83 (m, 2H), 2.66-2.48 (m, 2H), 2.40 (s, 1.5H), 2.35 (s, 1.5H), 2.20-1.73 (m, 1H), 1.73-1.51 (m, 6H), 1.35 (d, J=6.9 Hz, 1.5H), 1.24 (d, J=6.9 Hz, 1.5H), 1.18-0.99 (m, 6H), 0.84-0.72 (m, 0.5H), 0.39-0.30 (m, 0.5H) ppm; $^{13}$C NMR (CDCl$_3$, 75 MHz), mixture of rotomers: δ175.3, 174.8, 173.9, 172.1, 171.4, 171.2, 170.3, 143.9, 143.7, 143.6, 143.0, 128.2, 126.9, 126.8, 125.1, 125.0, 124.1, 123.9, 69.0, 68.3, 65.6, 63.3, 59.9, 59.8, 55.5, 55.3, 55.2, 54.4, 51.3, 51.2, 49.9, 48.6, 46.1, 44.7, 41.8, 40.7, 35.7, 34.9, 34.8, 34.3, 34.2, 33.4, 33.2, 33.1, 30.6, 30.5, 29.8, 29.5, 29.0, 28.8, 26.2, 26.1, 26.0, 25.9, 25.8, 21.1, 19.3, 18.9 ppm. Mass spectrum, m/z [574.7] (M+H)+.

EXAMPLE 13

N-{1-Cyclohexyl-2-[6-(1,3-dihydro-isoindole-2-carbonyl)-4-methanesulfonyl-hexahydro-pyrrolo[3,2-b]pyrrol-1-yl]-2-oxo-ethyl}-2-methylamino-propionamide: $^1$H NMR (CDCl$_3$, 300 MHz): δ7.69 (d, J=8.7 Hz, 1H), 7.36-7.28 (m, 4H), 5.49 (d, J=14.4 Hz, 1H), 4.85 (d, J=14.4 Hz, 1H), 4.79 (s, 2H), 4.55 (app t, J=8.1 Hz, 1H), 4.48 (d, J=4.8 Hz, 1H), 4.38-4.35 (m, 1H), 4.19 (app t, J=9.3 Hz, 1H), 3.78-3.54 (m, 4H), 3.08 (s, 3H), 2.64 (dd, J=5.7, 13.5 Hz, 1H), 2.40 (s, 3H), 2.26 (m, 1H), 2.06-1.99 (m, 1H), 1.81-1.64 (m, 6H), 1.32 (d, J=6.6 Hz, 3H), 1.27-1.04 (m, 6H) ppm; $^{13}$C NMR (CDCl$_3$, 75 MHz): δ174.9, 171.4, 170.9, 136.3, 135.7, 127.8, 127.7, 122.9, 122.9, 67.3, 63.7, 60.2, 55.4, 52.9, 52.5, 51.2, 46.2, 44.8, 40.7, 35.4, 35.0, 32.5, 29.8, 28.9, 26.1, 25.9, 25.8, 19.4 ppm. Mass spectrum, m/z [560.7] (M+H)+.

EXAMPLE 14

4-[2-Cyclohexyl-2-(2-methylamino-propionylamino)-acetyl]-1-methanesulfonyl-octahydro-pyrrolo[3,2-b]pyrrole-3-carboxylic acid indan-1-ylamide: $^1$H NMR (CDCl$_3$, 300 MHz), ~1:1 mixture of rotomers: δ8.74 (d, J=8.1 Hz, 0.5H), 7.88 (d, J=10.2 Hz, 0.5H), 7.64 (d, J=9.0 Hz, 0.5H), 7.33-7.19 (m, 4H), 7.06 (d, J=8.7 Hz, 0.5H), 5.48-5.37 (m, 1H), 4.55-4.44 (m, 2H), 4.22 (app t, J=4.8 Hz, 0.5H), 4.13 (app t, J=9.0 Hz, 0.5H), 3.98 (dd, J=2.4, 11.4 Hz, 0.5H), 3.75 (d, J=12.0 Hz, 0.5H), 3.68-3.53 (m, 1.5H), 3.36-3.22 (m, 1H), 3.17 (s, 1.5H), 3.05 (s, 1.5H), 3.03-2.99 (m, 1H), 2.93-2.82 (m, 1H), 2.64-2.51 (m, 3H), 2.48 (s, 1.5H), 2.35 (s, 1.5H), 2.12-2.03 (m, 1H), 1.95-1.81 (m, 1H), 1.75-1.56 (m, 6H), 1.30 (d, J=6.9 Hz, 1.5H), 1.19 (d, J=6.9 Hz, 1.5H), 1.09-0.97 (m, 6H), 0.83-0.80 (m, 0.5H) ppm; $^{13}$C NMR (CDCl$_3$, 75 MHz), mixture of rotomers: δ175.3, 174.9, 172.6, 171.5, 171.2, 170.3, 143.4, 143.3, 143.2, 143.0, 128.3, 128.1, 127.0, 126.9, 125.1, 124.8, 124.6, 124.3, 68.8, 68.1, 65.7, 63.3, 60.2, 60.1, 55.3, 55.2, 55.0, 54.9, 51.6, 51.4, 50.0, 48.5, 46.0, 44.7, 41.8, 40.8, 35.8, 35.3, 35.0, 34.8, 34.0, 33.4, 33.3, 33.2, 30.5, 30.4, 29.9, 28.8, 29.5, 29.0, 26.3, 26.2, 26.1, 26.0, 25.9, 19.6, 19.4 ppm. Mass spectrum, m/z [574.7] (M+H)+.

EXAMPLE 15

N-{1-Cyclohexyl-2-[6-(2,3-dihydro-indole-1-carbonyl)-4-methanesulfonyl-hexahydro-pyrrolo[3,2-b]pyrrol-1-yl]-2-oxo-ethyl}-2-methylamino-propionamide: $^1$H NMR (CDCl$_3$, 300 MHz): δ8.17 (d, J=7.5 Hz, 1H), 7.66 (d, J=8.4 Hz, 1H), 7.23-7.18 (m, 2H), 7.06 (t, J=7.5 Hz, 1H), 4.88-4.79 (m, 1H), 4.58-4.53 (m, 2H), 4.40 (app t, J=3.6 Hz, 1H), 4.22 (app t, J=9.9 Hz, 1H), 4.13-4.04 (m, 1H), 3.81 (d, J=10.8 Hz, 1H), 3.71-3.55 (m, 2H), 3.30-3.21 (m, 2H). 3.11 (s, 3H), 2.66 (dd, J=5.7, 13.2 Hz, 1H), 2.41 (s, 3H), 2.05-2.01 (m, 1H), 1.77-1.62 (m, 6H), 1.32 (d, J=6.9 Hz, 3H), 1.29-1.02 (m, 6H) ppm; $^{13}$C NMR (CDCl$_3$, 75 MHz): δ174.9, 171.5, 170.1, 142.6, 132.0, 127.5, 124.8, 124.4, 117.2, 67.3, 63.7, 60.1, 55.4, 51.4, 48.4, 46.3, 46.1, 40.7, 35.5, 35.0, 32.5, 29.7, 28.9, 28.2, 26.0, 25.9, 25.8, 19.4 ppm. Mass spectrum, m/z [560.7] (M+H)+.

EXAMPLE 16

4-[2-Cyclohexyl-2-(2-methylamino-propionylamino)-acetyl]-1-methanesulfonyl-octahydro-pyrrolo[3,2-b]pyrrole-3-carboxylic acid-phenethyl-amide: $^1$H NMR (CDCl$_3$, 300 MHz), ~2:1 mixture of rotomers: δ8.43 (t, J=5.4 Hz, 0.4H), 7.92 (d, J=10.5 Hz, 0.4H), 7.70 (d, J=8.7 Hz, 0.6H), 7.32-7.19 (m, 5H), 6.99 (t, J=5.4 Hz, 0.6H), 4.53-4.27 (m, 2H), 4.13-3.86 (m, 2H), 3.66-3.42 (m, 3H), 3.32-3.06 (m, 1H), 3.05 (s, 1 H), 2.98 (s, 2H), 2.90-2.79 (m, 2H), 2.58-2.49 (m, 1H), 2.45 (s, 1.2H), 2.39 (s, 0.8H), 2.06-1.97 (m, 4H), 1.76-1.56 (m, 4H), 1.36-0.98 (m, 6H) ppm; $^{13}$C NMR (CDCl$_3$, 75 MHz), mixture of rotomers: δ175.4, 174.8, 172.4, 171.5, 171.1, 170.2, 138.9, 129.1, 128.9, 128.7, 128.6, 126.7, 68.7, 67.9, 65.6, 63.1, 60.4, 55.2, 55.1, 51.3, 51.2, 49.7, 48.6, 46.1, 44.8, 41.9, 40.9, 40.8, 40.6, 36.0, 35.8, 35.4, 35.1, 34.8, 33.2, 29.9, 29.6, 29.4, 29.0, 26.2, 26.0, 25.9, 19.7, 19.6 ppm. Mass spectrum, m/z [562.5] (M+H)+.

EXAMPLE 17

4-[2-Cyclohexyl-2-(2-methylamino-propionylamino)-acetyl]-1-methanesulfonyl-octahydro-pyrrolo[3,2-b]pyrrole-3-carboxylic acid naphthalen-1-ylamide: $^1$H NMR (CDCl$_3$, 300 MHz), ~2:1 mixture of rotomers: δ10.36 (s, 0.4H), 9.72 (s, 0.6H), 8.22 (d, J=8.1 Hz, 0.6H), 8.15 (d, J=8.1 Hz, 0.4H), 8.10 (d, J=10.2 Hz, 0.4H), 8.02 (d, J=7.5 Hz, 0.6H), 7.93-7.68 (m, 2.6H), 7.53-7.43 (m, 2.4H), 4.84-4.54 (m, 2H), 4.23-4.05 (m, 2.4H), 3.89 (d, J=10.2 Hz, 0.4H), 3.78-3.65 (m, 1.6H), 3.51-3.41 (m, 0.6H), 3.23-3.15 (m, 1H), 3.10 (s, 1H), 3.03 (s, 2H), 2.68-2.56 (m, 1H), 2.48 (s, 1.2H), 2.43 (s, 0.8H), 2.22-2.13 (m, 1H), 2.06 (s, 1H), 1.92-1.67 (m, 6H), 1.38-1.05 (m, 6H) ppm; $^{13}$C NMR (CDCl$_3$, 75 MHz), mixture of rotomers: δ175.6, 174.8, 171.8, 170.2, 169.5, 134.2, 134.1, 132.4, 132.3, 128.7, 128.6, 127.6, 126.6, 126.2, 126.1, 125.9, 125.7, 125.6, 125.5, 121.7, 121.3, 120.9, 119.5, 69.1, 67.8, 65.6, 62.9, 60.2, 60.1, 55.4, 55.0, 51.5, 51.3, 49.9, 49.0, 45.9, 44.8, 41.6, 40.6, 35.8, 35.2, 34.9, 34.3, 33.1, 29.8, 29.6, 29.5, 28.8, 26.0, 25.9, 25.8, 25.7, 20.8, 19.5, 19.4 ppm. Mass spectrum, m/z [584.7] (M+H)+.

EXAMPLE 18

4-[2-Cyclohexyl-2-(2-methylamino-propionylamino)-acetyl]-1-methanesulfonyl-octahydro-pyrrolo[3,2-b]pyrrole-3-carboxylic acid naphthalen-2-ylamide: $^1$H NMR (CDCl₃, 300 MHz), ~1:1 mixture of rotomers: δ10.68 (s, 0.5H), 9.84 (s, 0.5H), 8.36 (s, 0.5H), 8.22 (s, 0.5H), 8.09 (d, J=10.2 Hz, 0.5 H), 7.83-7.77 (m, 2.5H), 7.59-7.38 (m, 2H), 4.71-4.53 (m, 2H), 4.21-4.02 (m, 2H), 3.86 (d, J=11.7 Hz, 0.5H), 3.74-3.64 (m, 1.5H), 3.40-3.30 (m, 1.5H), 3.20-3.13 (m, 1.5H), 3.05 (s, 1.5H), 2.68-2.56 (m, 1H), 2.49 (s, 1.5H), 2.45 (s, 0.5H), 2.16-1.99 (m, 2H), 1.84-1.64 (m, 6H), 1.44 (d, J=6.9 Hz, 1H), 1.36 (d, J=6.9 Hz, 1.5H), 1.27-1.05 (m, 4H) ppm; $^{13}$C NMR (CDCl₃, 75 MHz), mixture of rotomers: δ175.9, 175.2, 172.1, 171.0, 170.2, 169.2, 136.0, 135.8, 134.1, 134.0, 131.0, 130.9, 129.1, 129.0, 128.0, 127.8, 126.8, 126.7, 125.3, 125.2, 120.0, 119.9, 116.8, 116.6, 68.6, 68.1, 65.7, 63.3, 60.5, 60.4, 55.4, 55.3, 52.5, 51.4, 50.1, 49.3, 46.2, 44.8, 41.9, 40.8, 36.1, 35.5, 35.2, 34.5, 33.3, 32.8, 30.0, 29.7, 29.4, 29.1, 26.2, 26.1, 25.9, 25.8, 19.9, 19.7 ppm. Mass spectrum, m/z [584.6] (M+H)+.

EXAMPLE 19

4-[2-Cyclohexyl-2-(2-methylamino-propionylamino)-acetyl]-1-methanesulfonyl-octahydro-pyrrolo[3,2-b]pyrrole-3-carboxylic acid cyclohexylmethyl-amide: $^1$H NMR (CDCl₃, 300 MHz), ~2:1 mixture of rotomers: δ8.35 (br m, 0.4H), 7.95 (d, J=9.9 Hz, 0.4H), 7.71 (d, J=8.4 Hz, 0.6H), 6.96 (t, J=6.0 Hz, 0.6 H), 4.53-4.47 (m, 2H), 4.18-3.91 (m, 2H), 3.7-3.48 (m, 1.6H), 3.39-3.29 (m, 0.6H), 3.24-3.18 (m, 1 H), 3.13-3.08 (m, 2.4H), 3.03 (s, 1.4H), 2.95-2.84 (m, 0.6H), 2.63-2.51 (m, 1.4H), 2.45 (s, 1.4H), 2.41 (s, 1H), 2.12-2.01 (m, 0.6H), 1.83-1.42 (m, 10H), 1.37-0.86 (m, 6H) ppm; $^{13}$C NMR (CDCl₃, 75 MHz), mixture of rotomers: δ175.3, 174.4, 172.6, 171.5, 171.2, 170.3, 68.9, 68.2, 65.7, 63.2, 60.3, 60.2, 55.4, 55.3, 51.4, 51.2, 49.9, 48.6, 46.2, 46.1, 45.9, 44.8, 41.9, 40.8, 38.1, 35.8, 35.3, 34.7, 33.2, 33.1, 31.1, 31.0, 29.9, 29.4, 29.0, 26.6, 26.3, 26.2, 26.1, 26.0, 25.9, 19.7, 19.2 ppm. Mass spectrum, m/z [554.6] (M+H)+.

EXAMPLE 20

4-[3,3-Dimethyl-2-(2-methylamino-propionylamino)-butyryl]-1-methanesulfonyl-octahydro-pyrrolo[3,2-b]pyrrole-3-carboxylic acid benzylamide: $^1$H NMR (CDCl₃, 300 MHz): ~1:1 mixture of rotomers: δ8.94 (m, 0.5H), 8.11 (d, J=10.5 Hz, 0.5H), 7.83 (d, J=9.0 Hz, 1H), 7.38-7.28 (m, 5H), 4.72-4.64 (m, 0.5H), 4.57-4.38 (m, 4H), 4.26 (dd, J=3.9, 14.4 Hz, 0.5H), 4.18-4.11 (m, 1H), 4.00-3.94 (m, 1H), 3.74-3.49 (m, 2.5H), 3.49-3.30 (m, 0.5H), 3.18-3.12 (m, 1.5H), 3.09-3.07 (m, 1.5H), 3.02 (s, 2H), 2.68-2.50 (m, 3H), 2.17-2.00 (m, 1.5H), 1.86-1.78 (m, 0.5H), 1.34-1.28 (m, 3H), 1.01 (s, 6H), 0.85 (s, 3H) ppm; $^{13}$C NMR (CDCl₃, 75 MHz) mixture of rotomers: δ175.1, 174.6, 172.1, 170.9, 168.9, 138.2, 138.0, 128.7, 128.6, 127.7, 127.5, 127.4, 68.5, 68.1, 65.5, 63.0, 60.1, 56.8, 56.5, 51.1, 51.0, 49.6, 48.5, 46.5, 44.6, 43.6, 43.3, 35.8, 35.6, 35.3, 35.1, 34.8, 34.5, 33.0, 32.9, 26.5, 26.1, 19.4, 19.2 ppm. Mass spectrum, m/z [522.5] (M+H)+.

EXAMPLE 21

4-[3,3-Dimethyl-2-(2-methylamino-propionylamino)-butyryl]-1-methanesulfonyl-octahydro-pyrrolo[3,2-b]pyrrole-3-carboxylic acid 4-fluoro-benzylamide $^1$H NMR (CDCl₃, 300 MHz), ~1:1 mixture of rotomers: δ8.96 (m, 0.5H), 8.14 (d, J=10.5 Hz, 0.5H), 7.84 (d, J=9.0 Hz, 1H), 7.44 (t, J=6.3 Hz, 1H), 7.33-7.23 (m, 2.5H), 7.04-6.96 (m, 2.5H), 4.67-4.34 (m, 5H), 4.26-4.12 (m, 2H), 4.12-3.93 (m, 1.5H), 3.74-3.51 (m, 3H), 3.39-3.29 (m, 0.5H), 3.18-3.05 (m, 3.5H), 3.02 (s, 2.5H), 2.79-2.50 (m, 4H), 2.39 (s, 3H), 2.14-2.01 (m, 1.5H), 1.83-1.79 (m, 0.5H), 1.31-1.29 (m, 3H), 1.01 (s, 3H), 0.86 (s, 6H) ppm; $^{13}$C NMR (CDCl₃, 75 MHz), mixture of rotomers: δ175.2, 174.6, 174.1, 172.1, 171.0, 170.9, 170.8, 168.9, 163.8, 163.7, 160.6, 160.5, 134.1, 134.0, 133.9, 133.8, 129.6, 129.5, 129.3, 129.2, 115.7, 115.6, 115.4, 115.3, 68.5, 68.1, 65.5, 63.0, 60.1, 60.0, 56.9, 56.5, 51.2, 51.0, 49.5, 48.6, 46.5, 44.6, 42.9, 42.6, 35.9, 35.6, 35.3, 35.1, 34.7, 34.5, 32.9, 32.8, 26.6, 26.1, 19.4, 19.2 ppm. Mass spectrum, m/z [540.6] (M+H)+.

EXAMPLE 22

4-[3,3-Dimethyl-2-(2-methylamino-propionylamino)-butyryl]-1-methanesulfonyl-octahydro-pyrrolo[3,2-b]pyrrole-3-carboxylic acid phenylamide: $^1$H NMR (CDCl₃, 300 MHz), ~1:1 mixture of rotomers: δ10.58 (s, 0.5H), 9.51 (s, 0.5H), 8.30 (d, J=10.5 Hz, 0.5H), 7.93 (d, J=9.0 Hz, 0.5H), 7.65 (d, J=7.8 Hz, 1H), 7.57 (d, J=7.8 Hz, 1H), 7.34 (t, J=7.8 Hz, 2H), 7.15-7.09 (m, 1H), 4.70-4.58 (m, 2H), 4.49 (t, J=5.1 Hz, 0.5H), 4.20-4.14 (m, 1H), 4.10-3.97 (m, 1H), 3.82 (d, J=11.7 Hz, 0.5H), 3.76-3.59 (m, 1.5H), 3.44-3.34 (m, 0.5H), 3.28-3.25 (m, 0.5H), 3.21-3.19 (m, 1H), 3.14 (s, 1.5H), 3.02 (s, 1.5H), 2.65-2.54 (m, 1.5H), 2.45 (d, J=6 Hz, 3H), 2.39-2.32 (m, 1H), 2.18-2.05 (m, 1H), 1.86-1.80 (m, 0.5H), 1.39 (dd, J=7.2, 19.8 Hz, 3H), 1.03 (d, J=21 Hz, 9H) ppm; $^{13}$C NMR (CDCl₃, 75 MHz), mixture of rotomers: δ175.6, 174.7, 171.3, 170.6, 168.9, 168.8, 138.3, 137.9, 129.0, 124.5, 124.4, 119.8, 119.7, 68.4, 68.3, 65.4, 62.9, 60.1, 56.9, 56.7, 52.2, 51.1, 49.9, 49.0, 46.6, 44.6, 36.1, 35.7, 35.4, 35.2, 34.8, 34.3, 33.0, 32.7, 26.6, 26.3, 19.5, 19.3 ppm. Mass spectrum, m/z [508.6] (M+H)+.

EXAMPLE 23

4-[3,3-Dimethyl-2-(2-methylamino-propionylamino)-butyryl]-1-methanesulfonyl-octahydro-pyrrolo[3,2-b]pyrrole-3-carboxylic acid (1,2,3,4-tetrahydro-naphthalen-1-yl)-amide: $^1$H NMR (CDCl₃, 300 MHz), ~1:1 mixture of rotomers: δ9.00 (d, J=9.3 Hz, 0.5H), 8.01 (d, J=10.5 Hz, 0.5H), 7.77 (d, J=9.6 Hz, 0.5H), 7.31-7.28 (m, 0.5H), 7.24-7.16 (m, 1H), 7.14-7.03 (m, 3H), 5.25-5.22 (m, 0.5H), 5.14-5.11 (m, 0.5H), 4.54-4.49 (m, 1.5H), 4.29 (d, J=10.5 Hz, 0.5H), 4.22 (t, J=4.8 Hz, 0.5H), 4.13 (t, J=9.3 Hz, 0.5H), 4.01-3.95 (m, 1H), 3.76 (d, J=11.7 Hz, 0.5H), 3.68-3.51 (m, 1.5H), 3.37-3.31 (m, 0.5H), 3.21-3.18 (m, 0.5H), 3.15 (s, 1H), 3.01-2.99 (m, 2H), 2.84-2.76 (m, 1.5H), 2.64-2.52 (m, 1H), 2.35 (s, 1H), 2.30 (s, 1H), 2.18-1.77 (m, 5H), 1.25 (dd, J=7.2, 27.3 Hz, 3H), 0.99 (s, 3H), 0.68 (s, 3H) ppm; $^{13}$C NMR (CDCl₃, 75 MHz), mixture of rotomers: δ175.1, 171.5, 170.9, 170.6, 169.2, 137.8, 137.5, 136.6, 129.5, 128.7, 128.2, 127.5, 127.4, 126.5, 126.4, 68.8, 68.5, 65.7, 63.2, 60.4, 60.2, 56.9, 56.6, 51.3, 51.2, 49.9, 48.7, 48.2, 46.7, 46.5, 44.8, 35.8, 35.7, 35.5, 35.4, 34.8, 33.3, 33.1, 30.5, 29.8, 29.4, 29.2, 26.8, 26.1, 20.4, 19.6, 19.5, 19.3 ppm. Mass spectrum, m/z [562.6] (M+H)+.

EXAMPLE 24

4-[3,3-Dimethyl-2-(2-methylamino-propionylamino)-butyryl]-1-methanesulfonyl-octahydro-pyrrolo[3,2-b]pyrrole-3-carboxylic acid naphthalen-1-ylamide: $^1$H NMR (CDCl₃, 300 MHz), ~3:2 mixture of rotomers: δ10.42 (s, 0.4H), 9.82 (s, 0.6H), 8.33 (d, J=10.5 Hz, 0.4H), 8.26 (d, J=8.1 Hz, 0.6H), 8.19 (d, J=7.8 Hz, 0.4H), 8.04-7.99 (m, 0.6H), 7.92-7.86 (m, 0.6H), 7.76-7.68 (m, 1.4H), 7.53-7.43 (m, 3H), 4.85-4.74 (m, 1.4H), 4.64-4.55 (m, 1H), 4.25-4.19 (m, 2.4H), 4.07-4.01 (m, 0.4H), 3.89-3.85 (m, 0.4H), 3.80-3.65 (m, 2.4H), 3.50-3.39 (m, 1.4H), 3.21-3.14 (m, 1H), 3.10 (s, 0.6H), 3.03 (s, 2.4H), 2.70-2.56 (m, 1.4H), 2.48-2.39 (m, 4.6H), 2.25-2.14 (m, 1H), 2.04 (s, 0.4H), 1.92-1.82 (m, 0.6H), 1.38-1.35 (m, 3H), 1.10-1.06 (s, 9H) ppm; $^{13}$C NMR (CDCl₃, 75 MHz), mixture of rotomers: δ175.5, 174.8, 171.9, 171.4, 169.4, 169.1, 134.2, 134.1, 132.5, 132.4, 128.7, 128.6, 127.6, 126.5, 126.2, 126.1, 126.0, 125.9, 125.7, 125.5, 125.4, 121.8, 121.2, 121.0, 119.5, 69.2, 68.2, 65.8, 62.9, 60.4, 60.1, 56.8, 56.7, 51.5, 51.4, 50.1, 48.9, 46.5, 44.8, 35.8, 35.7, 35.4, 35.2, 35.1, 34.2, 33.1, 32.9, 26.6, 26.4, 19.6, 19.4 ppm. Mass spectrum, m/z [558.6] (M+H)+.

EXAMPLE 25

4-[3,3-Dimethyl-2-(2-methylamino-propionylamino)-butyryl]-1-methanesulfonyl-octahydro-pyrrolo[3,2-b]pyrrole-3-carboxylic acid naphthalen-2-ylamide: ¹H NMR (CDCl₃, 300 MHz), ~1:1 mixture of rotomers: δ10.77 (s, 0.5H), 9.78 (s, 0.5H), 8.37 (d, J=1.8 Hz, 0.5H), 8.32 (d, J=10.5 Hz, 0.5H), 8.23 (d, J=1.8 Hz, 0.5H), 7.94 (d, J=9.3 Hz, 0.5H), 7.81-7.77 (m, 2.5H), 7.59-7.38 (m, 2.5H), 4.74-4.67 (m, 1H), 4.61 (d, J=9.3 Hz, 0.5H), 4.54 (t, J=4.5 Hz, 0.5H), 4.21-3.99 (m, 2H), 3.87 (d, J=11.7 Hz, 0.5H), 3.78-3.63 (m, 1.5H), 3.46-3.22 (m, 1.5H), 3.19 (s, 2H), 3.05 (s, 1.5H), 2.78-2.56 (m, 1.5H), 2.48-2.46 (m, 3H), 2.19-2.05 (m, 1H), 1.89-1.80 (m, 0.5H), 1.41 (dd, J=6.9, 26.4 Hz, 3H), 1.04 (d, J=27 Hz, 9H) ppm; ¹³C NMR (CDCl₃, 75 MHz), mixture of rotomers: δ175.6, 174.6, 171.4, 170.8, 168.9, 135.8, 135.5, 133.8, 130.7, 130.6, 128.9, 128.8, 127.8, 127.6, 127.5, 126.5, 126.4, 125.1, 125.0, 119.8, 119.7, 116.5, 116.4, 68.4, 68.3, 65.5, 62.9, 60.1, 56.9, 56.8, 52.3, 51.2, 50.0, 49.0, 46.6, 44.6, 36.1, 35.8, 35.4, 35.2, 34.8, 34.3, 33.0, 32.6, 26.6, 26.3, 19.5, 19.3 ppm. Mass spectrum, m/z [558.7] (M+H)+.

EXAMPLE 26

4-[3,3-Dimethyl-2-(2-methylamino-propionylamino)-butyryl]-1-methanesulfonyl-octahydro-pyrrolo[3,2-b]pyrrole-3-carboxylic acid (5-methyl-2-phenyl-2H-pyrazol-3-yl)-amide: ¹H NMR (CDCl₃, 300 MHz), ~3:1 mixture of rotomers: δ10.23 (s, 0.25H), 9.57 (s, 0.75H), 8.17 (d, J=10.5 Hz, 0.25H), 7.76 (d, J=9.0 Hz, 0.75H), 7.52-7.34 (m, 5H), 6.43 (s, 0.75H), 6.30 (s, 0.25H), 4.52-4.36 (m, 2H), 4.12-3.91 (m, 2.25H), 3.69-3.50 (m, 1.75H), 3.38-3.28 (m, 0.25H), 3.22-3.12 (m, 1.75H), 3.05-2.93 (m, 3H), 2.61-2.43 (m, 1.25H), 2.37-2.14 (m, 5H), 2.39-2.32 (m, 1H), 2.14-2.02 (m, 1H), 1.35 (d, J=6.9 Hz, 2.25H), 1.24 (d, J=6.9 Hz, 0.75H), 0.96 (s, 6H), 0.89 (s, 1H) ppm; ¹³C NMR (CDCl₃, 75 MHz), mixture of rotomers: δ175.0, 174.3, 171.4, 170.9, 168.8, 168.2, 149.5, 149.3, 138.8, 138.1, 135.8, 135.2, 129.4, 129.1, 128.1, 127.9, 125.1, 101.6, 99.3, 68.1, 67.5, 65.3, 62.8, 60.1, 60.0, 56.6, 56.5, 50.9, 50.8, 49.3, 48.8, 46.4, 44.6, 35.8, 35.7, 35.4, 35.0, 34.8, 34.2, 32.9, 32.7, 26.5, 26.2, 19.2, 14.0 ppm. Mass spectrum m/z [588.7] (M+H)+.

EXAMPLE 27

4-[3,3-Dimethyl-2-(2-methylamino-propionylamino)-butyryl]-1-methanesulfonyl-octahydro-pyrrolo[3,2-b]pyrrole-3-carboxylic acid (1,2,3,4-tetrahydro-naphthalen-1-yl)-amide: ¹H NMR (CDCl₃, 300 MHz), ~1:1 mixture of rotomers: δ8.73 (d, J=8.7 Hz, 0.5H), 8.08 (d, J=10.5 Hz, 0.5H), 7.78 (d, J=9.0 Hz, 0.5H), 7.25-7.08 (m, 3H), 7.01 (d, J=9.3 Hz, 0.5H), 5.19-5.15 (m, 1H), 4.58-4.47 (m, 2H), 4.21-4.11 (m, 1H), 4.03-3.95 (m, 0.5H), 3.77-3.51 (m, 1.5H), 3.38-3.29 (m, 0.5H), 3.20 (d, J=6.3 Hz, 0.5H), 3.15-3.11 (m, 1.5H), 3.02 (s, 1.5H), 3.00-2.83 (m, 0.5H), 2.82-2.75 (m, 1.5H), 2.64-2.51 (m, 1H), 2.37 (d, J=9.9 Hz, 2H), 2.12-1.76 (m, 5H), 1.32 (d, J=6.6 Hz, 1.5H), 1.20 (d, J=6.9 Hz, 0.5H), 0.99 (d, J=7.2 Hz, 6.5H) ppm; ¹³C NMR (CDCl₃, 75 MHz), mixture of rotomers: δ174.8, 174.6, 171.9, 170.7, 170.6, 169.0, 137.4, 136.9, 136.5, 136.3, 129.2, 128.9, 128.5, 127.3, 127.2, 126.2, 68.7, 68.2, 65.7, 63.0, 60.0, 59.9, 56.9, 56.4, 51.4, 51.2, 49.7, 48.4, 47.6, 47.1, 46.5, 44.6, 35.8, 35.6, 35.2, 35.0, 34.7, 34.6, 33.1, 32.9, 30.2, 30.0, 29.1, 29.0, 26.6, 26.4, 20.0, 19.9, 19.2, 19.1 ppm. Mass spectrum, m/z [562.7] (M+H)+.

EXAMPLE 28

4-[3,3-Dimethyl-2-(2-methylamino-propionylamino)-butyryl]-1-methanesulfonyl-octahydro-pyrrolo[3,2-b]pyrrole-3-carboxylic acid (1S-cyclohexyl-ethyl)-amide: ¹H NMR (CDCl₃, 300 MHz), ~1:1 mixture of rotomers: δ8.23-8.14 (m, 1H), 7.86 (d, J=9.3 Hz, 1H), 6.86 (d, J=9.3 Hz, 1H), 4.60-4.48 (m, 2H), 4.18-4.12 (m, 1H), 3.98-3.94 (m, 1H), 3.80-3.76 (m, 2H), 3.70-3.49 (m, 2H), 3.43-3.38 (m, 1H), 3.17-3.13 (m, 1H), 3.12 (s, 1.5H), 3.04 (s, 1.5H), 2.92 (m, 1H), 2.64-2.53 (m, 1H), 2.41 (s, 3H), 1.76-1.73 (m, 5H), 1.36-1.33 (m, 3H), 1.16-1.10 (m, 3H), 1.02 (s, 9H) ppm; ¹³C NMR (CDCl₃, 75 MHz), mixture of rotomers: δ175.3, 175.2, 171.8, 171.1, 170.3, 169.3, 69.2, 68.4, 65.9, 63.2, 60.5, 60.4, 56.9, 56.7, 51.5, 51.0, 49.9, 49.7, 49.1, 46.7, 44.9, 43.3, 43.21, 43.17, 36.1, 35.9, 35.6, 35.4, 35.2, 34.6, 33.1, 29.7, 29.4, 29.2, 29.1, 26.8, 26.6, 26.5, 26.46, 26.4, 26.3, 19.8, 19.7, 18.3, 17.9 ppm. Mass spectrum, m/z [542.2] (M+H)+.

EXAMPLE 29

4-[3,3-Dimethyl-2-(2-methylamino-propionylamino)-butyryl]-1-methanesulfonyl-octahydro-pyrrolo[3,2-b]pyrrole-3-carboxylic acid (1R-cyclohexyl-ethyl)-amide: ¹H NMR (CDCl₃, 300 MHz), ~1:1 mixture of rotomers: δ8.37 (d, J=8.4 Hz, 0.5H), 8.14 (d, J=10.2 Hz, 0.5H), 7.83 (d, J=9.0 Hz, 1H), 6.81 (d, J=9.0 Hz, 1H), 4.56 (d, J=9.6 Hz, 1H), 4.51-4.40 (m, 4H), 4.18-4.09 (m, 1H), 4.03-3.96 (m, 0.5H), 3.91 (dd, J=3.0, 11.1 Hz, 0.5H), 3.81-3.71 (m, 1H), 3.69-3.49 (m, 2H), 3.38-3.25 (m, 1H), 3.19-3.13 (m, 0.5H), 3.08 (s, 1.5H), 3.02 (s, 1.5H), 2.63-2.49 (m, 1H), 2.45 (s, 2H), 2.43 (s, 1H), 2.06 (s, 3H), 1.76-1.68 (m, 5H), 1.38 (d, J=6.3 Hz, 3H), 1.25-1.17 (m, 2H), 1.12 (d, J=6.9 Hz, 3H), 1.04 (s, 6H), 0.99 (s, 3H) ppm; ¹³C NMR (CDCl₃, 75 MHz), mixture of rotomers: δ174.8, 174.1, 171.9, 170.9, 170.5, 169.3, 68.8, 68.3, 65.8, 63.3, 60.1, 59.9, 57.4, 56.8, 51.5, 512, 50.0, 49.8, 48.7, 46.8, 44.8, 43.2, 43.1, 36.1, 35.7, 35.6, 35.1, 34.7, 34.4, 33.2, 33.1, 29.3, 29.2, 29.1, 26.8, 26.6, 26.5, 26.4, 26.3, 19.3, 19.0, 18.1, 18.0 ppm. Mass spectrum, m/z [542.2] (M+H)+.

TABLE 2

| Example | Structure | XIAP, nM | cIAP1, nM | SKOV3, nM | Mass spectrum, m/z |
|---|---|---|---|---|---|
| 7 | 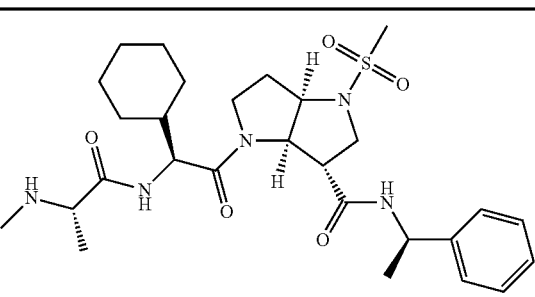 | B | A | B | 562.6 (M + H) |

TABLE 2-continued
| Example | Structure | XIAP, nM | cIAP1, nM | SKOV3, nM | Mass spectrum, m/z |
|---|---|---|---|---|---|
| 8 | 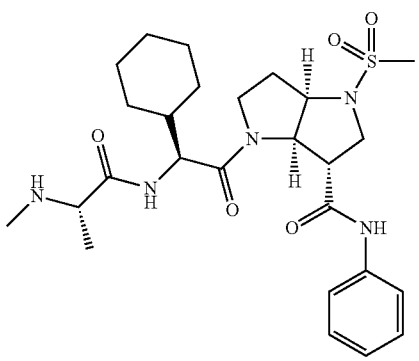 | B | A | A | 534.6 (M + H) |
| 9 | 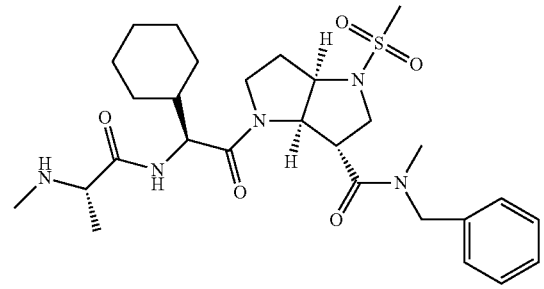 [SMILES: CN[C@@H](C)C(=O)N[C@H](C(=O)N1CC[C@@H]2[C@H]1[C@@H](C(=O)N(C)Cc1ccccc1)CN2S(C)(=O)=O)C1CCCCC1] | A | A | B | 562.6 (M + H) |
| 10 | 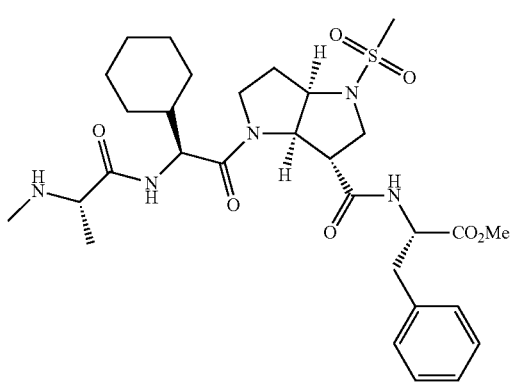 [SMILES: CN[C@@H](C)C(=O)N[C@H](C(=O)N1CC[C@@H]2[C@H]1[C@@H](C(=O)N[C@@H](Cc1ccccc1)C(=O)OC)CN2S(C)(=O)=O)C1CCCCC1] | B | B | C | 620.7 (M + H) |
| 11 | 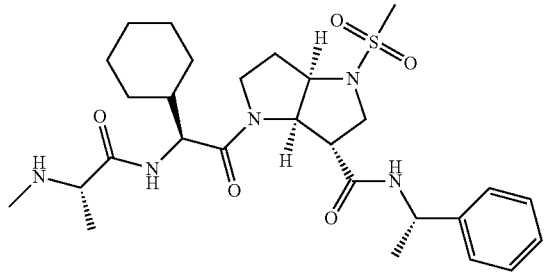 [SMILES: CN[C@@H](C)C(=O)N[C@H](C(=O)N1CC[C@@H]2[C@H]1[C@@H](C(=O)N[C@@H](C)c1ccccc1)CN2S(C)(=O)=O)C1CCCCC1] | A | A | B | 562.6 (M + H) |

TABLE 2-continued
| Example | Structure | XIAP, nM | cIAP1, nM | SKOV3, nM | Mass spectrum, m/z |
|---|---|---|---|---|---|
| 12 | 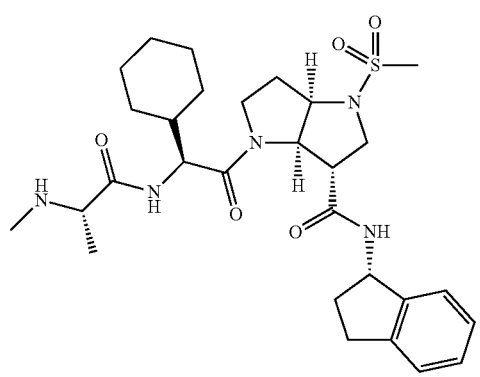 [SMILES: CN[C@@H](C)C(=O)N[C@H](C(=O)N1CC[C@@H]2[C@H]1[C@@H](C(=O)N[C@H]1CCc3ccccc31)CN2S(C)(=O)=O)C1CCCCC1] | B | A | B | 574.7 (M + H) |
| 13 | 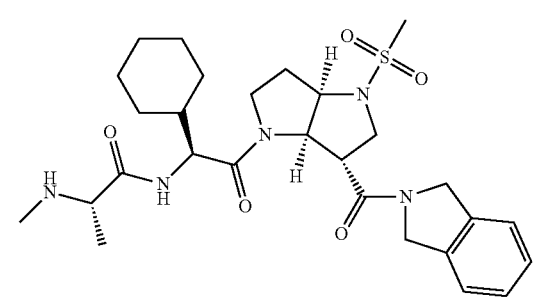 [SMILES: CN[C@@H](C)C(=O)N[C@H](C(=O)N1CC[C@@H]2[C@H]1[C@@H](C(=O)N1Cc3ccccc3C1)CN2S(C)(=O)=O)C1CCCCC1] | A | A | A | 560.7 (M + H) |
| 14 | 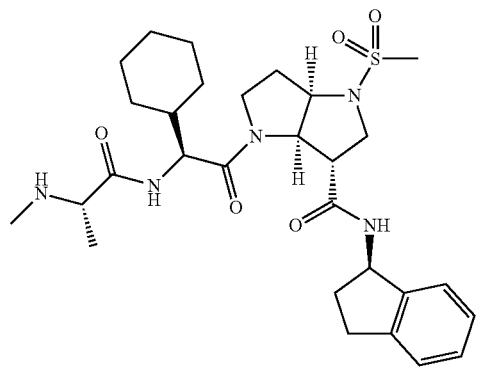 [SMILES: CN[C@@H](C)C(=O)N[C@H](C(=O)N1CC[C@@H]2[C@H]1[C@@H](C(=O)N[C@@H]1CCc3ccccc31)CN2S(C)(=O)=O)C1CCCCC1] | B | A | A | 574.7 (M + H) |
| 15 | 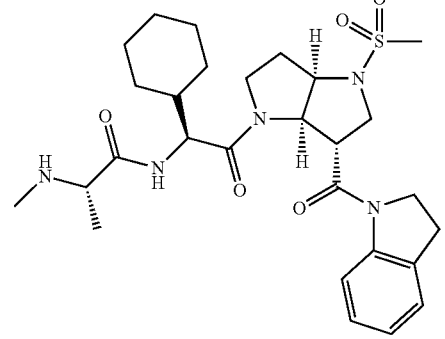 | B | B | A | 560.7 (M + H) |

TABLE 2-continued

| Example | Structure | XIAP, nM | cIAP1, nM | SKOV3, nM | Mass spectrum, m/z |
|---|---|---|---|---|---|
| 16 | 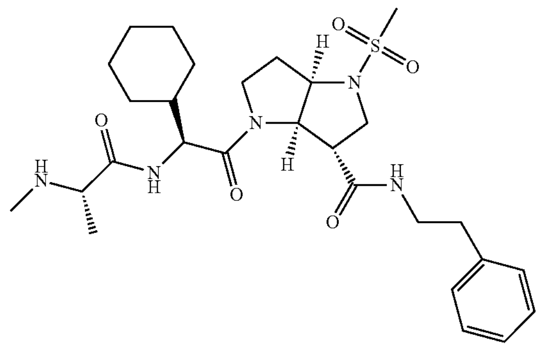 [SMILES: CN[C@@H](C)C(=O)N[C@H](C(=O)N1CC[C@@H]2[C@H]1[C@@H](C(=O)NCCc1ccccc1)CN2S(C)(=O)=O)C1CCCCC1] | A | A | B | 562.5 (M + H) |
| 17 | 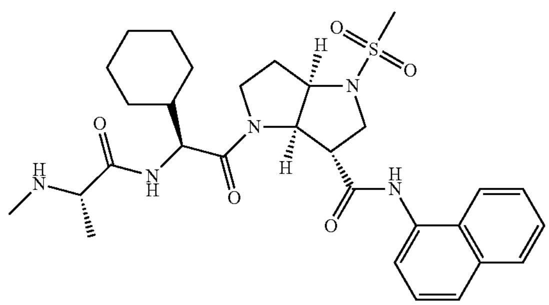 [SMILES: CN[C@@H](C)C(=O)N[C@H](C(=O)N1CC[C@@H]2[C@H]1[C@@H](C(=O)Nc1cccc3ccccc13)CN2S(C)(=O)=O)C1CCCCC1] | A | A | A | 584.7 (M + H) |
| 18 | 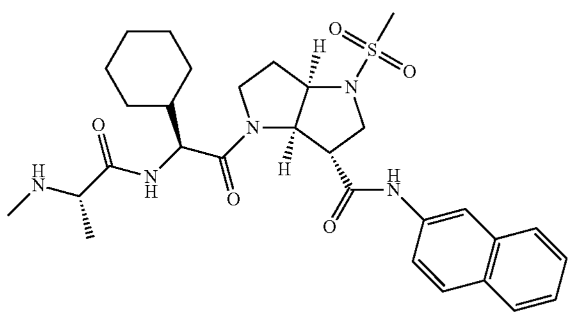 [SMILES: CN[C@@H](C)C(=O)N[C@H](C(=O)N1CC[C@@H]2[C@H]1[C@@H](C(=O)Nc1ccc3ccccc3c1)CN2S(C)(=O)=O)C1CCCCC1] | B | A | A | 584.6 (M + H) |
| 19 | 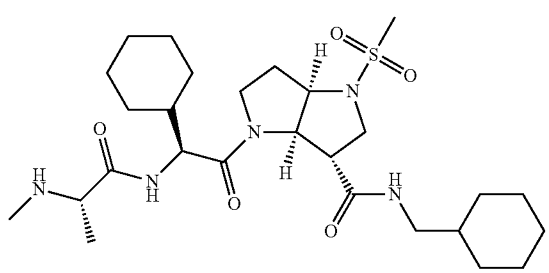 [SMILES: CN[C@@H](C)C(=O)N[C@H](C(=O)N1CC[C@@H]2[C@H]1[C@@H](C(=O)NCC1CCCCC1)CN2S(C)(=O)=O)C1CCCCC1] | A | A | A | 554.6 (M + H) |
| 20 | 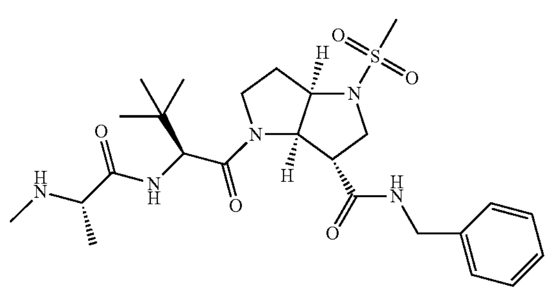 [SMILES: CN[C@@H](C)C(=O)N[C@H](C(=O)N1CC[C@@H]2[C@H]1[C@@H](C(=O)NCc1ccccc1)CN2S(C)(=O)=O)C(C)(C)C] | A | A | A | 522.5 (M + H) |

TABLE 2-continued
| Example | Structure | XIAP, nM | cIAP1, nM | SKOV3, nM | Mass spectrum, m/z |
|---|---|---|---|---|---|
| 21 | 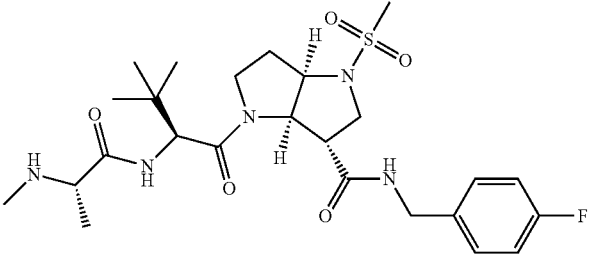 [SMILES: CN[C@@H](C)C(=O)N[C@H](C(=O)N1CC[C@@H]2[C@H]1[C@@H](C(=O)NCc1ccc(F)cc1)CN2S(C)(=O)=O)C(C)(C)C] | A | A | A | 540.6 (M + H) |
| 22 | 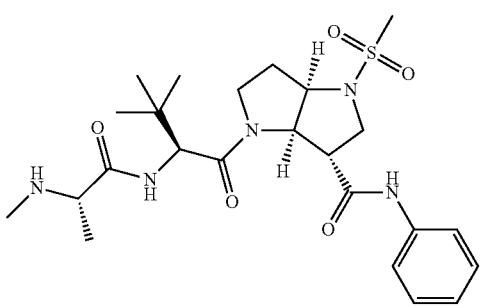 [SMILES: CN[C@@H](C)C(=O)N[C@H](C(=O)N1CC[C@@H]2[C@H]1[C@@H](C(=O)Nc1ccccc1)CN2S(C)(=O)=O)C(C)(C)C] | A | A | A | 508.6 (M + H) |
| 23 | 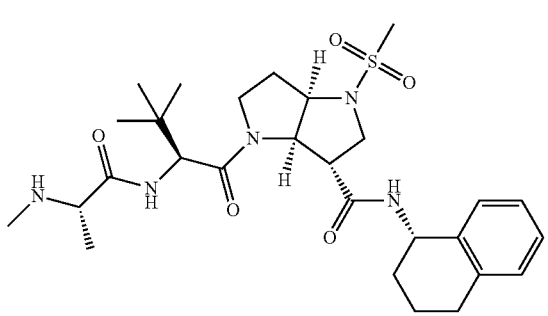 [SMILES: CN[C@@H](C)C(=O)N[C@H](C(=O)N1CC[C@@H]2[C@H]1[C@@H](C(=O)N[C@H]1CCCc3ccccc31)CN2S(C)(=O)=O)C(C)(C)C] | A | A | B | 562.6 (M + H) |
| 24 | 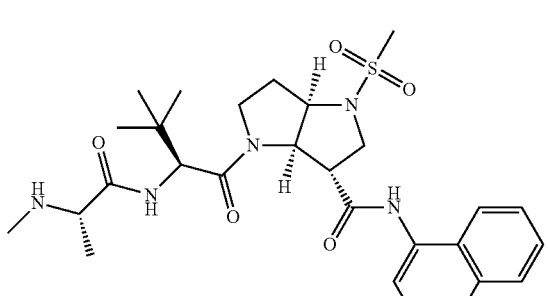 | A | A | A | 558.6 (M + H) |
| 25 | 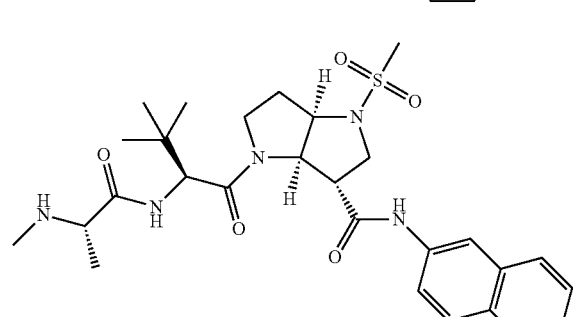 | A | A | A | 558.7 (M + H) |

TABLE 2-continued

| Example | Structure | XIAP, nM | cIAP1, nM | SKOV3, nM | Mass spectrum, m/z |
|---|---|---|---|---|---|
| 26 | 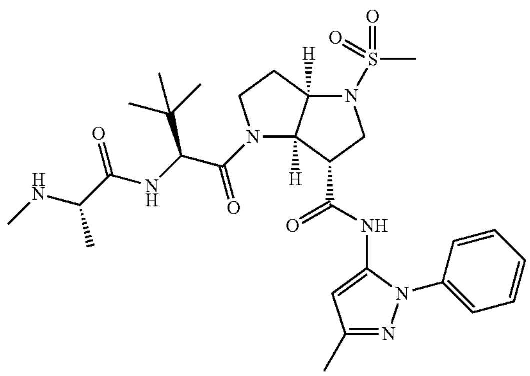 [SMILES: CN[C@@H](C)C(=O)N[C@H](C(=O)N1CC[C@@H]2[C@H]1[C@@H](C(=O)Nc1cc(C)nn1-c1ccccc1)CN2S(C)(=O)=O)C(C)(C)C] | A | A | B | 588.7 (M + H) |
| 27 | 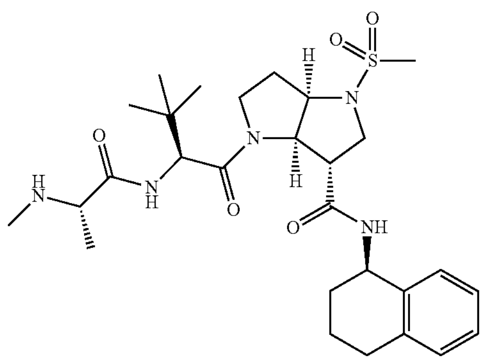 [SMILES: CN[C@@H](C)C(=O)N[C@H](C(=O)N1CC[C@@H]2[C@H]1[C@@H](C(=O)N[C@@H]1CCCc3ccccc31)CN2S(C)(=O)=O)C(C)(C)C] | A | A | A | 562.7 (M + H) |
| 28 | 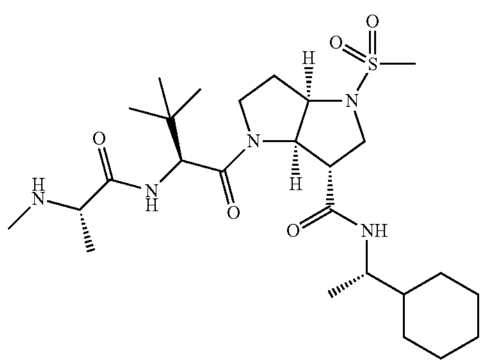 [SMILES: CN[C@@H](C)C(=O)N[C@H](C(=O)N1CC[C@@H]2[C@H]1[C@@H](C(=O)N[C@@H](C)C1CCCCC1)CN2S(C)(=O)=O)C(C)(C)C] | A | A | A | 542.2 (M + H) |
| 29 | 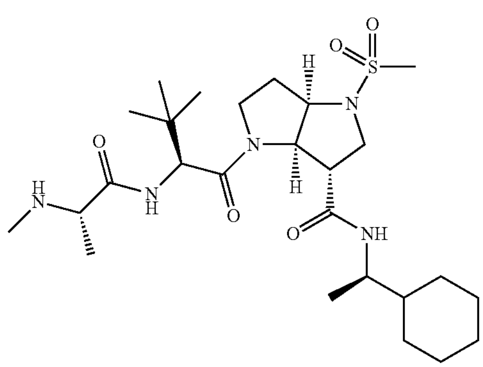 [SMILES: CN[C@@H](C)C(=O)N[C@H](C(=O)N1CC[C@@H]2[C@H]1[C@@H](C(=O)N[C@H](C)C1CCCCC1)CN2S(C)(=O)=O)C(C)(C)C] | C | A | C | 542.2 (M + H) |

Scheme XXXII

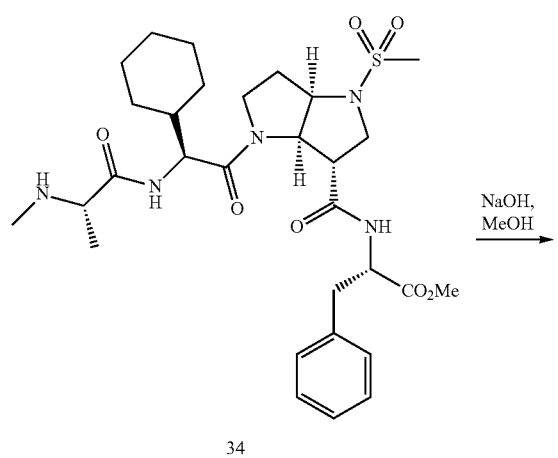

EXAMPLE 30

2-({4-[2-Cyclohexyl-2-(2-methylamino-propionylamino)-acetyl]-1-methanesulfonyl-octahydro-pyrrolo[3,2-b]pyrrole-3-carbonyl}-amino)-3-phenyl-propionic acid: A solution of 34 (61 mg, 0.1 mmol) [Example 10 from above] in MeOH (10 mL) was cooled to 0° C. and treated with 1M NaOH (0.5 mL). After 30 min, the solution was concentrated, diluted with ACN/H$_2$O containing 0.1% v/v HOAc and purified by reverse phase HPLC (2" Dynamax® C18, 10-70% ACN/H$_2$O, 30 min gradient). The product-containing fractions were combined, frozen, and lyophilized to give 35 as a white solid (24.2 mg). $^1$H NMR (CDCl$_3$, 300 MHz), ~2:1 mixture of rotomers: δ8.66 (d, J=9.0 Hz, 1H), 7.62 (d, J=8.4 Hz, 1H), 7.31-7.20 (m, 4H), 4.49 (d, J=5.7 Hz, 2H), 4.03 (app t, J=10.2 Hz, 1H), 3.80 (app q, J=6.9 Hz, 1H), 3.59-3.50 (m, 1H), 3.47-3.26 (m, 2H), 3.12 (d, J=6.3 Hz, 1H), 2.87-2.80 (m, 1H), 2.62 (s, 1.5H), 2.56 (s, 1.5H), 2.51-2.42 (m, 1H), 2.04-1.99 (m, 1H), 1.78-1.74 (m, 6H), 1.61-1.57 (m, 1H), 1.45 (d, J=7.2 Hz, 1.5H), 1.38 (d, J=6.9 Hz, 1.5H), 1.27-1.08 (m, 6H) ppm; $^{13}$C NMR (CDCl$_3$, 75 MHz), mixture of rotomers: δ171.5, 171.0, 170.2, 138.5, 129.8, 129.6, 128.5, 128.4, 126.8, 67.2, 64.0, 57.6, 56.4, 51.4, 46.4, 40.3, 38.9, 34.6, 33.0, 31.7, 29.7, 29.0, 26.1, 25.9, 16.7 ppm. Mass spectrum, m/z [606.9] (M+H)+.

TABLE 3

| Example | Structure | XIAP, nM | cIAP1, nM | SKOV3, nM | Mass spectrum, m/z |
|---|---|---|---|---|---|
| 30 | 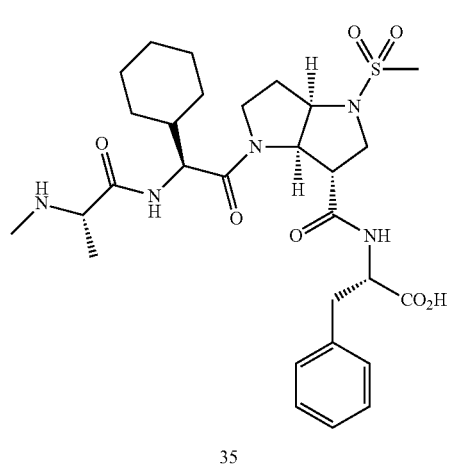 | C | A | C | 606.9 (M + H) |

Scheme XXXIII

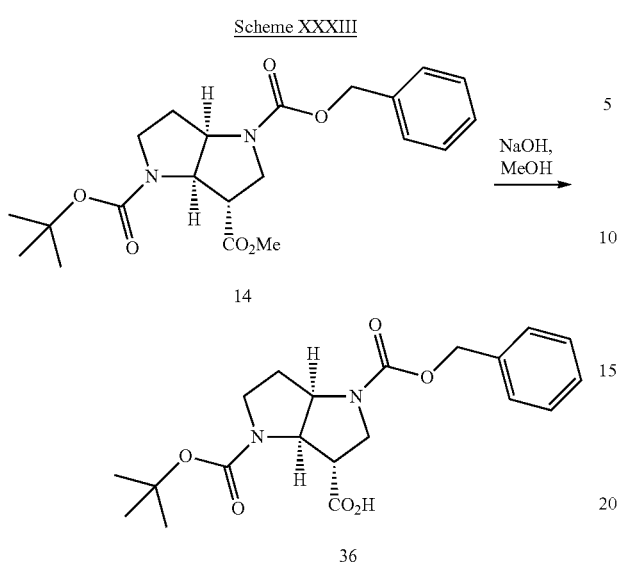

Hexahydro-pyrrolo[3,2-b]pyrrole-1,3,4-tricarboxylic acid 1-benzyl ester 4-tert-butyl ester (36): A solution of 14 (923 mg, 2.28 mmol) in MeOH (20 mL) was treated with 1M NaOH (7.8 mL) at ambient temperature. After 1.5 h, the solution was concentrated and diluted with EtOAc and 1M HCl. The layers were separated and the aqueous phase was extracted with EtOAc. The combined organic extracts were washed successively with 1M HCl, and brine, dried over anhydrous $Na_2SO_4$, filtered and concentrated to afford 36 as a yellow-colored foam (900 mg) which was used without further purification. Mass spectrum, m/z [391.4] (M+H)+.

Scheme XXXIV

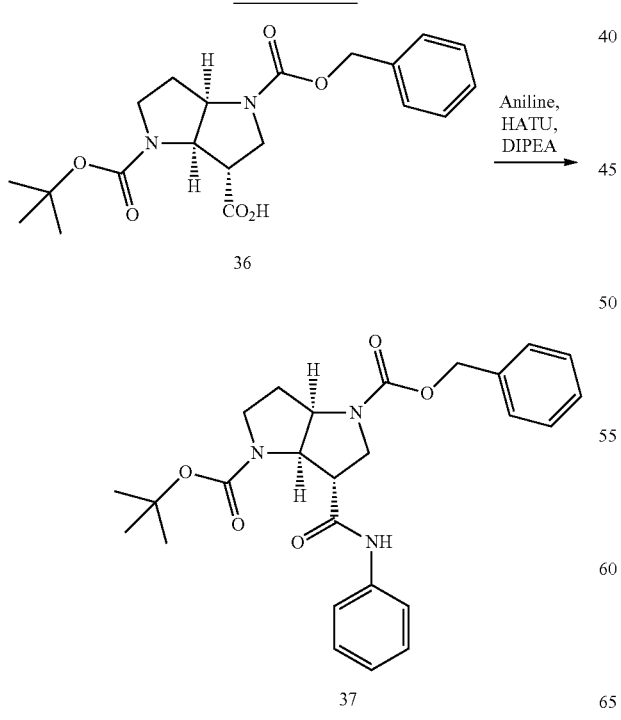

3-Phenylcarbamoyl-hexahydro-pyrrolo[3,2-b]pyrrole-1, 4-dicarboxylic acid 1-benzyl ester 4-tert-butyl ester (37): A solution of 36 (500 mg, 1.28 mmol) in NMP (7 mL) was cooled to 0° C. and treated with HATU (511 mg, 1.34 mmol) and DIPEA (0.33 mL, 1.92 mmol) followed in 15 min by the addition of aniline (0.14 mL, 1.54 mmol). The reaction mixture was allowed to warm to ambient temperature. After 3 h, the solution was diluted with EtOAc, washed with $H_2O$, 1M HCl, $H_2O$, sat $NaHCO_3$, brine, dried over anhydrous $Na_2SO_4$, filtered and concentrated to afford 37 (414 mg) as a white foam that was used without further purification. Mass spectrum, m/z [466.4] (M+H)+.

Scheme XXXV

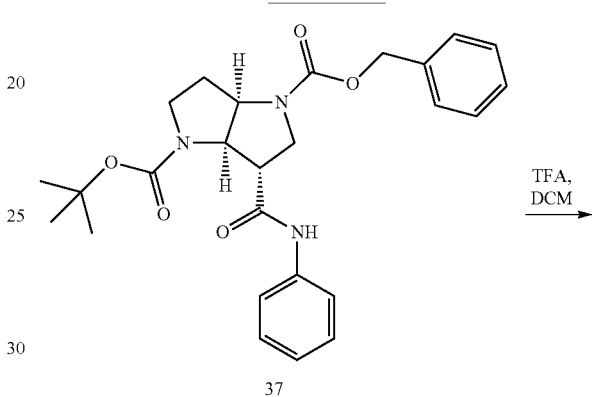

3-Phenylcarbamoyl-hexahydro-pyrrolo[3,2-b]pyrrole-1-carboxylic acid benzyl ester (38): A solution of 37 (410 mg, 0.88 mmol) in DCM (10 mL) was cooled to 0° C. and treated with TFA (4 mL). After 2 h, the solution was concentrated, diluted with EtOAc and washed with saturated aqueous $NaHCO_3$, brine, dried over anhydrous $Na_2SO_4$, filtered and concentrated to afford 38 (305 mg) as a white foam that was used without further purification. Mass spectrum, m/z [366.4] (M+H)+.

Scheme XXXVI

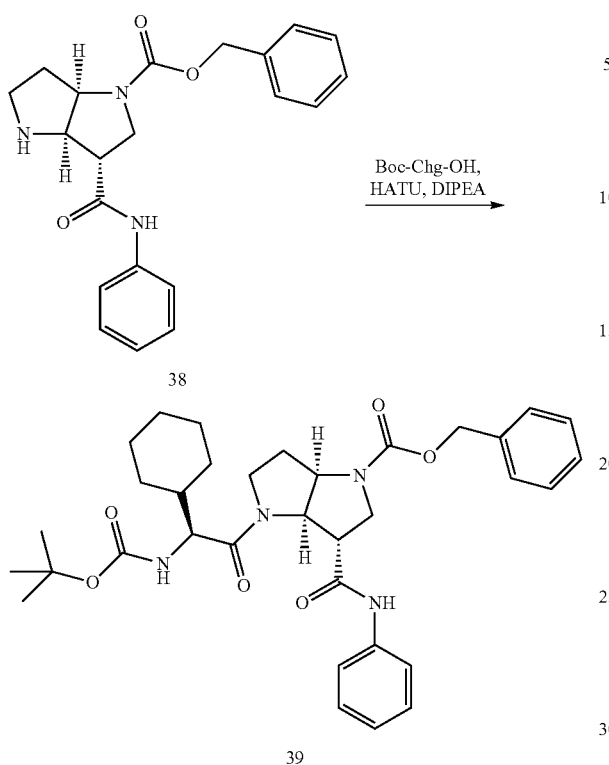

4-(2-tert-Butoxycarbonylamino-2-cyclohexyl-acetyl)-3-phenylcarbamoyl-hexahydro-pyrrolo[3,2-b]pyrrole-1-carboxylic acid benzyl ester (39): A solution of Boc-Chg-OH (222 mg, 0.86 mmol) in NMP (5 mL) was cooled to 0° C. and treated with HATU (328 mg, 0.86 mmol) and DIPEA (0.17 mL, 0.98 mmol) followed, in 15 min, by the addition of 38 (300 mg, 0.82 mmol). The reaction mixture was allowed to warm to ambient temperature. After 18 h, the solution was diluted with Et$_2$O, washed with H$_2$O, 1M HCl, H$_2$O, saturated aqueous NaHCO$_3$, brine, dried over anhydrous Na$_2$SO$_4$, filtered and concentrated. Purification by column chromatograhpy on silica gel with 2:1 hexane:EtOAc afforded 39 (460 mg) as a white foam. $^1$H NMR (CDCl$_3$, 300 MHz), mixture of rotamers: δ9.96 (d, J=18.9 Hz, 0.5H), 7.68 (d, J=9 Hz, 1H), 7.61 (d, J=7.5 Hz, 1H), 7.39-7.28 (m, 7H), 7.10 (dd, J=7.2, 15 Hz, 1H), 5.32-5.28 (m, 0.5H), 5.20-5.12 (m, 2.5H), 4.81-4.78 (m, 0.5H), 4.70 (d, J=6.6 Hz, 0.5H), 4.55-4.49 (m, 1H), 4.39-4.27 (m, 1.5H), 4.02-3.99 (m, 1H), 3.54-3.40 (m, 2H), 3.22-3.09 (m, 2H), 2.51-2.26 (m, 1H), 2.10-2.09 (m, 0.5H), 1.94-1.62 (m, 8H), 1.52-1.43 (m, 11H), 1.18-0.86 (m, 6H) ppm. Mass spectrum, m/z [605.7] (M+H)+.

Scheme XXXVII

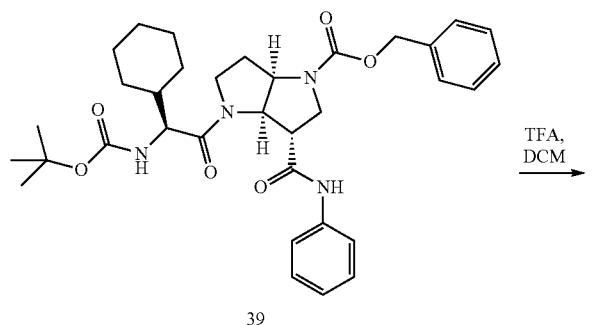

4-(2-Amino-2-cyclohexyl-acetyl)-3-phenylcarbamoyl-hexahydro-pyrrolo[3,2-b]pyrrole-1-carboxylic acid benzyl ester (40): A solution of 39 (460 mg, 0.76 mmol) in DCM (10 mL) was cooled to 0° C. and treated with TFA (4 mL). After 2 h, the solution was concentrated, diluted with EtOAc and washed with saturated aqueous NaHCO$_3$, brine, dried over anhydrous Na$_2$SO$_4$, filtered and concentrated to afford 40 (366 mg) as a pale yellow-colored foam that was used without further purification. Mass spectrum, m/z [505.5] (M+H)+.

Scheme XXXVIII

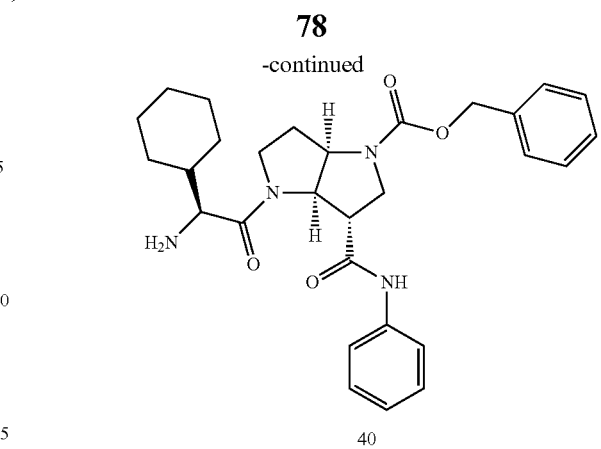

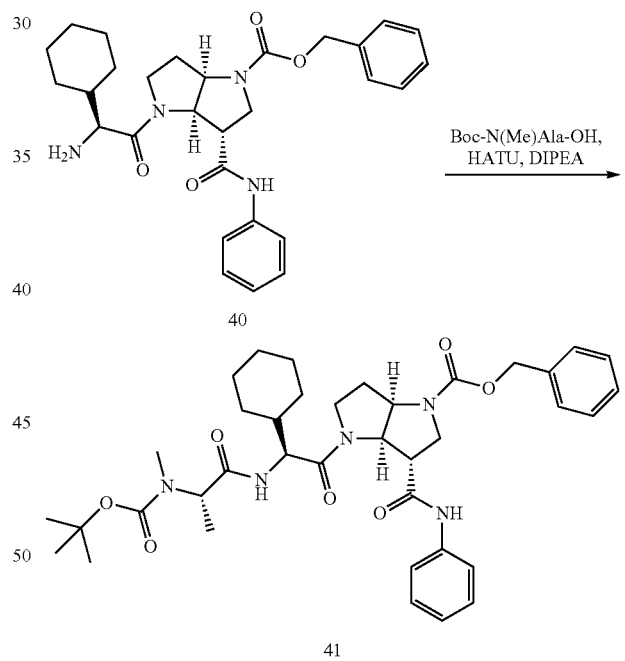

4-{2-[2-(tert-Butoxycarbonyl-methyl-amino)-propionylamino]-2-cyclohexyl-acetyl}-3-phenylcarbamoyl-hexahydro-pyrrolo[3,2-b]pyrrole-1-carboxylic acid benzyl ester (41): A solution of Boc-N(Me)Ala-OH (155 mg, 0.76 mmol) in NMP (5 mL) was cooled to 0° C. and treated with HATU (290 mg, 0.76 mmol) and DIPEA (0.15 mL, 0.87 mmol) followed in 15 min by the addition of 40 (366 mg, 0.73 mmol). The reaction mixture was allowed to warm to ambient temperature. After 18 h, the solution was diluted with Et$_2$O, washed with H$_2$O, 1M HCl, H$_2$O, saturated aqueous NaHCO$_3$, brine, dried over anhydrous Na$_2$SO$_4$, filtered and concentrated to afford 41 (443 mg) as a white foam that was used without further purification. Mass spectrum, m/z [690.8] (M+H)+.

Scheme XXXIX

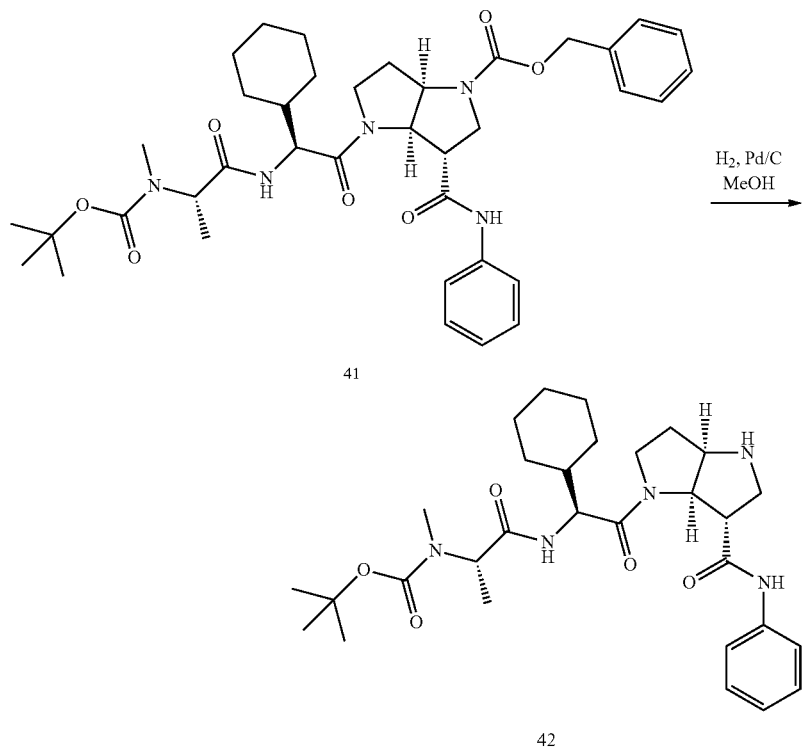

{1-[1-Cyclohexyl-2-oxo-2-(6-phenylcarbamoyl-hexahydro-pyrrolo[3,2-b]pyrrol-1-yl)-ethylcarbamoyl]-ethyl}-methyl-carbamic acid tert-butyl ester (42): A mixture of 41 (440 mg, 0.64 mmol) and 10% palladium-on-carbon (88 mg) in MeOH (15 mL) was shaken at 48 psi under a $H_2$ atmosphere. After 2 h, the mixture was filtered through a 0.45 μM filtering disc, washed with MeOH and concentrated to afford 42 (352 mg) as a white foam that was used without further purification. Mass spectrum, m/z [556.6] (M+H)+.

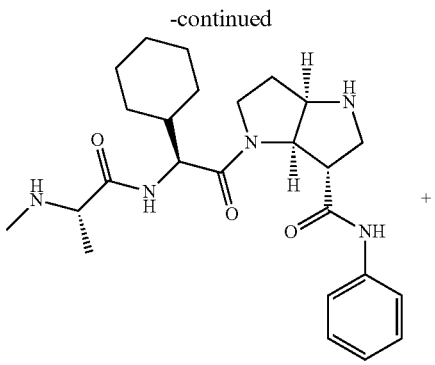

Scheme XL

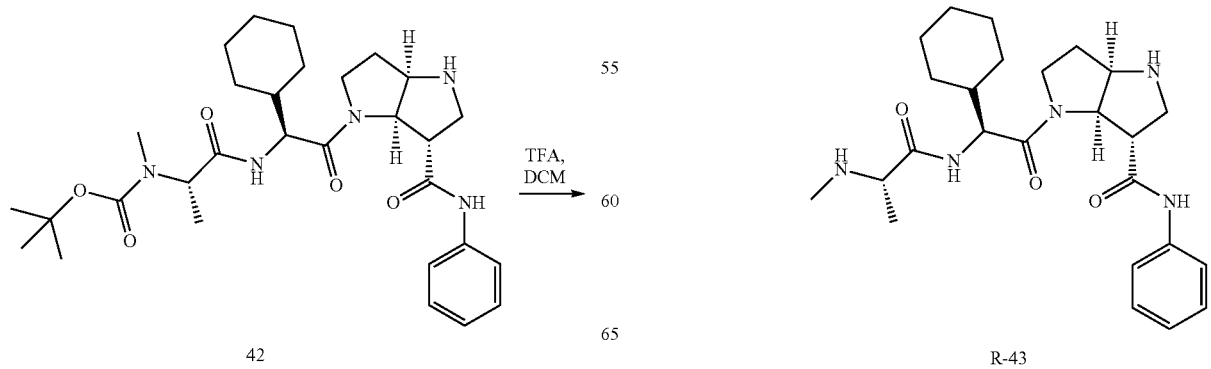

4-[2-Cyclohexyl-2-(2-methylamino-propionylamino)-acetyl]-1-methanesulfonyl-octahydro-pyrrolo[3,2-b]pyrrole-3S-carboxylic acid phenethyl-amide (S-43) and 4-[2-Cyclohexyl-2-(2-methylamino-propionylamino)-acetyl]-1-methanesulfonyl-octahydro-pyrrolo[3,2-b]pyrrole-3R-carboxylic acid phenethyl-amide (R-43): A solution of 42 (100 mg, 0.18 mmol) in DCM (8 mL) was cooled to 0° C. and treated with TFA (2 mL). After 2 h, the solution was concentrated, diluted with EtOAc and washed with saturated aqueous $NaHCO_3$, brine, dried over anhydrous $Na_2SO_4$, filtered and concentrated. Purification by reverse phase HPLC (2" Dynamax® C18, 10-70% ACN in $H_2O$ with 0.1% HOAc over 30 min) afforded S-43 (28 mg) and R-43 (4.6 mg) as white floculent solids following lyophilization of the purified fractions.

EXAMPLE 31

4-[2-Cyclohexyl-2-(2-methylamino-propionylamino)-acetyl]-1-methanesulfonyl-octahydro-pyrrolo[3,2-b]pyrrole-3-carboxylic acid phenethyl-amide (S-43): $^1$H NMR (CDCl$_3$, 300 MHz), ~2:1 mixture of rotomers: δ10.91 (s, 0.6H), 10.39 (s, 0.4H), 7.99 (d, J=10.5 Hz, 0.4H), 7.72 (d, J=9.0 Hz, 0.6H), 7.63 (d, J=8.7 Hz, 2H), 7.35-7.28 (m, 2H), 7.13-7.04 (m, 1H), 4.71-4.31 (m, 2.6H), 4.03-3.95 (m, 1.6H), 3.82-3.57 (m, 7.4H), 3.52-3.36 (m, 1H), 3.28-3.15 (m, 2.4H), 3.07-3.01 (m, 1.6H), 2.44 (d, J=6.0 Hz, 3.4H), 2.23-2.01 (m, 5H), 1.78-1.53 (m, 7H), 1.40-1.34 (m, 3.6H), 1.29-1.04 (m, 5H), 0.88-0.84 (m, 0.4H) ppm; $^{13}$C NMR (CDCl$_3$, 75 MHz), mixture of rotomers: δ175.8, 173.0, 172.6, 172.5, 170.6, 170.4, 139.2, 138.7, 129.1, 129.0, 124.4, 123.8, 120.0, 119.6, 67.9, 64.8, 62.4, 60.4, 56.0, 55.7, 55.1, 54.0, 51.0, 47.5, 46.9, 46.2, 41.6, 40.7, 35.2, 34.9, 30.9, 30.4, 30.0, 29.8, 29.3, 28.8, 26.3, 26.2, 26.0, 25.9, 19.8, 19.7 ppm. Mass spectrum, m/z [456.5] (M+H)+.

EXAMPLE 32

4-[2-Cyclohexyl-2-(2-methylamino-propionylamino)-acetyl]-1-methanesulfonyl-octahydro-pyrrolo[3,2-b]pyrrole-3-carboxylic acid phenethyl-amide (R-43): $^1$H NMR (CDCl$_3$, 300 MHz), ~2:1 mixture of rotomers: δ10.94 (s, 0.6H), 10.40 (s, 0.4H), 7.97 (d, J=9.9 Hz, 0.4H), 7.69-7.62 (m, 2.4H), 7.35-7.29 (m, 1.6H), 7.13-7.04 (m, 1H), 4.70-4.32 (m, 2.4H), 4.04-3.96 (m, 1.4H), 3.84-3.75 (m, 1H), 3.66-3.56 (m, 0.6H), 3.48-3.39 (m, 0.6H), 3.32-3.16 (m, 1.6H), 3.01-2.99 (m, 1H), 2.49 (s, 1.6H), 2.45 (s, 0.6H), 2.19-2.03 (m, 11H), 1.78-1.68 (m, 6.4H), 1.42-1.36 (m, 2.6H), 1.26-1.07 (m, 6H) ppm. Mass spectrum, m/z [456.6] (M+H)+.

TABLE 4

| Example | Structure | XIAP, nM | cIAP1, nM | SKOV3, nM | Mass spectrum, m/z |
|---|---|---|---|---|---|
| 31 | 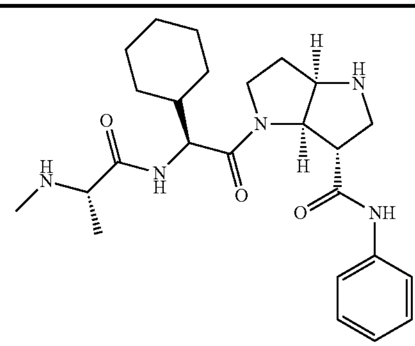 | B | A | B | 456.5 (M+H) |
| 32 | 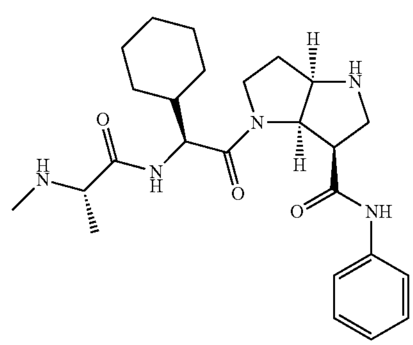 [SMILES: CN[C@@H](C)C(=O)N[C@H](C(=O)N1CC[C@H]2NC[C@@H](C(=O)Nc3ccccc3)[C@H]21)C1CCCCC1] | B | A | C | 456.6 (M+H) |

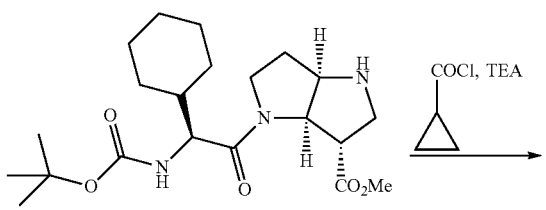

Scheme XLI

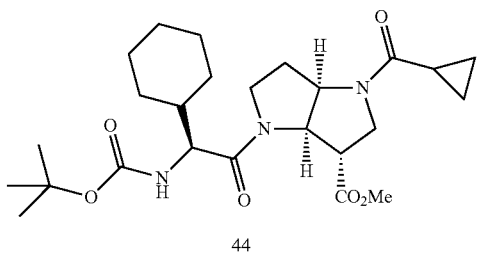

44

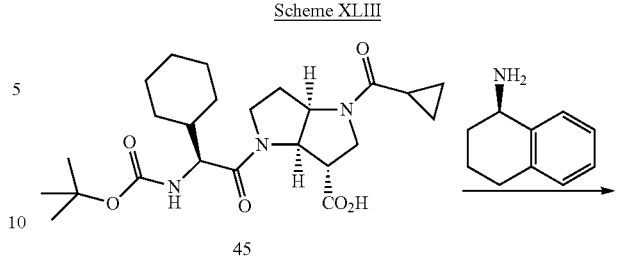

Scheme XLIII

45

4-(2-tert-Butoxycarbonylamino-2-cyclohexyl-acetyl)-1-cyclopropanecarbonyl-octahydro-pyrrolo[3,2-b]pyrrole-3-carboxylic acid methyl ester (44): A solution of 27 (500 mg, 1.22 mmol) in DCM (10 mL) was cooled to 0° C. and treated with TEA (0.26 mL, 1.83 mmol) and cyclopropanecarbonyl chloride (0.13 mL, 1.46 mmol). After 2 h, the reaction mixture was diluted with DCM, washed successively with 1M HCl, and brine, dried over anhydrous $Na_2SO_4$, filtered and concentrated to afford 44 (580 mg) as a pale yellow-colored foam that was used without further purification. Mass spectrum, m/z [478.6] (M+H)+.

Scheme XLII

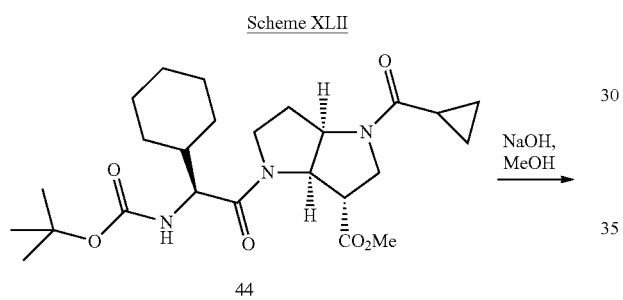

44

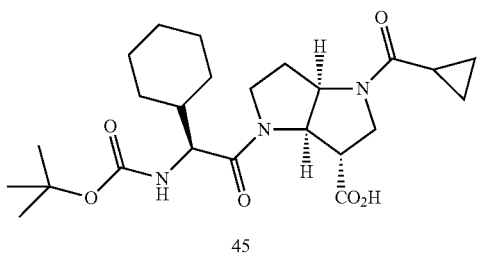

45

4-(2-tert-Butoxycarbonylamino-2-cyclohexyl-acetyl)-1-cyclopropanecarbonyl-octahydro-pyrrolo[3,2-b]pyrrole-3-carboxylic acid (45): A solution of 44 (580 mg, 1.21 mmol) in MeOH (20 mL) was treated with 1M NaOH (4 mL) at ambient temperature. After 4 h, the solution was concentrated and diluted with EtOAc and 1M HCl. The layers were separated and the aqueous phase was extracted with EtOAc. The combined organic extracts were washed successively with 1M HCl, and brine, dried over anhydrous $Na_2SO_4$, filtered and concentrated to afford 45 (613 mg) as a yellow-colored foam which was used without further purification. Mass spectrum, m/z [464.6] (M+H)+.

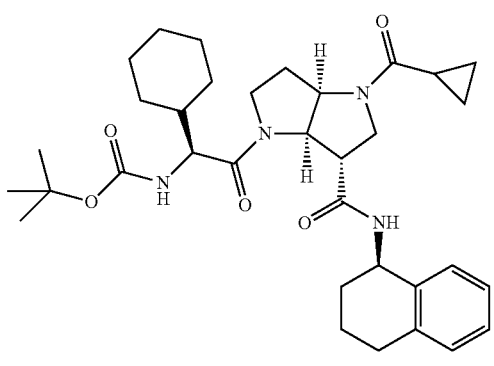

46

{1-Cyclohexyl-2-[4-cyclopropanecarbonyl-6-(1,2,3,4-tetrahydro-naphthalen-1-ylcarbamoyl)-hexahydro-pyrrolo[3,2-b]pyrrol-1-yl]-2-oxo-ethyl}-carbamic acid tert-butyl ester (46): A solution of 45 (563 mg, 1.21 mmol) in DCM (15 mL) was cooled to 0° C. and treated with R-(−)-tetrahydronaphthylamine (0.17 mL, 1.21 mmol), EDC (279 mg, 1.46 mmol), HOBt (197 mg, 1.46 mmol) and DIPEA (0.66 mL, 3.76 mmol), respectively. After 18 h, the solution was diluted with DCM, washed successively with 1M HCl, saturated aqueous $NaHCO_3$, and brine, dried over anhydrous $Na_2SO_4$, filtered and concentrated. Purification by reverse phase HPLC (2" Dynamax® C18, 20-100% ACN in $H_2O$ with 0.1% HOAc over 30 min) afforded 46 (430 mg) as a white foam. $^1$H NMR ($CDCl_3$, 300 MHz), ~1:1 mixture of rotamers: δ8.36 (d, J=8.4 Hz, 0.25H), 8.09 (d, J=8.7 Hz, 0.25H), 7.35 (d, J=9 Hz, 0.5H), 7.28-7.20 (m, 0.5H), 7.18-7.05 (m, 3.5H), 6.52 (d, J=8.4 Hz, 0.25H) 5.25-5.02 (m, 2H), 4.91-4.84 (m, 0.5H), 4.72-4.44 (m, 2H), 4.33-4.19 (m, 1.5H), 4.05-3.93 (m, 1H), 3.67-3.58 (m, 0.5H), 3.49-3.31 (m 1H), 3.15-2.98 (m, 1H), 2.86-2.71 (m, 2H), 2.44-2.35 (m, 1H), 1.98-1.54 (m, 10H), 1.44 (s, 5.5H), 1.17-0.75 (m, 15H) ppm. Mass spectrum, m/z [593.8] (M+H)+.

Scheme XLIV

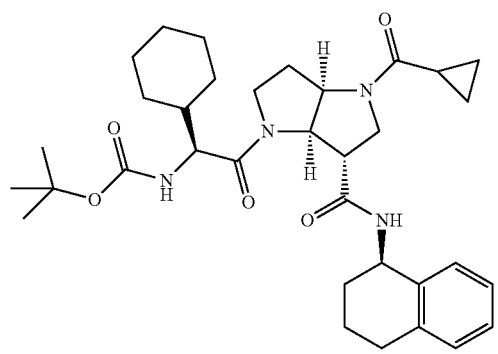

46

Scheme XLV

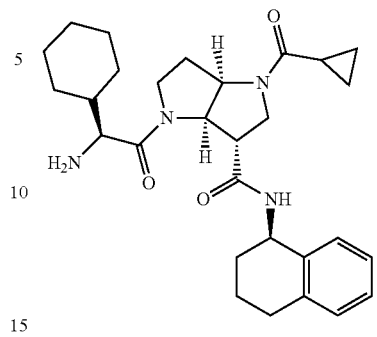

47

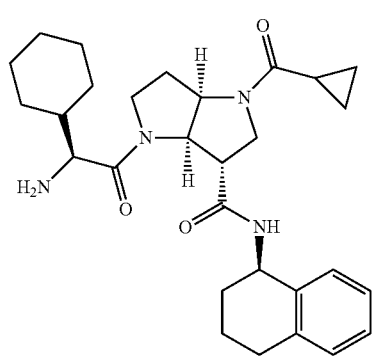

47

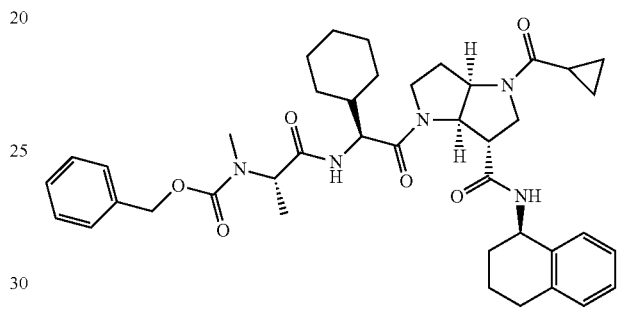

48

4-(2-Amino-2-cyclohexyl-acetyl)-1-cyclopropanecarbonyl-octahydro-pyrrolo[3,2-b]pyrrole-3-carboxylic acid (1,2,3,4-tetrahydro-naphthalen-1-yl)-amide (47): A solution of 46 (430 mg, 0.72 mmol) in DCM (10 mL) was cooled to 0° C. and treated with TFA (4 mL).). After 2 h, the solution was concentrated, diluted with DCM and washed successively with saturated aqueous NaHCO$_3$, and brine, dried over anhydrous Na$_2$SO$_4$, filtered and concentrated to afford 47 (332 mg) as a white foam that was used without further purification. Mass spectrum, m/z [493.7] (M+H)+.

(1-{1-Cyclohexyl-2-[4-cyclopropanecarbonyl-6-(1,2,3,4-tetrahydronaphthalen-1-ylcarbamoyl)-hexahydro-pyrrolo[3,2-b]pyrrol-1-yl]-2-oxo-ethylcarbamoyl}-ethyl) methyl-carbamic benzyl ester (48): A solution of 47 (330 mg, 0.67 mmol) in DCM (10 mL) was cooled to 0° C. and treated with Cbz-N(Me)Ala-OH (159 mg, 0.67 mmol), EDC (154 mg, 0.80 mmol), HOBt (109 mg, 0.80 mmol) and DIPEA (0.36 mL, 2.08 mmol), respectively. After 18 h, the solution was diluted with DCM, washed successively with 1M HCl, saturated aqueous NaHCO$_3$, and brine, dried over anhydrous Na$_2$SO$_4$, filtered and concentrated to afford 48 (454 mg) as a white foam that was used without further purification. Mass spectrum, m/z [712.9] (M+H)+.

Scheme XLVI

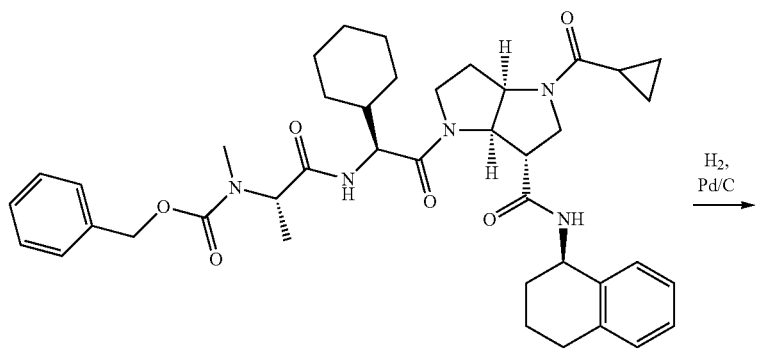

48

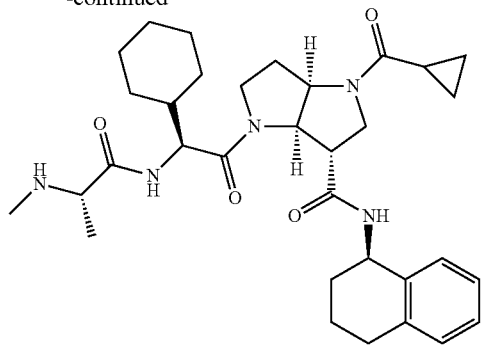

49

4-[2-Cyclohexyl-2-(2-methylamino-propionylamino)-acetyl]-1-cyclopropanecarbonyl-octahydro-pyrrolo[3,2-b]pyrrole-3-carboxylic acid (1,2,3,4-tetrahydro-naphthalen-1-yl)-amide (49): A mixture of 48 (450 mg, 0.63 mmol) and 10% palladium-on-carbon (wet, 90 mg) in MeOH (15 mL) was shaken at 50 psi under a $H_2$ atmosphere. After 1.5 h, the mixture was filtered through a 0.45 μM filtering disc, washed with MeOH and concentrated. Purification by reverse-phase HPLC (2" Dynamax® C18, 10-70% ACN in $H_2O$ with 0.1% HOAc over 30 min) afforded 49 (123 mg) as a white flocculent solid following lyophilization of the purified fractions.

EXAMPLE 33

4-[2-Cyclohexyl-2-(2-methylamino-propionylamino)-acetyl]-1-cyclopropanecarbonyl-octahydro-pyrrolo[3,2-b]pyrrole-3-carboxylic acid (1,2,3,4-tetrahydro-naphthalen-1-yl)-amide (49): $^1H$ NMR ($CDCl_3$, 300 MHz), mixture of rotomers: δ8.47 (d, J=8.1 Hz, 0.2H), 8.21 (d, J=8.4 Hz, 0.2H), 7.80 (d, J=9.9 Hz, 0.3H), 7.68 (d, J=8.7 Hz, 0.3H), 7.61 (d, J=9.0 Hz, 0.4H), 7.47 (d, J=8.7 Hz, 0.4H), 7.33-7.08 (m, 4H), 6.54 (d, J=8.7 Hz, 0.2H), 5.21-5.15 (m, 1H), 5.05 (t, J=5.4 Hz, 0.2H), 4.90 (t, J=5.1 Hz, 0.2H), 4.84 (t, J=4.8 Hz, 0.2H), 4.72-4.63 (m, 0.8H), 4.56-4.46 (m, 2.2H), 4.32-3.96 (m, 1.6H), 3.69-3.59 (m, 0.6H), 3.51-3.26 (m, 1.4H), 3.15-3.06 (m, 1.6H), 3.03-2.93 (m, 0.4H), 2.87-2.71 (m, 2.2H), 2.40-2.36 (m, 3H), 2.21-1.56 (m, 11H), 1.34-0.77 (m, 10H) ppm; $^{13}C$ NMR ($CDCl_3$, 75 MHz), mixture of rotomers: δ174.6, 172.5, 171.8, 171.3, 171.1, 170.2, 169.9, 137.4, 137.0, 136.9, 136.7, 129.1, 129.0, 128.9, 128.8, 127.3, 127.1, 127.0, 126.3, 126.1, 67.3, 67.0, 66.3, 65.7, 63.2, 62.8, 60.3, 60.1, 60.0, 55.0, 54.7, 51.5, 50.4, 49.5, 49.1, 48.2, 47.5, 47.4, 47.1, 47.0, 46.9, 46.2, 46.1, 44.8, 44.6, 41.4, 40.5, 35.0, 34.8, 33.1, 31.2, 30.6, 30.1, 29.8, 29.7, 29.3, 29.2, 28.6, 26.1, 26.0, 25.9, 25.8, 19.9, 19.7, 19.3, 19.2, 13.2, 13.0, 12.8, 8.1, 8.0, 7.6 ppm. Mass spectrum, m/z [578.8] (M+H)+.

EXAMPLES 34 through 39 were prepared using the chemistries described in Schemes XLI through XLVI by replacing Boc-Chg-OH with Boc-Tle-OH and/or cyclopropylcarbonyl chloride with acetic anhydride or methyl chloroformate and/or (1R)-1,2,3,4-tetrahydro-naphthalen-1-ylamine with naphthalen-1-ylamine, benzylamine, and 4-fluorobenzylamine.

EXAMPLE 34

1-Acetyl-4-[3,3-dimethyl-2-(2-methylamino-propionylamino)-butyryl]-octahydro-pyrrolo[3,2-b]pyrrole-3-carboxylic acid (1,2,3,4-tetrahydro-naphthalen-1-yl)-amide: $^1H$ NMR ($CDCl_3$, 300 MHz), mixture of rotomers: δ8.61 (d, J=8.4 Hz, 0.25H), 8.33 (d, J=9.0 Hz, 0.08H), 8.02 (d, J=10.2 Hz, 0.38H), 7.79 (d, J=9.3 Hz, 0.23H), 7.73 (d, J=9.6 Hz, 0.6H), 7.33-7.06 (m, 4H), 6.69 (d, J=7.8 Hz, 0.13 H), 5.23-5.18 (m, 1H), 4.91-4.79 (m, 0.4H), 4.70-4.53 (m, 2.6H), 4.35-4.24 (m, 3H), 4.09-3.86 (m, 1.4H), 3.53-3.30 (m, 1.5H), 3.22-2.97 (m, 2.4H), 2.88-2.71 (m, 2H), 2.48-2.33 (m, 3.5H), 2.25-2.09 (m, 3.5H), 2.03-1.81 (m, 6.5H), 1.30 (d, J=6.9 Hz, 2H), 1.23-1.17 (m, 1H), 1.01 (s, 3H), 0.96 (s, 6H) ppm; $^{13}C$ NMR ($CDCl_3$, 75 MHz), mixture of rotomers: δ174.9, 174.8, 174.5, 171.2, 170.7, 169.8, 169.7, 169.2, 169.1, 137.4, 137.1, 136.8, 136.7, 129.1, 129.0, 128.9, 128.6, 127.1, 127.0, 126.1, 126.0, 66.4, 66.3, 62.9, 59.9, 59.8, 59.7, 56.6, 56.5, 51.6, 50.2, 49.6, 47.8, 47.6, 47.1, 46.9, 44.9, 35.6, 35.4, 34.9, 34.6, 31.1, 30.5, 30.2, 30.0, 29.9, 29.2, 29.1, 29.0, 26.5, 26.4, 23.2, 22.9, 22.0, 20.9, 20.0, 19.7, 19.2, 19.1 ppm. Mass spectrum, m/z [526.7] (M+H)+.

EXAMPLE 35

1-Acetyl-4-[3,3-dimethyl-2-(2-methylamino-propionylamino)-butyryl]-octahydro-pyrrolo[3,2-b]pyrrole-3-carboxylic acid 4-fluoro-benzylamide: $^1H$ NMR ($CDCl_3$, 300 MHz), mixture of rotomers: δ8.32-8.08 (m, 0.3H), 8.55 (m, 0.2H), 8.14 (t, J=10.2 Hz, 0.5H), 7.89-7.71 (m, 1H), 7.35-7.26 (m, 2H), 7.05-6.96 (m, 2H), 6.32 (br s, 2.5 H), 4.87-4.76 (m, 0.5H), 4.62-4.54 (m, 2H), 4.49-4.36 (m, 1.5H), 4.28-4.20 (m, 1H), 4.10-3.86 (m, 1.5H), 3.54-3.07 (m, 4H), 2.44-2.41 (m, 3H), 2.16-2.05 (m, 7H), 2.03-1.81 (m, 6.5H), 1.37-1.31 (m, 3H), 1.02-0.88 (m, 8H) ppm; $^{13}C$ NMR ($CDCl_3$, 75 MHz), mixture of rotomers: δ175.5, 174.8, 173.7, 171.6, 171.4, 170.8, 170.3, 169.8, 169.3, 169.2, 169.1, 163.8, 163.7, 160.5, 134.4, 134.3, 134.2, 134.1, 129.8, 129.6, 129.5, 129.4, 129.3, 115.6, 115.5, 115.4, 115.3, 115.2, 115.1, 67.3, 67.1, 66.3, 66.2, 63.4, 62.7, 59.8, 59.7, 59.6, 59.3, 56.8, 56.7, 51.7, 50.6, 49.8, 49.6, 48.5, 47.6, 47.1, 46.9, 45.0, 44.9, 43.0, 42.9, 42.7, 42.5, 35.8, 35.7, 35.5, 35.4, 34.6, 34.0, 32.5, 31.0, 30.5, 26.5, 26.2, 23.1, 22.9, 22.0, 21.9, 21.1, 19.1, 18.9, 18.6 ppm. Mass spectrum, m/z [504.7] (M+H)+.

EXAMPLE 36

1-Acetyl-4-[2-cyclohexyl-2-(2-methylamino-propionylamino)-acetyl]-octahydro-pyrrolo[3,2-b]pyrrole-3-carboxylic acid (1,2,3,4-tetrahydro-naphthalen-1-yl)-amide: $^1H$ NMR ($CDCl_3$, 300 MHz), mixture of rotomers: δ8.52 (d, J=8.4 Hz, 0.25H), 8.22 (d, J=8.7 Hz, 0.12H), 7.87 (d, J=9.6 Hz, 0.25H), 7.64 (d, J=9.0 Hz, 0.5H), 7.45 (d, J=8.7 Hz, 0.5H), 7.32-7.25 (m, 1H) 7.22-7.09 (m, 2.5H), 6.79 (d, J=8.7 Hz, 0.12H), 5.22-5.16 (m, 1H), 4.89 (app t, J=5.7 Hz, 0.5 H), 4.82 (app t, J=5.1 Hz, 0.5H), 4.69-4.65 (m, 1H), 4.55-4.47 (m, 2H), 4.39-4.32 (m, 0.5H), 4.26 (d, J=10.8 Hz, 0.5H), 4.19-4.13 (m, 0.12H), 4.09-3.98 (m, 0.5H), 3.87 (d, J=11.4 Hz, 0.12H), 3.55-3.42 (m, 3H), 3.32-3.27 (m, 0.5H), 3.17-3.08 (m, 1H), 3.04-2.96 (m, 0.12H), 2.83-2.73 (m, 2H), 2.41-2.32 (m, 3H), 2.18 (s, 2H), 2.14 (s, 1H), 1.93-1.80 (m, 7H), 1.32 (d, J=6.6 Hz, 2H), 1.16 (d, J=6.9 Hz, 1H), 1.24-0.99 (m, 3H) ppm; $^{13}C$ NMR ($CDCl_3$, 75 MHz), mixture of rotomers: δ175.0, 174.8, 171.4, 171.3, 170.5, 170.4, 170.1, 175.3, 169.9, 169.4, 137.6, 137.3, 136.9, 136.8, 129.4, 129.3, 129.2, 129.1, 129.0, 127.5, 127.4, 127.3, 126.5, 126.3, 66.8, 66.1, 63.0, 60.1, 60.0, 55.3, 55.2, 55.0, 51.8, 50.4, 49.7, 48.0, 47.9, 47.6, 47.5, 47.3, 47.1, 46.6, 45.1, 41.6, 40.7, 35.1, 34.8, 31.3, 30.8, 30.4, 30.2, 30.1, 29.9, 29.6, 29.5, 29.4, 29.3, 29.2, 28.9, 28.8, 26.3, 26.2, 26.1, 26.0, 23.4, 23.2, 22.2, 21.6, 20.1, 19.9, 19.5 ppm. Mass spectrum, m/z [552.8] (M+H)+.

EXAMPLE 37

1-Acetyl-4-[3,3-dimethyl-2-(2-methylamino-propionylamino)-butyryl]-octahydro-pyrrolo[3,2-b]pyrrole-3-carboxylic acid naphthalen-1-ylamide: $^1$H NMR (CDCl$_3$, 300 MHz), mixture of rotomers: δ10.35 (br s, 0.3H), 10.13 (br s, 0.8H), 9.65 (br s, 0.2H), 8.35-8.26 (m, 1.7H), 8.16-8.14 (m, 1H), 8.08-7.96 (m, 1H), 7.89 (d, J=6.9 Hz, 1H), 7.74-7.68 (m, 1H), 7.53-7.48 (m, 3H), 4.99-4.84 (m, 1.5H), 4.80-4.76 (m, 1H), 4.69-4.62 (m, 1H), 4.52-4.49 (m, 1H), 4.19-4.02 (m, 1.5H), 3.77-56 (m, 2H), 3.45 (d, J=8.1 Hz, 1H), 3.24-3.19 (m, 1.5H), 2.49-2.34 (m, 9H), 2.23-2.16 (m, 3H), 1.41-1.39 (m, 3H), 1.13-1.09 (m, 9H) ppm; $^{13}$C NMR (CDCl$_3$, 75 MHz), mixture of rotomers: δ174.4, 171.3, 171.0, 169.7, 169.3, 168.9, 134.1, 132.9, 128.6, 128.5, 126.4, 125.9, 125.8, 125.7, 125.6, 125.0, 121.7, 121.1, 120.7, 118.9, 66.9, 66.3, 62.9, 60.3, 60.2, 59.7, 56.8, 56.5, 51.9, 51.3, 50.3, 47.1, 46.8, 45.2, 35.6, 35.5, 35.1, 34.9, 31.2, 30.5, 26.6, 26.4, 23.3, 23.0, 19.5 ppm. Mass spectrum, m/z [522.6] (M+H)+.

EXAMPLE 38

1-Acetyl-4-[3,3-dimethyl-2-(2-methylamino-propionylamino)-butyryl]-octahydro-pyrrolo[3,2-b]pyrrole-3-carboxylic acid benzylamide: $^1$H NMR (CDCl$_3$, 300 MHz), mixture of rotomers: δ8.83 (m, 0.25H), 8.456 (m, 0.12H), 8.09 (d, J=10.2 Hz, 0.25H), 7.78 (d, J=9.3 Hz, 0.5H), 7.67 (app t, J=5.7 Hz, 0.5H), 7.34-7.24 (m, 3H), 5.75 (br s, 2H), 4.84 (app t, J=5.7 Hz, 0.25H), 4.76-4.53 (m, 2H), 4.47 (d, J=6.0 Hz, 1H), 4.30-4.21 (m, 1H), 4.10-3.86 (m, 1H), 3.52-3.41 (m, 1H), 3.25-3.09 (m, 1.5H), 2.39 (s, 3H), 2.15 (s, 2H), 2.12 (s, 1H), 1.31 (d, J=6.9 Hz, 3H), 1.07 (s, 6H), 0.87 (s, 3H) ppm. Mass spectrum, m/z [486.2] (M+H)+.

EXAMPLE 39

4-[2-Cyclohexyl-2-(2-methylamino-propionylamino)-acetyl]-3-(1,2,3,4-tetrahydro-naphthalen-1-ylcarbamoyl)-hexahydro-pyrrolo[3,2-b]pyrrole-1-carboxylic acid methyl ester: $^1$H NMR (CDCl$_3$, 300 MHz), mixture of rotomers: δ8.41 (d, J=7.8 Hz, 0.4H), 8.29 (d, J=8.4 Hz, 0.4H), 7.81 (d, J=9.9 Hz, 0.4H), 7.62 (d, J=8.4 Hz, 0.6H), 7.31-7.23 (m, 1H), 7.20-7.05 (m, 3H), 5.20-5.17 (m, 1H), 4.76 (br s, 0.6H), 4.55-4.46 (m, 2.6H), 4.20 (dd, J=2.1, 11.4 Hz, 0.6H), 4.10-3.91 (m, 1.4H), 3.75 (s, 3H), 3.48-3.32 (m, 1.6H), 3.26-3.24 (m, 0.6H), 3.18-2.98 (m, 2H), 2.86-2.72 (m, 2H), 2.48-2.18 (m, 5.4H), 2.08-1.56 (m, 11.4H), 1.33 (d, J=6.9 Hz, 2H), 1.27-0.86 (m, 6.6H) ppm; $^{13}$C NMR (CDCl$_3$, 75 MHz), mixture of rotomers: δ174.7, 174.3, 171.6, 170.9, 170.3, 170.2, 155.2, 137.0, 136.7, 129.1, 129.0, 128.9, 127.2, 127.0, 126.2, 60.0, 59.9, 54.9, 52.6, 47.3, 46.9, 46.0, 44.6, 41.5, 40.6, 35.0, 34.6, 30.1, 30.0, 29.7, 29.3, 29.2, 29.1, 28.7, 26.1, 26.0, 25.9, 25.8, 19.9, 19.3, 19.2 ppm. Mass spectrum, m/z [568.8] (M+H)+.

TABLE 5

| Example | Structure | XIAP, nM | cIAP1, nM | SKOV3, nM | Mass spectrum, m/z |
|---------|-----------|----------|-----------|-----------|--------------------|
| 33 | 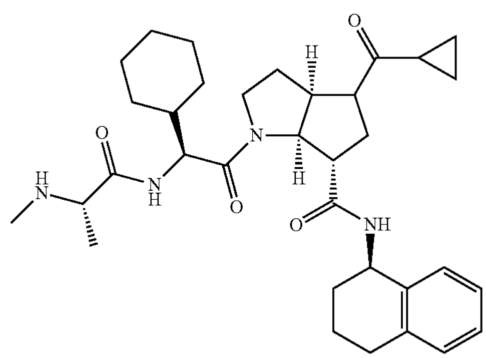 [SMILES: CN[C@@H](C)C(=O)N[C@H](C(=O)N1CC[C@H]2C(C(=O)C3CC3)C[C@H](C(=O)N[C@@H]3CCCc4ccccc43)[C@H]21)C1CCCCC1] | A | A | A | 578.8 (M + H) |
| 34 | 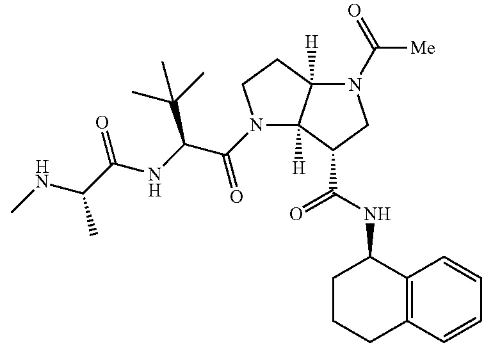 [SMILES: CN[C@@H](C)C(=O)N[C@H](C(=O)N1CC[C@@H]2[C@H]1[C@@H](C(=O)N[C@@H]1CCCc3ccccc31)CN2C(C)=O)C(C)(C)C] | A | A | A | 526.7 (M + H) |

TABLE 5-continued
| Example | Structure | XIAP, nM | cIAP1, nM | SKOV3, nM | Mass spectrum, m/z |
|---|---|---|---|---|---|
| 35 | 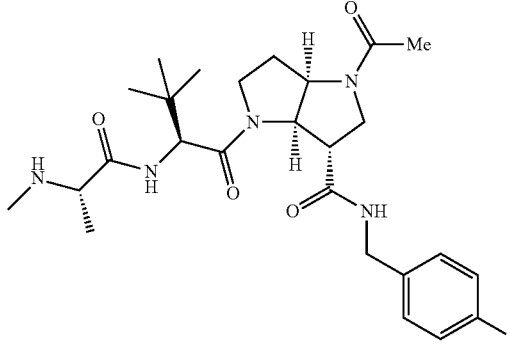 | A | A | A | 504.7 (M + H) |
| 36 | 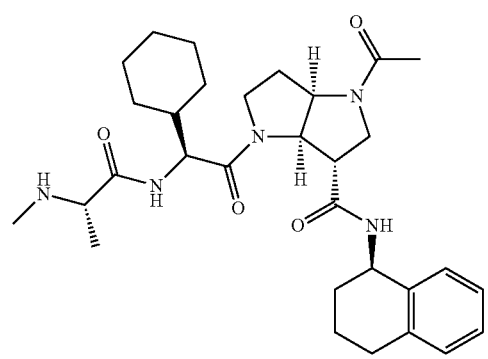 [SMILES: CN[C@@H](C)C(=O)N[C@H](C(=O)N1CC[C@@H]2[C@H]1[C@@H](C(=O)N[C@@H]1CCCc3ccccc31)CN2C(C)=O)C1CCCCC1] | A | A | A | 552.8 (M + H) |
| 37 | 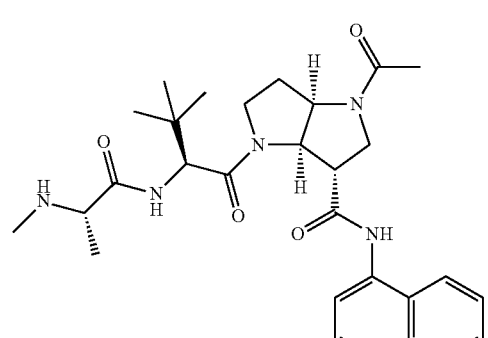 | A | A | A | 522.6 (M + H) |
| 38 | 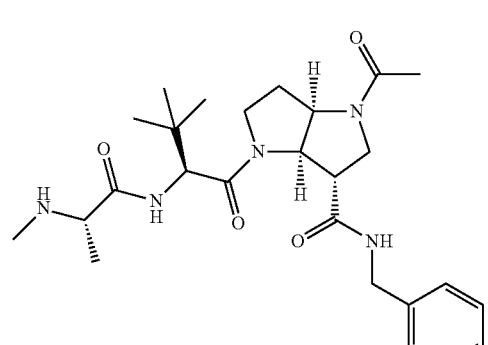 | A | A | A | 486.2 (M + H) |

TABLE 5-continued

| Example | Structure | XIAP, nM | cIAP1, nM | SKOV3, nM | Mass spectrum, m/z |
|---|---|---|---|---|---|
| 39 | 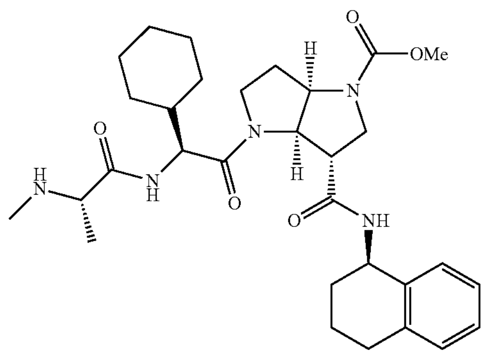 [SMILES: CN[C@@H](C)C(=O)N[C@H](C(=O)N1CC[C@@H]2[C@H]1[C@@H](C(=O)N[C@@H]1CCCc3ccccc31)CN2C(=O)OC)C1CCCCC1] | A | A | A | 568.8 (M + H) |

Intermediate 50 was prepared in 2 steps starting from 15 following the general procedures described in Schemes XIV and XXV and replacing Boc-Chg-OH with Boc-Tle-OH.

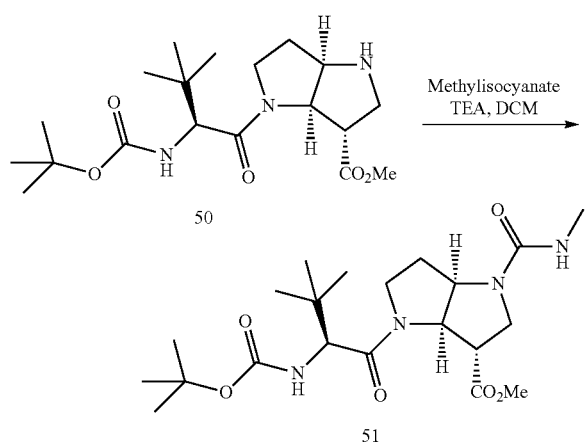

Scheme XLVII 4-(2-tert-butoxycarbonylamino-3,3-dimethyl-butyryl)-1-methylcarbamoyl-octahydro-pyrrolo[3,2-b]pyrrole-3-carboxylic acid methyl ester (51) A solution of amine 50 (950 mg, 2.48 mmol) in DCM (40 mL) was treated with TEA (0.69 mL, 4.95 mmol) followed by methyl isocyanate (0.29 mL, 4.95 mmol). After 1.5 h, the reaction mixture was quenched with MeOH (5 mL) followed by NH$_4$OH (15M, 10 drops). After 10 min, the solution was diluted with DCM, washed successively with 1M HCl, saturated aqueous NaHCO$_3$, and brine, dried over anhydrous Na$_2$SO$_4$, filtered and concentrated to afford the 51 as a pale yellow-colored foam (1.1 g) that was used without further purification. Mass spectrum, m/z [441.6] (M+H)+.

EXAMPLES 40 through 42 were prepared using Compound 51 following the general procedures described in Schemes XLII through XLVI.

EXAMPLE 40

4-[3,3-Dimethyl-2-(2-methylamino-propionylamino)-butyryl]-hexahydro-pyrrolo[3,2-b]pyrrole-1,3-dicarboxylic acid 1-methylamide 3-[(1,2,3,4-tetrahydro-naphthalen-1-yl)-amide]: $^1$H NMR (CDCl$_3$, 300 MHz), ~2:1 mixture of rotomers: δ8.51 (d, J=8.4 Hz, 0.3H), 8.04 (d, J=10.2 Hz, 0.3H), 7.73 (d, J=9.6 Hz, 0.7H), 7.58 (d, J=8.4 Hz, 0.7H), 7.31-7.23 (m, 1H), 7.19-7.05 (m, 3 H), 5.21-5.17 (m, 1H), 4.77 (t, J=4.5 Hz, 0.3H), 4.60 (d, J=10.2 Hz, 0.3H), 4.55-4.47 (m, 3H), 4.35 (m, 0.3H), 4.07-3.92 (m, 2H), 3.80 (d, J=9.9 Hz, 0.3H), 3.53-3.36 (m, 2H), 3.22-3.01 (m, 2.3H), 2.85-2.71 (m, 5.7H), 2.46-2.36 (m, 3.7H), 2.12-1.76 (m, 5.7H), 1.32 (d, J=6.6 Hz, 2H), 1.21 (d, J=7.2 Hz, 1H), 1.01 (s, 2H), 0.94 (s, 7H) ppm; $^{13}$C NMR (CDCl$_3$, 75 MHz), mixture of rotomers: δ174.6, 174.3, 171.5, 170.6, 170.1, 169.2, 157.3, 156.6, 137.4, 137.0, 136.8, 129.0, 128.9, 128.8, 128.6, 127.1, 127.0, 126.1, 66.9, 66.5, 63.2, 60.7, 59.9, 59.8, 56.6, 51.4, 49.5, 48.8, 47.6, 47.0, 46.9, 46.8, 44.8, 35.7, 35.4, 34.5, 31.6, 31.1, 30.1, 30.0, 29.2, 29.1, 27.5, 27.4, 26.5, 26.4, 20.0, 19.8, 19.2, 19.1 ppm. Mass spectrum, m/z [541.8] (M+H)+.

EXAMPLE 41

4-[3,3-Dimethyl-2-(2-methylamino-propionylamino)-butyryl]-hexahydro-pyrrolo[3,2-b]pyrrole-1,3-dicarboxylic acid 3-(4-fluoro-benzylamide) 1-methylamide: $^1$H NMR (CDCl$_3$, 300 MHz), ~2:1 mixture of rotomers: δ8.79 (t, J=6.0 Hz, 0.3H), 8.11 (d, J=10.2 Hz, 0.3H), 7.97 (t, J=5.7 Hz, 0.7H), 7.81 (d, J=9.6 Hz, 0.7H), 7.33-7.24 (m, 2H), 7.02-6.95 (m, 2H), 4.72 (t, J=5.4 Hz, 0.3H), 4.59-4.36 (m, 6H), 4.22 (dd, J=4.8, 14.7 Hz, 0.3H), 4.09-3.92 (m, 2H), 3.90 (m, 2H), 3.76 (d, J=10.2 Hz, 0.3H), 3.57-3.45 (m, 3H), 3.40-3.32 (m, 1H), 3.20-3.07 (m, 2.7 H), 2.82 (d, J=4.2 Hz, 3H), 2.47-2.35 (m, 4.3H), 2.16-2.04 (m, 2H), 1.82-1.73 (m, 0.3H), 1.34-1.27 (m, 3H), 0.99 (s, 6H), 0.88 (s, 3H) ppm; $^{13}$C NMR (CDCl$_3$, 75 MHz), mixture of rotomers: δ175.1, 174.4, 171.7, 170.8, 170.6, 169.0, 163.7, 160.4, 157.3, 156.6, 134.5, 134.3, 134.2, 129.7, 129.6, 129.4, 129.3, 115.5, 115.4, 115.3, 115.2, 66.9, 66.3, 62.9, 60.7, 60.0, 59.9, 56.6, 51.5, 49.6, 48.4, 46.9, 46.6, 42.9, 42.6, 35.8, 35.5, 34.9, 34.6, 31.6, 31.1, 27.4, 27.3, 26.5, 26.2, 21.0, 19.4, 19.2 ppm. Mass spectrum, m/z [519.8] (M+H)+.

EXAMPLE 42

4-[3,3-Dimethyl-2-(2-methylamino-propionylamino)-butyryl]-hexahydro-pyrrolo[3,2-b]pyrrole-1,3-dicarboxylic acid 1-methylamide 3-naphthalen-1-ylamide: $^1$H NMR (CDCl$_3$, 300 MHz), ~2:1 mixture of rotomers: δ10.31 (s, 0.7H), 10.22 (s, 0.3H), 8.34-8.31 (m, 1H), 8.27-8.22 (m, 0.3H), 8.11 (d, J=7.5 Hz, 0.7H), 8.01 (t, J=9.0 Hz, 1H), 7.87-7.84 (m, 1H), 7.70-7.65 (m, 1H), 7.51-7.40 (m, 3H), 4.88-4.78 (m, 1H), 4.72-4.53 (m, 2.7H), 4.36-4.34 (m, 0.3H), 4.28-4.20 (m, 0.7H), 4.15-4.09 (m, 0.7H), 4.03-3.93 (m, 0.3H), 3.73 (d, J=6.6 Hz, 0.3H), 3.66-3.57 (m, 0.7H), 3.52-3.42 (m, 1.7H), 3.24-3.15 (m, 1H), 2.84 (d, J=4.8 Hz, 2.7H), 2.57-2.51 (m, 0.7H), 2.46-2.39 (m, 3H), 2.32-2.12 (m, 3.3 H), 2.03 (s, 0.3H), 1.39-1.35 (m, 3H), 1.09-1.06 (m, 9H) ppm; $^{13}$C NMR (CDCl$_3$, 75 MHz), mixture of rotomers: δ174.4, 171.4, 171.2, 169.2, 169.1, 157.4, 156.5, 134.1, 133.1, 132.6, 128.6, 128.5, 127.2, 126.4, 125.9, 125.8, 125.7, 125.6, 124.9, 121.8, 121.3, 120.8, 119.0, 67.3, 66.0, 63.1, 60.9, 60.3, 60.1, 56.7, 56.6, 51.7, 51.1, 49.0, 46.7, 45.9, 45.0, 35.7, 35.6, 35.1, 34.9, 31.7, 31.0, 27.5, 27.4, 26.6, 26.4, 19.5, 19.3 ppm. Mass spectrum, m/z [537.7] (M+H)+.
Scheme XLVIII
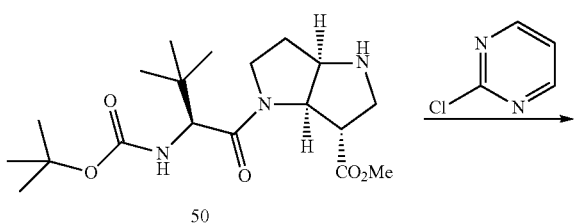
TABLE 6
| Example | Structure | XIAP, nM | cIAP1, nM | SKOV3, nM | Mass spectrum, m/z |
|---------|-----------|----------|-----------|-----------|--------------------|
| 40 | 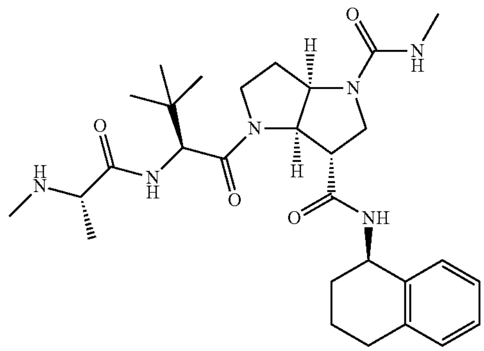 [SMILES: CNC(=O)N1C[C@H](C(=O)N[C@@H]2CCCc3ccccc32)[C@@H]2[C@H]1CCN2C(=O)[C@@H](NC(=O)[C@H](C)NC)C(C)(C)C] | A | A | A | 541.8 (M + H) |
| 41 | 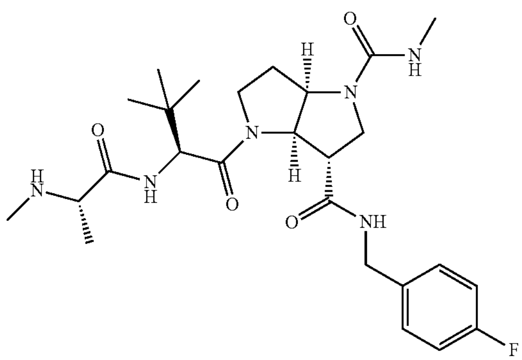 [SMILES: CNC(=O)N1C[C@H](C(=O)NCc2ccc(F)cc2)[C@@H]2[C@H]1CCN2C(=O)[C@@H](NC(=O)[C@H](C)NC)C(C)(C)C] | A | A | A | 519.8 (M + H) |
| 42 | 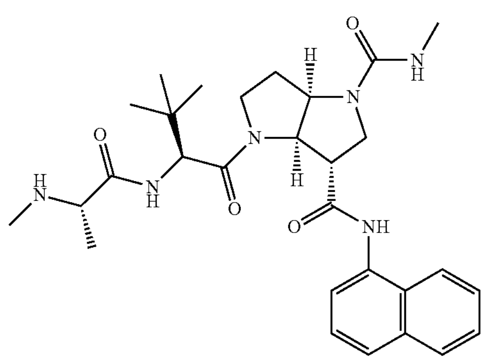 [SMILES: CNC(=O)N1C[C@H](C(=O)Nc2cccc3ccccc23)[C@@H]2[C@H]1CCN2C(=O)[C@@H](NC(=O)[C@H](C)NC)C(C)(C)C] | A | A | A | 537.7 (M + H) |

EXAMPLE 43

4-[2-Cyclohexyl-2-(2-methylamino-propionylamino)-acetyl]-1-pyrimidin-2-yl-octahydro-pyrrolo[3,2-b]pyrrole-3-carboxylic acid (1,2,3,4-tetrahydro-naphthalen-1-yl)-amide: $^1$H NMR (CDCl$_3$, 300 MHz), ~2:1 mixture of rotomers: δ8.38-8.66 (m, 2H), 7.81 (d, J=10.2 Hz, 0.33H), 7.62 (d, J=8.4 Hz, 0.66H), 7.27-7.25 (m, 1H), 7.16-6.99 (m, 3H), 6.60-6.58 (m, 1H), 5.19 (m, 1H), 5.05 (app t, J=4.8 Hz, 0.33H), 4.77 (app t, J=5.4 Hz, 0.66H), 4.64 (m, 1H), 4.57-4.47 (m, 1H), 4.32 (m, 0.66H), 4.11-4.00 (m, 1H), 3.62-3.47 (m, 1H), 3.43-3.37 (m, 2H), 3.22-3.09 (m, 2H), 3.02-3.00 (m, 0.66H), 2.78 (m, 2H), 2.54-2.49 (m, 1H), 2.38 (s, 2H), 2.35 (s, 1H), 2.18-2.14 (m, 1H), 1.95-1.68 (m, 9H), 1.30 (d, J=6.9 Hz, 1H), 1.20 (d, J=6.9 Hz, 2H), 1.04-0.96 (m, 3H) ppm; $^{13}$C NMR (CDCl$_3$, 75 MHz), mixture of rotomers: δ175.3, 175.1, 172.2, 171.1, 170.9, 170.5, 160.3, 159.8, 157.9, 137.6, 137.2, 137.1, 137.0, 129.3, 129.2, 129.1, 129.0, 127.4, 127.2, 126.4, 110.6, 110.5, 67.6, 66.8, 63.7, 61.1, 60.3, 60.1, 55.2, 55.0, 51.4, 50.1, 48.7, 48.5, 47.5, 47.1, 46.5, 45.0, 41.7, 40.9, 35.3, 35.1, 31.3, 31.0, 30.3, 30.2, 29.9, 29.5, 29.4, 29.3, 28.9, 26.4, 26.3, 26.2, 26.1, 26.0, 20.1, 19.7 ppm. Mass spectrum, m/z [588.9] (M+H)+.

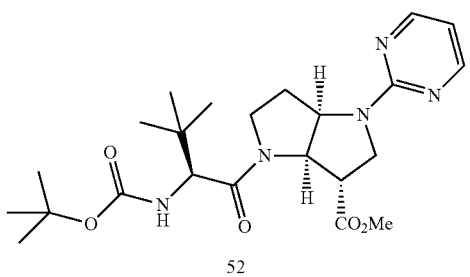

4-(2-tert-Butoxycarbonylamino-3,3-dimethyl-butyryl)-1-pyrimidin-2-yl-octahydro-pyrrolo[3,2-b]pyrrole-3-carboxylic acid methyl ester (52): A solution of 50 (302 mg, 0.74 mmol) in DMF (5 mL) was treated with DIPEA (0.2 mL, 1.2 mmol) followed by 2-chloropyrmidine (109 mg, 0.96 mmol) at room temperature. The reaction mixture was immersed into a pre-heated oil bath (70° C.). After 16 h, the solution was cooled to room temperature, diluted with Et$_2$O, washed successively with H$_2$O, and brine, dried over anhydrous Na$_2$SO$_4$, filtered and concentrated. The crude residue was purified by flash chromatography (SiO$_2$, 1:1 hexane/EtOAc to 1:2 hexane/EtOAc) to afford 52 as an off-white foam (212 mg). $^1$H NMR (CDCl$_3$, 300 MHz): δ8.34 (d, J=4.8 Hz, 2H), 6.58 (t, J=5.1 Hz, 1H), 5.24 (d, J=9.0 Hz, 1H), 4.89 (d, J=5.7 Hz, 1H), 4.75 (app t, J=5.1 Hz, 1H), 4.36-4.28 (m, 2H), 3.96 (app t, J=9.0 Hz, 1H), 3.71 (s, 3H), 3.58-3.51 (m, 1H), 3.46-3.34 (m, 2H), 2.47 (dd, J=6.3, 13.5 Hz, 1H), 2.18-2.13 (m, 1H), 1.81-1.63 (m, 6H), 1.43 (s, 9H), 1.21-1.01 (m, 6H), 0.94-0.85 (m, 1H) ppm. Mass spectrum, m/z [488.6] (M+H)+.

EXAMPLE 43 was prepared using Compound 41 following the general procedures described in Schemes XLII through XLVI.

EXAMPLES 44 through 52 can be synthesized using the procedures, reagents and similar starting materials as described above.

EXAMPLE 44

4-[3,3-Dimethyl-2-(2-methylamino-propionylamino)-butyryl]-1-methanesulfonyl-octahydro-pyrrolo[3,2-b]pyrrole-3-carboxylic acid isoquinolin-5-ylamide: $^1$H NMR (CDCl$_3$, 300 MHz), mixture of rotomers: δ10.57 (s, 0.3H), 10.26 (s, 0.7H), 9.27 (s, 1H), 8.51-8.47 (m, 1H), 8.41 (d, J=7.5 Hz, 1H), 8.30 (d, J=7.5 Hz, 0.3H), 8.19 (d, J=6.0 Hz, 0.7H), 8.12-8.04 (m, 1H), 7.86-7.79 (m, 1H), 7.68-7.60 (m, 1H), 4.82-4.72 (m, 1.3H), 4.68-4.57 (m, 1.3H), 4.28-4.01 (m, 2.6H), 3.86-3.68 (m, 2.3H), 3.47-3.44 (m, 1H), 3.21-3.08 (m, 1.7H), 3.03 (s, 2H), 2.69-2.57 (m, 1H), 2.48-2.39 (m, 5H), 2.22-2.18 (m, 1H), 2.08 (s, 0.3H), 1.92-1.85 (m, 0.3H), 1.42-1.32 (m, 3H), 1.26-1.01 (m, 9H) ppm; $^{13}$C NMR (CDCl$_3$, 75 MHz), mixture of rotomers: δ175.8, 175.2, 171.9, 171.7, 169.4, 168.9, 152.9, 142.9, 142.8, 132.3, 131.9, 129.7, 129.0, 128.7, 127.4, 127.2, 125.2, 124.2, 124.0, 122.2, 114.9, 114.2, 69.0, 68.1, 65.7,

TABLE 7

| Example | Structure | XIAP, nM | cIAP1, nM | SKOV3, nM | Mass spectrum, m/z |
| --- | --- | --- | --- | --- | --- |
| 43 | 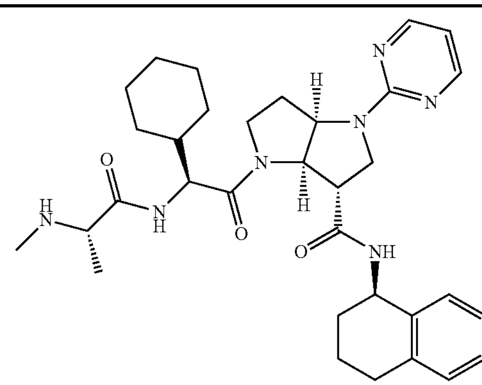 | B | A | A | 588.9 (M + H) |

62.9, 60.6, 60.1, 56.8, 51.5, 50.3, 48.7, 46.6, 44.8, 35.9, 35.8, 35.4, 35.3, 34.1, 32.9, 32.8, 26.6, 26.4, 19.9, 19.4 ppm. Mass spectrum, m/z [559.2] (M+H)+.

EXAMPLE 45

4-[3,3-Dimethyl-2-(2-methylamino-propionylamino)-butyryl]-1-methanesulfonyl-octahydro-pyrrolo[3,2-b]pyrrole-3-carboxylic acid isoquinolin-8-ylamide: $^1$H NMR (CDCl$_3$, 300 MHz), mixture of rotamers: δ10.86 (s, 0.3H), 10.49 (s, 0.7H), 9.76 (s, 0.7H), 9.64 (s, 0.3H), 8.58-8.56 (m, 1H), 8.37 (d, J=10.5 Hz, 0.3H), 8.20 (d, J=7.2 Hz, 0.7H), 8.04-8.01 (m, 1H), 7.75-7.63 (m, 3H), 4.84-4.76 (m, 1.3H), 4.67-4.56 (m, 1.3H), 4.25-4.17 (m, 2H), 4.07-4.01 (m, 0.3 H), 3.89 (d, J=11.7 Hz, 0.3H), 3.83-3.64 (m, 2H), 3.50-3.44 (m, 1H), 3.19-3.12 (m, 0.7H), 3.10 (s, 0.7H), 3.03 (s, 2H), 2.95-2.75 (m, 2.7H), 2.70-2.57 (m, 1H), 2.44 (d, J=3.0 Hz, 3H), 2.23-2.07 (m, 0.7H), 2.08 (s, 0.7H), 1.94-1.82 (m, 0.3H), 1.38 (d, J=7.2 Hz, 0.7H), 1.33 (d, J=7.2 Hz, 2.3H), 1.11 (s, 6H), 1.05 (s, 3H) ppm; $^{13}$C NMR (CDCl$_3$, 75 MHz), mixture of rotamers: δ175.9, 175.2, 172.1, 171.7, 169.6, 169.0, 147.3, 146.6, 143.1, 142.9, 136.7, 136.6, 133.9, 133.5, 130.7, 130.4, 124.5, 123.5, 122.6, 122.0, 121.7, 120.8, 120.7, 120.2, 68.8, 68.1, 65.7, 62.9, 60.2, 56.8, 51.6, 51.4, 50.2, 48.8, 46.6, 44.8, 35.9, 35.8, 35.4, 35.2, 35.0, 34.2, 33.0, 32, 26.7, 26.4, 19.5 ppm. Mass spectrum, m/z [559.2] (M+H)+.

EXAMPLE 46

4-[3,3-Dimethyl-2-(2-methylamino-propionylamino)-butyryl]-1-methanesulfonyl-octahydro-pyrrolo[3,2-b]pyrrole-3-carboxylic acid quinolin-8-ylamide: $^1$H NMR (CDCl$_3$, 300 MHz): δ10.39 (s, 1H), 8.86-8.84 (m, 1H), 8.66-8.61 (m, 1H), 8.17 (dd, J=1.8, 8.4 Hz, 1H), 7.88 (d, J=9.0 Hz, 1H), 7.57-7.41 (m, 3H), 4.80 (d, J=5.4 Hz, 1H), 4.66 (d, J=9.6 Hz, 1H), 4.35 (t, J=4.2 Hz, 1H), 4.18 (t, J=9.3 Hz, 1H), 4.03 (d, J=10.2 Hz, 1H), 3.73-3.59 (m, 3H), 3.20-3.12 (m, 1H), 3.06 (s, 3H), 2.63-2.57 (m, 2H), 2.46-2.43 (m, 3H), 2.12-2.05 (m, 2H), 1.33 (d, J=6.9 Hz, 3H), 1.09-1.05 (m, 9H) ppm; $^{13}$C NMR (CDCl$_3$, 75 MHz): δ174.7, 170.6, 169.9, 148.6, 138.7, 136.3, 134.2, 128.0, 127.1, 122.3, 121.8, 116.9, 67.9, 63.3, 60.2, 56.8, 50.4, 49.6, 46.6, 35.5, 35.0, 34.9, 33.2, 26.7, 19.4 ppm. Mass spectrum, m/z [559.2] (M+H)+.

EXAMPLE 47

4-[3,3-Dimethyl-2-(2-methylamino-propionylamino)-butyryl]-1-methanesulfonyl-octahydro-pyrrolo[3,2-b]pyrrole-3-carboxylic acid quinolin-5-ylamide: $^1$H NMR (CDCl$_3$, 300 MHz), mixture of rotamers: δ10.57 (s, 0.3H), 10.14 (s, 0.7H), 8.95 (d, J=4.2 Hz, 1H), 8.77-8.64 (m, 1.3H), 8.38 (d, J=10.5 Hz, 0.3H), 8.15 (d, J=7.5 Hz, 0.7H), 8.04-7.95 (m, 2H), 7.87 (d, J=9.6 Hz, 0.3H), 7.77-7.70 (m, 1H), 7.40-7.36 (m, 1H), 4.82-4.72 (m, 1.3H), 4.68-4.56 (m, 1.7H), 4.27-4.01 (m, 3H), 3.89-3.54 (m, 7H), 3.49-3.39 (m, 1H), 3.27-3.14 (m, 2.7H), 3.02 (s, 3H), 2.70-2.57 (m, 2H), 2.46 (s, 3H), 2.42 (s, 0.7H), 2.26-2.13 (m, 1H), 2.08 (s, 2H), 1.91-1.85 (m, 1H), 1.36 (d, J=6.9 Hz, 3H), 1.10-1.03 (m, 9H) ppm; $^{13}$C NMR (CDCl$_3$, 75 MHz), mixture of rotamers: δ175.8, 175.0, 171.9, 171.7, 169.4, 168.9, 150.3, 150.1, 148.4, 132.8, 130.8, 130.1, 129.5, 129.3, 127.2, 126.8, 126.3, 121.7, 121.1, 120.8, 120.7, 119.5, 69.2, 69.0, 68.1, 65.7, 62.9, 62.8, 60.3, 60.0, 56.9, 56.8, 51.5, 50.2, 49.7, 48.9, 46.6, 44.8, 35.9, 35.8, 35.3, 35.2, 35.1, 34.4, 34.2, 32.9, 32.8, 26.6, 26.4, 19.6, 19.4 ppm. Mass spectrum, m/z [559.1] (M+H)+.

EXAMPLE 48

4-[3,3-Dimethyl-2-(2-methylamino-propionylamino)-butyryl]-1-methanesulfonyl-octahydro-pyrrolo[3,2-b]pyrrole-3-carboxylic acid (2-methyl-quinolin-4-yl)-amide: $^1$H NMR (CDCl$_3$, 300 MHz), mixture of rotamers: δ10.66 (s, 0.3H), 10.57 (s, 0.7H), 8.41 (d, J=8.7 Hz, 1H), 8.32 (d, J=8.7 Hz, 0.3H), 8.19-8.18 (m, 1H), 8.08-8.02 (m, 1.7H), 7.71-7.66 (m, 1H), 7.46-7.36 (m, 1H), 4.77 (d, J=6.0 Hz, 0.7H), 4.72-4.68 (m, 0.3H), 4.62-4.58 (m, 1H), 4.28-4.17 (m, 2.3H), 4.08-4.01 (m, 0.3H), 3.89-3.66 (m, 2.3H), 3.48-3.39 (m, 1H), 3.22-3.05 (m, 4H), 2.76-2.58 (m, 4H), 2.47 (s, 2.7H), 2.34 (s, 0.3H), 2.26-2.09 (m, 1H), 1.90 (br s, 2H), 1.44 (d, J=6.6 Hz, 0.7H), 1.36 (d, J=6.9 Hz, 2.3H), 1.12 (s, 6.7H), 1.01 (s, 2.3 H) ppm; $^{13}$C NMR (CDCl$_3$, 75 MHz), mixture of rotamers: δ175.8, 175.2, 172.5, 171.7, 169.6, 169.0, 160.0, 159.8, 148.7, 148.6, 141.0, 140.9, 129.5, 129.4, 129.3, 125.4, 125.2, 121.0, 120.3, 119.2, 118.6, 112.4, 110.9, 68.8, 68.0, 65.7, 62.8, 60.6, 60.1, 56.8, 51.5, 50.6, 48.4, 46.5, 44.8, 36.1, 35.5, 35.4, 35.3, 34.2, 32.9, 32.8, 26.6, 26.4, 25.8, 19.9, 19.4 ppm. Mass spectrum, m/z [573.2] (M+H)+.

EXAMPLE 49

4-[3,3-Dimethyl-2-(2-methylamino-propionylamino)-butyryl]-1-methanesulfonyl-octahydro-pyrrolo[3,2-b]pyrrole-3-carboxylic acid isoquinolin-1-ylamide: $^1$H NMR (CDCl$_3$, 300 MHz): δ8.42-8.34 (m, 1H), 8.27-8.23 (m, 1H), 7.92 (d, J=9.0 Hz, 1H), 7.86-7.81 (m, 1H), 7.77-7.69 (m, 1H), 7.62-7.55 (dt, J=1.2, 6.9 Hz, 1H), 7.46 (d, J=5.7 Hz, 1H), 4.93-4.89 (m, 1H), 4.63 (d, J=9.6 Hz, 1H), 4.29-4.14 (m, 3H), 3.78-3.66 (m, 2H), 3.53-3.51 (m, 1H), 3.23-3.16 (m, 1H), 2.98 (s, 3H), 2.66-2.56 (m, 1H), 2.44 (s, 3H), 2.23-2.12 (m, 1H), 2.06 (s, 2H), 1.34 (d, J=6.9 Hz, 3H), 1.08-1.02 (m, 11H) ppm; $^{13}$C NMR (CDCl$_3$, 75 MHz): δ175.5, 174.7, 171.1, 169.2, 137.7, 131.0, 127.6, 127.1, 124.2, 122.4, 118.2, 68.2, 65.5, 63.2, 60.1, 56.9, 51.9, 51.2, 50.5, 49.6, 46.7, 44.8, 35.8, 35.7, 35.4, 35.0, 34.8, 34.3, 33.1, 26.6, 26.3, 21.3, 19.4 ppm. Mass spectrum, m/z [559.1] (M+H)+.

EXAMPLE 50

4-[3,3-Dimethyl-2-(2-methylamino-propionylamino)-butyryl]-1-methanesulfonyl-octahydro-pyrrolo[3,2-b]pyrrole-3-carboxylic acid quinolin-6-ylamide: $^1$H NMR (CDCl$_3$, 300 MHz), mixture of rotamers: δ10.92 (s, 0.5H), 10.14 (s, 0.5H), 8.86-8.83 (m, 1H), 8.48 (d, J=2.4 Hz, 0.5H), 8.34 (m, 1H), 8.14 (t, J=6.6 Hz, 1H), 8.07 (d, J=9.0 Hz, 1H), 7.89 (d, J=9.3 Hz, 0.5H), 7.75 (dd, J=2.4, 9.0 Hz, 0.5H), 7.68 (dd, J=2.4, 9.3 Hz, 0.5H), 7.42-7.38 (m, 1H), 4.74-4.68 (m, 1.5H), 4.62 (d, J=9.0 Hz, 0.5H), 4.54 (t, J=4.8 Hz, 0.5H), 4.22-3.99 (m, 2.5H), 3.87 (d, J=11.7 Hz, 0.5H), 3.79-3.64 (m, 1.5H), 3.46-3.36 (m, 0.5H), 3.34-3.22 (m, 1.5H), 3.05-2.81 (m, 3.5H), 2.69-2.56 (m, 1.5H), 2.53 (s, 1.5H), 2.48 (s, 1.5H), 2.21-2.08 (m, 1H), 1.92-1.80 (m, 0.5H), 1.47 (d, J=6.9 Hz, 1.5H), 1.40 (d, J=6.9 Hz, 1.5H), 1.09 (s, 5H), 1.00 (s, 4H) ppm; $^{13}$C NMR (CDCl$_3$, 75 MHz), mixture of rotamers: δ175.6, 173.9, 171.5, 171.0, 169.1, 168.8, 149.4, 149.3, 145.6, 145.4, 136.3, 136.1, 136.0, 135.9, 130.3, 130.2, 128.8, 128.7, 123.3, 123.2, 121.7, 121.6, 116.0, 115.8, 68.3, 68.2, 65.4, 63.0, 60.1, 59.8, 57.1, 56.8, 52.4, 51.1, 50.2, 49.0, 46.7, 44.6, 36.1, 35.8, 35.4, 35.1, 34.3, 33.0, 32.5, 26.6, 26.3, 19.5, 18.8 ppm. Mass spectrum, m/z [559.2] (M+H)+.

EXAMPLE 51

4-[3,3-Dimethyl-2-(2-methylamino-propionylamino)-butyryl]-1-methanesulfonyl-octahydro-pyrrolo[3,2-b]pyrrole-3-carboxylic acid quinolin-3-ylamide: $^1$H NMR (CDCl$_3$, 300 MHz), mixture of rotomers: δ 11.20 (s, 0.5H), 10.59 (s, 0.5H), 8.92-8.85 (m, 1.5H), 8.75 (d, J=2.1 Hz, 0.5H), 8.41 (d, J=11.1 Hz, 0.5H), 8.06-7.99 (m, 1.5H), 7.82 (t, J=7.8 Hz, 1H), 7.66-7.62 (m, 1H), 7.58-7.52 (m, 1H), 4.76-4.68 (m, 1.5H), 4.60 (d, J=9.0 Hz, 0.5H), 4.54 (t, J=5.1 Hz, 0.5H), 4.24-4.17 (m, 1H), 4.11-4.01 (m, 1H), 3.89 (d, J=11.7 Hz, 0.5H), 3.81-3.65 (m, 1.5H), 3.46-3.28 (m, 1.5H), 3.22-3.11 (m, 2.5H), 3.02 (s, 1.5H), 2.71-2.52 (m, 2.5H), 2.46 (d, J=3.3, Hz, 3H), 2.22-2.09 (m, 1H), 1.92-1.79 (m, 0.5H), 1.40 (dd, J=6.6, 28.2 Hz, 3H), 1.09 (s, 5H), 1.00 (s, 4H) ppm; $^{13}$C NMR (CDCl$_3$, 75 MHz), mixture of rotomers: δ 175.9, 175.2, 171.8, 171.4, 169.4, 168.8, 145.2, 145.1, 144.2, 144.1, 132.0, 131.9, 129.0, 128.9, 128.4, 128.2, 128.2, 128.1, 127.8, 127.7, 127.3, 123.4, 123.3, 68.3, 67.9, 65.4, 63.1, 60.3, 60.1, 56.9, 56.8, 52.4, 51.0, 50.3, 49.1, 46.7, 44.6, 36.1, 35.9, 35.3, 35.2, 35.1, 34.2, 33.1, 32.2, 26.6, 26.3, 19.5 ppm. Mass spectrum, m/z [559.1] (M+H)+.

EXAMPLE 52

4-[3,3-Dimethyl-2-(2-methylamino-propionylamino)-butyryl]-1-methanesulfonyl-octahydro-pyrrolo[3,2-b]pyrrole-3-carboxylic acid quinolin-2-ylamide: $^1$H NMR (CDCl$_3$, 300 MHz): δ 9.82 (br s, 1H), 8.29-8.22 (m, 1H), 8.18-8.13 (m, 1H), 7.94-7.86 (m, 2H), 7.78 (d, J=8.1 Hz, 1H), 7.68 (td, J=1.5, 6.9 Hz, 1H), 7.50-7.43 (m, 1H), 4.78-4.74 (m, 1H), 4.63 (d, J=9.3 Hz, 1H), 4.27-4.16 (m, 2H), 4.06 (dd, J=2.4, 11.7 Hz, 1H), 3.75-3.60 (m, 2H), 3.46 (d, J=6.6 Hz, 1H), 3.17-3.10 (m, 1H), 3.05 (s, 3H), 2.81 (br s, 2H), 2.61 (dd, J=5.4, 13.8 Hz, 1H), 2.46 (s, 3H), 2.14-2.05 (m, 2H), 1.34 (d, J=6.9 Hz, 3H), 1.07 (s, 7H), 1.02 (s, 2H) ppm; $^{13}$C NMR (CDCl$_3$, 75 MHz): δ175.0, 171.0, 170.3, 150.6, 146.6, 138.7, 130.1, 127.5, 126.3, 125.4, 114.2, 68.0, 65.5, 63.0, 60.2, 56.8, 51.9, 49.6, 49.4, 46.6, 35.9, 35.7, 35.5, 35.2, 35.0, 34.8, 33.0, 26.6, 26.4, 19.4 ppm. Mass spectrum, m/z [559.1] (M+H)+.

TABLE 8

| Example | Structure | XIAP, nM | cIAP1, nM | SKOV3, nM | Mass spectrum, m/z |
|---|---|---|---|---|---|
| 44 | 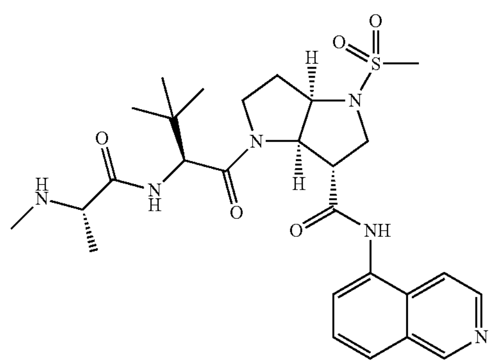 [SMILES: CN[C@@H](C)C(=O)N[C@H](C(=O)N1CC[C@@H]2[C@H]1[C@@H](C(=O)Nc1cccc3cnccc13)CN2S(C)(=O)=O)C(C)(C)C] | B | A | A | 559.2 (M + H) |
| 45 | 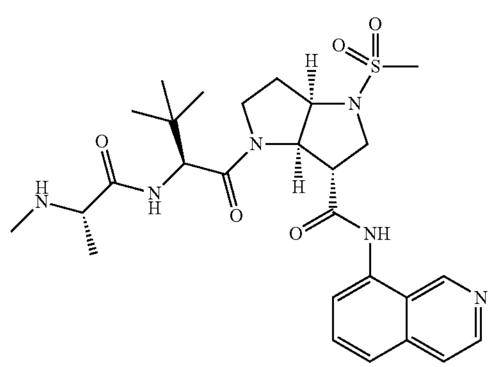 [SMILES: CN[C@@H](C)C(=O)N[C@H](C(=O)N1CC[C@@H]2[C@H]1[C@@H](C(=O)Nc1cccc3ccncc13)CN2S(C)(=O)=O)C(C)(C)C] | B | A | B | 559.2 (M + H) |

TABLE 8-continued

| Example | Structure | XIAP, nM | cIAP1, nM | SKOV3, nM | Mass spectrum, m/z |
|---|---|---|---|---|---|
| 46 | 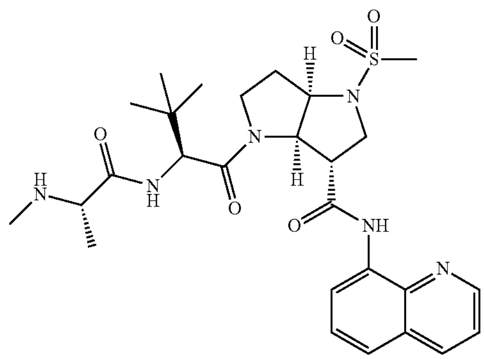 [SMILES: CN[C@@H](C)C(=O)N[C@H](C(=O)N1CC[C@@H]2[C@H]1[C@@H](C(=O)Nc1cccc3cccnc13)CN2S(C)(=O)=O)C(C)(C)C] | B | A | A | 559.2 (M + H) |
| 47 | 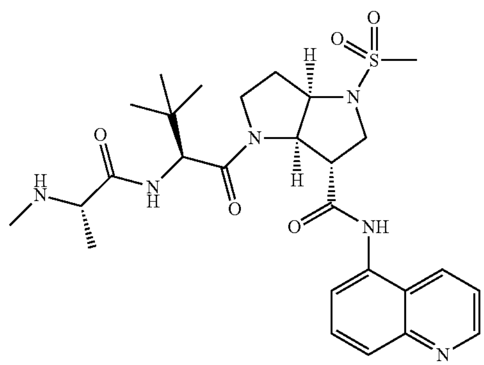 [SMILES: CN[C@@H](C)C(=O)N[C@H](C(=O)N1CC[C@@H]2[C@H]1[C@@H](C(=O)Nc1cccc3ncccc13)CN2S(C)(=O)=O)C(C)(C)C] | A | A | A | 559.1 (M + H) |
| 48 | 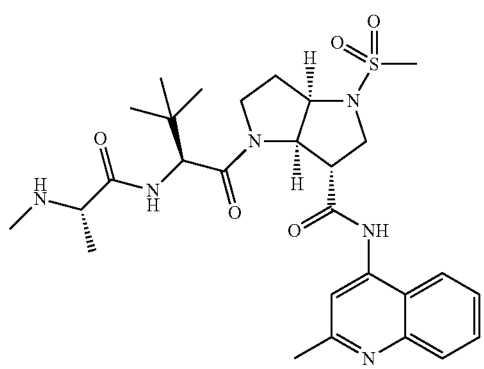 [SMILES: CN[C@@H](C)C(=O)N[C@H](C(=O)N1CC[C@@H]2[C@H]1[C@@H](C(=O)Nc1cc(C)nc3ccccc13)CN2S(C)(=O)=O)C(C)(C)C] | A | A | A | 573.2 (M + H) |
| 49 | 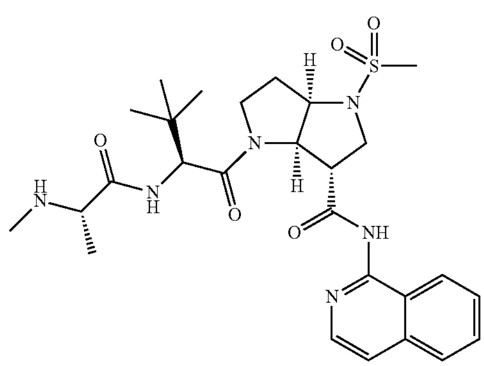 [SMILES: CN[C@@H](C)C(=O)N[C@H](C(=O)N1CC[C@@H]2[C@H]1[C@@H](C(=O)Nc1nccc3ccccc13)CN2S(C)(=O)=O)C(C)(C)C] | A | A | A | 559.1 (M + H) |

TABLE 8-continued

| Example | Structure | XIAP, nM | cIAP1, nM | SKOV3, nM | Mass spectrum, m/z |
|---|---|---|---|---|---|
| 50 | 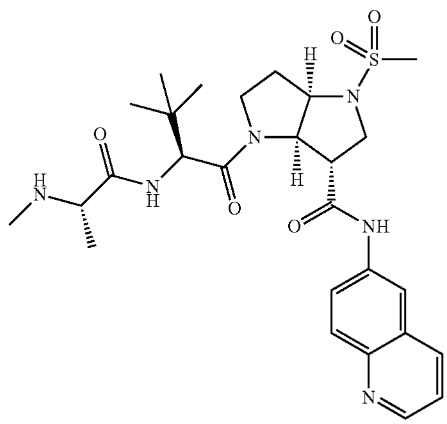 [SMILES: CN[C@@H](C)C(=O)N[C@H](C(=O)N1CC[C@@H]2[C@H]1[C@@H](C(=O)Nc1ccc3ncccc3c1)CN2S(C)(=O)=O)C(C)(C)C] | B | A | A | 559.2 (M + H) |
| 51 | 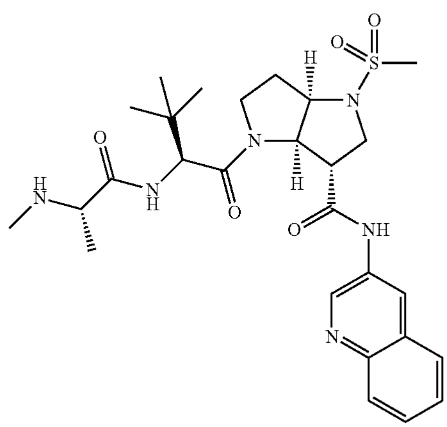 [SMILES: CN[C@@H](C)C(=O)N[C@H](C(=O)N1CC[C@@H]2[C@H]1[C@@H](C(=O)Nc1cnc3ccccc3c1)CN2S(C)(=O)=O)C(C)(C)C] | B | A | A | 559.1 (M + H) |
| 52 | 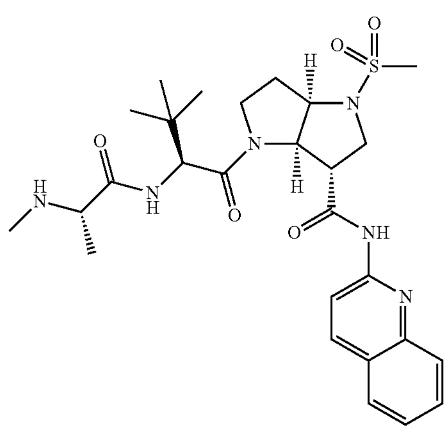 | B | A | A | 559.1 (M + H) |

As noted above, dimers of the compounds generally and specifically described above can be prepared by a person of skill in the art. Illustrative dimers of the invention can be prepared, e.g., in accordance with the following general synthetic schemes and examples:

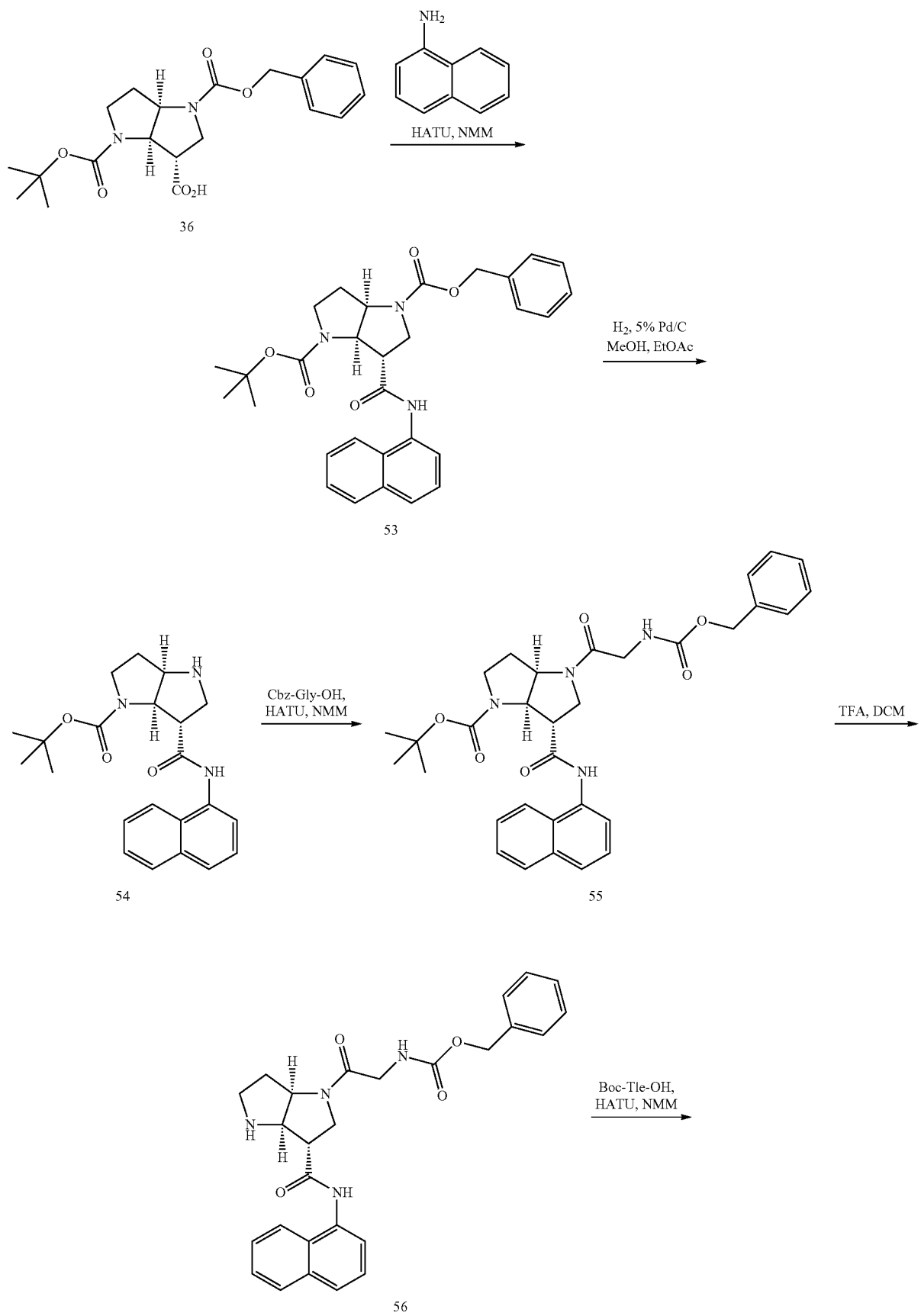

-continued
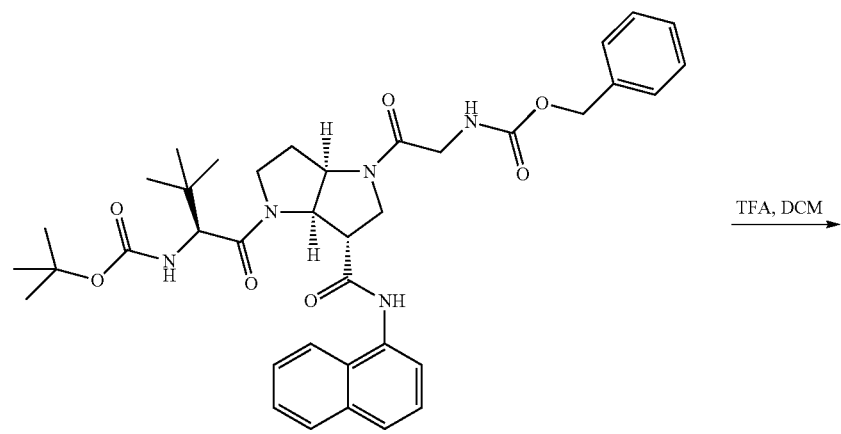
57
TFA, DCM →
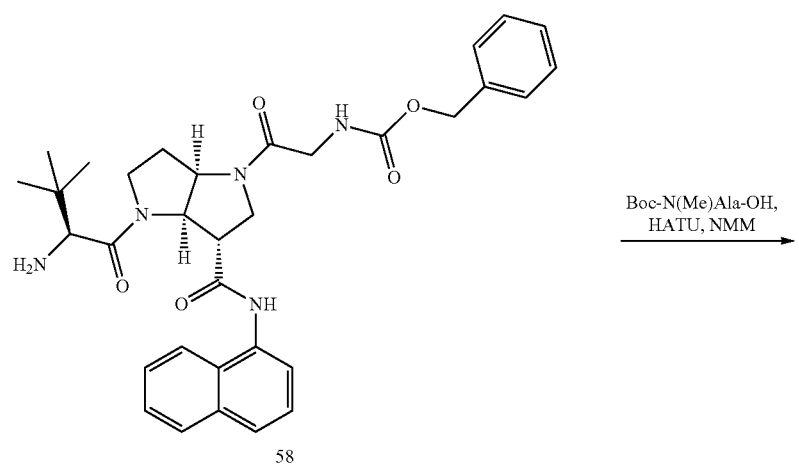
58
Boc-N(Me)Ala-OH, HATU, NMM →
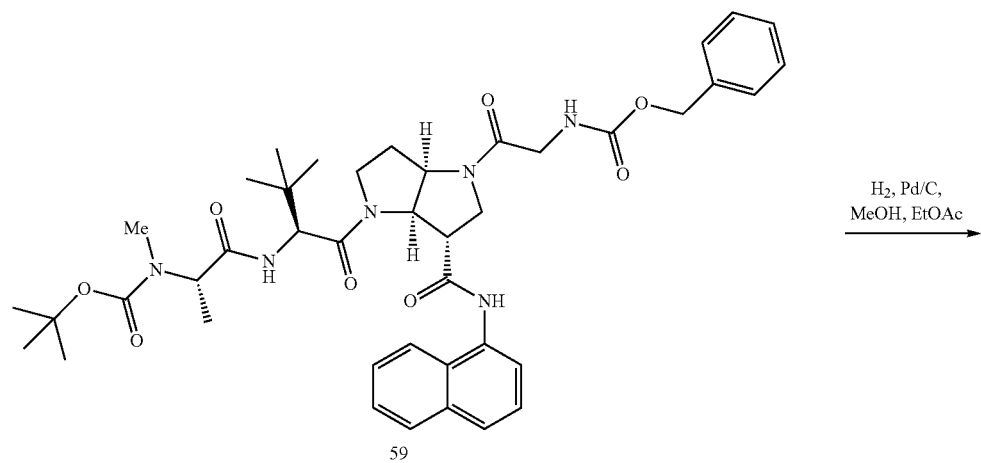
59
H₂, Pd/C, MeOH, EtOAc →

-continued
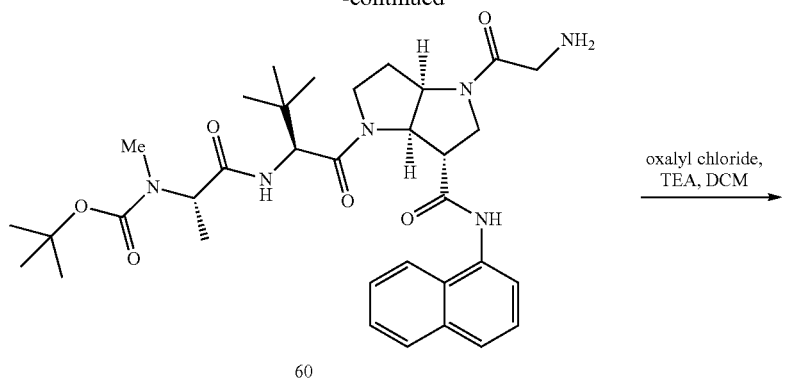
60
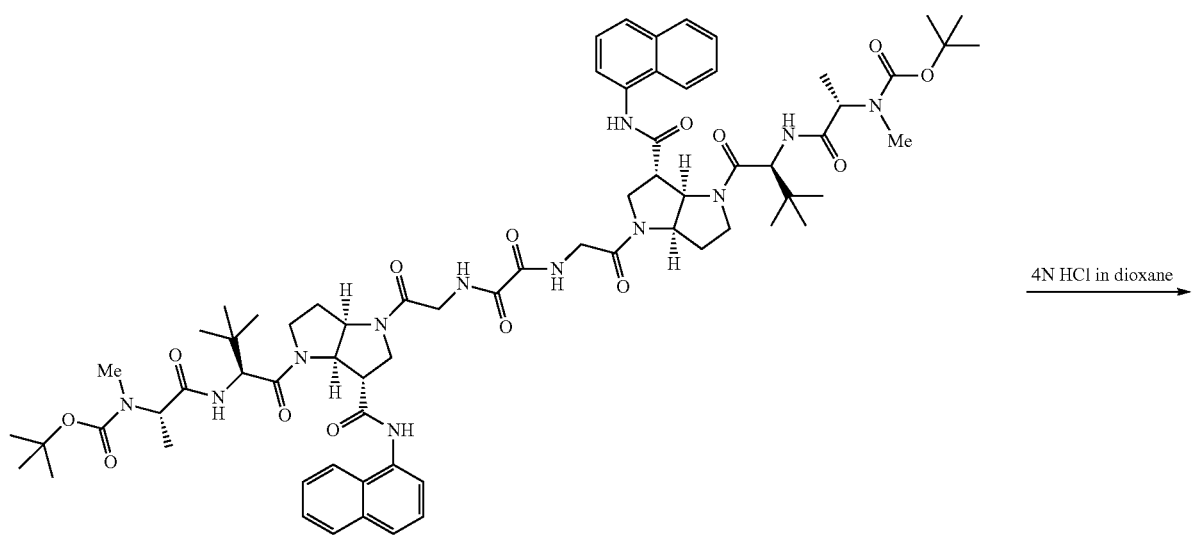
61
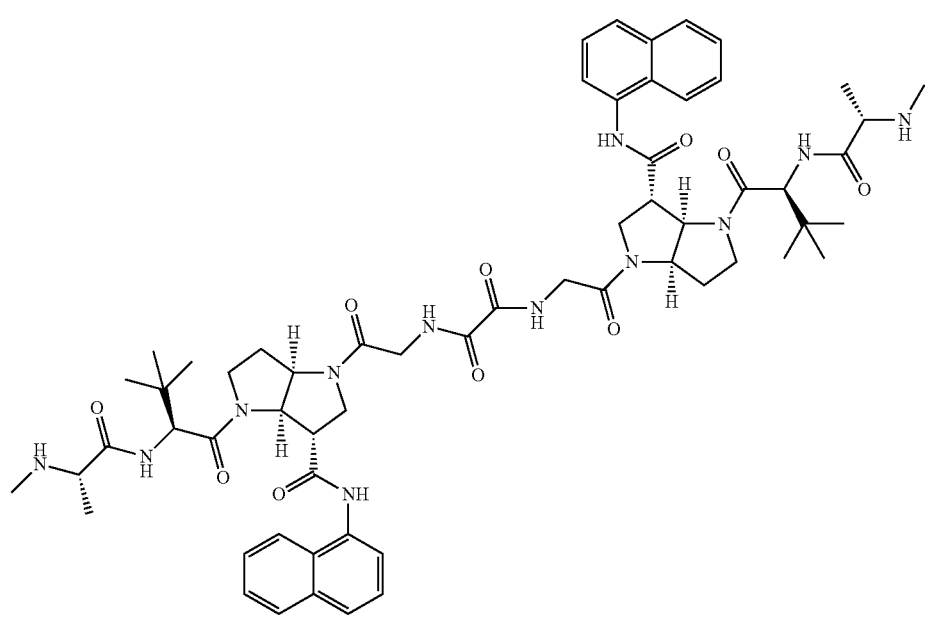
62

Scheme XLIX

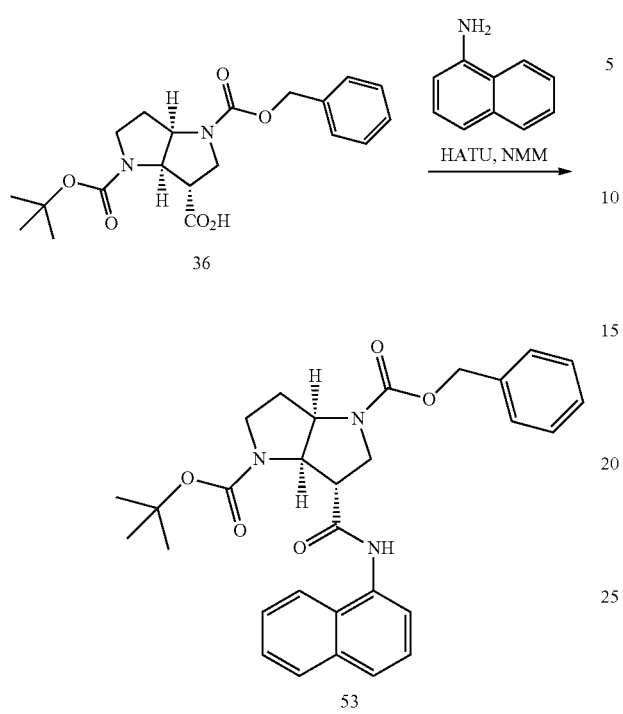

3-(Naphthalen-1-ylcarbamoyl)-hexahydro-pyrrolo[3,2-b]pyrrole-1,4-dicarboxylic acid 1-benzyl ester 4-tert-butyl ester (53): A solution of 36 (390 mg, 1.00 mmol) in NMP (5 mL) was cooled to 0° C. and treated with HATU (420 mg, 1.10 mmol) and NMM (0.17 mL, 1.50 mmol) followed in 15 min by the addition of 1-aminonaphthalene (145 mg, 1.00 mmol). The reaction mixture was allowed to warm to ambient temperature. After 3 h, the solution was diluted with EtOAc, washed with $H_2O$, 1M HCl, $H_2O$, sat $NaHCO_3$, brine, dried over anhydrous $Na_2SO_4$, filtered and concentrated. Purification by reverse phase HPLC (2" Dynamax® C18, 10-70% ACN in $H_2O$ with 0.1% HOAc over 30 min) afforded 53 (490 mg) as a white foam. $^1$H NMR (CDCl$_3$, 300 MHz), ~2:1 mixture of rotomers: δ8.32 (d, J=8.4 Hz, 1H), 8.15 (d, J=7.80 Hz, 1H), 7.84 (m, 1H), 7.64 (d, J=8.40 Hz, 1H), 7.42-7.56 (m, 4H), 7.26-7.42 (m, 4H), 5.17 (br s, 2H), 4.62 (m, 2H), 4.48 (dd, J=11.6, 2.5 Hz, 1H), 3.30-3.70 (m, 5H), 2.0-2.20 (m, 2H), 1.55 (s, 9H) ppm. Mass spectrum, m/z [516.1] (M+H)+.

Scheme L

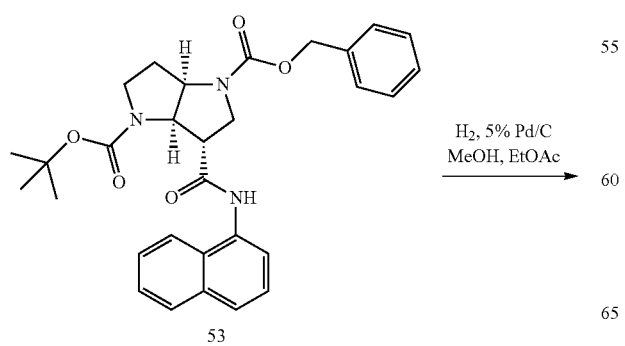

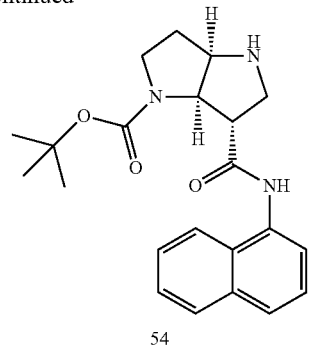

6-(Naphthalen-1-ylcarbamoyl)-hexahydro-pyrrolo[3,2-b]pyrrole-1-carboxylic acid tert-butyl ester (54): A solution of 53 (490 mg, 0.95 mmol) in 1:1 MeOH/EtOAc (4 mL) was treated with Pd/C (5% wet, ca. 100 mg) and placed under $H_2$ (50 psi) using a Parr apparatus. After 1.5 h, the reaction mixture was filtered through syringe filter disc (Acrodisc-PSF-0.45 µM) and rinsed with MeOH. The filtrate was concentrated to afford crude 54 (360 mg) which was used without further purification. Mass spectrum, m/z [382.2] (M+H)+.

Scheme LI

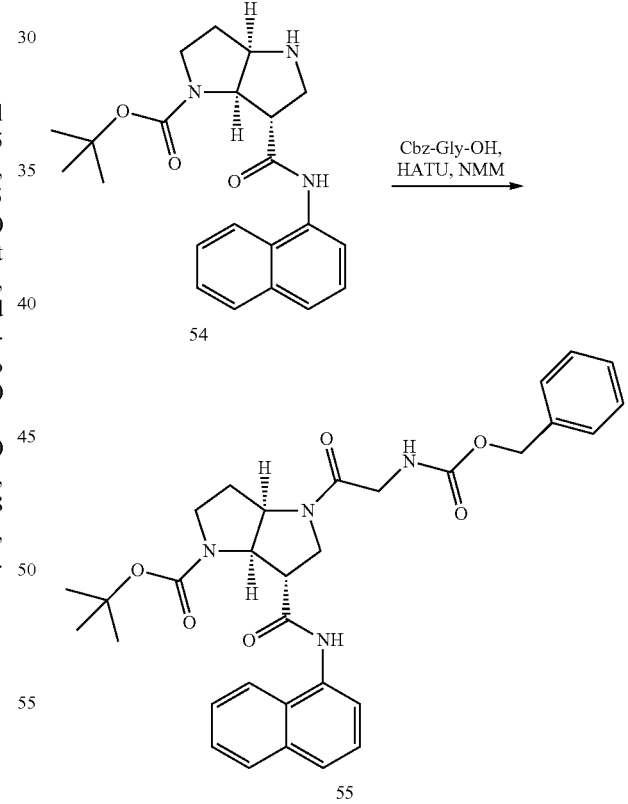

4-(2-Benzyloxycarbonylamino-acetyl)-6-(naphthalen-1-ylcarbamoyl)-hexahydro-pyrrolo[3,2-b]pyrrole-1-carboxylic acid tert-butyl ester (55): A solution of Cbz-Gly-OH (250 mg, 1.20 mmol) in NMP (2 mL) was cooled to 0° C. and treated with HATU (502 mg, 1.32 mmol) followed by NMM (0.2 mL). After 10 min, 54 (360 mg, 0.95 mmol) in NMP (2 mL) was added. The reaction mixture was allowed to warm to ambient temperature overnight. The solution was diluted with EtOAc, washed successively with 1M HCl, saturated NaHCO$_3$, dried over anhydrous Na$_2$SO$_4$, filtered and concentrated. Purification by reverse phase HPLC (2" Dynamax® C18, 10-70% ACN in H$_2$O with 0.1% HOAc over 30 min) afforded 55 as a white solid (400 mg). Mass spectrum, m/z [573.2] (M+H)+.

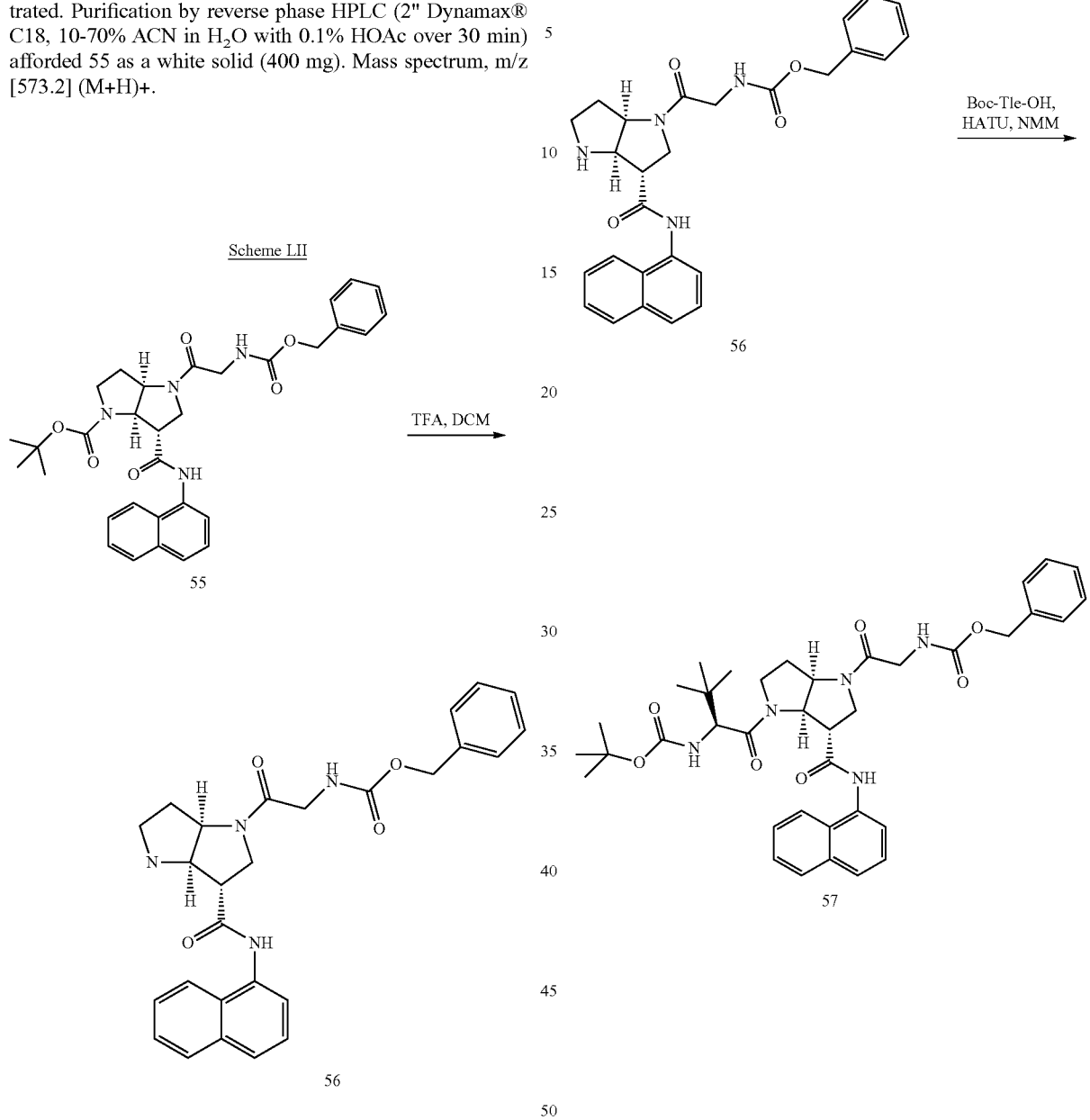

{2-[3-(Naphthalen-1-ylcarbamoyl)-hexahydro-pyrrolo[3,2-b]pyrrol-1-yl]-2-oxo-ethyl}-carbamic acid benzyl ester (56): A solution of 55 (400 mg, 0.69 mmol) in DCM (10 mL) was treated with TFA (3 mL) at ambient temperature. After 1 h, the solution was concentrated, diluted with EtOAc, and washed with saturated NaHCO$_3$. The aqueous phase was back extracted with DCM and the combined organic extracts were washed with brine, dried over anhydrous Na$_2$SO$_4$, filtered and concentrated to afford 56 (360 mg) which was used without further purification. Mass spectrum, m/z [473.2] (M+H)+.

{1-[4-(2-Benzyloxycarbonylamino-acetyl)-6-(naphthalen-1-ylcarbamoyl)-hexahydro-pyrrolo[3,2-b]pyrrole-1-carbonyl]-2,2-dimethyl-propyl}-carbamic acid tert-butyl ester (57): A solution of Boc-Tle-OH (176 mg, 0.76 mmol) in NMP (3 mL) was cooled to 0° C. and treated with HATU (318 mg, 0.83 mmol) followed by NMM (0.15 mL). After 10 min, 56 (360 mg, 0.76 mmol) in NMP (2 mL) was added. The reaction mixture was allowed to warm to ambient temperature overnight. The solution was diluted with EtOAc, washed successively with 1M HCl, saturated NaHCO$_3$, dried over anhydrous Na$_2$SO$_4$, filtered and concentrated to afford 57 (570 mg) which was used without further purification. Mass spectrum, m/z [686.4] (M+H)+.

Scheme LIV

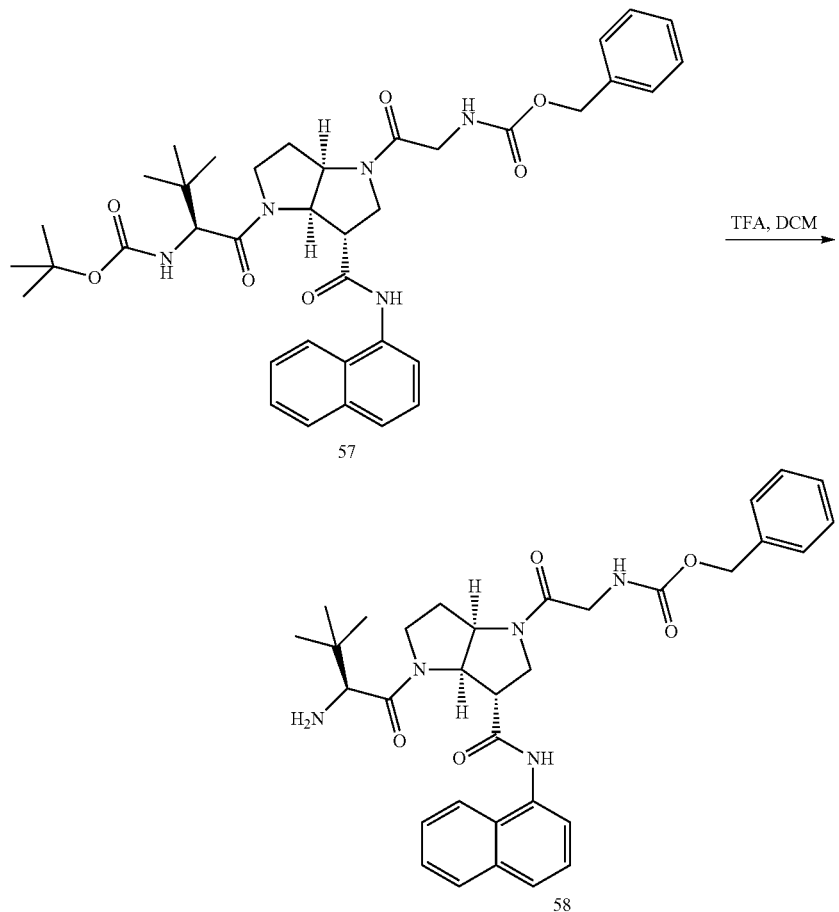

{2-[4-(2-Amino-3,3-dimethyl-butyryl)-3-(naphthalen-1-ylcarbamoyl)-hexahydro-pyrrolo[3,2-b]pyrrol-1-yl]-2-oxo-ethyl}-carbamic acid benzyl ester (58): A solution of 57 (570 mg) in DCM (10 mL) was treated with TFA (3 mL) at ambient temperature. After 2 h, the solution was concentrated, diluted with EtOAc, and washed with saturated NaHCO$_3$. The aqueous phase was back extracted with DCM and the combined organic extracts were washed with brine, dried over anhydrous Na$_2$SO$_4$, filtered and concentrated to afford 58 (450 mg) which was used without further purification. Mass spectrum, m/z [586.4] (M+H)+.

Scheme LV

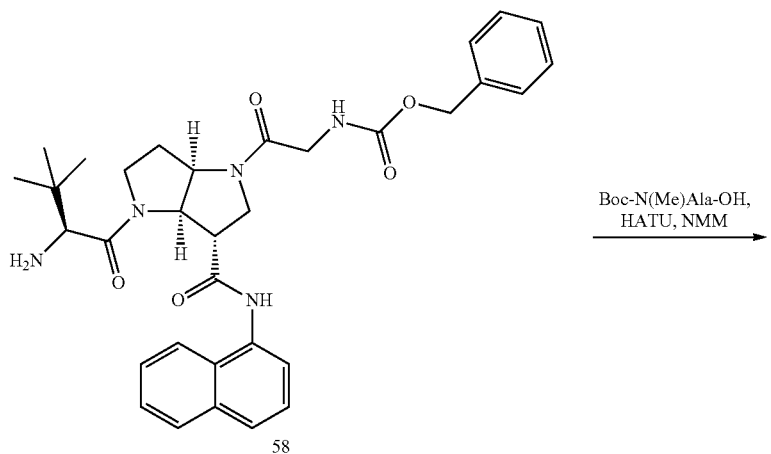

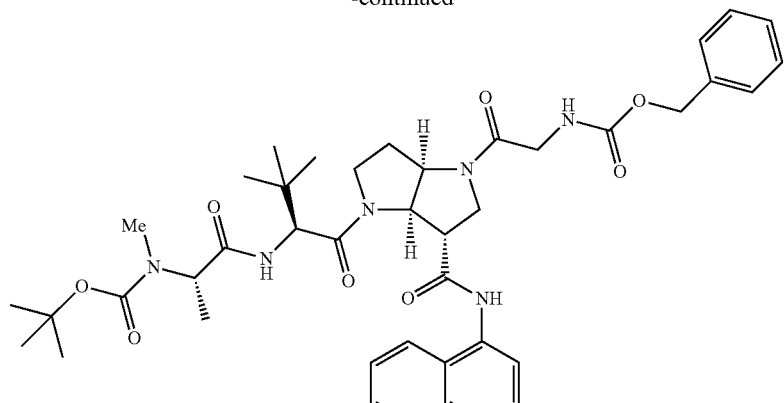

59

(1-{1-[4-(2-Benzyloxycarbonylamino-acetyl)-6-(naphthalen-1-ylcarbamoyl)-hexahydro-pyrrolo[3,2-b]pyrrole-1-carbonyl]-2,2-dimethyl-propylcarbamoyl}-ethyl)-methyl-carbamic acid tert-butyl ester (59): A solution of Boc-N(Me)Ala-OH (152 mg, 0.74 mmol) in NMP (3 mL) was cooled to 0° C. and treated with HATU (313 mg, 0.83 mmol) followed by NMM (0.15 mL). After 10 min, 58 (450 mg) in NMP (2 mL) was added. The reaction mixture was allowed to warm to ambient temperature overnight. The solution was diluted with EtOAc, washed successively with 1M HCl, saturated NaHCO$_3$, dried over anhydrous Na$_2$SO$_4$, filtered and concentrated. Purification by reverse phase HPLC (2" Dynamax® C18, 10-70% ACN in H$_2$O with 0.1% HOAc over 30 min) afforded 59 as a white solid (430 mg). Mass spectrum, m/z [771.3] (M+H)+.

Scheme LVI

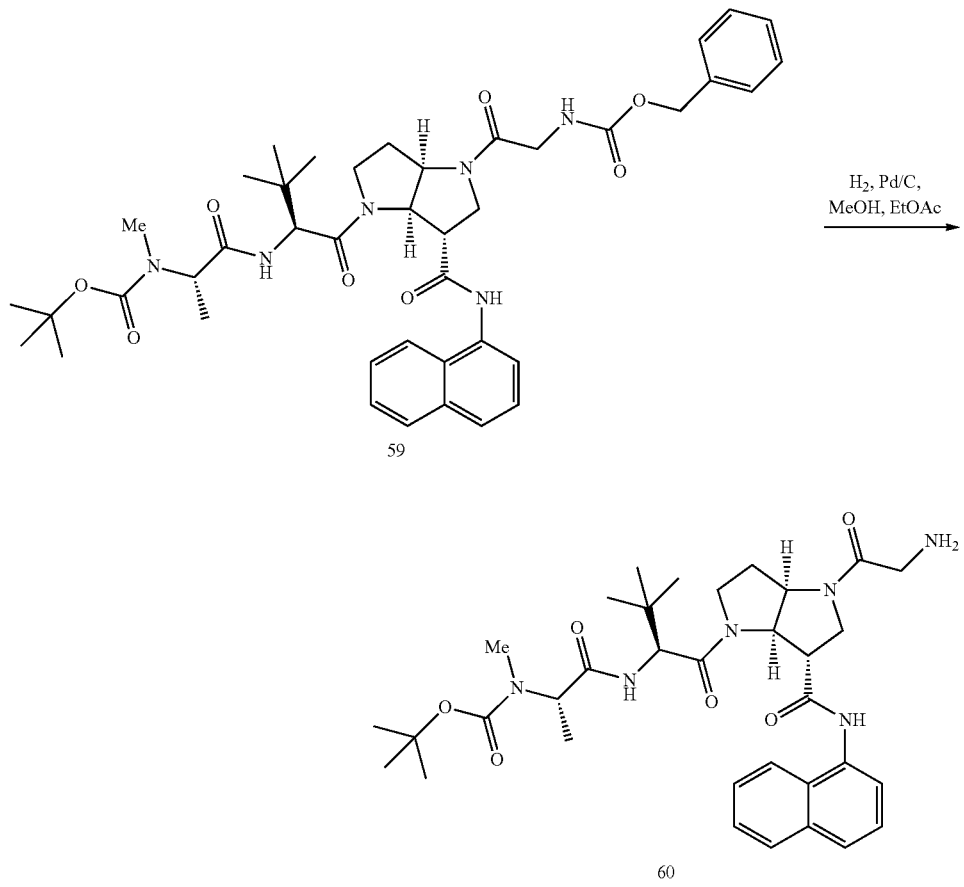

(1-{1-[4-(2-Amino-acetyl)-6-(naphthalen-1-ylcarbamoyl)-hexahydro-pyrrolo[3,2-b]pyrrole-1-carbonyl]-2,2-dimethyl-propylcarbamoyl}-ethyl)-methyl-carbamic acid tert-butyl ester (60): A solution of 59 (430 mg, 0.56 mmol) in 1:1 MeOH/EtOAc (4 mL) was treated with Pd/C (5% wet, ca. 100 mg) and placed under H$_2$ (35 psi) using a Parr apparatus. After 3 h, the reaction mixture was filtered through syringe filter disc (Acrodisc-PSF-0.45 μM) and rinsed with MeOH. The filtrate was concentrated to afford crude 60 (350 mg) which was concentrated twice from anhydrous toluene (50 mL) and then used without further purification. Mass spectrum, m/z [637.5] (M+H)+.

N,N'-Bis-{2-[4-[3,3-dimethyl-2-(2-Boc-methylamino-propionylamino)-butyryl]-3-(naphthalen-1-ylcarbamoyl)-hexahydro-pyrrolo[3,2-b]pyrrol-1-yl]-2-oxo-ethyl}-oxalamide (61): A solution containing crude 60 (350 mg, 0.57 mmol) in anhydrous DCM (20 mL) was cooled to −20° C. Oxalyl chloride (2M in DCM, 0.11 mL, 0.22 mmol) was added in portions until all 60 had been consumed by LC/MS analysis. The reaction mixture was quenched by the addition of saturated aqueous NaHCO$_3$ and the part-aqueous mixture was extracted with EtOAc. The combined organic extracts were washed with brine then dried over anhydrous Na$_2$SO$_4$, filtered, and concentrated to afford 61 which was used directly in the next reaction. Mass spectrum, m/z [1328.5] (M+H)+.

Scheme LVIIa

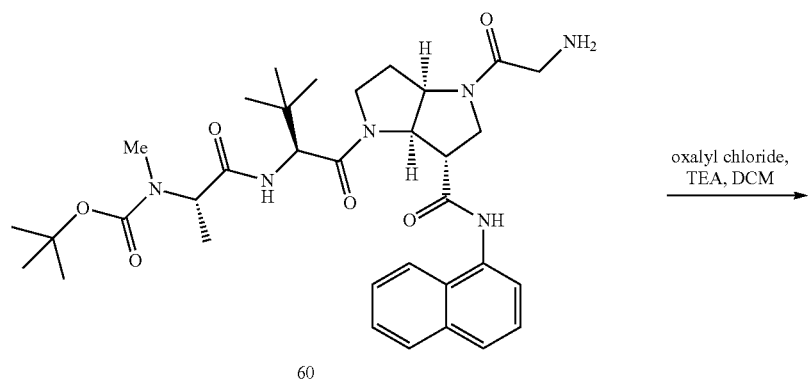

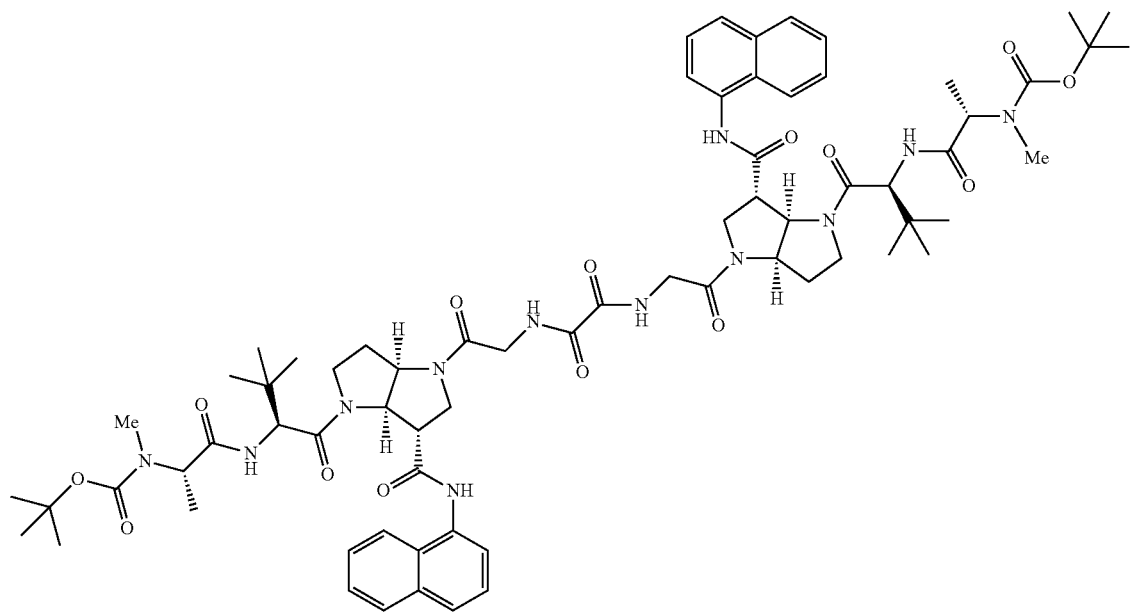

Scheme LVIIb

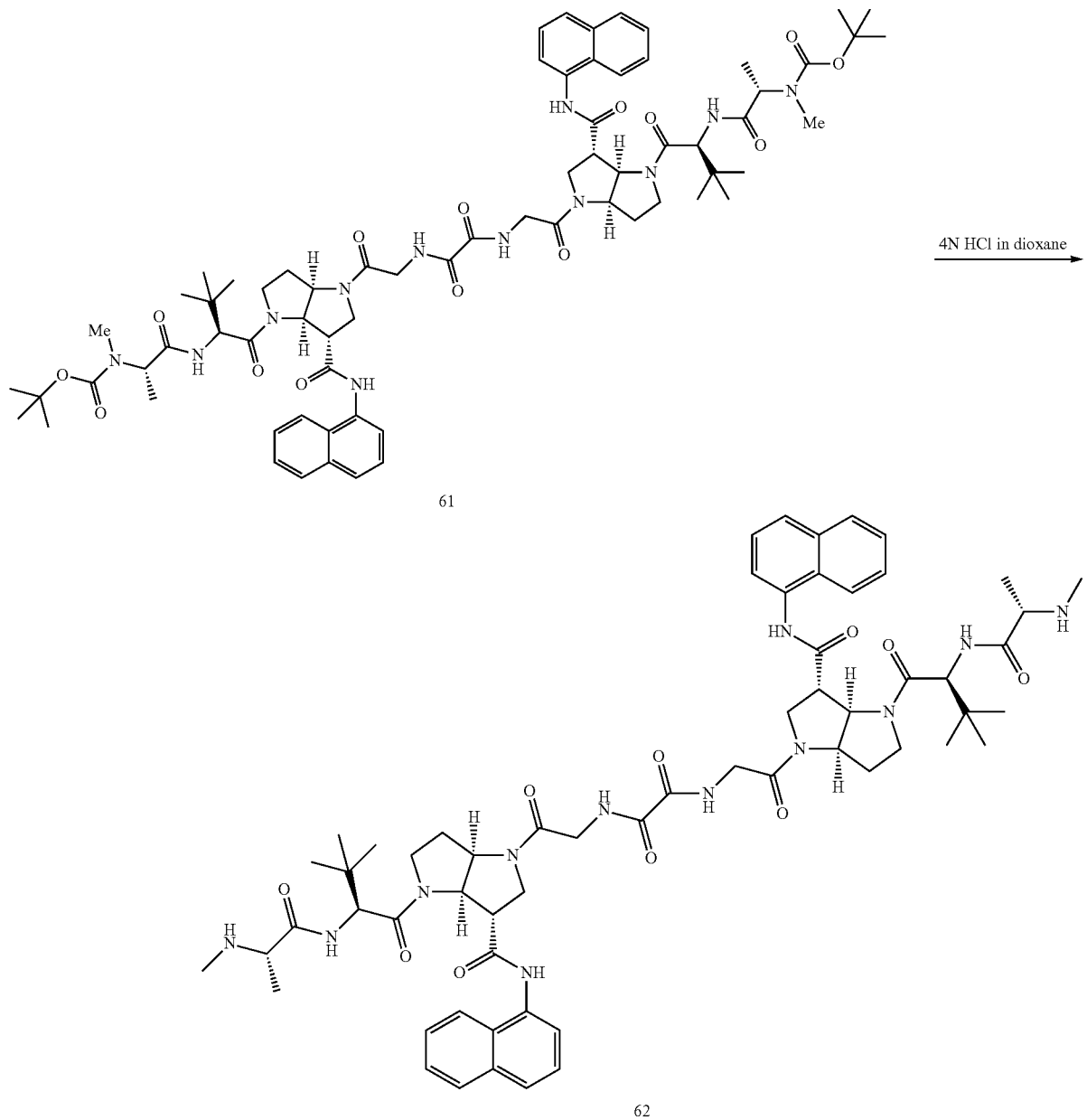

N,N'-Bis-{2-[4-[3,3-dimethyl-2-(2-methylamino-propionylamino)-butyryl]-3-(naphthalen-1-ylcarbamoyl)-hexahydro-pyrrolo[3,2-b]pyrrol-1-yl]-2-oxo-ethyl}-oxalamide (62): Bis-Boc intermediate 61 was dissolved in 4N HCl in dioxane (10 mL) at ambient temperature. After 2 h, the solvent was removed in vacuo and the crude residue was purified by reverse phase HPLC (2" Dynamax® C18, 10-70% ACN in H$_2$O with 0.1% HOAc over 30 min). The product-containing fractions were combined, frozen, and lyophilized to afford 62 (58 mg) as a white solid.

EXAMPLE 53

N,N'-Bis-{2-[4-[3,3-dimethyl-2-(2-methylamino-propionylamino)-butyryl]- 3-(naphthalen-1-ylcarbamoyl)-hexahydro-pyrrolo[3,2-b]pyrrol-1-yl]-2-oxo-ethyl}-oxalamide (62): $^1$H NMR (CDCl$_3$+d$_4$-methanol, 300 MHz): δ8.20 (m, 2H), 7.96 (m, 2H), 7.86 (m, 2H), 7.69 (m, 2H), 7.49 (m, 6H), 4.88 (m, 2H), 4.78 (m, 2H), 4.65 (br s, 2H), 3.90-4.38 (m, 6H), 3.20-3.80 (m, 20H), 2.45 (s, 6H), 2.60 (m, 2H), 1.36 (d, J=6.30 Hz, 6H), 1.10 (s, 18H) ppm; $^{13}$C NMR (CDCl$_3$, 75 MHz): δ174.5, 171.4, 171.0, 170.9, 169.6, 169.5, 169.3, 166.4, 165.9, 159.5, 134.3, 132.6, 128.8, 127.0, 126.3, 126.2, 125.8, 125.7, 121.8, 121.3, 120.1, 66.5, 65.9, 63.7, 60.8, 59.7, 57.1, 52.1, 50.7, 49.9, 49.6, 49.3, 49.1, 48.7, 47.3, 46.0, 45.5, 42.4, 35.8, 35.7, 34.8, 34.4, 31.0, 30.4, 26.7, 26.5, 19.2, 19.1 ppm. Mass spectrum, m/z [1127.8] (M+H)+.

EXAMPLE 54 was prepared using Compound 36 following the general procedures described in Schemes XLIX through LVII.

EXAMPLE 54

N,N'-Bis-{2-[4-[3,3-dimethyl-2-(2-methylamino-propionylamino)-butyryl]-3-(4-fluoro-phenylcarbamoyl)-hexahydro-pyrrolo[3,2-b]pyrrol-1-yl]-2-oxo-ethyl}-oxalamide: $^1$H NMR (CDCl$_3$, 300 MHz), δ7.52 (m, 4H), 7.01 (m, 4H), 4.60-4.80 (m, 4H), 3.90-4.10 (m, 6H), 3.20-3.80 (m, 20H), 2.57 (s, 6H), 2.10-2.50 (m, 4H), 1.44 (d, J=6.6 Hz, 6H), 1.06 (s, 18H) ppm. Mass spectrum, m/z [1063.1] (M+H)+.

Additional bivalent ("dimeric") compounds can be prepared by linking two independently substituted monovalent compounds through the R2 positions, such that the R2 group on one monomer and the R2 group on the other monomer together from -L-.

The synthetic preparation of such R2-linked bivalent compounds is described in Schemes LVIII and LIX following chemistry outlined in this application and U.S. Pat. Nos. 7,517,906, 7,309,792 which are herein incorporated by reference in their entireties.

TABLE 9

| Example | Structure | XIAP, nM | cIAP1, nM | SKOV3, nM | Mass spectrum, m/z |
|---------|-----------|----------|-----------|-----------|--------------------|
| 53 | 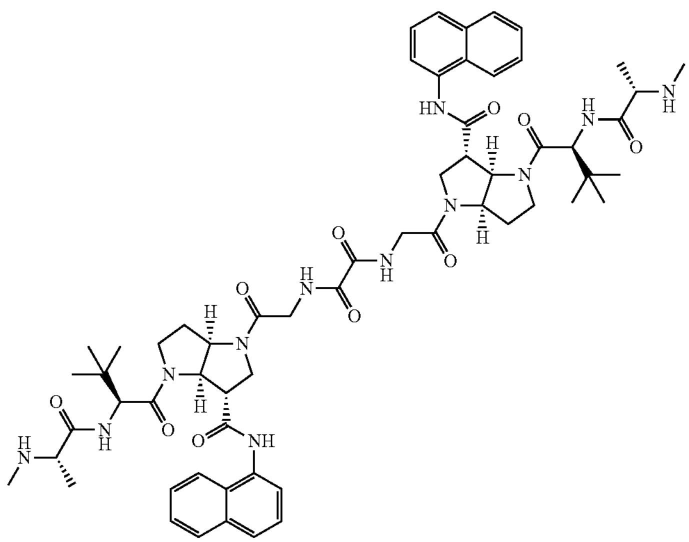 | A | A | A | 1127.8 |
| 54 | 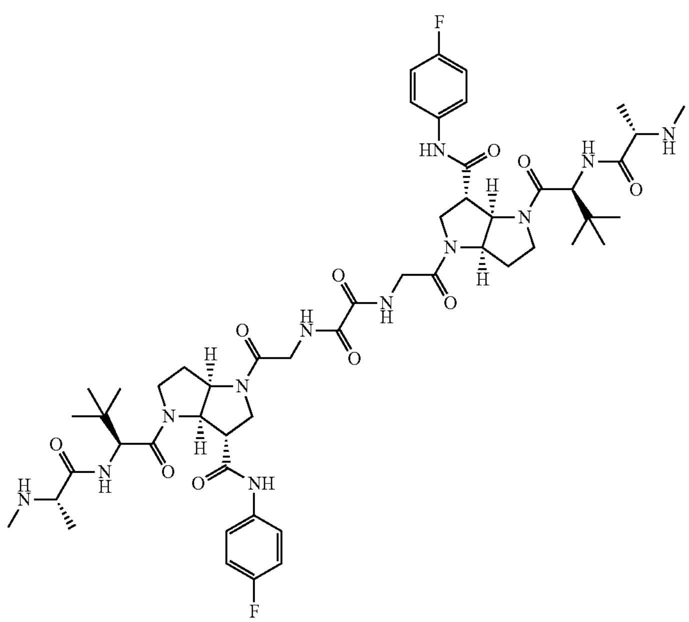 | A | A | A | 1063.1 |

Scheme LVIII
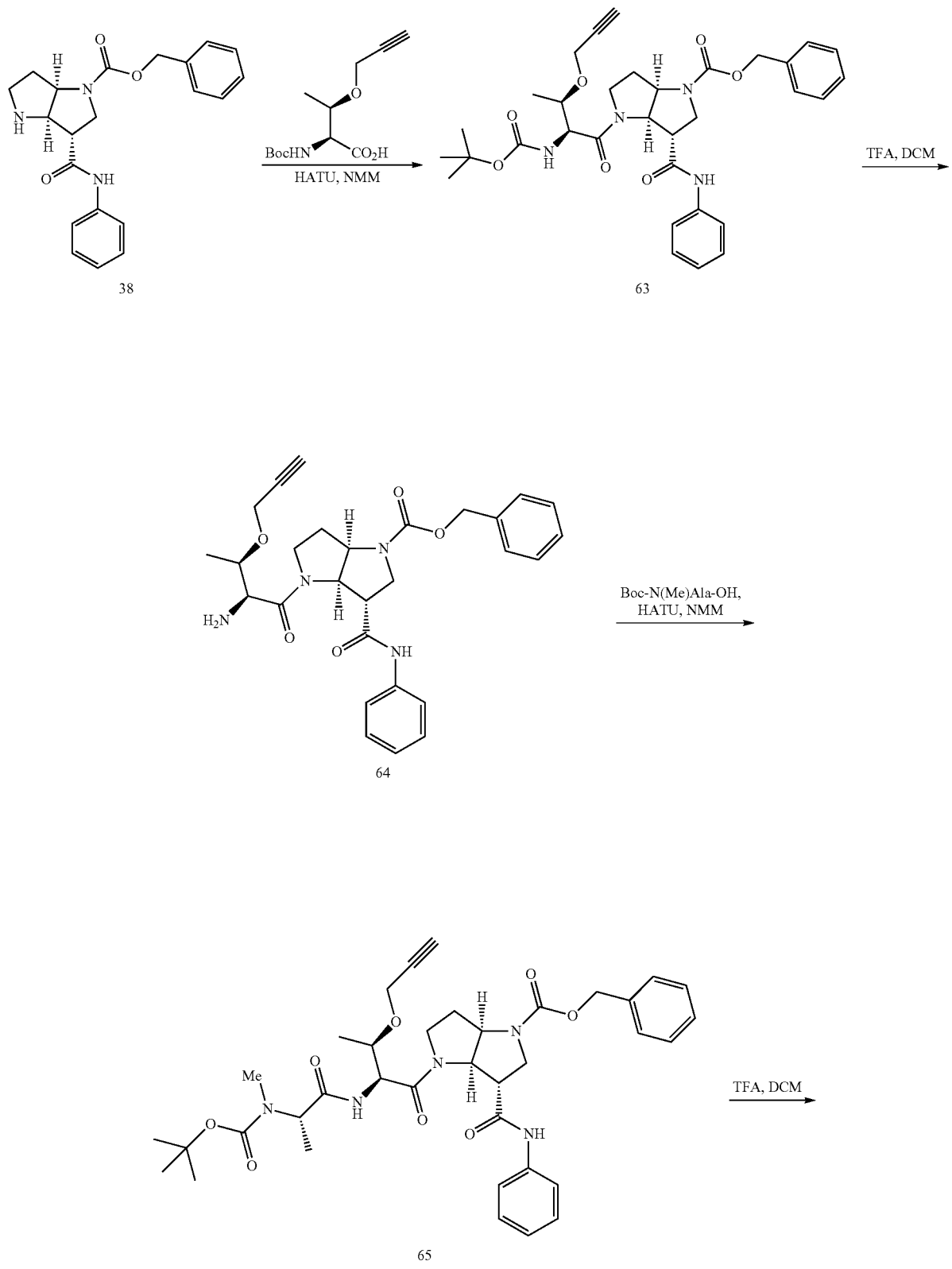

-continued
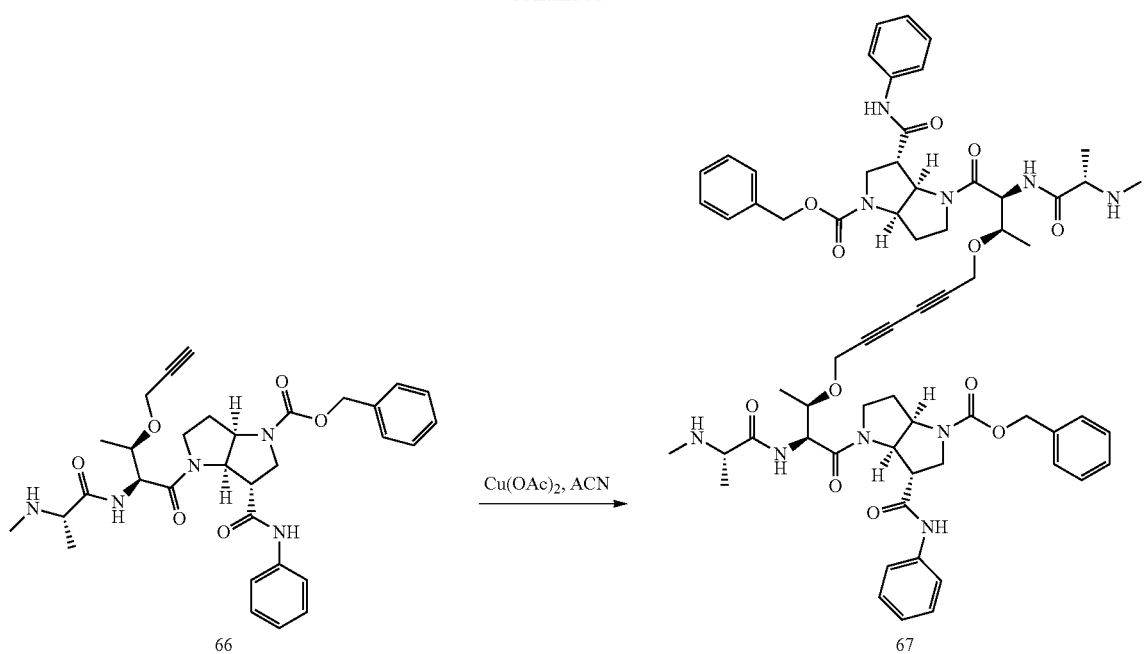
Scheme LIX
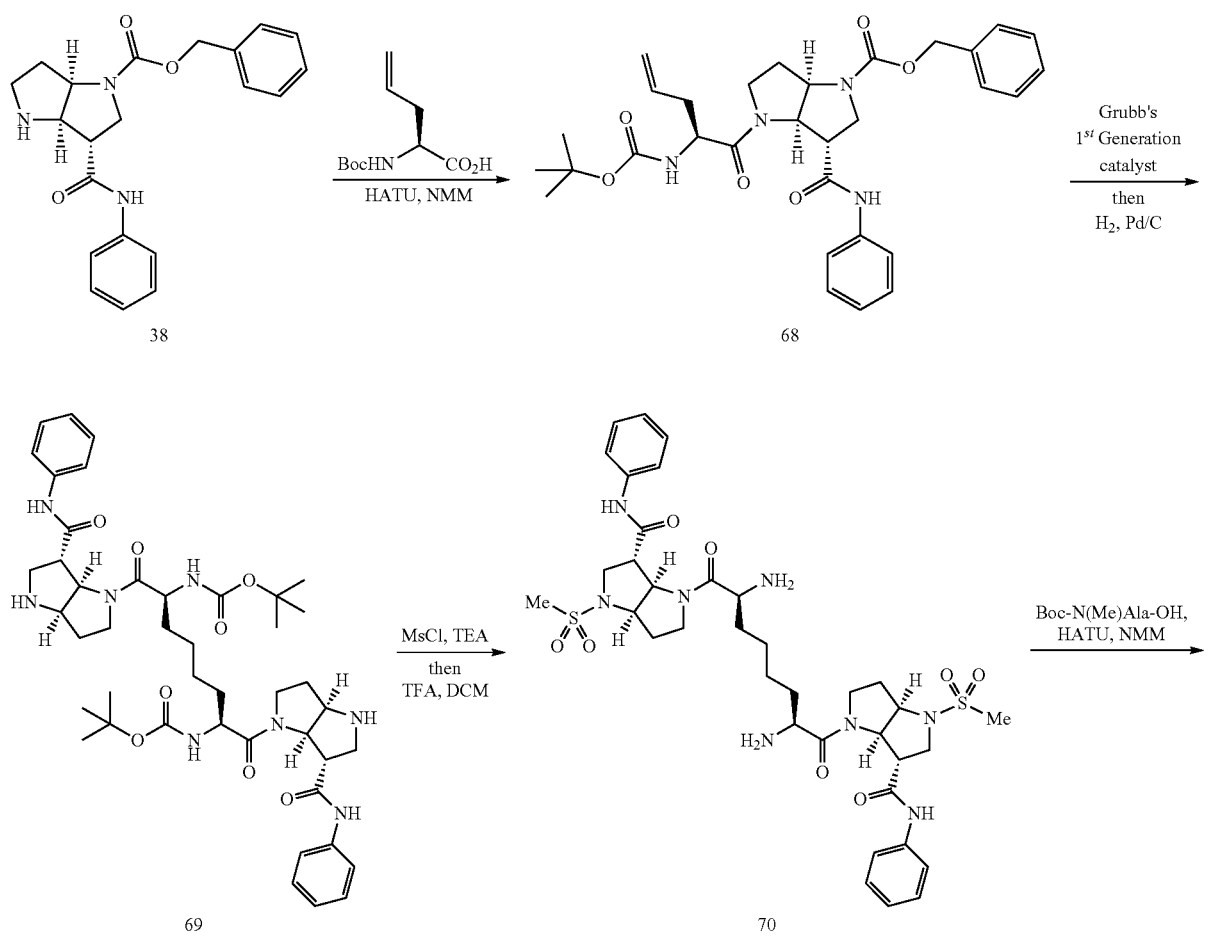

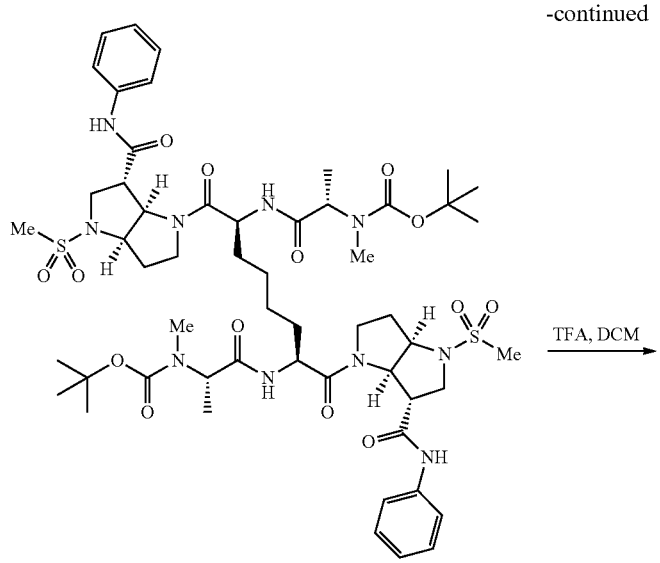

71

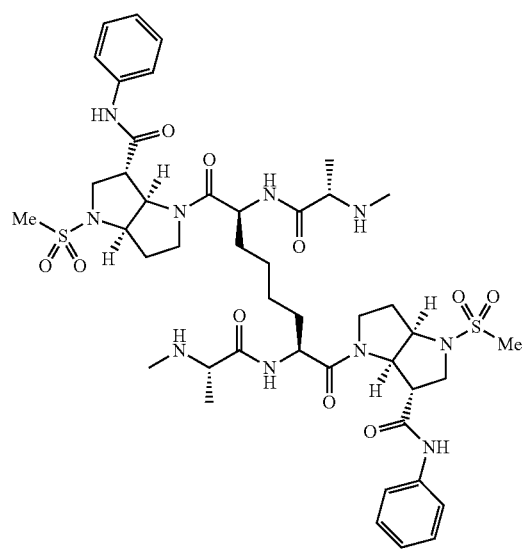

72

It is intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-enriched compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically enriched compounds of this invention can generally be prepared by substituting a readily available isotopically labelled reagent for a non-isotopically labelled reagent.

The compounds of the present invention may exist in unsolvated forms as well as solvated forms, including hydrated forms. The compounds of the present invention (e.g., compounds of Formula I, IS, and IR) also are capable of forming both pharmaceutically acceptable salts, including but not limited to acid addition and/or base addition salts. Furthermore, compounds of the present invention may exist in various solid states including an amorphous form (noncrystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present invention.

A "polymorph" refers to solid crystalline forms of a compound. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing.

A "clathrate" means a compound or a salt thereof in the form of a crystal lattice that contains spaces (e.g., channels) that have a guest molecule (e.g., a solvent or water) trapped within.

As noted above, the compounds of the present invention can be administered, inter alia, as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

Compounds and salts of the present invention may also exist in tautomeric forms, such as an enol and an imine form, and the corresponding keto and enamine forms and geometric isomers and mixtures thereof. Tautomers exist as mixtures of a tautomeric set in solution. In solid form, usually one tautomer predominates. Even though only one tautomer may be described by the formulae above, the present invention includes all tautomers of the present compounds.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water, ethanol, and the like. The present invention contemplates and encompasses both the solvated and unsolvated forms.

The compounds of the present invention can be administered to a patient either alone or a part of a pharmaceutical composition in a therapeutically effective amount. A variety of non-limiting methods for administering the compounds and related compositions to patients include orally, rectally, parenterally (intravenously, intramuscularly, or subcutaneously), intracisternally, intravaginally, intraperitoneally, intravesically, locally (powders, ointments, or drops), or as a buccal or nasal spray. In addition, the substance or compositions containing the active substances can be administered all at once, as for example, by a bolus injection, multiple times, such as by a series of tablets, or delivered substantially uniformly over a period of time, as for example, using transdermal delivery. It is also noted that the dose of the substances can be varied over time.

The compounds and related compositions of the present invention can be administered alone, or in combination with other pharmaceutically active substances. The other pharmaceutically active substances can be intended to treat the same disease or condition as the substances of the present invention or a different disease or condition. If the patient is to receive, or is receiving multiple pharmaceutically active substances, the substances can be administered simultaneously, or sequentially. For example, in the case of tablets, the active substances may be found in one tablet or in separate tablets, which can be administered at once or sequentially in any order. In addition, it should be recognized that the compositions may be different forms. For example, one or more substance may be delivered via a tablet, while another is administered via injection or orally as a syrup. All combinations, delivery methods and administration sequences are contemplated.

Pharmaceutical compositions to be used comprise a therapeutically effective amount of a compound as described above, or a pharmaceutically acceptable salt or other form thereof together with one or more pharmaceutically acceptable excipients. The phrase "pharmaceutical composition" refers to a composition suitable for administration in medical or veterinary use. It should be appreciated that the determinations of proper dosage forms, dosage amounts, and routes of administration for a particular patient are within the level of ordinary skill in the pharmaceutical and medical arts.

Compositions suitable for parenteral administration conveniently comprise a sterile aqueous preparation of a compound or composition of the invention, which is preferably isotonic with the blood of the recipient. This aqueous preparation may be formulated according to known methods using suitable dispersing or wetting agents, emulsifying and suspending agents. Various antibacterial and antifungal agents, for example, parabens, chlorobutanol, phenol, and sorbic acid also may be included. The sterile injectable preparation also may be a sterile injectable solution or suspension in a nontoxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Prolonged absorption of the injectable pharmaceutical form can be brought about by the use of agents delaying absorption, for example, aluminum monostearate and gelatin. Carrier formulation suitable for subcutaneous, intravenous, intramuscular, etc. administrations can be found in Remington's Pharmaceutical Sciences, Mack Publishing Co., Easton, Pa. which is incorporated herein in its entirety by reference thereto.

Solid dosage forms for oral administration include capsules, tablets, pills, powders, and granules. In such solid dosage forms, the compound is admixed with at least one inert pharmaceutically acceptable excipient such as (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, dragees, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a substance of the present invention, and a second pharmaceutical substance. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a substance of the present invention can consist of one tablet or capsule, while a daily dose of the second substance can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Liquid dosage forms for oral administration include pharmaceutically acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

Compositions for rectal administrations are preferably suppositories which can be prepared by mixing compounds of the present invention with suitable non-irritating excipients or carriers such as cocoa butter, polyethyleneglycol or a low-melting, suppository wax, which are solid at ordinary temperatures but liquid at body temperature and therefore, melt in the rectum or vaginal cavity and release the active compound.

Dosage forms for topical administration of a compound of this invention include ointments, powders, sprays, and inhalants. The active compound is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds and compositions of the present invention also may benefit from a variety of delivery systems, including time-released, delayed release or sustained release delivery systems. Such option may be particularly beneficial when the compounds and composition are used in conjunction with other treatment protocals as described in more detail below.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active compound for at least 30 days, and preferably 60 days. Long-term sustained release implants are well-known to those of ordinary skill in the art and include some of the release systems described above.

In practicing the methods of the present invention, the compounds and compositions of the present invention are administered in a therapeutically effective amount. Generally, doses of active compounds would be from about 0.01 mg/kg per day to 1000 mg/kg per day. It is expected that doses ranging from 50-500 mg/kg will be suitable, preferably intravenously, intramuscularly, or intradermally, and in one or several administrations per day. The compounds of the present invention may also be used in combination with radiation therapy, hormone therapy, surgery and immunotherapy, which therapies are well know to those skilled in the art.

When practicing the conjoint or combination therapy described in more detail below, the administration of the compounds and compositions of the presnt invention can occur simultaneous with, subsequent to, or prior to chemotherapy or radiation, so long as the chemotherapeutic agent or radiation sensitizes the system to the compounds and compositions of the present invention.

In general, routine experimentation in clinical trials will determine specific ranges for optimal therapeutic effect for a particular compound and composition of the presnt invention and each administrative protocol, and administration to specific patients will be adjusted to within effective and safe ranges depending on the patient condition and responsiveness to initial administrations. However, the ultimate administration protocol will be regulated according to the judgment of the attending clinician considering such factors as age, condition and size of the patient, the potency of the compound or composition, the duration of the treatment and the severity of the disease being treated. For example, a dosage regimen of the compound or composition can be an oral administration of from 1 mg to 2000 mg/day, preferably 1 to 1000 mg/day, more preferably 50 to 600 mg/day, in two to four (preferably two) divided doses, to reduce tumor growth. Intermittent therapy (e.g., one week out of three weeks or three out of four weeks) may also be used.

In the event that a response in a subject is insufficient at the initial doses applied, higher doses (or effectively higher doses by a different, more localized delivery route) may be employed to the extent that the patient tolerance permits. Multiple doses per day are contemplated to achieve appropriate systemic levels of compounds. Generally, a maximum dose is used, that is, the highest safe dose according to sound medical judgment. Those of ordinary skill in the art will understand, however, that a patient may insist upon a lower dose or tolerable dose for medical reasons, psychological reasons or for virtually any other reason.

The compounds of the present invention and pharmaceutical compositions comprising a compound of the present invention can be administered to a subject suffering from cancer, an autoimmune disease or another disorder where a defect in apoptosis is implicated. In connection with such treatments, the patient can be treated prophylactically, acutely, or chronically using compounds and compositions of the present invention, depending on the nature of the disease. Typically, the host or subject in each of these methods is human, although other mammals may also benefit from the administration of a compound of the present invention.

As described in U.S. Pat. No. 7,244,851, the disclosure of which is incorporated herein by reference, IAP antagonists can be used for the treatment of all cancer types which fail to undergo apoptosis. Thus, compounds of the present invention can be used to provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia is also contemplated by this invention. Indications may include, but are not limited to brain cancers, skin cancers, bladder cancers, ovarian cancers, breast cancers, gastric cancers, pancreatic cancers, colon cancers, blood cancers, lung cancers and bone cancers. Examples of such cancer types include neuroblastoma, intestine carcinoma such as rectum carcinoma, colon carcinoma, familiarly adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

The inventors believe that the IAP antagonists of the present invention will be particularly active for treating human malignancies where cIAP1 and cIAP2 are over-expressed (e.g., lung cancers, see Dai et al, Hu. Molec. Genetics, 2003 v 12 pp 791-801; leukemias (multiple references), and other cancers (Tamm et al, Clin Cancer Res, 2000, v 6, 1796-1803). The inventors also expect that the IAP antagonists of the present invention will be active in disorders that may be driven by inflammatory cytokines such as TNF playing a pro-survival role (for example, there is a well defined role for TNF acting as a survival factor in ovarian carcinoma, similarly for gastric cancers (see Kulbe, et al, Cancer Res 2007, 67, 585-592).

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erthematosus or rheumatoid arthritis.

Examples of such autoimmune diseases include collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barré syndrome (Müller-Fischer syndrome), stiff-man syndrome, cerebellar degeneration, ataxia, opsoklonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

The present invention also is directed to the use of the compounds and compositions as a chemopotentiating agent with other treatment approaches. The term "chemopotentiating agent" refers to an agent that acts to increase the sensitivity of an organism, tissue, or cell to a chemical compound, or treatment namely "chemotherapeutic agents" or "chemo drugs" or to radiation treatment. Thus, compounds and compositions of the present invention can be used for inhibiting tumor growth in vivo by administering them in combination with a biologic or chemotherapeutic agent or by using them in combination with chemoradiation. In these applications, the administration of the compounds and compositions of the present invention may occur prior to, and with sufficient time, to cause sensitization of the site to be treated. Alternatively, the compounds and compositions of the present invention may be used contemporaneously with radiation and/or additional anti-cancer chemical agents (infra). Such systems can avoid repeated administrations of the compounds and compositions of the present invention, increasing convenience to the subject and the physician, and may be particularly suitable for certain compositions of the present invention.

Biological and chemotherapeutics/anti-neoplastic agents and radiation induce apoptosis by activating the extrinsic or intrinsic apoptotic pathways, and, since the compounds and compositions of the present invention relieve antagonists of apoptotic proteins (IAPs) and, thus, remove the block in apoptosis, the combination of chemotherapeutics/anti-neoplastic agents and radiation with the compounds and compositions of the present invention should work synergistically to facilitate apoptosis.

A combination of a compound of the present invention and a chemotherapeutic/anti neoplastic agent and/or radiation therapy of any type that activates the intrinsic pathway may provide a more effective approach to destroying tumor cells. Compounds of the present invention interact with IAP's, such as XIAP, cIAP-1, cIAP-2, ML-IAP, etc., and block the IAP mediated inhibition of apoptosis while chemotherapeutics/ anti neoplastic agents and/or radiation therapy kills actively dividing cells by activating the intrinsic apoptotic pathway leading to apoptosis and cell death. As is described in more detail below, embodiments of the invention provide combinations of a compound of the present invention and a chemotherapeutic/anti-neoplastic agent and/or radiation which provide a synergistic action against unwanted cell proliferation. This synergistic action between a compound of the present invention and a chemotherapeutic/anti-neoplastic agent and/ or radiation therapy can improve the efficiency of the chemotherapeutic/anti-neoplastic agent and/or radiation therapies. This will allow for an increase in the effectiveness of current chemotherapeutic/anti-neoplastic agents or radiation treatments allowing the dose of the chemotherapeutic/anti-neoplastic agent to be lowered, therein providing both a more effective dosing schedule as well as use of a more tolerable dose of chemotherapeutic/anti-neoplastic agent and/or radiation.

In an embodiment of the present invention, the patient is treated by administering a compound or a pharmaceutical composition of the present invention at a time the patient is subject to concurrent or antecedent radiation or chemotherapy for treatment of a neoproliferative pathology of a tumor such as, but not limited to, bladder cancer, breast cancer, prostate cancer, lung cancer, pancreatic cancer, gastric cancer, colon cancer, ovarian cancer, renal cancer, hepatoma, melanoma, lymphoma, sarcoma, and combinations thereof.

In another embodiment of the present invention, the compound or composition of the present invention can be administered in combination with a chemotherapeutic and/or for use in combination with radiotherapy, immunotherapy, and/or photodynamic therapy, promoting apoptosis and enhancing the effectiveness of the chemotherapeutic, radiotherapy, immunotherapy, and/or photodynamic therapy.

Embodiments of the invention also include a method of treating a patient afflicted with cancer by the contemporaneous or concurrent administration of a chemotherapeutic agent. Such chemotherapeutic agents include but are not limited to the chemotherapeutic agents described in "Modern Pharmacology with Clinical Applications", Sixth Edition, Craig & Stitzel, Chpt. 56, pg 639-656 (2004), herein incorporated by reference. The chemotherapeutic agent can be, but is not limited to, alkylating agents, antimetabolites, anti-tumor antibiotics, plant-derived products such as taxanes, enzymes, hormonal agents, miscellaneous agents such as cisplatin, monoclonal antibodies, glucocorticoids, mitotic inhibitors, topoisomerase I inhibitors, topoisomerase II inhibitors, immunomodulating agents such as interferons, cellular growth factors, cytokines, and nonsteroidal anti-inflammatory compounds, cellular growth factors and kinase inhibitors. Other suitable classifications for chemotherapeutic agents include mitotic inhibitors and nonsteroidal anti-estrogenic analogs.

Specific examples of suitable biological and chemotherapeutic agents include, but are not limited to, cisplatin, carmustine (BCNU), 5-fluorouracil (5-FU), cytarabine (Ara-C), gemcitabine, methotrexate, daunorubicin, doxorubicin, dexamethasone, topotecan, etoposide, paclitaxel, vincristine, tamoxifen, TNF-alpha, TRAIL, interferon (in both its alpha and beta forms), thalidomide, and melphalan. Other specific examples of suitable chemotherapeutic agents include nitrogen mustards such as cyclophosphamide, alkyl sulfonates, nitrosoureas, ethylenimines, triazenes, folate antagonists, purine analogs, pyrimidine analogs, anthracyclines, bleomycins, mitomycins, dactinomycins, plicamycin, vinca alkaloids, epipodophyllotoxins, taxanes, glucocorticoids, L-asparaginase, estrogens, androgens, progestins, luteinizing hormones, octreotide actetate, hydroxyurea, procarbazine, mitotane, hexamethylmelamine, carboplatin, mitoxantrone, monoclonal antibodies, levamisole, interferons, interleukins, filgrastim and sargramostim. Chemotherapeutic compositions also comprise other members, i.e., other than TRAIL, of the TNF superfamily of compounds.

Another embodiment of the present invention relates to the use of a compound or composition of the present invention in combination with topoismerase inhibitors to potentiate their apoptotic inducing effect. Topoisomerase inhibitors inhibit DNA replication and repair, thereby promoting apoptosis and have been used as chemothemotherapeutic agents. Topoisomerase inhibitors promote DNA damage by inhibiting the enzymes that are required in the DNA repair process. Therefore, export of Smac from the mitochondria into the cell cytosol is provoked by the DNA damage caused by topoisomerase inhibitors. Topoisomerase inhibitors of both the Type I class (camptothecin, topotecan, SN-38 (irinotecan active metabolite)) and the Type II class (etoposide) are expected to show potent synergy with compounds of the present invention. Further examples of topoisomerase inhibiting agents that may be include, but are not limited to, irinotecan, topotecan, etoposide, amsacrine, exatecan, gimatecan, etc. Other topoisomerase inhibitors include, for example, Aclacinomycin A, camptothecin, daunorubicin, doxorubicin, ellipticine, epirubicin, and mitaxantrone.

In another embodiment of the invention, the chemotherapeutic/anti-neoplastic agent for use in combination with the compounds and compositions of the present invention may be a platinum containing compound. In one embodiment of the invention, the platinum containing compound is cisplatin. Cisplatin can synergize with a compound of the present invention and potentiate the inhibition of an IAP, such as but not limited to XIAP, cIAP-1, c-IAP-2, ML-IAP, etc. In another embodiment a platinum containing compound is carboplatin. Carboplatin can synergize with a compound of the present invention and potentiate the inhibition of an IAP, including, but not limited to, XIAP, cIAP-1, c-IAP-2, ML-IAP, etc. In another embodiment a platinum containing compound is oxaliplatin. The oxaliplatin can synergize with a compound of the present invention and potentiate the inhibition of an IAP, including, but not limited to, XIAP, cIAP-1, c-IAP-2, ML-IAP, etc.

Platinum chemotherapy drugs belong to a general group of DNA modifying agents. DNA modifying agents may be any highly reactive chemical compound that bonds with various nucleophilic groups in nucleic acids and proteins and cause mutagenic, carcinogenic, or cytotoxic effects. DNA modifying agents work by different mechanisms, disruption of DNA function and cell death; DNA damage/the formation of cross-bridges or bonds between atoms in the DNA; and induction of mispairing of the nucleotides leading to mutations, to achieve the same end result. Three non-limiting examples of a platinum containing DNA modifying agents are cisplatin, carboplatin and oxaliplatin.

Cisplatin is believed to kill cancer cells by binding to DNA and interfering with its repair mechanism, eventually leading to cell death. Carboplatin and oxaliplatin are cisplatin derivatives that share the same mechanism of action. Highly reactive platinum complexes are formed intracellularly and inhibit DNA synthesis by covalently binding DNA molecules to form intrastrand and interstrand DNA crosslinks.

Non-steroidal anti-inflammatory drugs (NSAIDs) have been shown to induce apoptosis in colorectal cells. NSAIDs appear to induce apoptosis via the release of Smac from the mitochondria (PNAS, Nov. 30, 2004, vol. 101:16897-16902). Therefore, the use of NSAIDs in combination with the compounds and compositions of the present invention would be expected to increase the activity of each drug over the activity of either drug independently.

Many naturally occurring compounds isolated from bacterial, plant, and animals can display potent and selective biological activity in humans including anticancer and antineoplastic activities. In fact, many natural products, or semi-synthetic derivatives thereof, which possess anticancer activity, are already commonly used as therapeutic agents; these include paclitaxel, etoposide, vincristine, and camptothecin amongst others. Additionally, there are many other classes of natural products such as the indolocarbazoles and epothilones that are undergoing clinical evaluation as anti-cancer agents. A reoccurring structural motif in many natural products is the attachment of one or more sugar residues onto an aglycone core structure. In some instances, the sugar portion of the natural product is critical for making discrete protein-ligand interactions at its site of action (i.e., pharmacodynamics) and removal of the sugar residue results in significant reductions in biological activity. In other cases, the sugar moiety or moieties are important for modulating the physical and pharmacokinetic properties of the molecule. Rebeccamycin and staurosporine are representative of the sugar-linked indolocarbazole family of anticancer natural products with demonstrated anti-kinase and anti-topoisomerase activity.

Taxanes are anti-mitotic, mitotic inhibitors or microtubule polymerization agents. Taxanes are characterized as compounds that promote assembly of microtubules by inhibiting tubulin depolymerization, thereby blocking cell cycle progression through centrosomal impairment, induction of abnormal spindles and suppression of spindle microtubule dynamics. Taxanes include but are not limited to, docetaxel and paclitaxel. The unique mechanism of action of taxane is in contrast to other microtubule poisons, such as Vinca alkaloids, colchicine, and cryptophycines, which inhibit tubulin polymerization. Microtubules are highly dynamic cellular polymers made of alpha-beta-tubulin and associated proteins that play key roles during mitosis by participating in the organization and function of the spindle, assuring the integrity of the segregated DNA. Therefore, they represent an effective target for cancer therapy.

Yet another embodiment of the present invention is the therapeutic combination or the therapeutic use in combination of a compound or composition of the present invention with TRAIL or other chemical or biological agents which bind to and activate the TRAIL receptor(s). TRAIL has received considerable attention recently because of the finding that many cancer cell types are sensitive to TRAIL-induced apoptosis, while most normal cells appear to be resistant to this action of TRAIL. TRAIL-resistant cells may arise by a variety of different mechanisms including loss of the receptor, presence of decoy receptors, or overexpression of FLIP which competes for zymogen caspase-8 binding during DISC formation. In TRAIL resistance, a compound or composition of the present invention may increase tumor cell sensitivity to TRAIL leading to enhanced cell death, the clinical correlations of which are expected to be increased apoptotic activity in TRAIL resistant tumors, improved clinical response, increased response duration, and ultimately, enhanced patient survival rate. In support of this, reduction in XIAP levels by in vitro antisense treatment has been shown to cause sensitization of resistant melanoma cells and renal carcinoma cells to TRAIL (Chawla-Sarkar, et al., 2004). The compounds of the present invention bind to IAPs and inhibit their interaction with caspases, therein potentiating TRAIL-induced apoptosis.

Compounds and compositions of the present invention also can be used to augment radiation therapy (or radiotherapy), i.e., the medical use of ionizing radiation as part of cancer treatment to control malignant cells. Although radiotherapy is often used as part of curative therapy, it is occasionally used as a palliative treatment, where cure is not possible and the aim is for symptomatic relief. Radiotherapy is commonly used for the treatment of tumors. It may be used as the primary therapy. It is also common to combine radiotherapy with surgery and/or chemotherapy. The most common tumors treated with radiotherapy are breast cancer, prostate cancer, rectal cancer, head & neck cancers, gynecological tumors, bladder cancer and lymphoma. Radiation therapy is commonly applied just to the localized area involved with the tumor. Often the radiation fields also include the draining lymph nodes. It is possible but uncommon to give radiotherapy to the whole body, or entire skin surface. Radiation therapy is usually given daily for up to 35-38 fractions (a daily dose is a fraction). These small frequent doses allow healthy cells time to grow back, repairing damage inflicted by the radiation. Three main divisions of radiotherapy are external beam radiotherapy or teletherapy, brachytherapy or sealed source radiotherapy and unsealed source radiotherapy, which are all suitable examples of treatment protocol in the present invention. The differences relate to the position of the radiation source; external is outside the body, while sealed and unsealed source radiotherapy has radioactive material delivered internally. Brachytherapy sealed sources are usually extracted later, while unsealed sources are injected into the body.

Administration of the compounds and compositions of the present invention may occur prior to, concurrently with, or subsequent to the combination treatment protocol. A variety of administration routes are available. The particular mode selected will depend, of course, upon the particular chemotherapeutic drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, inhalation, intra-peritoneal, or parenteral routes. The term "parenteral" includes subcutaneous, intravenous, intramuscular, or infusion. Intravenous or intramuscular routes are particularly suitable for purposes of the present invention.

In further embodiments numbered 1-30 hereafter, the present invention includes

1. A compound of Formula (I):

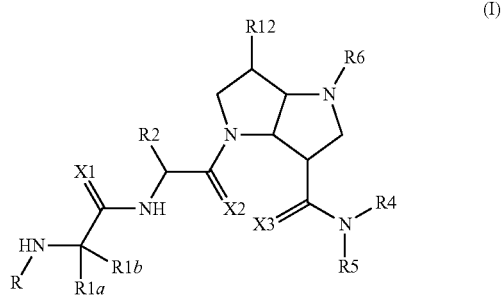

or a pharmaceutically acceptable salt thereof, wherein:
X1, X2 and X3 are each independently O or S:
R is selected from H; alkyl; substituted alkyl; alkenyl; substituted alkenyl; cycloalkyl; substituted cycloalkyl; aryl; substituted aryl; heteroaryl; or substituted heteroaryl;
R1a and R1b are each independently selected from H; alkyl; or substituted alkyl;
R2 is selected from H; alkyl; substituted alkyl; cycloalkyl; substituted cycloalkyl; heterocycloalkyl; substituted heterocycloalkyl; aryl; substituted aryl; heteroaryl; or substituted heteroaryl;
R4 and R5 are each independently selected from H; alkyl; substituted alkyl; cycloalkyl; substituted cycloalkyl; aryl; substituted aryl; heterocycloalkyl; substituted heterocycloalkyl; heteroaryl; or substituted heteroaryl; or R4 and R5 together with the nitrogen to which they are attached represent heterocycloalkyl; or substituted heterocycloalkyl;
R6 is selected from H; alkyl; substituted alkyl; alkoxy; substituted alkoxy; alkylsulfonyl; arylsulfonyl; cycloalkyl; substituted cycloalkyl; heterocycloalkyl; substituted heterocycloalkyl; aryl; substituted aryl; heteroaryl; or substituted heteroaryl; and
R12 is selected from H or hydroxy.

2. The compound of embodiment 1, or a pharmaceutically acceptable salt thereof, wherein:
R is selected from H; alkyl; substituted alkyl; alkenyl; substituted alkenyl; aryl; substituted aryl; cycloalkyl; substituted cycloalkyl; heteroaryl; or substituted heteroaryl; wherein the alkyl, alkenyl, aryl, cycloalkyl, and heteroaryl substitutents are selected from the group consisting of halogen, hydroxy, oxo, mercapto, carboxyl, alkyl, cycloalkyl, aryl, alkoxy, amino, heteroaryl, and nitro;
R1a and R1b are each independently selected from H; alkyl; or substituted alkyl; wherein the alkyl substitutents are selected from the group consisting of halogen, hydroxy, oxo, mercapto, carboxyl, cycloalkyl, aryl, alkoxy, amino, heteroaryl, and nitro;
R2 is selected from alkyl; substituted alkyl, wherein the alkyl substituents are selected from the group consisting of halogen, hydroxy, oxo, alkoxy, cycloalkyl, aryl, heterocycloalkyl and heteroaryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the heteroaryl substituents are selected from the group consisting of halogen, hydroxy, mercapto, carboxyl, alkyl, cycloalkyl, aryl, alkoxy, amino, heteroaryl, and nitro;
R4 and R5 are each independently selected from H; alkyl; substituted alkyl, wherein the alkyl substituents are selected from the groups consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;
R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

3. The compound of embodiment 1 or 2, or a pharmaceutically acceptable salt thereof, wherein:
X1, X2 and X3 are O;
R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;
R1a and R1b are each independently selected from H; alkyl; or substituted alkyl, wherein the substitutents are selected from the group consisting of halogen, hydroxy, oxo, mercapto, carboxyl, alkyl, cyclopropyl, alkoxy, amino, and nitro.
R2 is alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;
R4 and R5 are each independently selected from H; alkyl; substituted alkyl, wherein the alkyl substituents are selected from the group consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

4. The compound of embodiment 1, 2, or 3, or a pharmaceutically acceptable salt thereof, wherein:
R is selected from H or lower alkyl;
R1a and R1b are each independently selected from H or lower alkyl;
R2 is selected from H; lower alkyl; cycloalkyl; or substituted lower alkyl, wherein the substituents are selected from the group consisting of hydroxy, cycloalkyl and alkoxy;
R4 is H or methyl and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;
R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen.

5. The compound of embodiment 1, 2, 3, or 4, or a pharmaceutically acceptable salt thereof, wherein:
R is methyl;
R1a is H and R1b is methyl;
R2 is lower alkyl or cycloalkyl;
R4 is H and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;
R6 is selected from H; methylsulfonyl; substituted lower alkyl, wherein the substituents are selected from the group consisting of oxo, lower alkoxy, —NH$_2$, mono-lower alkyl amino, and heteroaryl optionally substituted with lower alkyl or halogen.

6. The compound of embodiment 1, 2, 3, 4, or 5 wherein:
R is methyl;
R2 is selected from t-butyl or cyclohexyl;
R4 is H and R5 is selected from cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;
R12 is —H.

7. A compound of embodiment 1 having the structure of formula (I-S):

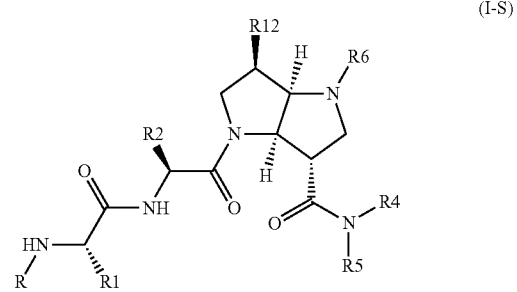

(I-S)

or a pharmaceutically acceptable salt thereof, wherein:
R is selected from H; alkyl; substituted alkyl; alkenyl; substituted alkenyl; cycloalkyl; substituted cycloalkyl; aryl; substituted aryl; heteroaryl; or substituted heteroaryl;
R1 is selected from alkyl or substituted alkyl;
R2 is selected from H; alkyl; substituted alkyl; cycloalkyl; substituted cycloalkyl; heterocycloalkyl; substituted heterocycloalkyl; aryl; substituted aryl; heteroaryl; or substituted heteroaryl;
R4 and R5 are each independently selected from H; alkyl; substituted alkyl; cycloalkyl; substituted cycloalkyl; aryl; substituted aryl; heterocycloalkyl; substituted heterocycloalkyl; heteroaryl; or substituted heteroaryl; or R4 and R5 together with the nitrogen to which they are attached represent heterocycloalkyl, or substituted heterocycloalkyl;

R6 is selected from H; alkylsulfonyl; arylsulfonyl; alkyl; substituted alkyl; alkoxy; substituted alkoxy; cycloalkyl; substituted cycloalkyl; heterocycloalkyl; substituted heterocycloalkyl; aryl; substituted aryl; heteroaryl; or substituted heteroaryl; and R12 is selected from H or hydroxy.

8. A compound of embodiment 7, or a pharmaceutically acceptable salt thereof, wherein:

R is selected from H; alkyl; substituted alkyl; alkenyl; substituted alkenyl; aryl; substituted aryl; cycloalkyl; substituted cycloalkyl; heteroaryl; or substituted heteroaryl; wherein the alkyl, alkenyl, aryl, cycloalkyl and heteroaryl substitutents are selected from the group consisting of halogen, hydroxy, oxo, mercapto, carboxyl, alkyl, cycloalkyl, aryl, alkoxy, amino, heteroaryl, and nitro;

R1 is alkyl; or substituted alkyl, wherein the substitutents are selected from the group consisting of halogen, hydroxy, oxo, mercapto, carboxyl, alkyl, cycloalkyl, aryl, alkoxy, amino, heteroaryl, and nitro;

R2 is alkyl; substituted alkyl, wherein the alkyl substituents are selected from the group consisting of halogen, hydroxy, oxo, alkoxy, cycloalkyl, aryl, heterocycloalkyl and heteroaryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the heteroaryl substituents are selected from the group consisting of halogen, hydroxy, mercapto, carboxyl, alkyl, cycloalkyl, aryl, alkoxy, amino, heteroaryl, and nitro;

R4 and R5 are each independently selected from H; alkyl; substituted alkyl, wherein the alkyl substituents are selected from the group consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

9. A compound of embodiment 7 or 8, or a pharmaceutically acceptable salt thereof, wherein:

R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;

R1 is selected from H; alkyl; or substituted alkyl, wherein the substitutents are selected from the group consisting of halogen, hydroxy, oxo, mercapto, carboxyl, alkyl, cyclopropyl, alkoxy, amino, and nitro.

R2 is selecteyed from alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

R4 and R5 are each independently selected from H; alkyl; substituted alkyl, wherein the alkyl substituents are selected from the groups consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;

R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

10. The compound of embodiment 7, 8, or 9, or a pharmaceutically acceptable salt thereof, wherein:

R is selected from H, or lower alkyl;
R1 is lower alkyl;
R2 is selected from lower alkyl; cycloalkyl; or substituted lower alkyl, wherein the substituents are selected from the group consisting of hydroxy, cycloalkyl and alkoxy;
R4 is H or methyl and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;
R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen.

11. The compound of embodiment 7, 8, 9, or 10, or a pharmaceutically acceptable salt thereof, wherein R is lower alkyl;
R1 is lower alkyl;
R2 is selected from a lower alkyl; a cycloalkyl; or a substituted lower alkyl, wherein the substituents are selected from the group consisting of hydroxy, cycloalkyl and alkoxy;
R4 is H and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl.

12. A compound of embodiment 7, 8, 9, 10, or 11, or a pharmaceutically acceptable salt thereof, wherein R is methyl;
R1 is methyl;
R2 is selected from cyclohexyl, tert-butyl, cyclohexylmethyl, or cyclohexylethyl:
R4 is H and R5 is selected from cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;
R6 is selected from H, methylsulfonyl, cyclopropylcarbonyl, methylcarbonyl, methoxycarbonyl, methylaminocarbonyl, or pyrimidin-2-yl, and
R12 is H.

13. The compound of any of embodiments 1 through 12, or a pharmaceutically acceptable salt thereof, wherein the structure:

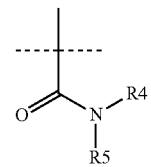

consists of a residue of an L-amino acid or L-amino acid ester.

14. The compound of any of embodiments 1 through 12, or a pharmaceutically acceptable salt thereof, wherein R4 and R5 together with the nitrogen to which they are both attached, are:

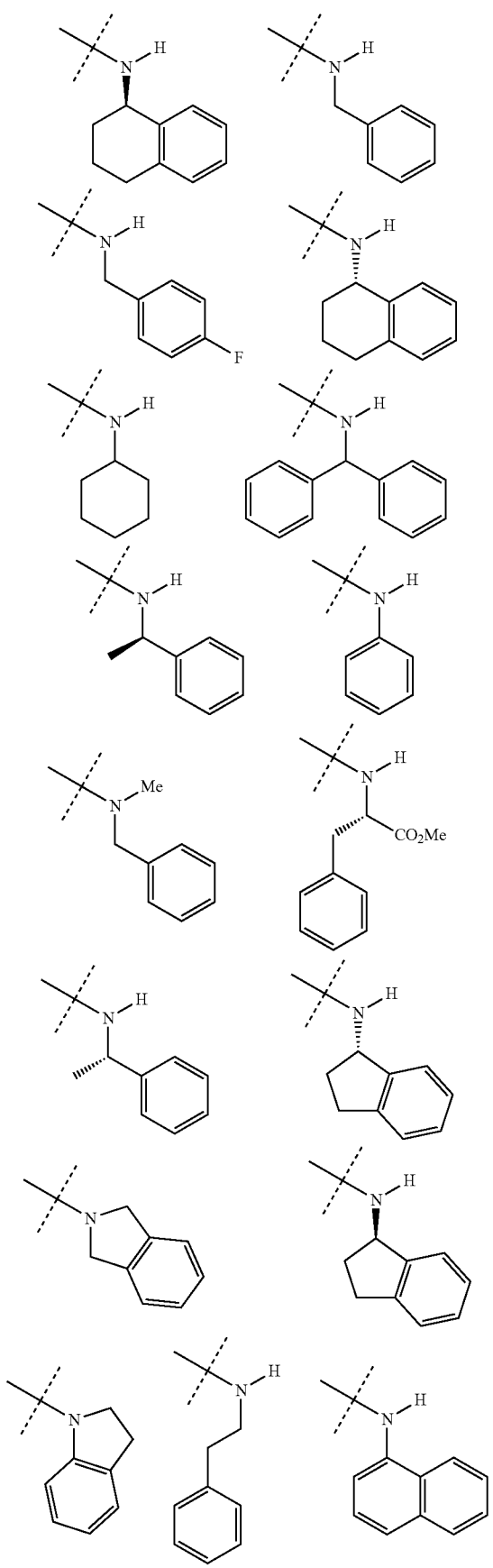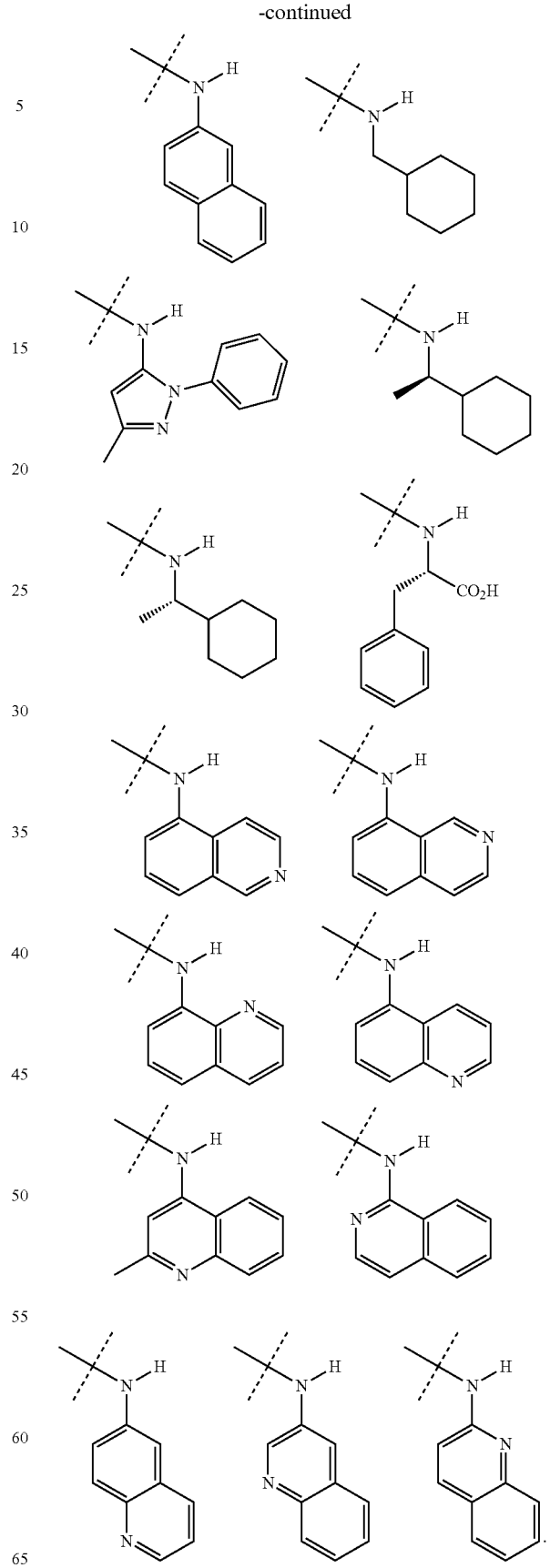

15. The compound of embodiment 1, selected from the group consisting of:
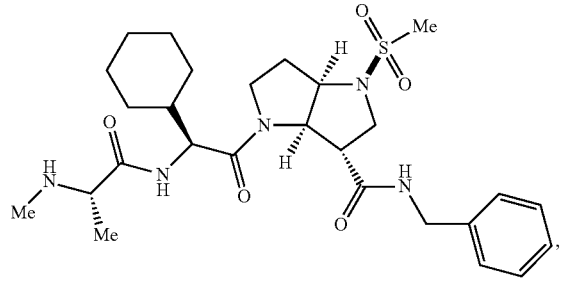
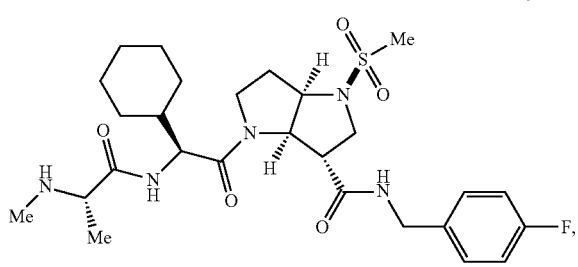
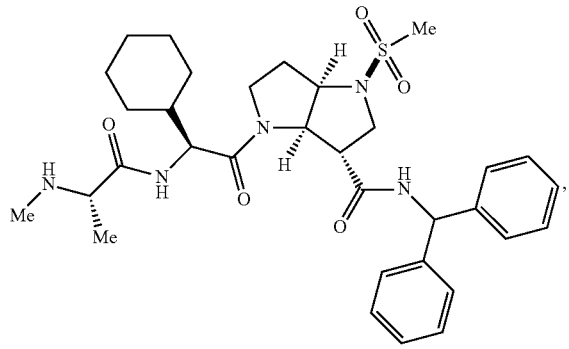
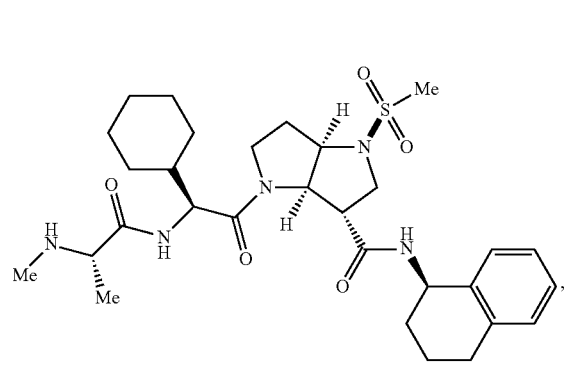
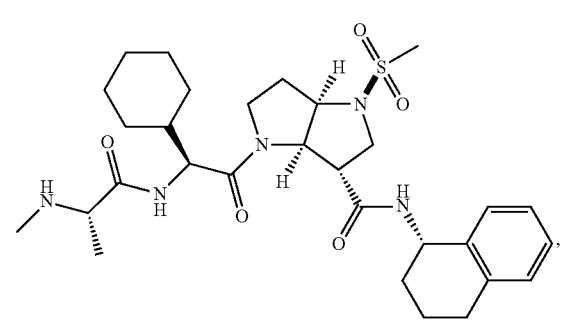
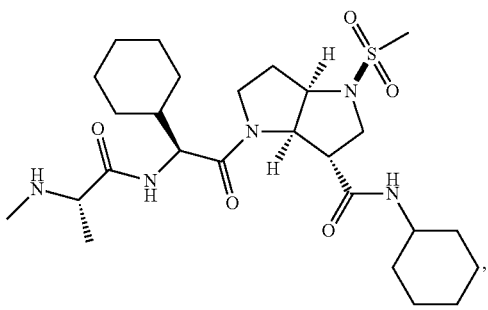
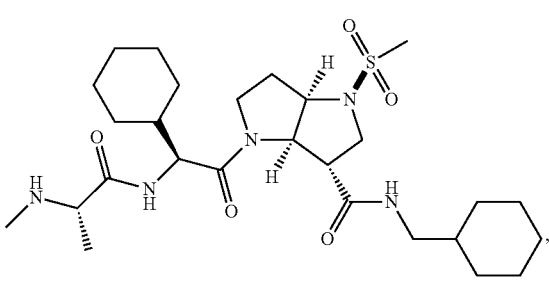
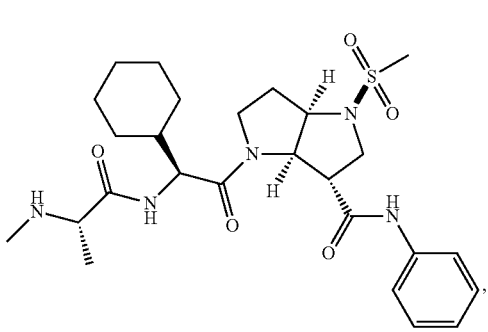
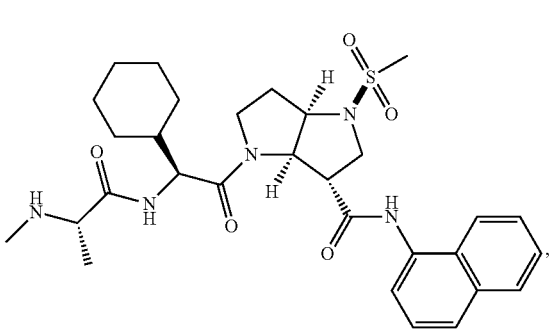
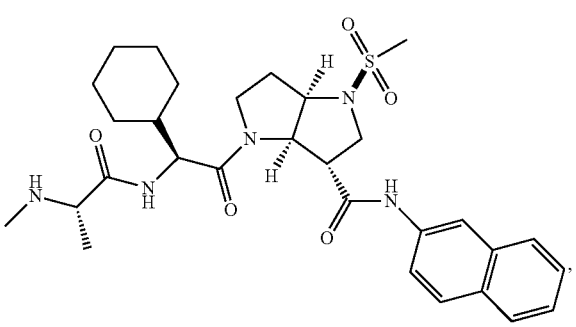

157
-continued
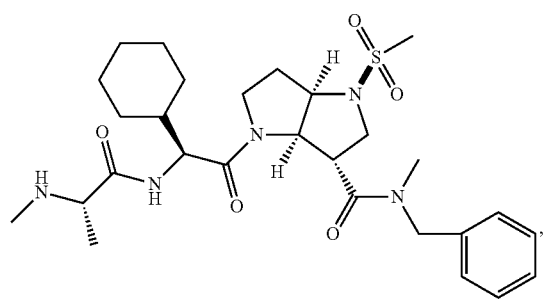
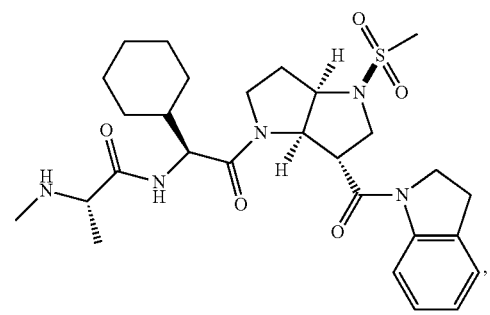
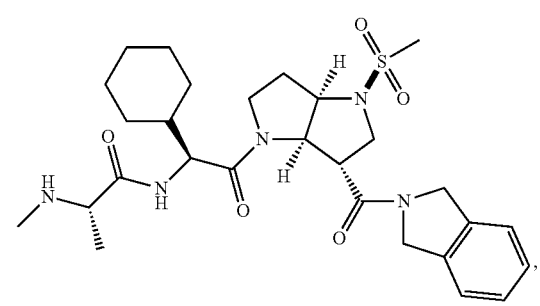
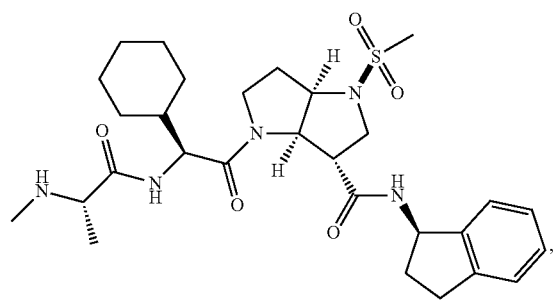
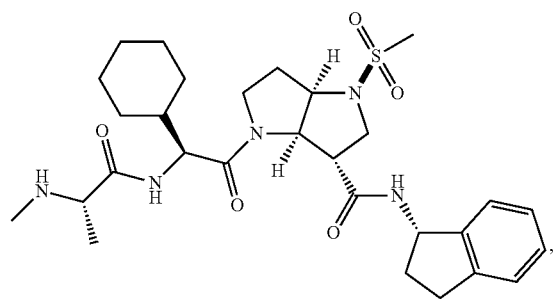
158
-continued
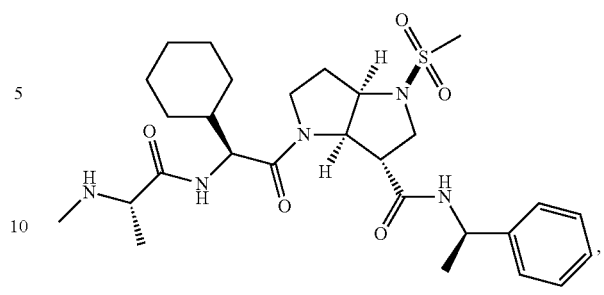
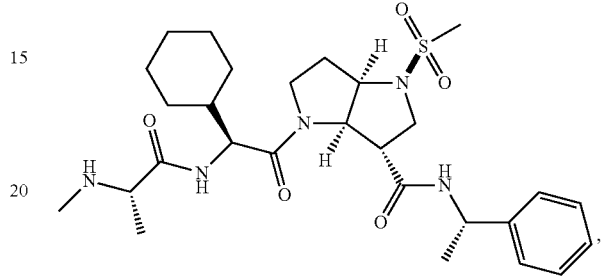
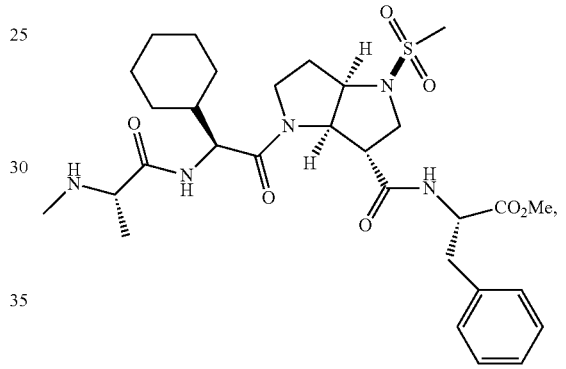
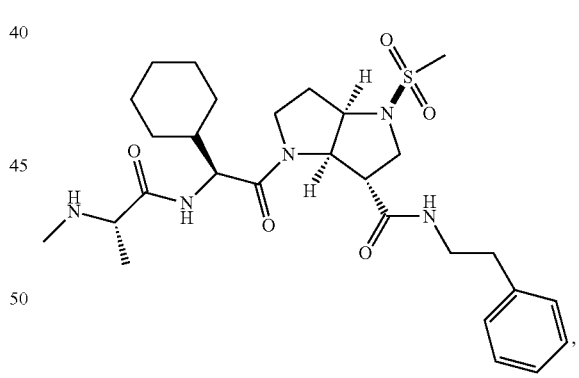
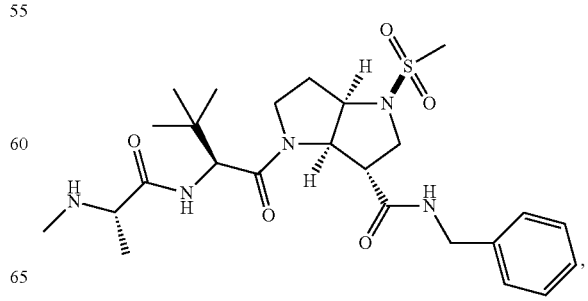

159
-continued
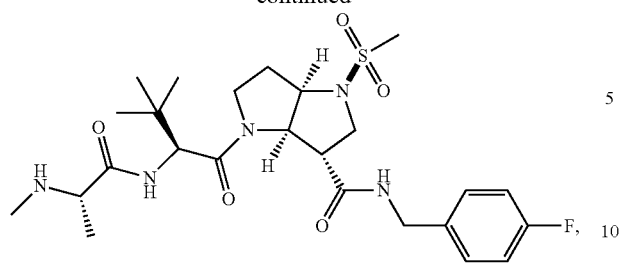
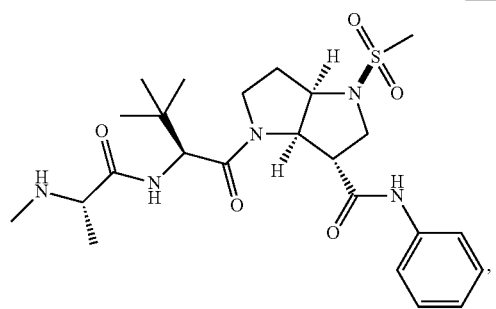
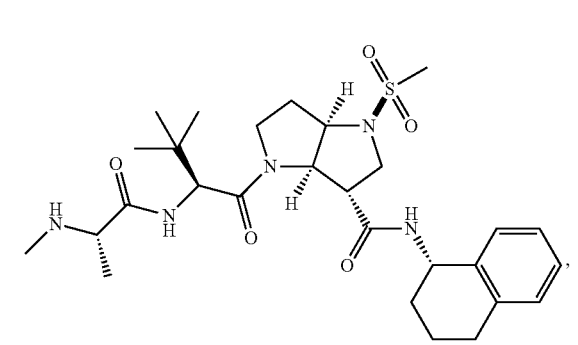
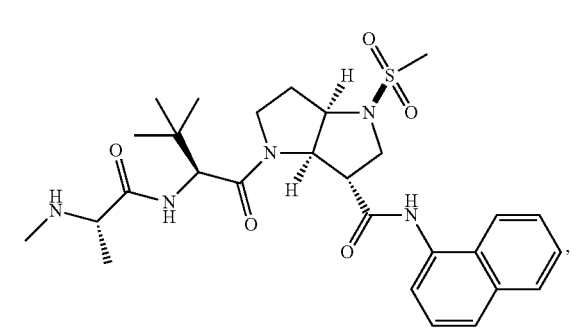
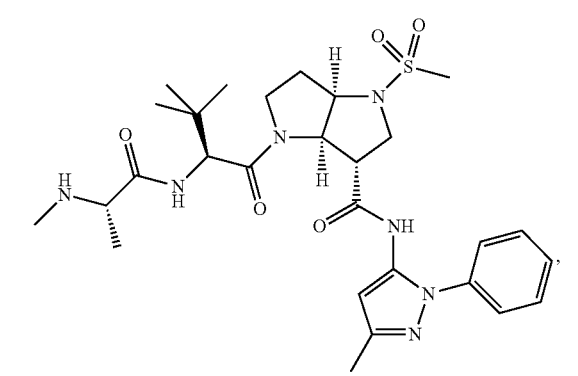
160
-continued
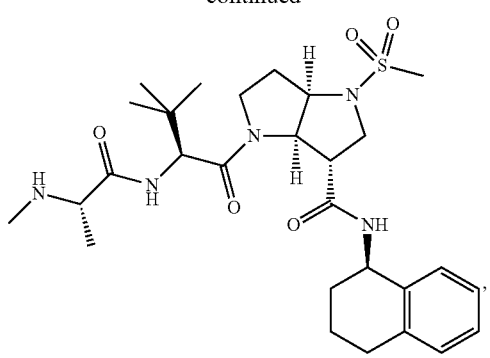
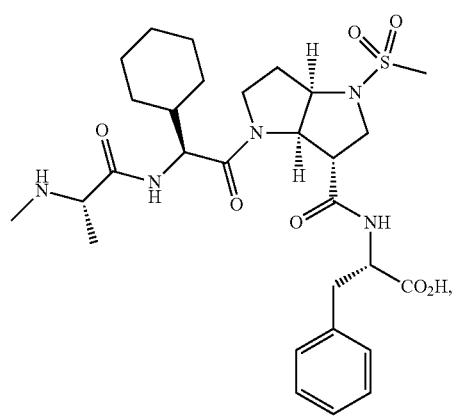
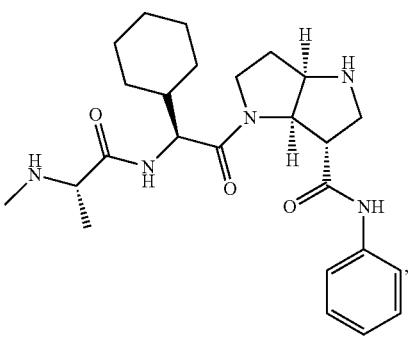
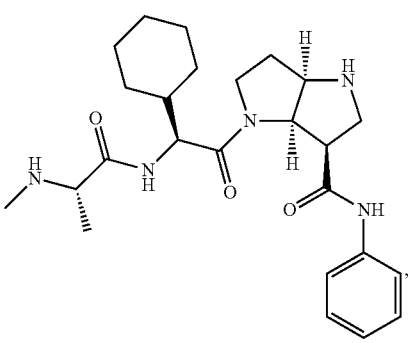

161
-continued
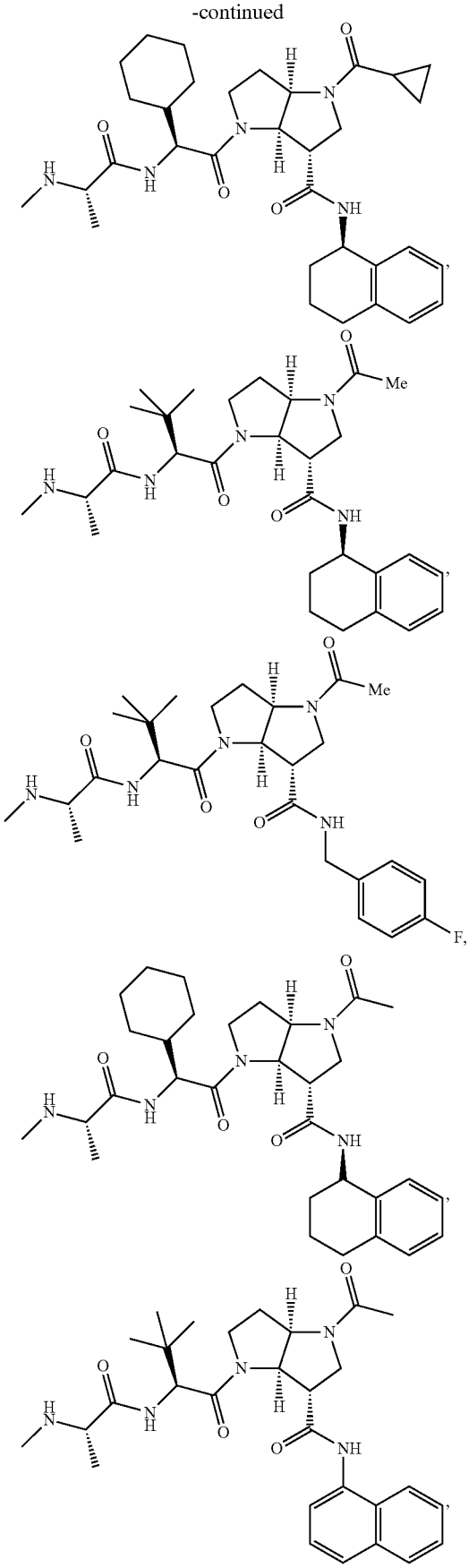
162
-continued
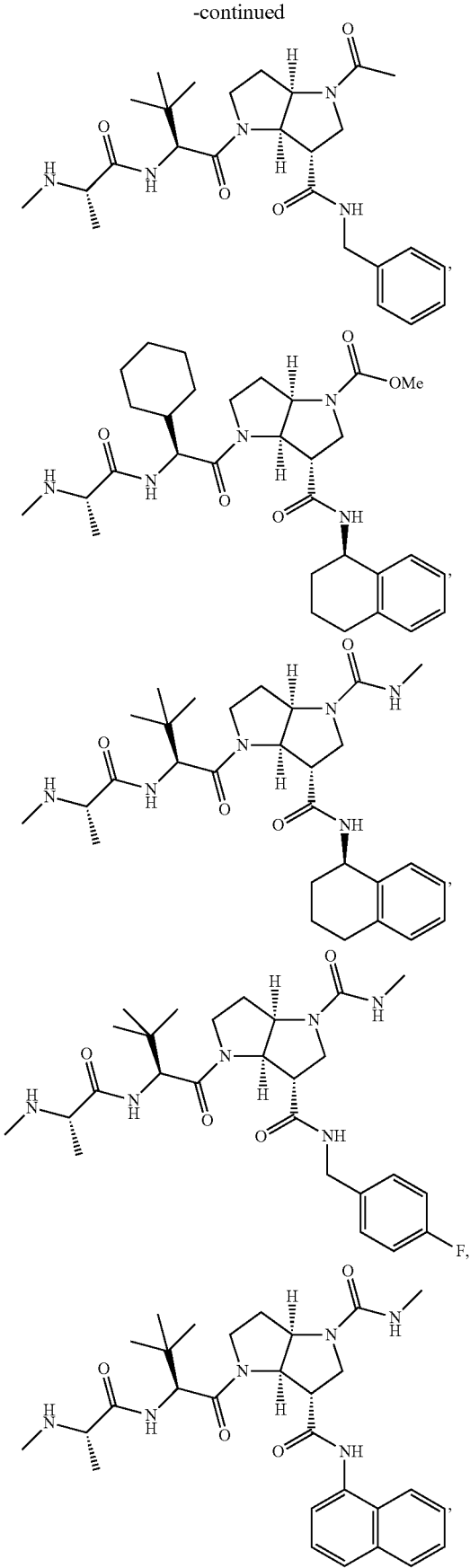

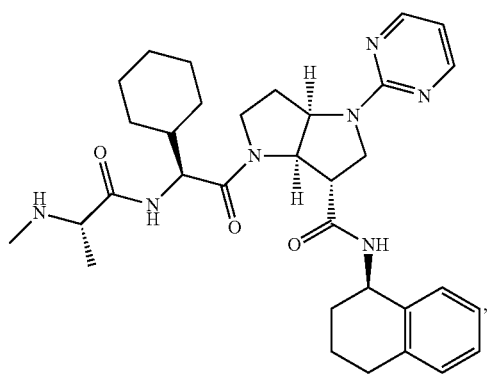
and
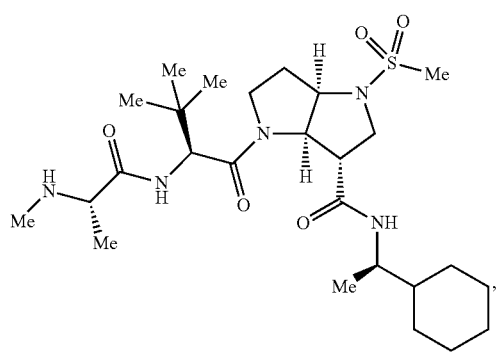
and
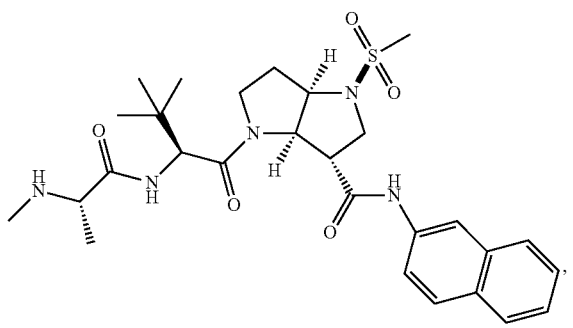
or a pharmaceutically acceptable salt thereof.
16. A compound of embodiment 1, selected from the group consisting of:
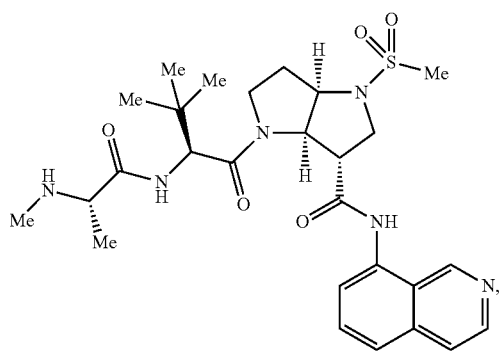
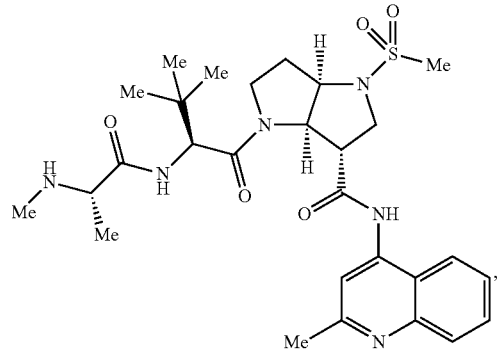

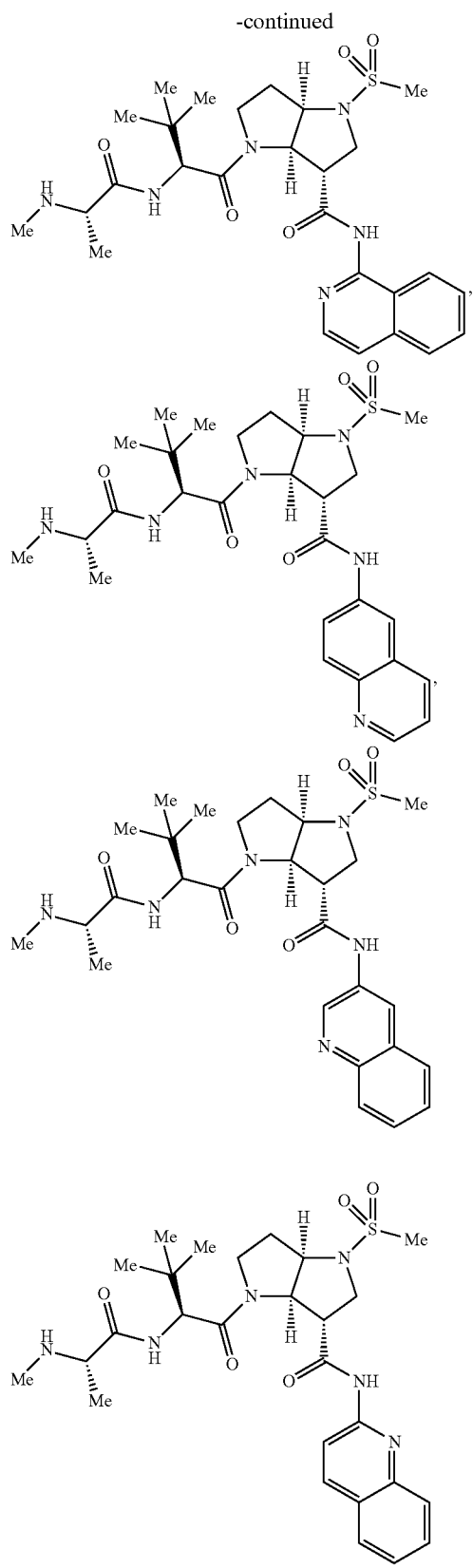

a pharmaceutically acceptable salt thereof.

17. A compound that is a dimer of two monomers of Formula (I) or of two monomers of Formula (I-S) or of one monomer of Formula (I-S) and one monomer of Formula (I-R), or a pharmaceutically acceptable salt of any such dimer, wherein:

X1 is O or S:
X2 is O or S:
X3 is O or S:
R is selected from H; alkyl; substituted alkyl; alkenyl; substituted alkenyl; cycloalkyl; substituted cycloalkyl; aryl; substituted aryl; heteroaryl; or substituted heteroaryl;
R1a is H; alkyl; or substituted alkyl;
R1b is H; alkyl; or substituted alkyl;
R1 is H; alkyl; or substituted alkyl;
both R2 groups together, or both R6 groups together, form -L-, linking the two monomers;
when both R6 groups together form -L-, then each R2 is independently selected from H; alkyl; substituted alkyl; cycloalkyl; substituted cycloalkyl; heterocycloalkyl; substituted heterocycloalkyl; aryl; substituted aryl; heteroaryl; or substituted heteroaryl;
R4 is H; alkyl; substituted alkyl; cycloalkyl; substituted cycloalkyl; aryl; substituted aryl; heterocycloalkyl; substituted heterocycloalkyl; heteroaryl; or substituted heteroaryl and
R5 is H; alkyl; substituted alkyl; cycloalkyl; substituted cycloalkyl; aryl; substituted aryl; heterocycloalkyl; substituted heterocycloalkyl; heteroaryl; or substituted heteroaryl or R4 and R5 together with the nitrogen to which each are attached represent heterocycloalkyl; or substituted heterocycloalkyl;
when both R2 groups together form -L-, each R6 is independently selected from H; alkyl; substituted alkyl; alkoxy; substituted alkoxy; alkylsulfonyl; arylsulfonyl; cycloalkyl; substituted cycloalkyl; heterocycloalkyl; substituted heterocycloalkyl; aryl; substituted aryl; heteroaryl; or substituted heteroaryl; and
R12 is H or hydroxy;
L is a single or double covalent bond or is a contiguous chain, branched or unbranched, substituted or unsubstituted, of 1 to about 100 atoms.

18. The compound of embodiment 17, or a pharmaceutically acceptable salt thereof, wherein:
in R, the alkyl, alkenyl, aryl, cycloalkyl, and heteroaryl substitutents are selected from the group consisting of halogen, hydroxy, oxo, mercapto, carboxyl, alkyl, cycloalkyl, aryl, alkoxy, amino, heteroaryl, and nitro;
in R1a, R1b and R1, the alkyl substitutents are selected from the group consisting of halogen, hydroxy, oxo, mercapto, carboxyl, cycloalkyl, aryl, alkoxy, amino, heteroaryl, and nitro;
in R2, the alkyl substituents are selected from the group consisting of halogen, hydroxy, oxo, alkoxy, cycloalkyl, aryl, heterocycloalkyl and heteroaryl; cycloalkyl; the cycloalkyl substituents are selected from the group consisting of halogen, hydroxy, oxo, mercapto, carboxyl, alkyl, cycloalkyl, aryl, alkoxy, amino, heteroaryl, and nitro; aryl; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro;

in R4, the alkyl substituents are selected from the groups consisting of oxo, alkoxy, carboxy, carboalkoxy, cycloalkyl, aryl, and substituted aryl; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro;

in R5, the alkyl substituents are selected from the groups consisting of oxo, alkoxy, carboxy, carboalkoxy, cycloalkyl, aryl, and substituted aryl; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro;

in R6, the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, oxo, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro.

19. The compound of embodiment 17 or 18, or a pharmaceutically acceptable salt thereof, wherein:

$X_1$, $X_2$ and $X_3$ are O;

R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;

$R_{1a}$ is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

$R_{1b}$ is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

$R_1$ is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

$R_2$ is alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

$R_4$ and $R_5$ are each independently selected from H; alkyl; substituted alkyl, wherein the alkyl substituents are selected from the group consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or $R_4$ and $R_5$ together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;

both $R_6$ groups together form -L-;

L is a single or double covalent bond or is a contiguous chain, branched or unbranched, substituted or unsubstituted, of 1 to 100 atoms.

20. The compound of embodiment 17, 18, or 19, or a pharmaceutically acceptable salt thereof, wherein:

R is selected from H or lower alkyl;

$R_{1a}$ is H or lower alkyl;

$R_{1b}$ is H or lower alkyl;

$R_1$ is H or lower alkyl;

$R_2$ is selected from H; lower alkyl; cycloalkyl; or substituted lower alkyl, wherein the substituents are selected from the group consisting of hydroxy, cycloalkyl and alkoxy;

R4 is H or methyl and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; both R6 groups together form -L-;

L is a single or double covalent bond or is a contiguous chain, branched or unbranched, substituted or unsubstituted, of 1 to 300 atoms.

21. The compound of embodiment 17, 18, 19, or 20, or a pharmaceutically acceptable salt thereof, wherein:
R is methyl;
R1a is H;
R1b is methyl;
R1 is methyl;
R2 is lower alkyl or cycloalkyl;
R4 is H and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;
R6 is selected from H; methylsulfonyl; substituted lower alkyl, wherein the substituents are selected from the group consisting of oxo, lower alkoxy, —NH$_2$, mono-lower alkyl amino, and heteroaryl optionally substituted with lower alkyl or halogen;
L is optionally substituted alkyl, alkylene, alkylyne, cycloalkyl, alkylcycloalkyl, alkylarylalkyl chain of 2 to 20 atoms with 1-3 heteroatoms selected from —O—, —NH— and —S—.

22. The compound of embodiment 17, 18, 19, 20, or 21 wherein:
R1a is —H
R1b is methyl;
R1 is methyl;
R2 is selected from t-butyl or cyclohexyl;
R4 is H and R5 is selected from cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;
R12 is —H;
L is —C(O)CH$_2$NHC(O)C(O)NHCH$_2$C(O)—.

23. The compound of embodiment 17 selected from the group consisting of:

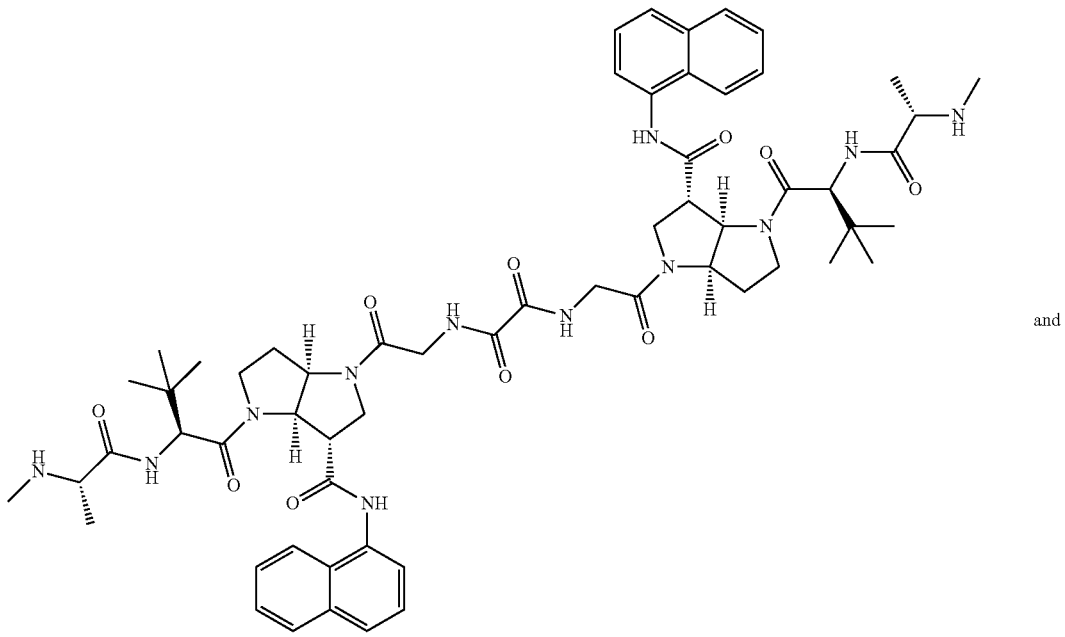

and

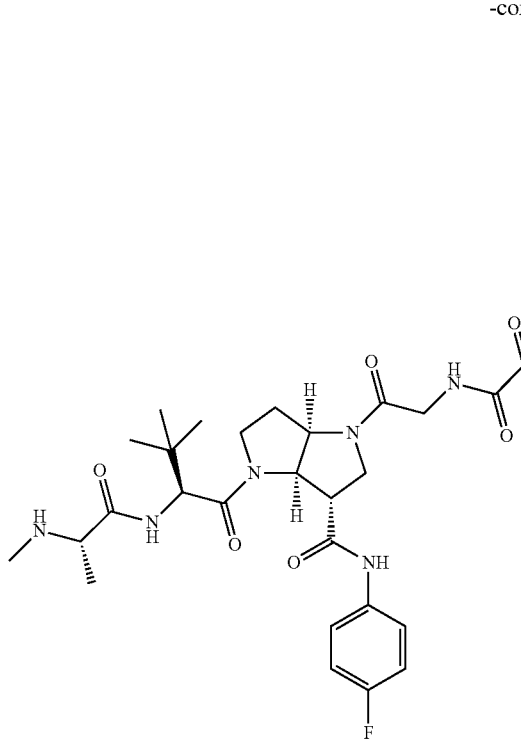

24. A pharmaceutical composition comprising a compound, or a pharmaceutically acceptable salt thereof, selected from any one or more of embodiments 1 to 23 and a pharmaceutically acceptable excipient.
25. A method for inducing apoptosis in a cell comprising contacting the cell with a compound, or a pharmaceutically acceptable salt thereof, selected from any one or more of embodiments 1 to 23, in an amount sufficient to induce apoptosis in the cell.
26. The method of embodiment 25 wherein the cell is a cancer cell.
27. A method of treating cancer selected from the group consisting of; sarcomas, bladder cancers, ovarian cancers, breast cancers, brain cancers, pancreatic cancers, colon cancers, blood cancers, skin cancers, lung cancers and bone cancers, the method comprising administering a therapeutically effective amount of a compound, or a pharmaceutically acceptable salt thereof, selected from any one or more of embodiments 1 to 23, to a patient in need thereof.
28. The method of embodiment 27 wherein the cancers are selected from the group consisting of colorectal cancer, renal carcinoma, ovarian carcinoma, pancreatic carcinoma, prostate carcinoma, breast carcinoma, melanoma, glioblastoma, acute myeloid leukemia (AML), small cell lung carcinoma, non-small cell lung carcinoma, rhabdomyosarcoma, and basal cell carcinoma.
29. The method of embodiment 27 further comprising administering a second therapy selected from radiation, chemotherapy, immunotherapy, photodynamic therapy, or combinations thereof.
30. A method of treating an autoimmune disease selected from the group consisting of; systemic lupus erythematosus, psoriasis and idiopathic thrombocytopenic purpura (Morbus Werlhof); the method comprising administering a therapeutically effective amount of a compound, or a pharmaceutically acceptable salt thereof, selected from any one or more of embodiments 1 to 23, to a patient in need thereof.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:
1. A compound of Formula (I):

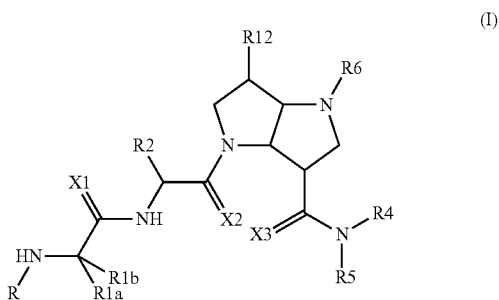

or a pharmaceutically acceptable salt thereof, wherein:
X1, X2 and X3 are each independently O or S:
R is selected from H; alkyl; substituted alkyl; alkenyl; substituted alkenyl; cycloalkyl; substituted cycloalkyl; aryl; substituted aryl; heteroaryl; or substituted heteroaryl;
R1a and R1b are each independently selected from H; alkyl; or substituted alkyl;

R2 is selected from H; alkyl; substituted alkyl; cycloalkyl; substituted cycloalkyl; heterocycloalkyl; substituted heterocycloalkyl; aryl; substituted aryl; heteroaryl; or substituted heteroaryl;

R4 and R5 are each independently selected from H; alkyl; substituted alkyl; cycloalkyl; substituted cycloalkyl; aryl; substituted aryl; heterocycloalkyl; substituted heterocycloalkyl; heteroaryl; or substituted heteroaryl; or R4 and R5 together with the nitrogen to which they are attached represent heterocycloalkyl; or substituted heterocycloalkyl;

R6 is selected from H; alkyl; substituted alkyl; alkoxy; substituted alkoxy; alkylsulfonyl; arylsulfonyl; cycloalkyl; substituted cycloalkyl; heterocycloalkyl; substituted heterocycloalkyl; aryl; substituted aryl; heteroaryl; or substituted heteroaryl; and R12 is selected from H or hydroxy.

2. The compound of claim 1, or a pharmaceutically acceptable salt thereof, wherein:

R is selected from H; alkyl; substituted alkyl; alkenyl; substituted alkenyl; aryl; substituted aryl; cycloalkyl; substituted cycloalkyl; heteroaryl; or substituted heteroaryl; wherein the alkyl, alkenyl, aryl, cycloalkyl, and heteroaryl substitutents are selected from the group consisting of halogen, hydroxy, oxo, mercapto, carboxyl, alkyl, cycloalkyl, aryl, alkoxy, amino, heteroaryl, and nitro;

R1a and R1b are each independently selected from H; alkyl; or substituted alkyl; wherein the alkyl substituents are selected from the group consisting of halogen, hydroxy, oxo, mercapto, carboxyl, cycloalkyl, aryl, alkoxy, amino, heteroaryl, and nitro;

R2 is selected from alkyl; substituted alkyl, wherein the alkyl substituents are selected from the group consisting of halogen, hydroxy, oxo, alkoxy, cycloalkyl, aryl, heterocycloalkyl and heteroaryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the heteroaryl substituents are selected from the group consisting of halogen, hydroxy, mercapto, carboxyl, alkyl, cycloalkyl, aryl, alkoxy, amino, heteroaryl, and nitro;

R4 and R5 are each independently selected from H; alkyl; substituted alkyl, wherein the alkyl substituents are selected from the groups consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; and R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

3. The compound of claim 1, or a pharmaceutically acceptable salt thereof, wherein:

X1, X2 and X3 are O;

R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;

R1a and R1b are each independently selected from H; alkyl; or substituted alkyl, wherein the substitutents are selected from the group consisting of halogen, hydroxy, oxo, mercapto, carboxyl, alkyl, cyclopropyl, alkoxy, amino, and nitro;

R2 is alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

R4 and R5 are each independently selected from H; alkyl; substituted alkyl, wherein the alkyl substituents are selected from the group consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; and R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

4. The compound of claim 1, or a pharmaceutically acceptable salt thereof, wherein:
R is selected from H or lower alkyl;
R1a and R1b are each independently selected from H or lower alkyl;
R2 is selected from H; lower alkyl; cycloalkyl; or substituted lower alkyl, wherein the substituents are selected from the group consisting of hydroxy, cycloalkyl and alkoxy;
R4 is H or methyl and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; and R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen.

5. The compound of claim 2, or a pharmaceutically acceptable salt thereof, wherein:
R is methyl;
R1a is H and R1b is methyl;
R2 is lower alkyl or cycloalkyl;
R4 is H and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl; and R6 is selected from H; methylsulfonyl; substituted lower alkyl, wherein the substituents are selected from the group consisting of oxo, lower alkoxy, —NH2, mono-lower alkyl amino, and heteroaryl optionally substituted with lower alkyl or halogen.

6. The compound of claim 5 wherein:
R is methyl;
R2 is selected from t-butyl or cyclohexyl;
R4 is H and R5 is selected from cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl; and
R12 is —H.

7. A compound of claim 1 having the structure of formula (I-S):

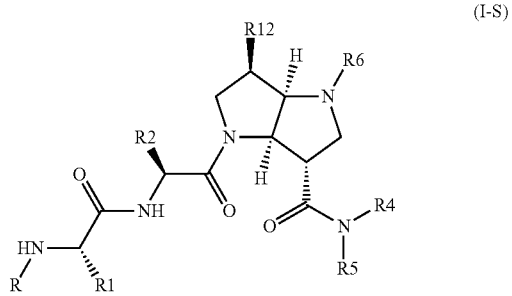

or a pharmaceutically acceptable salt thereof, wherein:
R is selected from H; alkyl; substituted alkyl; alkenyl; substituted alkenyl; cycloalkyl; substituted cycloalkyl; aryl; substituted aryl; heteroaryl; or substituted heteroaryl;
R1 is selected from alkyl or substituted alkyl;

R2 is selected from H; alkyl; substituted alkyl; cycloalkyl; substituted cycloalkyl; heterocycloalkyl; substituted heterocycloalkyl; aryl; substituted aryl; heteroaryl; or substituted heteroaryl;

R4 and R5 are each independently selected from H; alkyl; substituted alkyl; cycloalkyl; substituted cycloalkyl; aryl; substituted aryl; heterocycloalkyl; substituted heterocycloalkyl; heteroaryl; or substituted heteroaryl; or R4 and R5 together with the nitrogen to which they are attached represent heterocycloalkyl, or substituted heterocycloalkyl;

R6 is selected from H; alkylsulfonyl; arylsulfonyl; alkyl; substituted alkyl; alkoxy; substituted alkoxy; cycloalkyl; substituted cycloalkyl; heterocycloalkyl; substituted heterocycloalkyl; aryl; substituted aryl; heteroaryl; or substituted heteroaryl; and R12 is selected from H or hydroxy.

8. A compound of claim 7, or a pharmaceutically acceptable salt thereof, wherein:

R is selected from H; alkyl; substituted alkyl; alkenyl; substituted alkenyl; aryl; substituted aryl; cycloalkyl; substituted cycloalkyl; heteroaryl; or substituted heteroaryl; wherein the alkyl, alkenyl, aryl, cycloalkyl and heteroaryl substituents are selected from the group consisting of halogen, hydroxy, oxo, mercapto, carboxyl, alkyl, cycloalkyl, aryl, alkoxy, amino, heteroaryl, and nitro;

R1 is alkyl; or substituted alkyl, wherein the substituents are selected from the group consisting of halogen, hydroxy, oxo, mercapto, carboxyl, alkyl, cycloalkyl, aryl, alkoxy, amino, heteroaryl, and nitro;

R2 is alkyl; substituted alkyl, wherein the alkyl substituents are selected from the group consisting of halogen, hydroxy, oxo, alkoxy, cycloalkyl, aryl, heterocycloalkyl and heteroaryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl wherein the heteroaryl substituents are selected from the group consisting of halogen, hydroxy, mercapto, carboxyl, alkyl, cycloalkyl, aryl, alkoxy, amino, heteroaryl, and nitro;

R4 and R5 are each independently selected from H; alkyl; substituted alkyl, wherein the alkyl substituents are selected from the group consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; and R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

9. A compound of claim 7, or a pharmaceutically acceptable salt thereof, wherein:

R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;

R1 is selected from H; alkyl; or substituted alkyl, wherein the substitutents are selected from the group consisting of halogen, hydroxy, oxo, mercapto, carboxyl, alkyl, cyclopropyl, alkoxy, amino, and nitro;

R2 is selected from alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

R4 and R5 are each independently selected from H; alkyl; substituted alkyl, wherein the alkyl substituents are selected from the groups consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl;

heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; and R6 is selected from H; alkylsulfonyl; arylsulfonyl; alkyl; substituted alkyl, wherein the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; alkoxy; substituted alkoxy, wherein the alkoxy substituents are selected from the groups consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heterocycloalkyl; substituted heterocycloalkyl, wherein the heterocycloalkyl substituents are selected from the group consisting of halogen, hydroxy, oxo, mercapto, carboxyl, alkyl, cycloalkyl, aryl, alkoxy, amino, heteroaryl, and nitro; heteroaryl; or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro.

10. The compound of claim 9, or a pharmaceutically acceptable salt thereof, wherein:

R is selected from H, or lower alkyl;

R1 is lower alkyl;

R2 is selected from lower alkyl; cycloalkyl; or substituted lower alkyl, wherein the substituents are selected from the group consisting of hydroxy, cycloalkyl and alkoxy;

R4 is H or methyl and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; and R6 is selected from H; lower alkylsulfonyl; alkyl; substituted alkyl, wherein the alkyl substituents are selected from the group consisting of hydroxy, oxo, halogen, alkoxy, cycloalkyl, aryl, and heteroaryl optionally substituted with lower alkyl or halogen; cycloalkyl; or heteroaryl optionally substituted with lower alkyl or halogen.

11. The compound of claim 10, or a pharmaceutically acceptable salt thereof, wherein R is lower alkyl;

R1 is lower alkyl;

R2 is selected from a lower alkyl; a cycloalkyl; or a substituted lower alkyl, wherein the substituents are selected from the group consisting of hydroxy, cycloalkyl and alkoxy;

R4 is H and

R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl;

or R4 and R5 together with the nitrogen to which they are attached represent indolinyl or isoindolinyl.

12. A compound of claim 11, or a pharmaceutically acceptable salt thereof, wherein R is methyl;

R1 is methyl;

R2 is selected from cyclohexyl, tert-butyl, cyclohexylmethyl, or cyclohexylethyl:

R4 is H;

R5 is selected from cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;

R6 is selected from H, methylsulfonyl, cyclopropylcarbonyl, methylcarbonyl, methoxycarbonyl, methylaminocarbonyl, or pyrimidin-2-yl: and R12 is H.

13. The compound of claim 1, or a pharmaceutically acceptable salt thereof, wherein the structure:

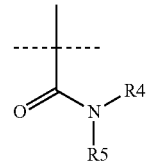

consists of a residue of an L-amino acid or an L-amino acid ester.

14. The compound of claim 1, or a pharmaceutically acceptable salt thereof, wherein R4 and R5 together with the nitrogen to which they are both attached, are:

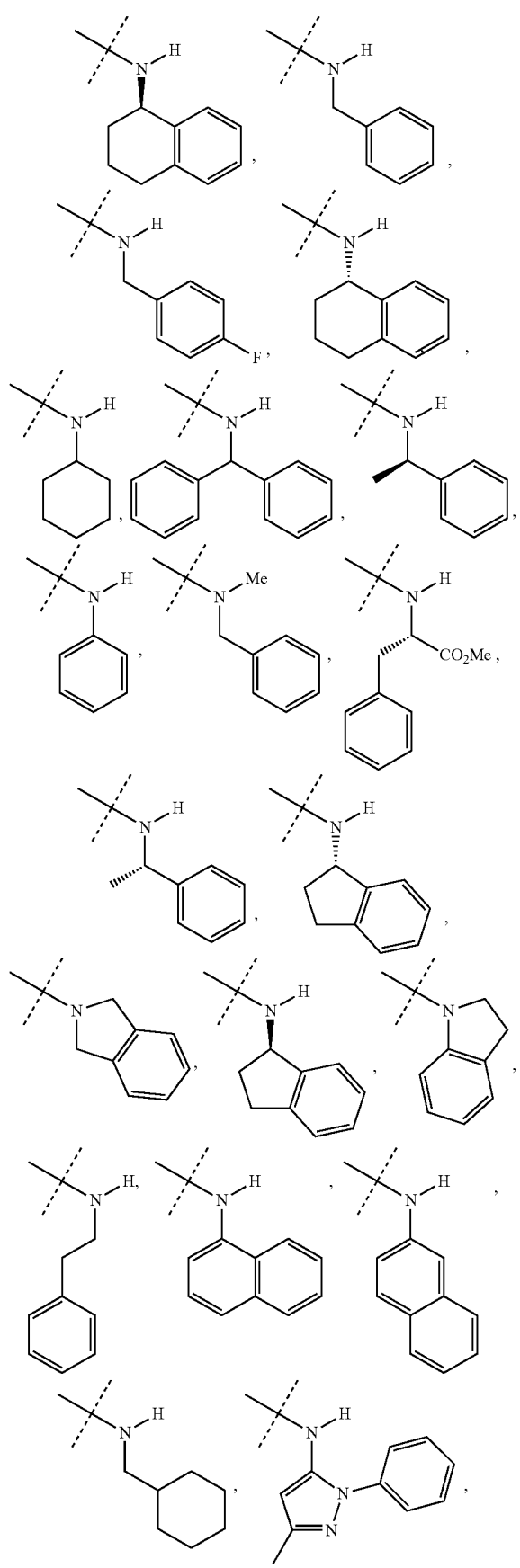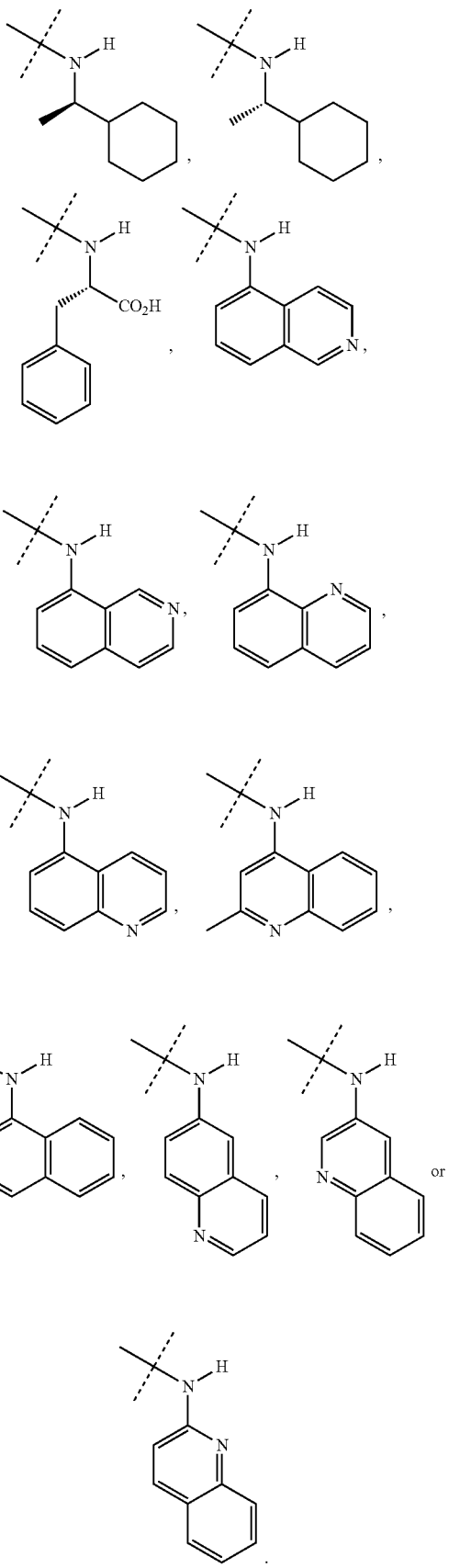

15. The compound of claim 1, selected from the group consisting of:
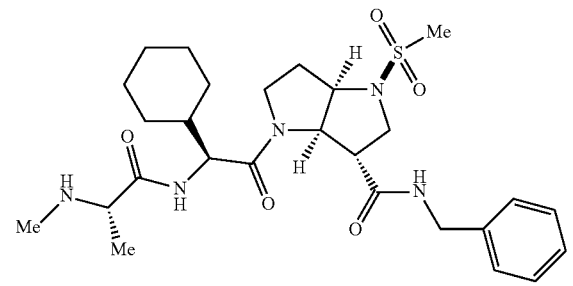
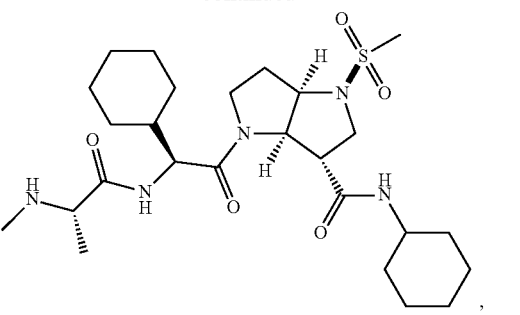
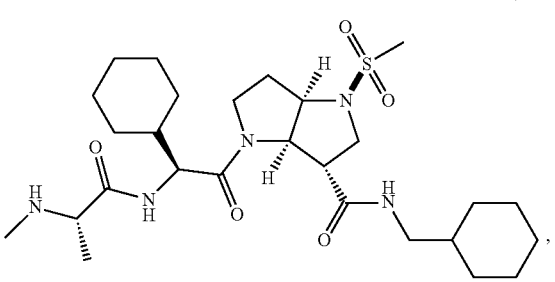
-continued
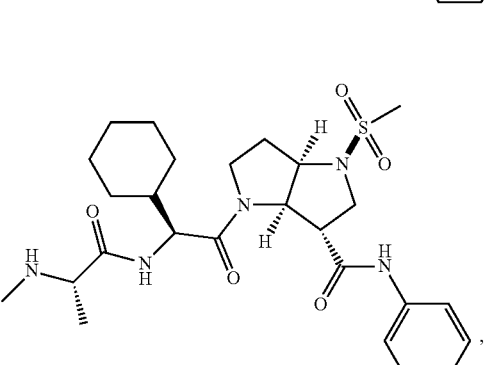
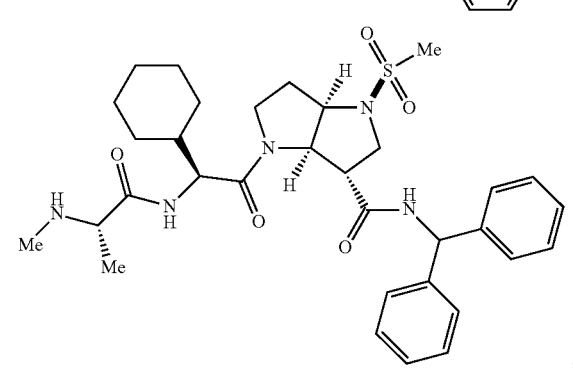
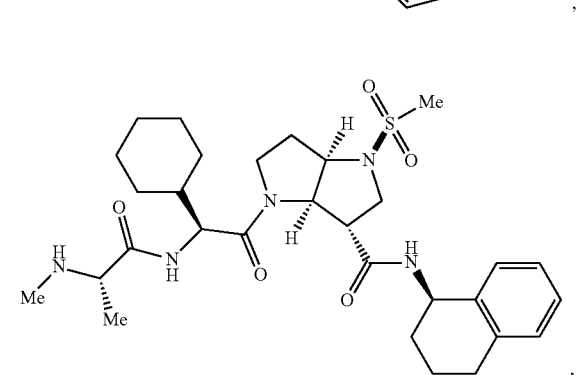
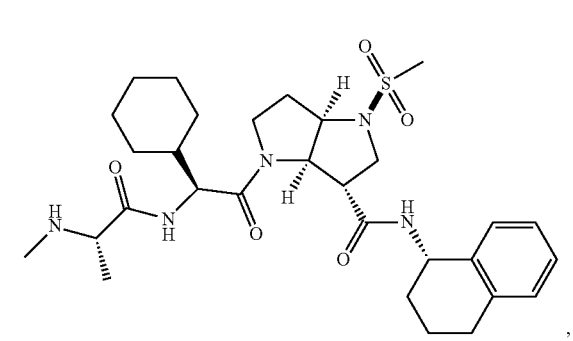

185
-continued
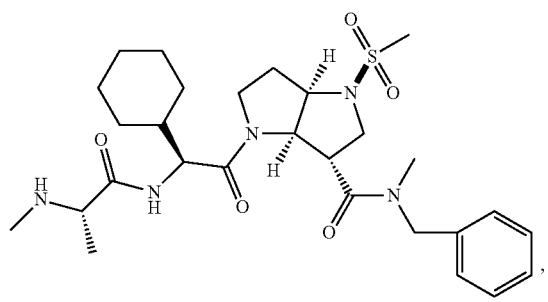
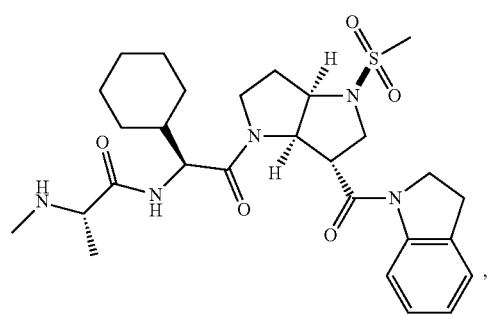
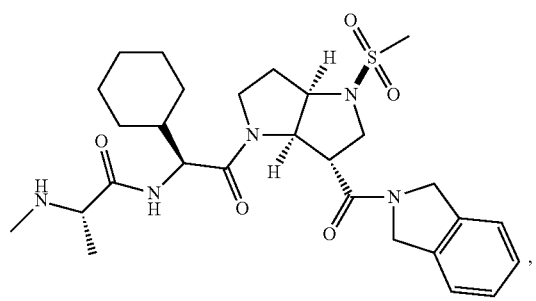
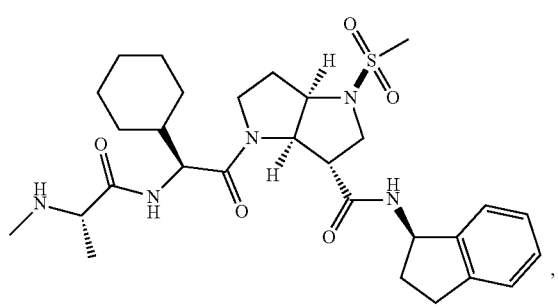
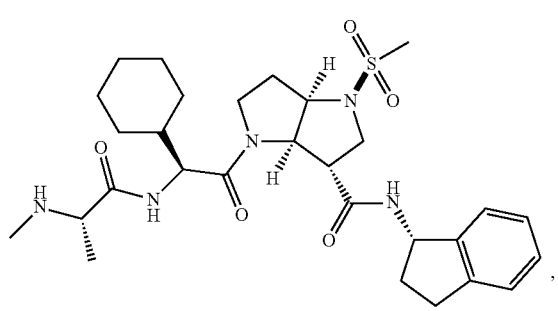
186
-continued
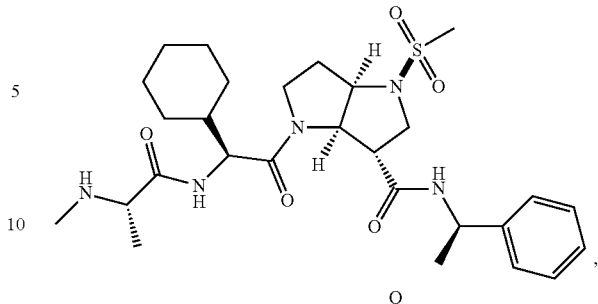
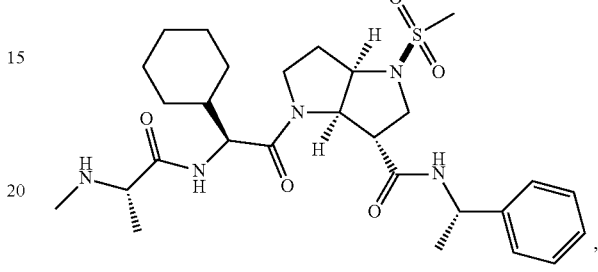
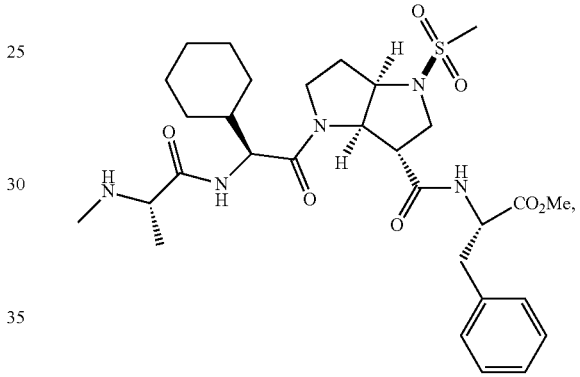
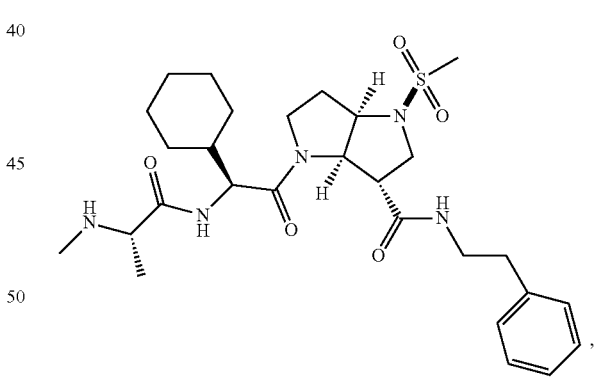
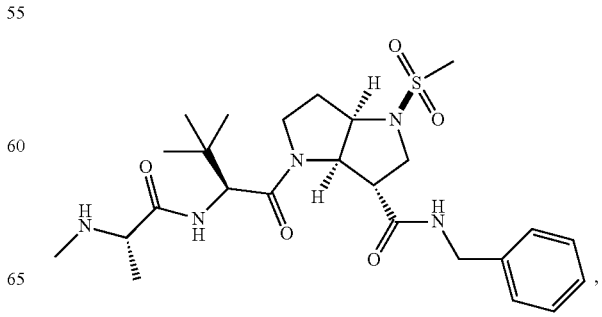

187
-continued
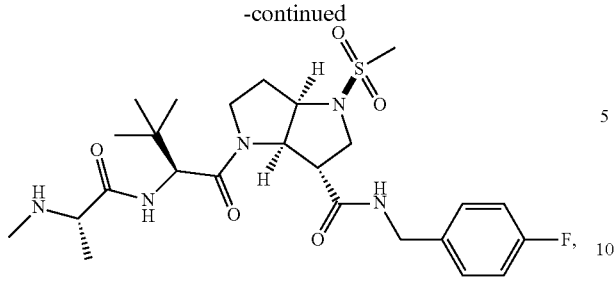
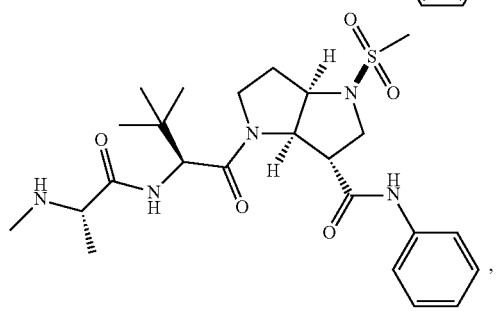
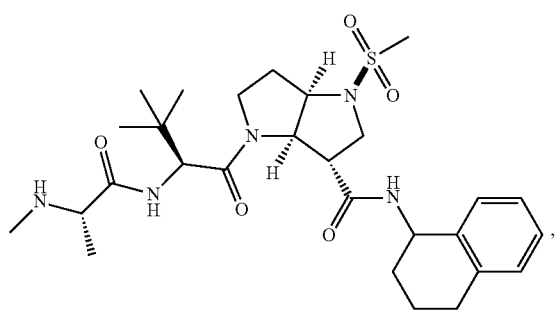
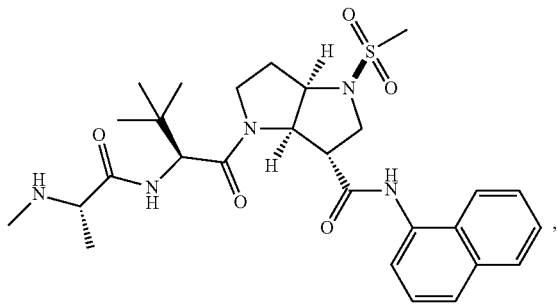
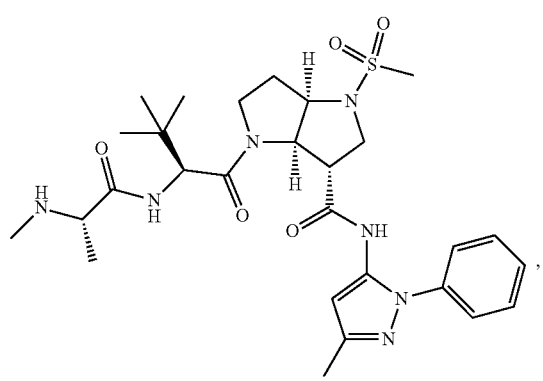
188
-continued
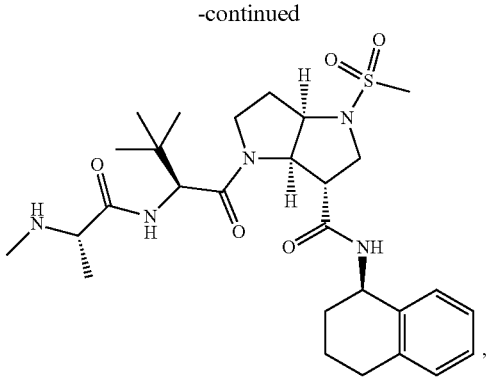
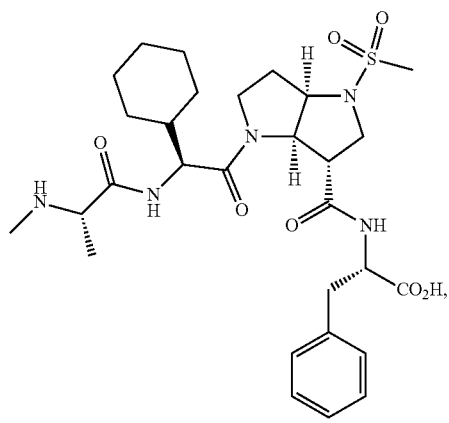
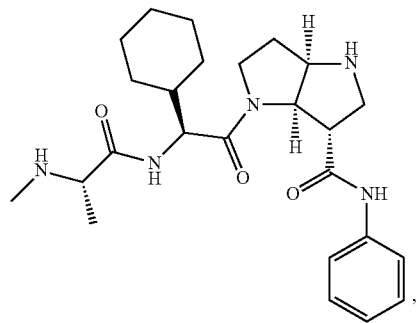
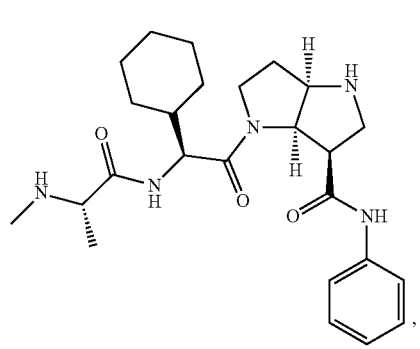

189
-continued
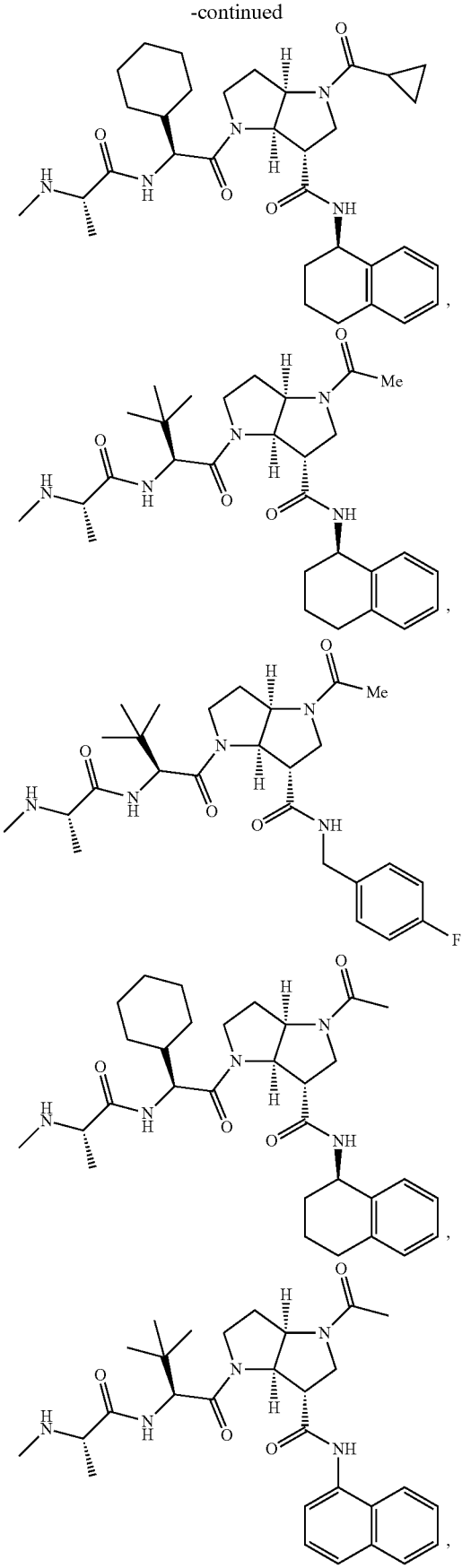
190
-continued
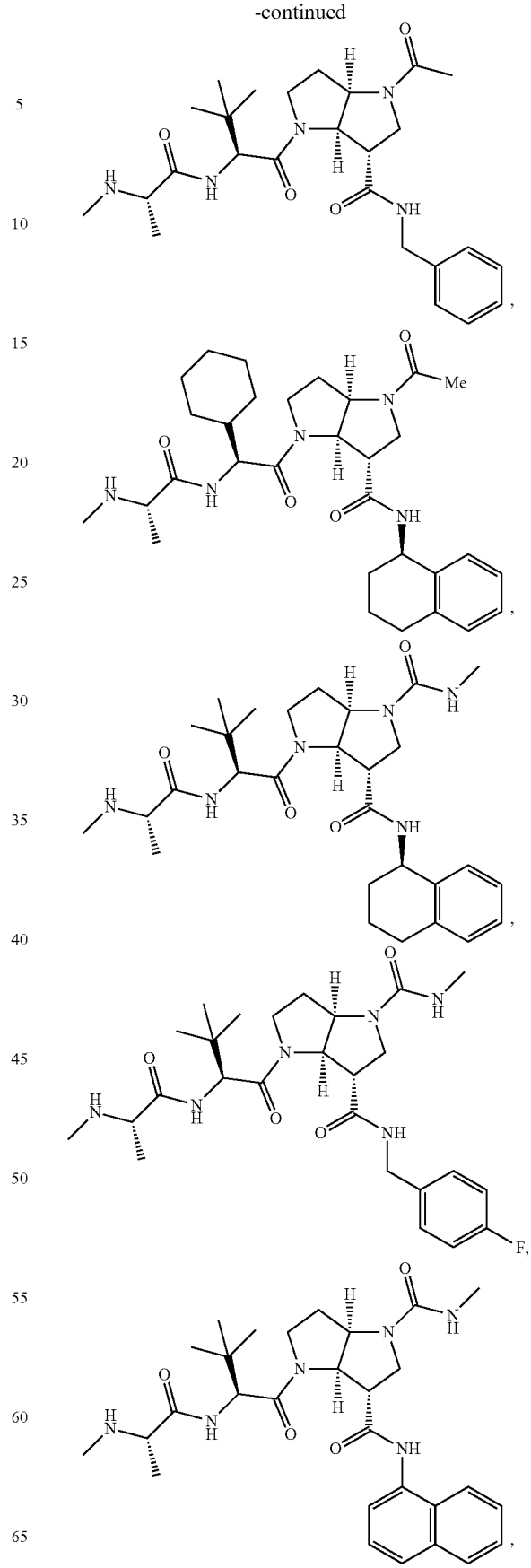

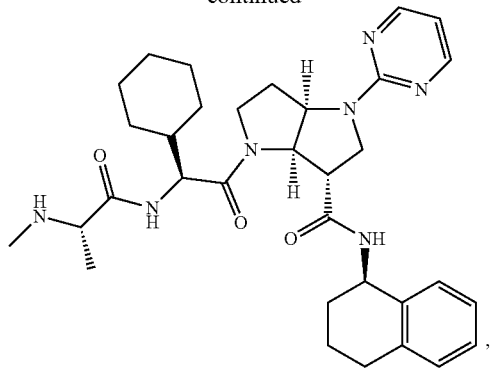
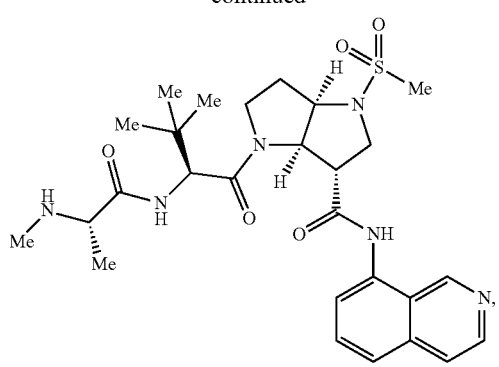
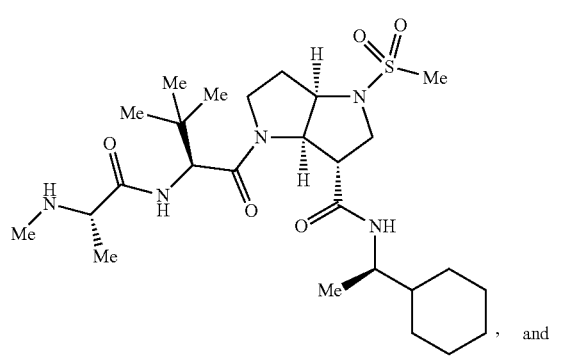
, and
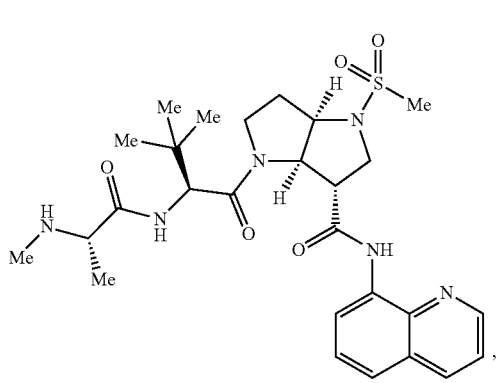
,
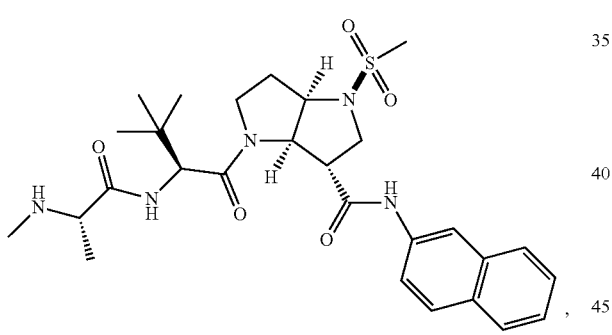
,
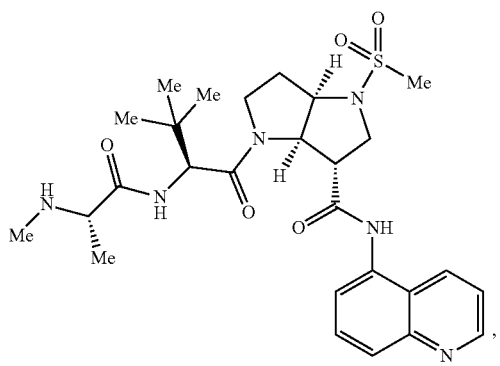
,
or a pharmaceutically acceptable salt thereof.
16. A compound of claim 1, selected from the group consisting of:
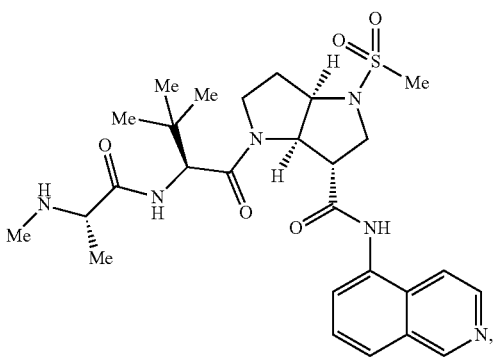
,
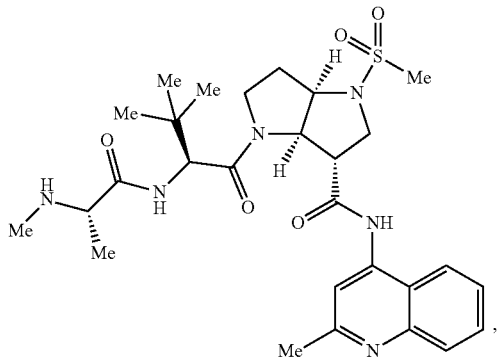
, -continued

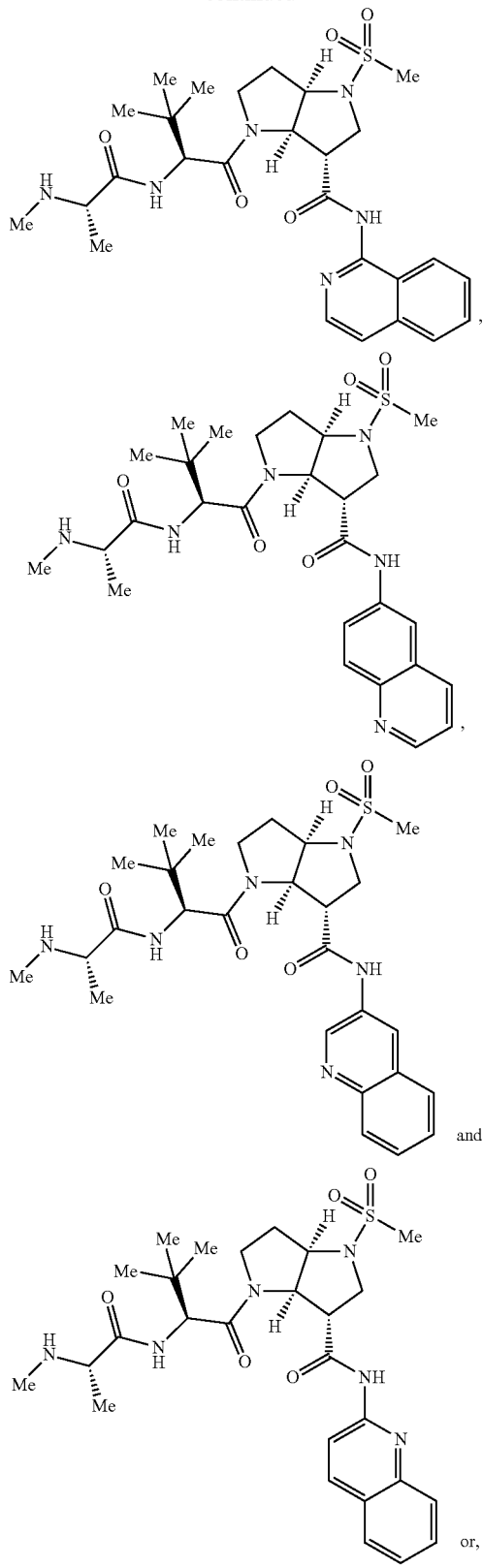

a pharmaceutically acceptable salt thereof.

17. A compound that is a dimer of two monomers of Formula (I), or of two monomers of Formula (I-S), or of one monomer of Formula (I-S) and one monomer of Formula (I-R), or a pharmaceutically acceptable salt of any such dimer,

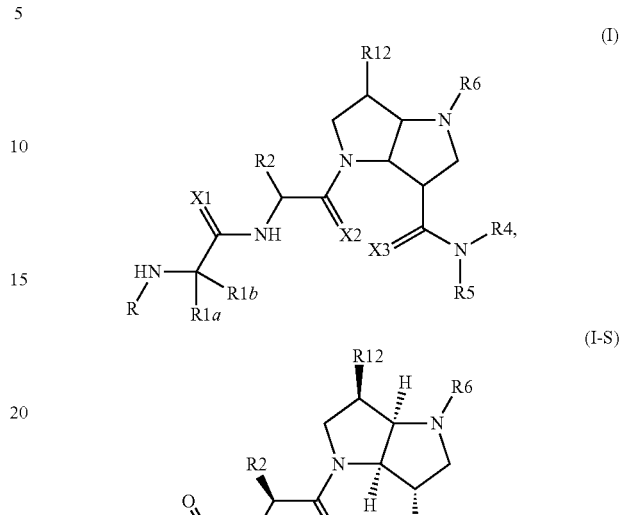 (I)

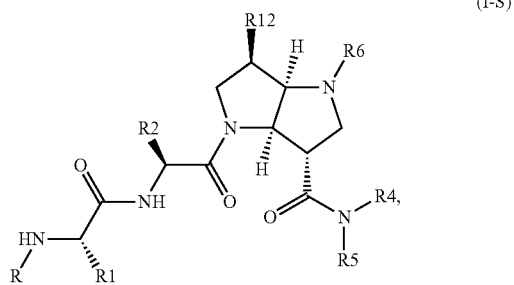 (I-S)

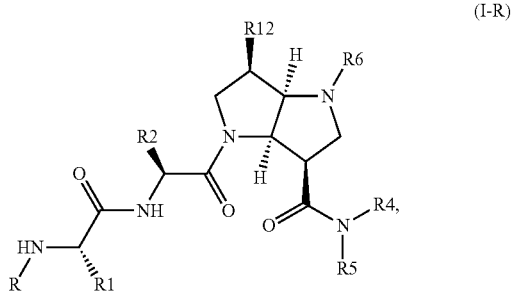 (I-R)

wherein:
X1 is O or S;
X2 is O or S;
X3 is O or S;
R is selected from H; alkyl; substituted alkyl; alkenyl; substituted alkenyl; cycloalkyl; substituted cycloalkyl; aryl; substituted aryl; heteroaryl; or substituted heteroaryl;
R1a is H; alkyl; or substituted alkyl;
R1b is H; alkyl; or substituted alkyl;
R1 is H; alkyl; or substituted alkyl;
both R2 groups together, or both R6 groups together, form -L-, linking the two monomers;
when both R2 groups together form -L-, each R6 is independently selected from H; alkyl; substituted alkyl; alkoxy; substituted alkoxy; alkylsulfonyl; arylsulfonyl; cycloalkyl; substituted cycloalkyl; heterocycloalkyl; substituted heterocycloalkyl; aryl; substituted aryl; heteroaryl; or substituted heteroaryl;
when both R6 groups together form -L-, then each R2 is independently selected from H; alkyl; substituted alkyl; cycloalkyl; substituted cycloalkyl; heterocycloalkyl; substituted heterocycloalkyl; aryl; substituted aryl; heteroaryl; or substituted heteroaryl;
R4 is H; alkyl; substituted alkyl; cycloalkyl; substituted cycloalkyl; aryl; substituted aryl; heterocycloalkyl; substituted heterocycloalkyl; heteroaryl; or substituted heteroaryl;

R5 is H; alkyl; substituted alkyl; cycloalkyl; substituted cycloalkyl; aryl; substituted aryl; heterocycloalkyl; substituted heterocycloalkyl; heteroaryl; or substituted heteroaryl or R4 and R5 together with the nitrogen to which each are attached represent heterocycloalkyl; or substituted heterocycloalkyl;

R12 is H or hydroxy; and

L is a single or double covalent bond or is a contiguous chain, branched or unbranched, substituted or unsubstituted, of 1 to about 100 atoms.

18. The compound of claim 17, or a pharmaceutically acceptable salt thereof, wherein:

in R, the alkyl, alkenyl, aryl, cycloalkyl, and heteroaryl substituents are selected from the group consisting of halogen, hydroxy, oxo, mercapto, carboxyl, alkyl, cycloalkyl, aryl, alkoxy, amino, heteroaryl, and nitro;

in R1a, R1b and R1, the alkyl substituents are selected from the group consisting of halogen, hydroxy, oxo, mercapto, carboxyl, cycloalkyl, aryl, alkoxy, amino, heteroaryl, and nitro;

in R2, the alkyl substituents are selected from the group consisting of halogen, hydroxy, oxo, alkoxy, cycloalkyl, aryl, heterocycloalkyl and heteroaryl; cycloalkyl; the cycloalkyl substituents are selected from the group consisting of halogen, hydroxy, oxo, mercapto, carboxyl, alkyl, cycloalkyl, aryl, alkoxy, amino, heteroaryl, and nitro; aryl; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro;

in R4, the alkyl substituents are selected from the groups consisting of oxo, alkoxy, carboxy, carboalkoxy, cycloalkyl, aryl, and substituted aryl; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro;

in R5, the alkyl substituents are selected from the groups consisting of oxo, alkoxy, carboxy, carboalkoxy, cycloalkyl, aryl, and substituted aryl; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro; and in R6, the alkyl substituents are selected from the group consisting of halogen, hydroxy, oxo, mercapto, carboxyl, alkoxy, amino, nitro, cycloalkyl, aryl, alkylsulfonyl, arylsulfonyl, and heteroaryl optionally substituted with lower alkyl or halogen; the alkoxy substituents are selected from the group consisting of halogen, hydroxy, oxo, mercapto, carboxyl, alkoxy, amino, nitro, cycloalkyl, aryl, alkylsulfonyl, arylsulfonyl and heteroaryl optionally substituted with lower alkyl or halogen; the cycloalkyl substituents are selected from the group consisting of halogen, hydroxy, oxo, mercapto, carboxyl, alkyl, cycloalkyl, aryl, alkoxy, amino, heteroaryl, and nitro; the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; the heterocycloalkyl substituents are selected from the group consisting of halogen, hydroxy, oxo, mercapto, carboxyl, alkyl, cycloalkyl, aryl, alkoxy, amino, heteroaryl, and nitro; the heteroaryl substituents are selected from the group consisting of halogen, hydroxy, mercapto, carboxyl, alkyl, cycloalkyl, aryl, alkoxy, amino, heteroaryl, and nitro.

19. The compound of claim 17, or a pharmaceutically acceptable salt thereof, wherein:

X1, X2 and X3 are O;

R is selected from H; alkyl; substituted alkyl; alkenyl; or substituted alkenyl; wherein the alkyl and alkenyl substitutents are selected from the group consisting of halogen, hydroxy, oxo, mercapto, carboxyl, alkyl, cyclopropyl, alkoxy, amino, and nitro;

R1a is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R1b is selected from H, alkyl, or substituted alkyl, wherein the substitutents are selected from the group consisting of halogen, hydroxy, oxo, mercapto, carboxyl, alkyl, cyclopropyl, alkoxy, amino, and nitro.

R1 is selected from H, alkyl, or substituted alkyl, wherein the substitutents are selected from the group consisting of halogen, hydroxy, oxo, mercapto, carboxyl, alkyl, cyclopropyl, alkoxy, amino, and nitro;

R2 is alkyl; cycloalkyl; aryl; heterocycloalkyl; heteroaryl; or substituted alkyl, wherein the substituents are selected from the group consisting of halogen, hydroxy, oxo, alkoxy, cycloalkyl, aryl, heterocycloalkyl and heteroaryl;

R4 and R5 are each independently selected from H; alkyl; substituted alkyl, wherein the alkyl substituents are selected from the group consisting of oxo, alkoxy, carboxy, carboalkoxy, cycloalkyl, aryl, and substituted aryl; cycloalkyl; substituted cycloalkyl, wherein the cycloalkyl substituents are selected from the group consisting of halogen, hydroxy, oxo, mercapto, carboxyl, alkyl, cycloalkyl, aryl, alkoxy, amino, heteroaryl, and nitro; aryl; substituted aryl, wherein the aryl substituents are selected from the group consisting of alkyl, halogen, hydroxy, mercapto, carboxyl, cycloalkyl, aryl, alkoxy, amino, heteroaryl, nitro, alkylsulfonyl and arylsulfonyl; heteroaryl, or substituted heteroaryl, wherein the heteroaryl substituents are selected from the group consisting of halogen, hydroxy, mercapto, carboxyl, alkyl, cycloalkyl, aryl, alkoxy, amino, heteroaryl, and nitro; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro;

both R6 groups together form -L-; and

L is a single or double covalent bond or is a contiguous chain, branched or unbranched, substituted or unsubstituted, of 1 to 100 atoms.

20. The compound of claim 17, or a pharmaceutically acceptable salt thereof, wherein:
R is selected from H or lower alkyl;
R1a is H or lower alkyl;
R1b is H or lower alkyl;
R1 is H or lower alkyl;
R2 is selected from H; lower alkyl; cycloalkyl; or substituted lower alkyl, wherein the substituents are selected from the group consisting of hydroxy, cycloalkyl and alkoxy;
R4 is H or methyl and R5 is selected from substituted lower alkyl, wherein the substituents are selected from the group consisting of oxo, lower alkoxy, carboxy, substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent heterocycloalkyl; or substituted heterocycloalkyl, wherein the heterocycloalkyl substituents are selected from the group consisting of halogen, hydroxy, mercapto, carboxyl, alkyl, cycloalkyl, aryl, alkoxy, amino, heteroaryl, and nitro; both R6 groups together form -L-; and
L is a single or double covalent bond or is a contiguous chain, branched or unbranched, substituted or unsubstituted, of 1 to 300 atoms.

21. The compound of claim 20, or a pharmaceutically acceptable salt thereof, wherein:
R is methyl;
R1a is H;
R1b is methyl;
R1 is methyl;
R2 is lower alkyl or cycloalkyl;
R4 is H and R5 is selected from substituted lower alkyl, wherein the substituents are selected from the group consisting of oxo, lower alkoxy, carboxy, cyclohexyl, and phenyl optionally substituted with fluoro; cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;
R6 is selected from H; methylsulfonyl; substituted lower alkyl, wherein the substituents are selected from the group consisting of oxo, lower alkoxy, —NH$_2$, mono-lower alkyl amino, and heteroaryl optionally substituted with lower alkyl or halogen; and
L is optionally substituted alkyl, alkylene, alkylyne, cycloalkyl, alkylcycloalkyl, alkylarylalkyl chain of 2 to 20 atoms with 1-3 heteroatoms selected from —O—, —NH— and —S—.

22. The compound of claim 21 wherein:
R1a is —H
R1b is methyl;
R1 is methyl;
R2 is selected from t-butyl or cyclohexyl;
R4 is H and R5 is selected from cyclohexyl; indanyl; tetrahydro-naphthyl; phenyl; naphthyl; substituted phenyl, wherein the phenyl substituents are selected from the group consisting of lower alkyl and fluoro; a heteroaryl selected from pyrazolyl, quinazolinyl, quinolyl, or isoquinolyl, each optionally substituted with one or more substituents selected from the group consisting of lower alkyl, halogen and phenyl; or R4 and R5 together with the nitrogen to which they are attached represent indolinyl or isoindolinyl;
R12 is —H; and
L is —C(O)CH$_2$NHC(O)C(O)NHCH$_2$C(O)—.

23. The compound of claim 17 selected from the group consisting of:

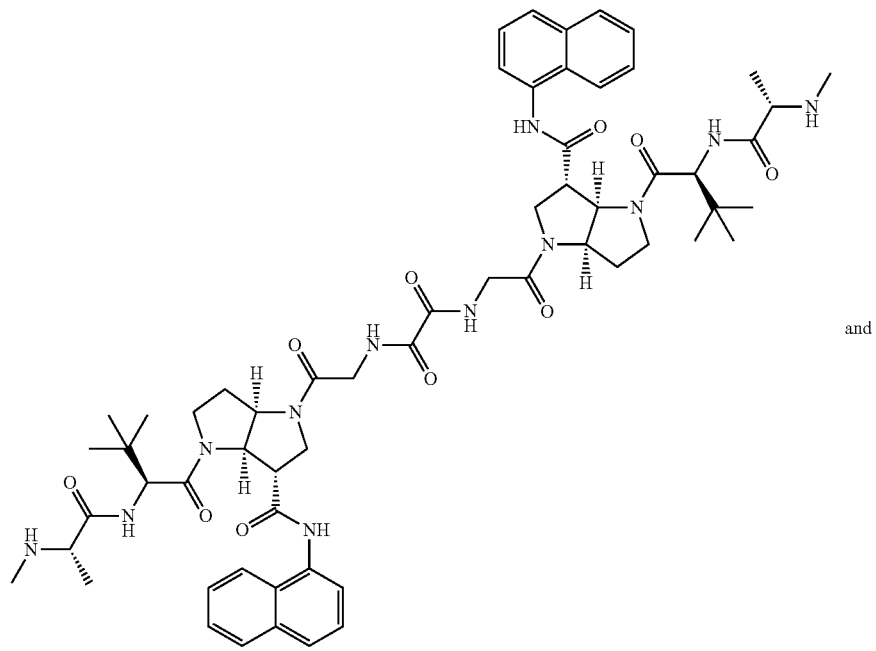

and

-continued

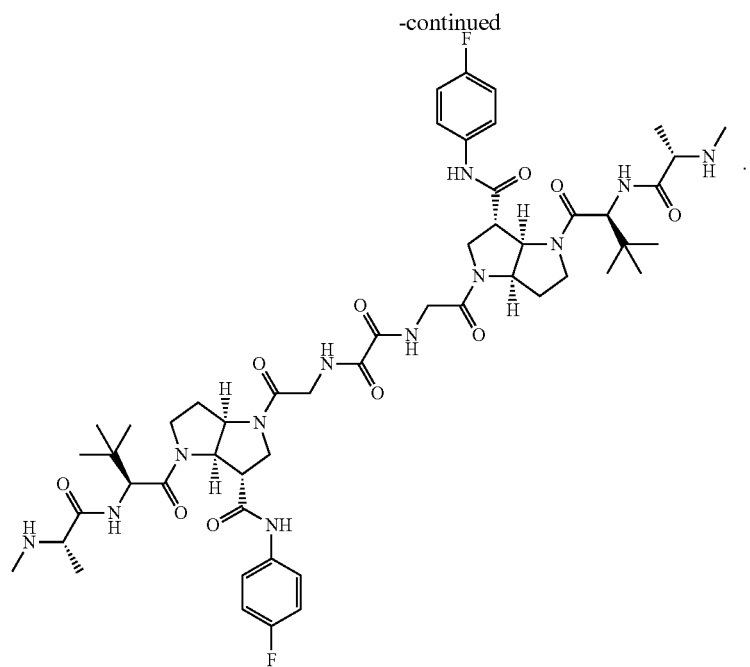

24. A pharmaceutical composition comprising a compound, or a pharmaceutically acceptable salt thereof, selected from claim 1 and a pharmaceutically acceptable excipient.

25. A method for inducing apoptosis in a cell comprising contacting the cell with a compound, or a pharmaceutically acceptable salt thereof, selected from claim 1 in an amount sufficient to induce apoptosis in the cell.

26. The method of claim 25 wherein the cell is a cancer cell.

27. A method of treating ovarian cancer the method comprising administering a therapeutically effective amount of a compound, or a pharmaceutically acceptable salt thereof, selected from claim 1, to a patient in need thereof.

28. The method of claim 27 further comprising administering a second therapy selected from radiation, chemotherapy, immunotherapy, and photodynamic therapy, or combinations thereof.

* * * * *